(12) United States Patent
Ni et al.

(10) Patent No.: US 9,163,008 B2
(45) Date of Patent: Oct. 20, 2015

(54) PYRIMIDINES AS SODIUM CHANNEL BLOCKERS

(75) Inventors: Chiyou Ni, Belle Mead, NJ (US); Bin Shao, Richboro, PA (US); Laykea Tafesse, Robbinsville, NJ (US); Jiangcho Yao, Princeton, NJ (US); Mark Youngman, North Wales, PA (US); Minnie Park, Princeton Junction, NJ (US)

(73) Assignee: Purdue Pharma, L.P., Stamford, CT (US)

( * ) Notice: Subject to any disclaimer, the term of this patent is extended or adjusted under 35 U.S.C. 154(b) by 0 days.

(21) Appl. No.: 14/342,054

(22) PCT Filed: Aug. 31, 2012

(86) PCT No.: PCT/IB2012/001871
§ 371 (c)(1),
(2), (4) Date: Jun. 24, 2014

(87) PCT Pub. No.: WO2013/030665
PCT Pub. Date: Mar. 7, 2013

(65) Prior Publication Data
US 2014/0303139 A1     Oct. 9, 2014

Related U.S. Application Data

(60) Provisional application No. 61/530,678, filed on Sep. 2, 2011, provisional application No. 61/651,611, filed on May 25, 2012.

(51) Int. Cl.
| | |
|---|---|
| A61K 31/506 | (2006.01) |
| C07D 413/04 | (2006.01) |
| C07D 403/12 | (2006.01) |
| C07D 401/14 | (2006.01) |
| C07D 405/14 | (2006.01) |
| C07D 233/90 | (2006.01) |
| C07D 401/12 | (2006.01) |
| C07D 403/04 | (2006.01) |
| C07D 405/12 | (2006.01) |
| C07D 239/34 | (2006.01) |
| C07D 239/42 | (2006.01) |
| C07D 401/04 | (2006.01) |

(52) U.S. Cl.
CPC .......... *C07D 413/04* (2013.01); *C07D 233/90* (2013.01); *C07D 239/34* (2013.01); *C07D 239/42* (2013.01); *C07D 401/04* (2013.01); *C07D 401/12* (2013.01); *C07D 401/14* (2013.01); *C07D 403/04* (2013.01); *C07D 403/12* (2013.01); *C07D 405/12* (2013.01); *C07D 405/14* (2013.01); *A61K 31/506* (2013.01)

(58) Field of Classification Search
CPC .. C07D 403/12; C07D 401/14; C07D 405/14; C07D 233/90; C07D 401/12; C07D 413/04; C07D 405/12; C07D 239/34; C07D 401/04; C07D 239/42; C07D 403/04; A61K 31/506
See application file for complete search history.

(56) References Cited

U.S. PATENT DOCUMENTS

| | | | |
|---|---|---|---|
| 6,281,211 B1 | 8/2001 | Cai et al. |
| 6,335,354 B2 | 1/2002 | Hogenkamp |
| 6,414,011 B1 | 7/2002 | Hogenkamp et al. |
| 6,479,484 B1 | 11/2002 | Lan et al. |
| 6,500,825 B2 | 12/2002 | Lan et al. |
| 6,613,803 B1 | 9/2003 | Wang et al. |
| 6,638,947 B2 | 10/2003 | Wang et al. |
| 6,696,442 B2 | 2/2004 | Wang et al. |
| 6,737,418 B2 | 5/2004 | Hogenkamp et al. |
| 6,770,661 B2 | 8/2004 | Shao et al. |
| 6,867,210 B2 | 3/2005 | Hogenkamp et al. |

(Continued)

FOREIGN PATENT DOCUMENTS

| | | |
|---|---|---|
| CN | 101223146 A | 7/2008 |
| EP | 1911753 A1 | 4/2008 |

(Continued)

OTHER PUBLICATIONS

CAS Registry No. 380476-49-3 (Jan. 4, 2002).*
V.I. Ilyin et al., 318 The Journal of Pharmacology and Experimental Therapeutics, 1083-1093 (2006).*
A.F. El-Kafrawy Journal of the Chemical Society of Pakistan, 59-66 (1992).*
V. I. Ilyin, "Pharmacology of 2-[4-(4 Chloro-2-fluorophenoxy)phenyl]-pyrimidine-4-carboxamide: A Potent, Broad Spectrum State-Dependent Sodium Channel Blocker for Treat Pain States", Journal of Pharmacology and Experimental Therapeutics, Jan. 1, 2006, vol. 318, No. 3, pp. 1083-1093.

(Continued)

*Primary Examiner* — Alexander R Pagano
(74) *Attorney, Agent, or Firm* — Purdue Pharma, L.P.; Alan L. Koller; Weiying Yang

(57) ABSTRACT

The present disclosure provides substituted pyrimidine compounds of Formula (I), and the pharmaceutically acceptable salts, prodrugs, and solvates thereof, wherein $A^1$, X, $A^2$, $W^1$, $W^2$, E, Z, and $R^4$ are defined as set forth in the specification. The present disclosure is also directed to the use of compounds of Formula (I) to treat a disorder responsive to the blockade of sodium channels. Compounds of the present disclosure are especially useful for treating pain.

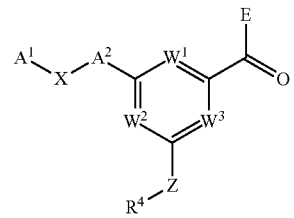

21 Claims, No Drawings

(56) References Cited

U.S. PATENT DOCUMENTS

| | | | |
|---|---|---|---|
| 6,919,363 | B2 | 7/2005 | Hogenkamp et al. |
| 7,022,714 | B2 | 4/2006 | Sun et al. |
| 7,078,426 | B2 | 7/2006 | Hogenkamp et al. |
| 7,091,210 | B2 | 8/2006 | Lan et al. |
| 7,105,549 | B2 | 9/2006 | Shao et al. |
| 7,169,782 | B2 | 1/2007 | Sun et al. |
| 7,229,993 | B2 | 6/2007 | Goehring et al. |
| 7,393,872 | B2 | 7/2008 | Lan |
| 7,541,465 | B2 | 6/2009 | Lan et al. |
| 7,579,367 | B2 | 8/2009 | Shao et al. |
| 7,872,127 | B2 | 1/2011 | Lan et al. |
| 7,943,643 | B2 | 5/2011 | Shao et al. |
| 8,048,881 | B2 | 11/2011 | Caroff et al. |
| 8,426,431 | B2 | 4/2013 | Lan et al. |
| 2002/0037926 | A1 | 3/2002 | Lan et al. |
| 2002/0040025 | A1 | 4/2002 | Hogenkamp et al. |
| 2003/0225080 | A1 | 12/2003 | Wang et al. |
| 2004/0097569 | A1 | 5/2004 | Sun et al. |
| 2004/0152696 | A1 | 8/2004 | Sun et al. |
| 2004/0176364 | A1 | 9/2004 | Sun et al. |
| 2004/0192691 | A1 | 9/2004 | Hogenkamp et al. |
| 2005/0043305 | A1 | 2/2005 | Hogenkamp et al. |
| 2005/0222027 | A1 | 10/2005 | Chiang et al. |
| 2007/0197391 | A1 | 8/2007 | Clark et al. |
| 2008/0318932 | A1 | 12/2008 | Lan |
| 2010/0221259 | A1 | 9/2010 | Habashita et al. |
| 2013/0289044 | A1 | 10/2013 | Goehring et al. |
| 2013/0296281 | A1 | 11/2013 | Kyle et al. |
| 2013/0303526 | A1 | 11/2013 | Ni et al. |
| 2013/0303568 | A1 | 11/2013 | Lan et al. |
| 2013/0345211 | A1 | 12/2013 | Kyle et al. |
| 2014/0005212 | A1 | 1/2014 | Ni et al. |
| 2014/0249128 | A1 | 9/2014 | Tadesse et al. |
| 2014/0288092 | A1 | 9/2014 | Yao |
| 2014/0309228 | A1 | 10/2014 | Engel |
| 2014/0315783 | A1 | 10/2014 | Shao |
| 2015/0045397 | A1 | 2/2015 | Tafesse et al. |
| 2015/0057300 | A1 | 2/2015 | Tafesse et al. |

FOREIGN PATENT DOCUMENTS

| | | | |
|---|---|---|---|
| EP | 2382865 | A1 | 11/2011 |
| WO | 01/68612 | A2 | 9/2001 |
| WO | WO-2004048365 | | 6/2004 |
| WO | 2004/084824 | A2 | 10/2004 |
| WO | 2004/087679 | A1 | 10/2004 |
| WO | 2005/113514 | A2 | 12/2005 |
| WO | 2006/003378 | A1 | 1/2006 |
| WO | 2006/127588 | A2 | 11/2006 |
| WO | 2007/080382 | A1 | 7/2007 |
| WO | 2008/125833 | A1 | 10/2008 |
| WO | 2009/007751 | A2 | 1/2009 |
| WO | 2009/066084 | A1 | 5/2009 |
| WO | WO-2010030027 | | 3/2010 |
| WO | 2011/076723 | A1 | 6/2011 |
| WO | 2011/080568 | A2 | 7/2011 |
| WO | WO-2011080568 | | 8/2011 |
| WO | 2012/052390 | A1 | 4/2012 |
| WO | WO-2013030665 | | 3/2013 |
| WO | WO-2014016673 | | 1/2014 |
| WO | WO-2014096941 | | 1/2014 |
| WO | WO-2014/135955 | | 9/2014 |
| WO | WO-2014151393 | | 12/2014 |
| WO | WO-2015031036 | | 3/2015 |

OTHER PUBLICATIONS

Daniel P. McNamara et al., "Use of a Glutaric Acid Cocrystal to Improve Oral Bioavailability of Low Solubility API", Pharmaceutical Research, Kluwer Academic Publishers—Plenum Publishers, NL, Jul. 11, 2006, vol. 23, No. 8, pp. 1888-1897.

Obrecht D et al, "5. A Novel and Efficient Approach for the Combinatorial Synthesis of Structurally Diverse Pyrimidines on Solid Suppoer", Helvetica Chimica Acta, Verlag Helvetica Chimica Acta, Basel, CH, Jan. 1, 1997, vol. 80, pp. 65-72.

International Search Report mailed Dec. 10, 2012 in corresponding International Application No. PCT/IB2012/001871 and Written Opinion.

Hubner, C., et al., "Ion Channel Diseases," Human Molecular Genetics 11:2435-2445, Oxford University Press (2002).

Yogeeswari, P., et al., "Ion Channels as Important Targets for Antiepileptic Drug Design," Curr. Drug Targets 5 (7):589-602, Bentham Science Publishers Ltd., Netherlands (2004).

Noble, D., "Unraveling the genetics and mechanisms of cardiac arrhythmia," Proc.Natl. Acad. Sci. USA 99 (9):5755-5756, National Academy of Sciences, United States (2002).

Cannon, S.C., "Spectrum of sodium channel disturbances in the nondystrophic myotonias and periodic paralyses," Kidney Int. 57(3):772-779, International Society of Nephrology, United States (2000).

Wood, J.N., et al., "Voltage-Gated Sodium Channels and Pain Pathways," J. Neurobiol. 61(1):55-71, Wiley Periodicals, Inc., United States (2004).

Chahine, M., et al., "Voltage-Gated Sodium Channels in Neurological Disorders," CNS Neurol. Disord. Drug Targets 7(2):144-158, Bentham Science Publishers Ltd., United Arab Emirates (2008).

Kyle, D.J., and Ilyin, V.I., "Sodium Channel Blockers," J. Med. Chem. 50(11):2583-2588, American Chemical Society, United States (2007).

Liu, H., et al., "Mutations in Cardiac Sodium Channels: Clinical Implications," Am. J. Pharmacogenomics 3(3):173-179, Adis Data Information BV, New Zealand (2003).

Srivatsa, U., et al., "Mechanisms of Antiarrhythmic Drug Actions and Their Clinical Relevance for Controlling Disorders of Cardiac Rhythm," Curr. Cardiol. Rep. 4(5):401-410, Current Science Inc., United States (2002).

Black, J.A., et al., "Sensory neuron-specific sodium channel SNS is abnormally expressed in the brains of mice with experimental allergic encephalomyelitis and humans with multiple sclerosis," Proc. Natl. Acad. Sci. USA 97 (21):11598-11602, National Academy of Sciences, United States (2000).

Majumdar, B., et al., "An electrocochleographic study of the effects of lignocaine on patients with tinnitus," Clin. Otolaryngol. Allied Sci. 8(3):175-180, Blackwell Scientific Publications, England (1983).

Toledo-Aral, J.J., et al., "Identification of PN1, a predominant voltage-dependent sodium channel expressed principally in peripheral neurons," Proc. Natl. Acad. Sci. USA 94(4):1527-1532, The National Academy of Sciences, United States (1997).

Nassar, M.A., et al., "Nociceptor-specific gene deletion reveals a major role for Nav1.7 (PN1) in acute and inflammatory pain," Proc. Natl. Acad. Sci. USA 101(34):12706-12711, National Academy of Sciences, United States (2004).

Clare, J.J., et al., "Voltage-gated sodium channels as therapeutic targets," Drug Discov. Today 5(11):506-520, Elsevier Science Ltd., England (2000).

Lai, J., et al., "Voltage-Gated Sodium Channels and Hyperalgesia," Annu. Rev. Pharmacol. Toxicol. 44:371-397, Annual Reviews, United States (2004).

Anger. T., et al., "Medicinal Chemistry of Neuronal Voltage-Gated Sodium Channel Blockers," J. Med. Chem. 44 (2):115-137, American Chemical Society, United States (2001).

Catterall, W.A., "Common modes of drug action on Na+ channels: local anesthetics, antiarrhythmics and anticonvulsants," Trends Pharmacol. Sci. 8:57-65, Elsevier Science Publishers, B.V., Netherlands (1987).

Graham, S.H., et al., "Neuroprotective Effects of a Use-Dependent Blocker of Voltage-Dependent Sodium Channels, BW619C89, in Rat Middle Cerebral Artery Occlusion," J. Pharmacol. Exp. Ther. 269(2):854-859, The American Society for Pharmacology and Experimental Therapeutics, United States (1994).

Brown, C.M., et al., "Neuroprotective properties of lifarizine compared with those of other agents in a mouse model of focal cerebral ischaemia," Br. J. Pharmacol. 115(8):1425-1432, Stockton Press, England (1995).

Donaldson, I., "Tegretol: a double blind trial in tinnitus," J. Laryngol. Otol. 95(9):947-951, Cambridge University Press, England (1981).

(56) References Cited

OTHER PUBLICATIONS

Baker, M.D. and Wood, J.N., "Involvement of Na+ channels in pain pathways," Trends Pharmacol. Sci. 22(1):27-31, Elsevier Science Ltd., England (2001).

Lai, J., et al., "The role of voltage-gated sodium channels in neuropathic pain," Curr. Opin. Neurobiol. 13(3):291-297, Elsevier Science Ltd., England (2003).

Meisler, M.H. and Kearney, J.A., "Sodium channel mutations in epilepsy and other neurological disorders," J. Clin. Invest. 115(8):2010-2017, American Society for Clinical Investigation, United States (2005).

Taylor, C.P. and Meldrum, B.S., "Na+ channels as targets for neuroprotective drugs," Trends Pharmacol. Sci. 16 (9):309-316, Elsevier Science Ltd., England (1995).

Moller, A., "Similiarities Between Chronic Pain and Tinnitus," The American Journal of Ontology 18:577-585 (1997).

Tonndorf, J., "The analogy between tinnitus and pain: A suggestion for physiological basis of chronic tinnitus," Hearing Research 28(2-3):271-275, Elsevier Science Publishers B.V., Netherlands (1987).

Simpson, J.J. and Davies, W.E., "Recent advances in the pharmacological treatment of tinnitus," Trends Pharmacol. Sci. 20(1):12-18, Elsevier Science, England (1999).

\* cited by examiner

PYRIMIDINES AS SODIUM CHANNEL BLOCKERS

CROSS-REFERENCE TO RELATED APPLICATIONS

This application is the U.S. national phase, pursuant to 35 U.S.C. §371, of PCT International Application Ser. No. PCT/IB2012/001871, filed Aug. 31, 2012, designating the United States and published in English on Mar. 7, 2013 as publication WO 2013/030665 A1, which claims priority to U.S. Provisional Application Ser. No. 61/530,678, filed Sep. 2, 2011, and U.S. Provisional Application Ser. No. 61/651,611, filed May 25, 2012. The contents of the afore-mentioned patent applications are incorporated herein by their entirety.

BACKGROUND OF THE INVENTION

1. Field of the Invention

This invention is in the field of medicinal chemistry. The invention provides novel substituted pyrimidine compounds and the use of these compounds as blockers of voltage-gated sodium ($Na^+$) channels.

2. Background Art

Voltage-gated sodium channels (VGSCs) are found in all excitable cells. In neuronal cells of the central nervous system (CNS) and peripheral nervous system (PNS) sodium channels are primarily responsible for generating the rapid upstroke of the action potential. In this manner sodium channels are essential to the initiation and propagation of electrical signals in the nervous system. Proper function of sodium channels is therefore necessary for normal function of the neuron. Consequently, aberrant sodium channel function is thought to underlie a variety of medical disorders (See Hubner et al., *Hum. Mol. Genet.* 11:2435-2445 (2002) for a general review of inherited ion channel disorders) including epilepsy (Yogeeswari et al, *Curr. Drug Target* 5:589-602 (2004)), arrhythmia (Noble, *Proc. Natl. Acad. Sci. USA* 99:5755-5756 (2002)), myotonia (Cannon, *Kidney Int.* 57:772-779 (2000)), and pain (Wood et al., *J. Neurobiol.*, 61:55-71 (2004)).

VGSCs are composed of one α-subunit, which forms the core of the channel and is responsible for voltage-dependent gating and ion permeation, and several auxiliary β-subunits (see, e.g., Chahine et al., *CNS & Neurological Disorders-Drug Targets* 7:144-158 (2008) and Kyle and Ilyin, *J. Med. Chem.* 50:2583-2588 (2007)). α-Subunits are large proteins composed of four homologous domains. Each domain contains six α-helical transmembrane spanning segments. There are currently nine known members of the family of voltage-gated sodium channel α-subunits. Names for this family include SCNx, SCNAx, and $Na_v$x.x (see Table 1, below). The VGSC family has been phylogenetically divided into two subfamilies $Na_v$1.x (all but SCN6A) and $Na_v$2.x (SCN6A). The $Na_v$1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v$1.5, H1) is almost exclusively expressed in cardiac tissue and has been shown to underlie a variety of cardiac arrhythmias and other conduction disorders (Liu et al., *Am. J. Pharmacogenomics* 3:173-179 (2003)). Consequently, blockers of $Na_v$1.5 have found clinical utility in treatment of such disorders (Srivatsa et al., *Curr. Cardiol. Rep.* 4:401-410 (2002)). The remaining TTX-resistant sodium channels, $Na_v$1.8 (SCN10A, PN3, SNS) and $Na_v$1.9 (SCN11A, NaN, SNS2) are expressed in the peripheral nervous system and show preferential expression in primary nociceptive neurons. Human genetic variants of these channels have not been associated with any inherited clinical disorder. However, aberrant expression of $Na_v$1.8 has been found in the CNS of human multiple sclerosis (MS) patients and also in a rodent model of MS (Black et al., *Proc. Natl. Acad. Sci. USA* 97:11598-115602 (2000)). Evidence for involvement in nociception is both associative (preferential expression in nociceptive neurons) and direct (genetic knockout). $Na_v$1.8-null mice exhibited typical nociceptive behavior in response to acute noxious stimulation but had significant deficits in referred pain and hyperalgesia (Laird et al., *J. Neurosci.* 22:8352-8356 (2002)).

TABLE 1

Voltage-gated sodium channel gene family

| Type | Gene Symbol | Tissue Distribution | TTX $IC_{50}$ (nM) | Disease Association | Indications |
|---|---|---|---|---|---|
| $Na_v$1.1 | SCN1A | CNS/PNS | 10 | Epilepsy | Pain, seizures, neurodegeneration |
| $Na_v$1.2 | SCN2A | CNS | 10 | Epilepsy | Epilepsy, neurodegeneration |
| $Na_v$1.3 | SCN3A | CNS | 15 | — | Pain |
| $Na_v$1.4 | SCN4A | Skeletal muscle | 25 | Myotonia | Myotonia |
| $Na_v$1.5 | SCN5A | Heart muscle | 2,000 | Arrhythmia | Arrhythmia |
| $Na_v$1.6 | SCN8A | CNS/PNS | 6 | — | Pain, movement disorders |
| $Na_v$1.7 | SCN9A | PNS | 25 | Erythermalgia | Pain |
| $Na_v$1.8 | SCN10A | PNS | 50,000 | — | Pain |
| $Na_v$1.9 | SCN11A | PNS | 1,000 | — | Pain |

The $Na_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA* 94:1527-1532 (1997)).

An increasing body of evidence suggests that $Na_v$1.7 plays a key role in various pain states, including acute, inflammatory and/or neuropathic pain. Deletion of the SCN9A gene in nociceptive neurons of mice led to an increase in mechanical and thermal pain thresholds and reduction or abolition of inflammatory pain responses (Nassar et al., *Proc. Natl. Acad. Sci. USA* 101:12706-12711 (2004)).

Sodium channel-blocking agents have been reported to be effective in the treatment of various disease states, and have found particular use as local anesthetics, e.g., lidocaine and bupivacaine, and in the treatment of cardiac arrhythmias, e.g., propafenone and amiodarone, and epilepsy, e.g., lamotrigine, phenyloin and carbamazepine (see Clare et al., *Drug Discovery Today* 5:506-510 (2000); Lai et al., *Annu. Rev. Pharmacol. Toxicol.* 44:371-397 (2004); Anger et al., *J. Med. Chem.* 44:115-137 (2001), and Catterall, *Trends Pharmacol. Sci.* 8:57-65 (1987)). Each of these agents is believed to act by interfering with the rapid influx of sodium ions.

Other sodium channel blockers such as BW619C89 and lifarizine have been shown to be neuroprotective in animal models of global and focal ischemia (Graham et al., *J. Pharmacol. Exp. Ther.* 269:854-859 (1994); Brown et al., *British J. Pharmacol.* 115:1425-1432 (1995)).

It has also been reported that sodium channel-blocking agents can be useful in the treatment of pain, including acute, chronic, inflammatory, neuropathic, and other types of pain such as rectal, ocular, and submandibular pain typically associated with paroxysmal extreme pain disorder; see, for example, Kyle and Ilyin., *J. Med. Chem.* 50:2583-2588 (2007); Wood et al., *J. Neurobiol.* 61:55-71 (2004); Baker et al., *TRENDS in Pharmacological Sciences* 22:27-31 (2001); and Lai et al., *Current Opinion in Neurobiology* 13:291-297 (2003); the treatment of neurological disorders such as epilepsy, seizures, epilepsy with febrile seizures, epilepsy with benign familial neonatal infantile seizures, inherited pain disorders, e.g., primary erthermalgia and paroxysmal extreme pain disorder, familial hemiplegic migraine, and movement disorder; and the treatment of other psychiatric disorders such as autism, cerebellar atrophy, ataxia, and mental retardation; see, for example, Chahine et al., *CNS & Neurological Disorders-Drug Targets* 7:144-158 (2008) and Meisler and Kearney, *J. Clin. Invest.* 115:2010-2017 (2005). In addition to the above-mentioned clinical uses, carbamazepine, lidocaine and phenyloin are used to treat neuropathic pain, such as from trigeminal neuralgia, diabetic neuropathy and other forms of nerve damage (Taylor and Meldrum, *Trends Pharmacol. Sci.* 16:309-316 (1995)). Furthermore, based on a number of similarities between chronic pain and tinnitus, (Moller, *Am. J. Otol.* 18:577-585 (1997); Tonndorf, *Hear. Res.* 28:271-275 (1987)) it has been proposed that tinnitus should be viewed as a form of chronic pain sensation (Simpson, et al., *Tip.* 20:12-18 (1999)). Indeed, lidocaine and carbamazepine have been shown to be efficacious in treating tinnitus (Majumdar, B. et al., *Clin. Otolaryngol.* 8:175-180 (1983); Donaldson, *Laryngol. Otol.* 95:947-951 (1981)).

Many patients with either acute or chronic pain disorders respond poorly to current pain therapies, and the development of resistance or insensitivity to opiates is common. In addition, many of the currently available treatments have undesirable side effects.

In view of the limited efficacy and/or unacceptable side-effects of the currently available agents, there is a pressing need for more effective and safer analgesics that work by blocking sodium channels.

BRIEF SUMMARY OF THE INVENTION

In one aspect, the present disclosure provides substituted pyrimidine compounds represented by Formulae I-XV, below, and the pharmaceutically acceptable salts, prodrugs, and solvates thereof, collectively referred to herein as "Compounds of the Invention."

In another aspect, the present disclosure provides the use of Compounds of the Invention as blockers of one or more sodium (Na$^+$) channels.

In another aspect, the present disclosure provides a method for treating a disorder responsive to the blockade of one or more sodium channels in a mammal, comprising administering to the mammal an effective amount of a Compound of the Invention.

In another aspect, the present disclosure provides a method for treating pain (e.g., acute pain, chronic pain, which includes but is not limited to, neuropathic pain, postoperative pain, and inflammatory pain, or surgical pain), comprising administering an effective amount of a Compound of the Invention to a mammal in need of such treatment. Specifically, the present disclosure provides a method for preemptive or palliative treatment of pain by administering an effective amount of a Compound of the Invention to a mammal in need of such treatment.

In another aspect, the present disclosure provides a method for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, comprising administering an effective amount of a Compound of the Invention to a mammal in need of such treatment.

In another aspect, the present disclosure provides a pharmaceutical composition comprising a Compound of the Invention and one or more pharmaceutically acceptable carriers.

In another aspect, the present disclosure provides a pharmaceutical composition for treating a disorder responsive to the blockade of sodium ion channels, wherein the pharmaceutical composition comprises an effective amount of a Compound of the Invention in a mixture with one or more pharmaceutically acceptable carriers.

In another aspect, the present disclosure provides a method of modulating sodium channels in a mammal, comprising administering to the mammal an effective amount of at least one Compound of the Invention.

In another aspect, the present disclosure provides Compounds of the Invention for use in treating pain in a mammal, e.g., acute pain, chronic pain, which includes but is not limited to, neuropathic pain, postoperative pain, and inflammatory pain, or surgical pain.

In another aspect, the present disclosure provides Compounds of the Invention for use in treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

In another aspect, the present disclosure provides a radiolabeled Compound of the Invention and the use of such compounds as radioligands in any appropriately selected competitive binding assays and screening methodologies. Thus, the present disclosure further provides a method for screening a candidate compound for its ability to bind to a sodium channel or sodium channel subunit using a radiolabeled Compound of the Invention. In certain embodiments, the compound is radiolabeled with $^3$H, $^{11}$C, or $^{14}$C. This competitive binding assay can be conducted using any appropriately selected methodology. In one embodiment, the screening method comprises: i) introducing a fixed concentration of the radiolabeled compound to an in vitro preparation comprising a soluble or membrane-associated sodium channel, subunit or fragment under conditions that permit the radiolabeled compound to bind to the channel, subunit or fragment, respectively, to form a conjugate; ii) titrating the conjugate with a candidate compound; and iii) determining the ability of the candidate compound to displace the radiolabeled compound from said channel, subunit or fragment.

In another aspect, the present disclosure provides a Compound of the Invention for use in the manufacture of a medicament for treating pain in a mammal. In one embodiment, the present disclosure provides the use of a Compound of the Invention in the manufacture of a medicament for palliative or preemptive treatment of pain, such as acute pain, chronic pain, or surgical pain.

In another aspect, the present disclosure provides a Compound of the Invention for use in the manufacture of a medicament for treating stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, or cardiac arrhythmia, or providing local anesthesia, in a mammal.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

One aspect of the present disclosure is based on the use of Compounds of the Invention as blockers of $Na^+$ channels. In view of this property, Compounds of the Invention are useful for treating disorders responsive to the blockade of sodium ion channels.

In one embodiment, Compounds of the Invention are compounds represented by Formula I:

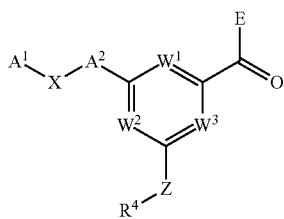

I and the pharmaceutically acceptable salts, solvates, and prodrugs thereof,
wherein:
$W^1$ and $W^2$ are N and $W^3$ is $CR^3$; or
$W^1$ and $W^3$ are N and $W^2$ is $CR^3$; or
$W^2$ and $W^3$ are N and $W^1$ is $CR^3$;
$A^1$ is selected from the group consisting of:
a) optionally substituted aryl;
b) optionally substituted heteroaryl;
c) optionally substituted cycloalkyl;
d) optionally substituted heterocyclo; and
e) aralkyl;
X is selected from the group consisting of:
a) —O—;
b) —S—;
c) —SO—;
d) —SO$_2$—;
e) —($CR^{7a}R^{7b}$)$_m$—;
f) —$NR^8$—;
g) —$SO_2NR^9$—; and
h) —$NR^9SO_2$—;
each $R^{7a}$ and $R^{7b}$, which can be identical or different, is selected from the group consisting of:
a) hydrogen;
b) halo;
c) alkyl; and
d) aryl; or
each $R^{7a}$ and $R^{7b}$ taken together with the carbon atom to which they are attached form a 3- to 8-membered optionally substituted cycloalkyl or a 3- to 8-membered optionally substituted heterocyclo;
m is 0, 1, 2, or 3;
$R^8$ is selected from the group consisting of hydrogen and alkyl;
$R^9$ is selected from the group consisting of hydrogen and alkyl;
$A^2$ is selected from the group consisting of:
a) optionally substituted aryl;
b) optionally substituted heteroaryl;
c) optionally substituted heterocyclo; and
d) optionally substituted cycloalkyl; or
$A^2$ is absent;
E is selected from the group consisting of:
a) hydroxy;
b) alkoxy; and
c) —$NR^1R^2$;
$R^1$ is selected from the group consisting of:
a) hydrogen;
b) alkyl;
c) aralkyl;
d) (heterocyclo)alkyl;
e) (heteroaryl)alkyl;
f) (amino)alkyl;
g) (alkylamino)alkyl;
h) (dialkylamino)alkyl;
i) (carboxamido)alkyl;
j) (cyano)alkyl;
k) alkoxyalkyl;
l) hydroxyalkyl; and
m) heteroalkyl;
$R^2$ is selected from the group consisting of hydrogen and alkyl; or
$R^1$ and $R^2$ taken together with the nitrogen atom to which they are attached form a 3- to 8-membered optionally substituted heterocyclo;
$R^3$ is selected from the group consisting of:
a) hydrogen;
b) halo;
c) nitro;
d) cyano;
e) hydroxy;
f) amino;
g) alkylamino;
h) dialkylamino;
i) haloalkyl;
j) hydroxyalkyl;
k) alkoxy;
l) haloalkoxy; and
m) alkoxyalkyl;
Z is selected from the group consisting of —$NR^5$— and —O—;

$R^4$ is selected from the group consisting of:

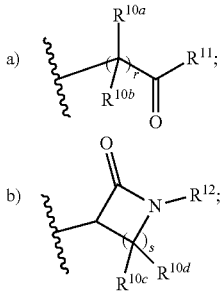

c) hydroxyalkyl;
d) hydroxy(cycloalkyl)alkyl; and
e) (heterocyclo)alkyl;
each $R^{10a}$, $R^{10b}$, $R^{10c}$, and $R^{10d}$ is independently selected from the group consisting of:
a) hydrogen;
b) hydroxy;
c) optionally substituted alkyl;
d) aralkyl;
e) (heterocyclo)alkyl;
f) (heteroaryl)alkyl;
g) (amino)alkyl;
h) (alkylamino)alkyl;
i) (dialkylamino)alkyl;
j) (carboxamido)alkyl;
k) (cyano)alkyl;
l) alkoxyalkyl;
m) hydroxyalkyl;
n) heteroalkyl;
o) optionally substituted cycloalkyl;
p) optionally substituted aryl;
q) optionally substituted heterocyclo; and
r) optionally substituted heteroaryl; or
$R^{10a}$ and $R^{10b}$ taken together with the carbon atom to which they are attached form a 3- to 8-membered optionally substituted cycloalkyl or a 3- to 8-membered optionally substituted heterocyclo;
r is 1, 2, or 3;
s is 1, 2, or 3;
$R^{11}$ is selected from the group consisting of:
a) hydroxy;
b) alkoxy; and
c) —$NR^{1a}R^{2a}$;
$R^{1a}$ is selected from the group consisting of:
a) hydrogen;
b) alkyl;
c) aralkyl;
d) (heterocyclo)alkyl;
e) (heteroaryl)alkyl;
f) (amino)alkyl;
g) (alkylamino)alkyl;
h) (dialkylamino)alkyl;
i) (carboxamido)alkyl;
j) (cyano)alkyl;
k) alkoxyalkyl;
l) hydroxyalkyl; and
m) heteroalkyl;
$R^{2a}$ is selected from the group consisting of hydrogen and alkyl; or
$R^{1a}$ and $R^{2a}$ taken together with the nitrogen atom to which they are attached form a 3- to 8-membered optionally substituted heterocyclo;

$R^{12}$ is selected from the group consisting of:
a) hydrogen;
b) optionally substituted alkyl;
c) (amino)alkyl;
d) (alkylamino)alkyl;
e) (dialkylamino)alkyl;
f) (carboxamido)alkyl;
g) (cyano)alkyl;
h) alkoxyalkyl;
i) hydroxyalkyl; and
j) heteroalkyl;
$R^5$ is selected from the group consisting of:
a) hydrogen
b) alkyl;
c) hydroxyalkyl; and
d) alkylsulfonyl; or
$R^4$ and $R^5$ taken together with the nitrogen atom to which they are attached form a 3- to 8-membered optionally substituted heterocyclo.

In another embodiment, Compounds of the Invention are compounds represented by Formula I, and the pharmaceutically acceptable salts, prodrugs and solvates thereof, wherein when Z is —$NR^5$— and $R^4$ and $R^5$ taken together with the nitrogen atom to which they are attached form a 3- to 8-membered optionally substituted heterocyclo, then $R^1$ is selected from the group consisting of:
a) hydrogen;
b) (heterocyclo)alkyl;
c) (heteroaryl)alkyl;
d) (amino)alkyl;
e) (alkylamino)alkyl;
f) (dialkylamino)alkyl;
g) (carboxamido)alkyl;
h) (cyano)alkyl;
i) alkoxyalkyl;
j) hydroxyalkyl; and
k) heteroalkyl.

In another embodiment, Compounds of the Invention are compounds represented by Formula I, and the pharmaceutically acceptable salts, prodrugs and solvates thereof, wherein when Z is —$NR^5$—, $R^4$ and $R^5$ taken together with the nitrogen atom to which they are attached form a 3- to 8-membered optionally substituted heterocyclo, and $A^2$ is absent, then X is selected from the group consisting of:
a) —O—;
b) —S—;
c) —SO—;
d) —$SO_2$—
e) —$(CR^{7a}R^{7b})_m$—;
f) —$SO_2NR^9$—; and
g) —$NR^9SO_2$—.

In another embodiment, Compounds of the Invention are compounds represented by Formula I, and the pharmaceutically acceptable salts, prodrugs and solvates thereof, wherein $A^2$ is selected from the group consisting of:
a) optionally substituted aryl;
b) optionally substituted heteroaryl;
c) optionally substituted heterocyclo; and
d) optionally substituted cycloalkyl.

In another embodiment, Compounds of the Invention are compounds represented by Formula I, and the pharmaceutically acceptable salts, prodrugs and solvates thereof, wherein X is selected from the group consisting of:
a) —O—;
b) —S—;
c) —SO—;
d) —$SO_2$— e) —(CR$^{7a}$R$^{7b}$)$_m$—;
f) —SO$_2$NR$^9$—; and
g) —NR$^9$SO$_2$—.

In another embodiment, Compounds of the Invention are compounds represented by Formula I, and the pharmaceutically acceptable salts, prodrugs and solvates thereof, wherein:

W$^1$ and W$^2$ are N and W$^3$ is CH;

A$^1$ is selected from the group consisting of optionally substituted aryl and optionally substituted heteroaryl;

X is —O—;

A$^2$ is selected from the group consisting of:
a) optionally substituted aryl, e.g., optionally substituted phenyl;
b) optionally substituted heteroaryl, e.g., optionally substituted pyridyl;
c) optionally substituted heterocyclo, e.g., optionally substituted piperidinyl, optionally substituted piperazinyl, or optionally substituted azetidinyl; and
d) optionally substituted cycloalkyl, e.g., optionally substituted cyclohexenyl, or optionally substituted cyclohexyl; and E is selected from the group consisting of —OH, —OMe, -OtBu, and —NH$_2$.

In another embodiment, Compounds of the Invention are compounds represented by Formula I, and the pharmaceutically acceptable salts, prodrugs and solvates thereof, wherein when Z is —NR$^5$— and R$^4$ and R$^5$ taken together with the nitrogen atom to which they are attached form a 3- to 8-membered optionally substituted heterocyclo, then R$^1$ is selected from the group consisting of:
a) hydrogen;
b) (heterocyclo)alkyl;
c) (heteroaryl)alkyl;
d) (amino)alkyl;
e) (alkylamino)alkyl;
f) (dialkylamino)alkyl;
g) (carboxamido)alkyl;
h) (cyano)alkyl;
i) alkoxyalkyl;
j) hydroxyalkyl; and
k) heteroalkyl, and A$^2$ is selected from the group consisting of:
a) optionally substituted aryl;
b) optionally substituted heteroaryl;
c) optionally substituted heterocyclo; and
d) optionally substituted cycloalkyl.

In another embodiment, Compounds of the Invention are compounds represented by Formula II:

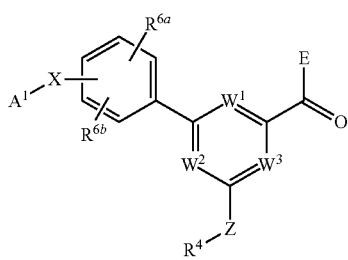

II and the pharmaceutically acceptable salts, solvates, and prodrugs thereof, wherein A$^1$, X, E, R$^4$, W$^1$, W$^2$, W$^3$, and Z are as defined above in connection with Formula I, and R$^{6a}$ and R$^{6b}$ are each independently selected from the group consisting of:
a) hydrogen;
b) halo;
c) nitro;
d) cyano;
e) hydroxy;
f) amino;
g) alkylamino;
h) dialkylamino;
i) haloalkyl;
j) hydroxyalkyl;
k) alkoxy;
l) haloalkoxy;
m) carboxy; and
n) alkoxycarbonyl.

In another embodiment, Compounds of the Invention are compounds represented by Formula III:

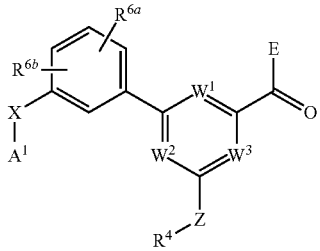

III and the pharmaceutically acceptable salts, solvates, and prodrugs thereof, wherein A$^1$, X, E, R$^4$, W$^1$, W$^2$, W$^3$, and Z are as defined above in connection with Formula I, and R$^{6a}$ and R$^{6b}$ are as defined above in connection with Formula II.

In another embodiment, Compounds of the Invention are compounds represented by Formula IV:

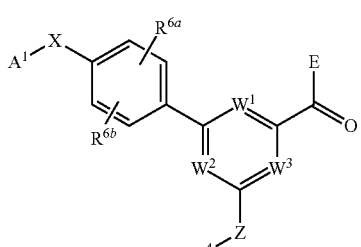

IV and the pharmaceutically acceptable salts, solvates, and prodrugs thereof, wherein A$^1$, X, E, R$^4$, W$^1$, W$^2$, W$^3$, and Z are as defined above in connection with Formula I, and R$^{6a}$ and R$^{6b}$ are as defined above in connection with Formula II.

In another embodiment, Compounds of the Invention are compounds represented by Formula V:

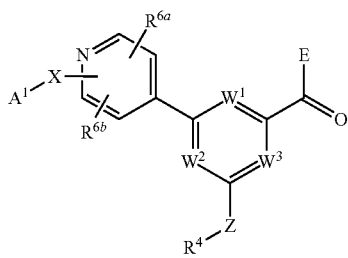

and the pharmaceutically acceptable salts, solvates, and prodrugs thereof, wherein $A^1$, X, E, $R^4$, $W^1$, $W^2$, $W^3$, and Z are as defined above in connection with Formula I, and $R^{6a}$ and $R^{6b}$ are as defined above in connection with Formula II.

In another embodiment, Compounds of the Invention are compounds represented by Formula VI:

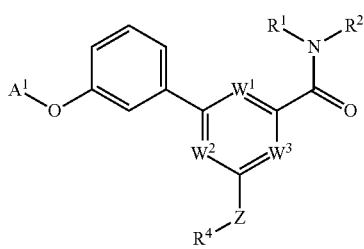

and the pharmaceutically acceptable salts, prodrugs and solvates thereof, wherein $A^1$, $R^1$, $R^2$, $R^4$, $W^1$, $W^2$, $W^3$, and Z are as defined above in connection with Formula I.

In another embodiment, Compounds of the Invention are compounds represented by Formula VII:

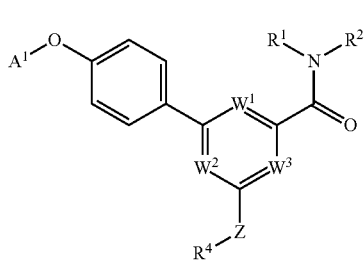

and the pharmaceutically acceptable salts, prodrugs and solvates thereof, wherein $A^1$, $R^1$, $R^2$, $R^4$, $W^1$, $W^2$, $W^3$, and Z are as defined above in connection with Formula I.

In another embodiment, Compounds of the Invention are compounds represented by Formula VII, and the pharmaceutically acceptable salts, prodrugs and solvates thereof, wherein:

$W^1$ and $W^2$ are N and $W^3$ is CH;

$A^1$ is selected from the group consisting of optionally substituted aryl, e.g., optionally substituted phenyl, and optionally substituted heteroaryl, e.g., optionally substituted pyridyl; and $R^1$ and $R^2$ are hydrogen.

In another embodiment, Compounds of the Invention are compounds represented by Formula VIII:

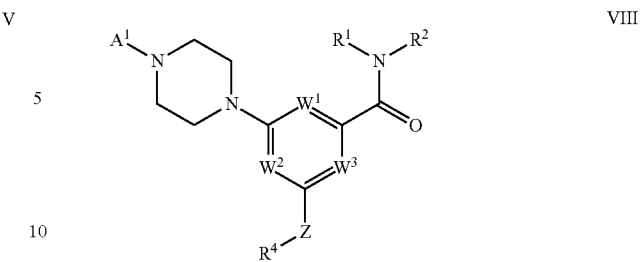

and the pharmaceutically acceptable salts, prodrugs and solvates thereof, wherein $A^1$, $R^1$, $R^2$, $R^4$, $W^1$, $W^2$, $W^3$, and Z are as defined above in connection with Formula I.

In another embodiment, Compounds of the Invention are compounds represented by Formula VIII, and the pharmaceutically acceptable salts, prodrugs and solvates thereof, wherein:

$W^1$ and $W^2$ are N and $W^3$ is CH;

$A^1$ is selected from the group consisting of optionally substituted aryl, e.g., optionally substituted phenyl, and aralkyl, e.g., benzyl, or —CH(4-F-Ph)$_2$; and $R^1$ and $R^2$ are hydrogen.

In another embodiment, Compounds of the Invention are compounds represented by Formula IX:

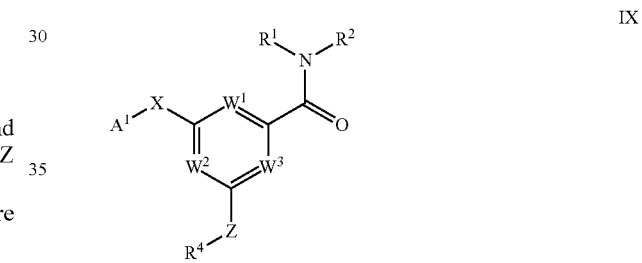

and the pharmaceutically acceptable salts, prodrugs and solvates thereof, wherein $A^1$, $R^1$, $R^2$, $R^4$, $W^1$, $W^2$, $W^3$, X, and Z are as defined above in connection with Formula I.

In another embodiment, Compounds of the Invention are compounds represented by Formula IX, and the pharmaceutically acceptable salts, prodrugs and solvates thereof, wherein:

$W^1$ and $W^2$ are N and $W^3$ is CH;

X is —O—;

$A^1$ is optionally substituted aryl, e.g., optionally substituted phenyl; and $R^1$ and $R^2$ are hydrogen.

In another embodiment, Compounds of the Invention are compounds represented by Formula XII:

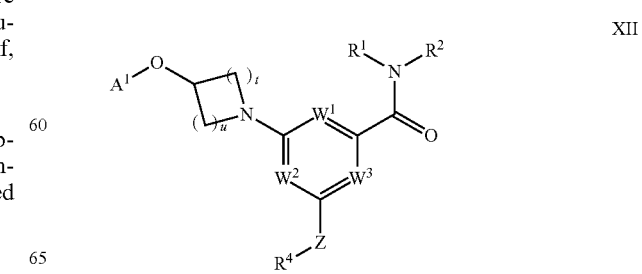

and the pharmaceutically acceptable salts, prodrugs and solvates thereof, wherein $A^1$, $R^1$, $R^2$, $R^4$, $W^1$, $W^2$, $W^3$, and Z are as defined above in connection with Formula I, t is 1, 2, 3, or 4, and u is 1, 2, 3, or 4.

In another embodiment, Compounds of the Invention are compounds represented by Formula XII, and the pharmaceutically acceptable salts, prodrugs and solvates thereof, wherein t and u are 1.

In another embodiment, Compounds of the Invention are compounds represented by Formula XII, and the pharmaceutically acceptable salts, prodrugs and solvates thereof, wherein t and u are 2.

In another embodiment, Compounds of the Invention are compounds represented by Formula XII, and the pharmaceutically acceptable salts, prodrugs and solvates thereof, wherein:

$W^1$ and $W^2$ are N and $W^3$ is CH;
$A^1$ is optionally substituted aryl, e.g., phenyl;
$R^1$ and $R^2$ are hydrogen; and
t and u are 1; or
t and u are 2.

In another embodiment, Compounds of the Invention are compounds represented by Formula XIII:

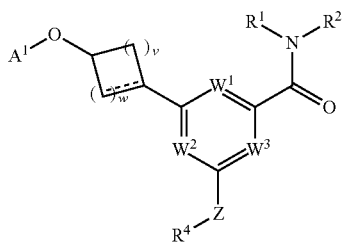

XIII and the pharmaceutically acceptable salts, prodrugs and solvates thereof, wherein $A^1$, $R^1$, $R^2$, $R^4$, $W^1$, $W^2$, $W^3$, and Z are as defined above in connection with Formula I, v is 1, 2, 3, or 4, w is 1, 2, 3, or 4, and ═ represents a single bond or a double bond.

In another embodiment, Compounds of the Invention are compounds represented by Formula XIII, and the pharmaceutically acceptable salts, prodrugs and solvates thereof, wherein v and w are 2.

In another embodiment, Compounds of the Invention are compounds represented by Formula XIII, and the pharmaceutically acceptable salts, prodrugs and solvates thereof, wherein:

$W^1$ and $W^2$ are N and $W^3$ is CH;
$A^1$ is optionally substituted aryl, e.g., optionally substituted phenyl;
$R^1$ and $R^2$ are hydrogen; and
v and w are 2.

In another embodiment, Compounds of the Invention are compounds of any of Formulae I-IX, XII, or XIII, and the pharmaceutically acceptable salts, prodrugs and solvates thereof, wherein $R^3$ is hydrogen.

In another embodiment, Compounds of the Invention are compounds of any of Formulae I-IX, XII, or XIII, and the pharmaceutically acceptable salts, prodrugs and solvates thereof, wherein $W^1$ and $W^2$ are N and $W^3$ is CH.

In another embodiment, Compounds of the Invention are compounds of any of Formulae I-IX, XII, or XIII, and the pharmaceutically acceptable salts, prodrugs and solvates thereof, wherein $W^1$ and $W^3$ are N and $W^2$ is CH.

In another embodiment, Compounds of the Invention are compounds of any of Formulae I-IX, XII, or XIII, and the pharmaceutically acceptable salts, prodrugs and solvates thereof, wherein $W^2$ and $W^3$ are N and $W^1$ is CH.

In another embodiment, Compounds of the Invention are compounds of any of Formulae I-IX, XII, or XIII, and the pharmaceutically acceptable salts, prodrugs and solvates thereof, wherein Z is —O—.

In another embodiment, Compounds of the Invention are compounds of any of Formulae I-IX, XII, or XIII, and the pharmaceutically acceptable salts, prodrugs and solvates thereof, wherein Z is —$NR^5$—.

In another embodiment, Compounds of the Invention are compounds of any of Formulae I-IX, XII, or XIII, and the pharmaceutically acceptable salts, prodrugs and solvates thereof, wherein Z is —$NR^5$— and $R^4$ and $R^5$ taken together with the nitrogen atom to which they are attached form a 5- or 6-membered optionally substituted heterocyclo.

In another embodiment, Compounds of the Invention are compounds of any of Formulae I-IX, XII, or XIII, and the pharmaceutically acceptable salts, prodrugs and solvates thereof, wherein Z is —$NR^5$— and $R^4$ and $R^5$ taken together with the nitrogen atom to which they are attached form a 5- or 6-membered optionally substituted heterocyclo selected from the group consisting of:

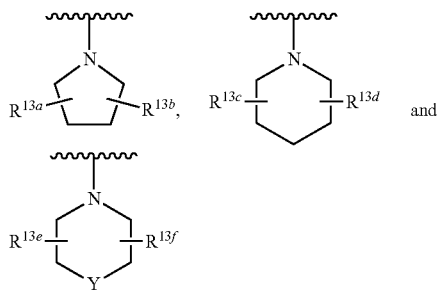

wherein:

$R^{13a}$, $R^{13b}$, $R^{13c}$, $R^{13d}$, $R^{13e}$, and $R^{13f}$ are each independently selected from the group consisting of:

a) hydrogen;
b) hydroxy;
c) hydroxyalkyl;
d) carboxy;
e) alkoxycarbonyl; and
f) carboxamido;

Y is selected from the group consisting of O, S, and $NR^{14}$; and $R^{14}$ is selected from the group consisting of hydrogen and alkyl.

In another embodiment, Compounds of the Invention are compounds of any of Formulae I-IX, XII, or XIII, and the pharmaceutically acceptable salts, prodrugs and solvates thereof, wherein Z is —$NR^5$— and $R^4$ and $R^5$ taken together with the nitrogen atom to which they are attached form a 6-membered optionally substituted heterocyclo selected from the group consisting of:

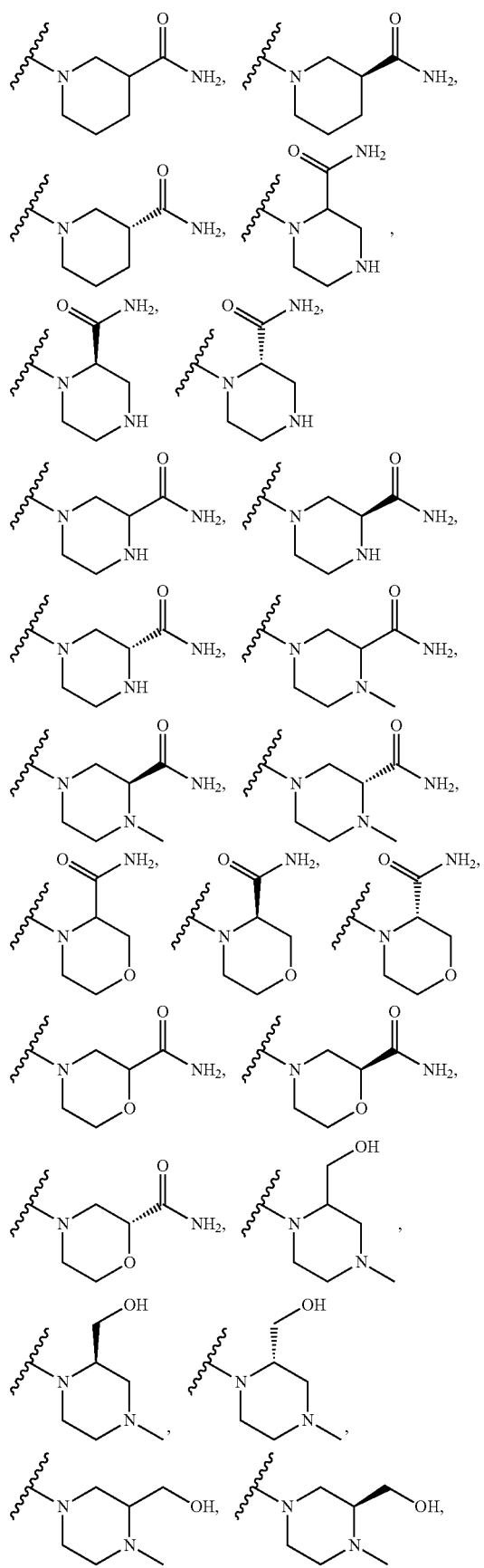

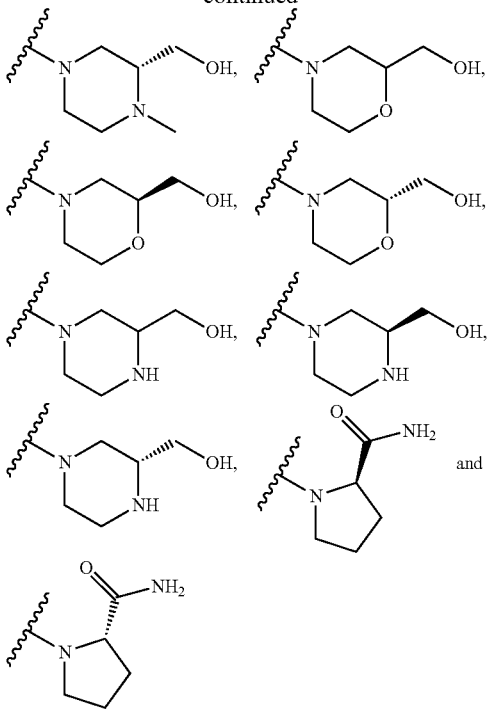

In another embodiment, Compounds of the Invention are compounds of any of Formulae I-IX, XII, or XIII, and the pharmaceutically acceptable salts, prodrugs and solvates thereof, wherein:

$R^4$ is selected from the group consisting of:

a)

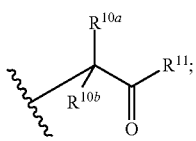

b) hydroxyalkyl; and
c) hydroxy(cycloalkyl)alkyl;

$R^{10a}$ is selected from the group consisting of:
a) hydrogen;
b) optionally substituted alkyl;
c) aralkyl;
e) (heteroaryl)alkyl;
f) (amino)alkyl;
g) (alkylamino)alkyl;
h) (dialkylamino)alkyl;
i) (carboxamido)alkyl;
k) alkoxyalkyl; and
l) hydroxyalkyl;

$R^{10b}$ is selected from the group consisting of hydrogen and alkyl; or $R^{10a}$ and $R^{10b}$ taken together with the carbon atom to which they are attached form a 3- to 6-membered cycloalkyl; and $R^5$ is selected from the group consisting of hydrogen and alkylsulfonyl; or $R^4$ and $R^5$ taken together with the nitrogen atom to which they are attached form a 3- to 8-membered optionally substituted heterocyclo.

In another embodiment, Compounds of the Invention are compounds of any of Formulae I-IX, XII, or XIII, and the pharmaceutically acceptable salts, prodrugs and solvates thereof, wherein $R^4$ is:

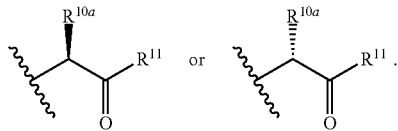

In another embodiment, Compounds of the Invention are compounds of any of Formulae I-IX, XII, or XIII, and the pharmaceutically acceptable salts, prodrugs and solvates thereof, wherein $R^4$ is:

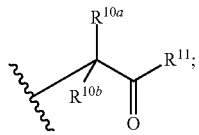

and $R^{10a}$ and $R^{10b}$ taken together with the carbon atom to which they are attached form a 3- to 6-membered cycloalkyl.

In another embodiment, Compounds of the Invention are compounds of any of Formulae I-IX, XII, or XIII, and the pharmaceutically acceptable salts, prodrugs and solvates thereof, wherein $R^{11}$ is $-NR^{1a}R^{2a}$, and $R^{1a}$ and $R^{2a}$ are as defined above.

In another embodiment, Compounds of the Invention are compounds of any of Formulae I-IX, XII, or XIII, and the pharmaceutically acceptable salts, prodrugs and solvates thereof, wherein $R^{11}$ is $-NR^{1a}R^{2a}$, $R^{1a}$ is selected from the group consisting of alkyl and hydroxyalkyl, and $R^{2a}$ is hydrogen.

In another embodiment, Compounds of the Invention are compounds of any of Formulae I-IX, XII, or XIII, and the pharmaceutically acceptable salts, prodrugs and solvates thereof, wherein $R^{11}$ is $-NR^{1a}R^{2a}$ and $R^{1a}$ and $R^{2a}$ taken together with the nitrogen atom to which they are attached form a 5- or 6-membered optionally substituted heterocyclo.

In another embodiment, Compounds of the Invention are compounds of any of Formulae I-IX, XII, or XIII, and the pharmaceutically acceptable salts, prodrugs and solvates thereof, wherein $R^{11}$ is $-NR^{1a}R^{2a}$ and $R^{1a}$ and $R^{2a}$ are hydrogen, i.e., $R^{11}$ is amino.

In another embodiment, Compounds of the Invention are compounds of any of Formulae I-IX, XII, or XIII, and the pharmaceutically acceptable salts, prodrugs and solvates thereof, wherein $R^4$ is:

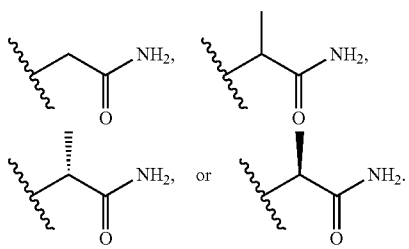

In another embodiment, Compounds of the Invention are compounds of any of Formulae I-IX, XII, or XIII, and the pharmaceutically acceptable salts, prodrugs and solvates thereof, wherein $R^4$ is selected from the group consisting of:

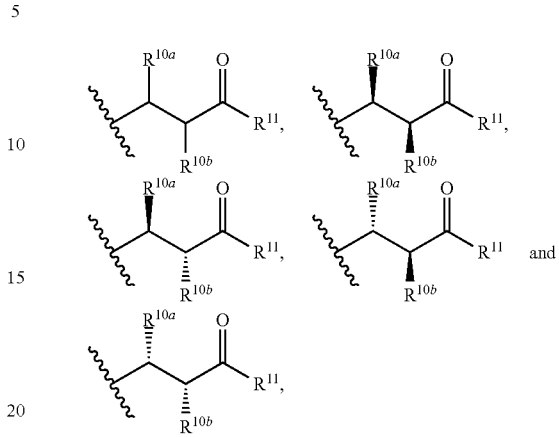

wherein, $R^{10a}$ is selected from the group consisting of hydrogen and alkyl; and
$R^{10b}$ is selected from the group consisting of:
a) hydrogen;
b) hydroxy; and
c) alkyl.

In another embodiment, Compounds of the Invention are compounds of any of Formulae I-IX, XII, or XIII, and the pharmaceutically acceptable salts, prodrugs and solvates thereof, wherein $R^4$ is selected from the group consisting of:

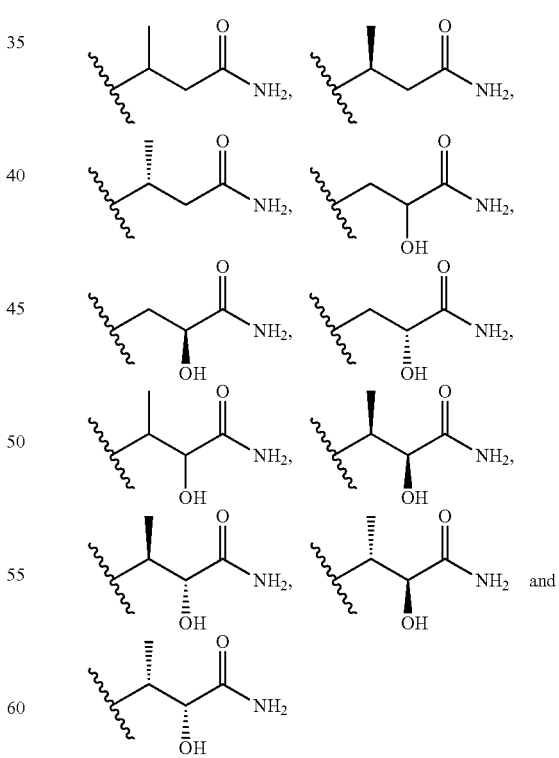

In another embodiment, Compounds of the Invention are compounds of any of Formulae I-IX, XII, or XIII, and the pharmaceutically acceptable salts, prodrugs and solvates thereof, wherein $R^4$ is selected from the group consisting of:

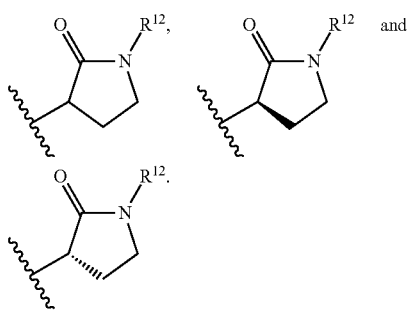

In another embodiment, Compounds of the Invention are compounds of any of Formulae I-IX, XII, or XIII, and the pharmaceutically acceptable salts, prodrugs and solvates thereof, wherein $R^4$ is hydroxyalkyl or hydroxy(cycloalkyl)alkyl.

In another embodiment, Compounds of the Invention are compounds of any of Formulae I-IX, XII, or XIII, and the pharmaceutically acceptable salts, prodrugs and solvates thereof, wherein $R^4$ is hydroxyalkyl.

In another embodiment, Compounds of the Invention are compounds of any of Formulae I-IX, XII, or XIII, and the pharmaceutically acceptable salts, prodrugs and solvates thereof, wherein $R^4$ is a hydroxyalkyl or hydroxy(cycloalkyl)alkyl selected from the group consisting of:

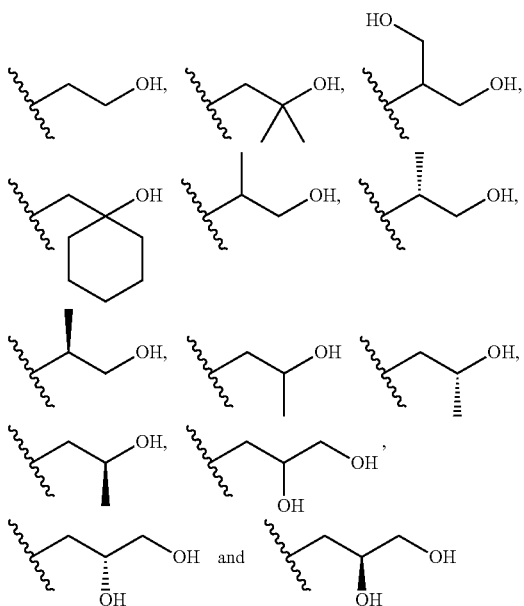

In another embodiment, Compounds of the Invention are compounds of any of Formulae I-IX, XII, or XIII, and the pharmaceutically acceptable salts, prodrugs and solvates thereof, wherein $A^1$ is selected from the group consisting of optionally substituted aryl and optionally substituted heteroaryl.

In another embodiment, Compounds of the Invention are compounds of any of Formulae I-IX, XII, or XIII, and the pharmaceutically acceptable salts, prodrugs and solvates thereof, wherein $A^1$ is optionally substituted aryl.

In another embodiment, Compounds of the Invention are compounds of Formula VIII, XII, or XIII, and the pharmaceutically acceptable salts, prodrugs and solvates thereof, wherein $A^1$ is selected from the group consisting of optionally substituted aryl and aralkyl.

In another embodiment, Compounds of the Invention are compounds of Formula I, with the proviso that when $A^2$ is absent, then X is —O— and $A^1$ is optionally substituted aryl.

In another embodiment, Compounds of the Invention are compounds represented by Formula I, and the pharmaceutically acceptable salts, prodrugs and solvates thereof, with the proviso that when $A^2$ is absent, then X is —$(CR^{7a}R^{7b})_m$—, m is 0, and $A^1$ is optionally substituted heterocyclo.

In another embodiment, Compounds of the Invention are compounds represented by Formula I, and the pharmaceutically acceptable salts, prodrugs and solvates thereof, wherein $A^2$ is an optionally substituted $C_{4-8}$ cycloalkyl that is partially unsaturated, i.e., $A^2$ is an optionally substituted $C_{4-8}$ cycloalkenyl. In another embodiment, $A^2$ is a $C_6$ cycloalkenyl.

In another embodiment, Compounds of the Invention are compounds of Formula IX, wherein $A^1$ is optionally substituted aryl and X is —O—.

In another embodiment, Compounds of the Invention are compounds of any of Formulae I-IX, XII, or XIII, and the pharmaceutically acceptable salts, prodrugs and solvates thereof, wherein $A^1$ is optionally substituted aryl and the optional substituents are chosen from the group consisting of halo, cyano, haloalkyl, hydroxyalkyl, alkoxy, and haloalkoxy.

In another embodiment, Compounds of the Invention are compounds of any of Formulae I-IX, XII, or XIII, and the pharmaceutically acceptable salts, prodrugs and solvates thereof, wherein E is —$NR^1R^2$.

In another embodiment, Compounds of the Invention are compounds of any of Formulae I-IX, XII, or XIII, and the pharmaceutically acceptable salts, prodrugs and solvates thereof, wherein E is —$NR^1R^2$, $R^1$ is selected from the group consisting of:
a) hydrogen;
b) (heterocyclo)alkyl;
c) (heteroaryl)alkyl;
d) (amino)alkyl;
e) (alkylamino)alkyl;
f) (dialkylamino)alkyl;
g) (carboxamido)alkyl;
h) (cyano)alkyl;
i) alkoxyalkyl;
j) hydroxyalkyl; and
k) heteroalkyl, and
$R^2$ is hydrogen.

In another embodiment, Compounds of the Invention are compounds of any of Formulae I-IX, XII, or XIII, and the pharmaceutically acceptable salts, prodrugs and solvates thereof, wherein E is —$NH_2$.

In another embodiment, Compounds of the Invention are compounds of any of Formulae I-V, and the pharmaceutically acceptable salts, prodrugs and solvates thereof, wherein X is selected from the group consisting of:
a) —O—;
b) —S—;
c) —$(CR^{7a}R^{7b})_m$—; and
d) —$NR^8$—;
wherein $R^{7a}$, $R^{7b}$, and $R^8$ are hydrogen, and m is 0 or 1.

In another embodiment, Compounds of the Invention are compounds of any of Formulae I-V, and the pharmaceutically acceptable salts, prodrugs and solvates thereof, wherein $R^3$ is selected from the group consisting of:
a) hydrogen;
b) halo;
c) nitro;

d) cyano;
e) amino;
f) alkylamino;
g) dialkylamino;
h) haloalkyl;
i) hydroxyalkyl;
j) alkoxy;
k) haloalkoxy; and
l) alkoxyalkyl.

In another embodiment, Compounds of the Invention are compounds of Formula X:

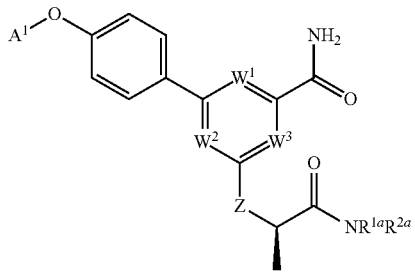

X and the pharmaceutically acceptable salts, solvates, and prodrugs thereof, wherein $A^1$, $R^{1a}$, $R^{2a}$, $W^1$, $W^2$, $W^3$, and Z are as defined above in connection with Formula I.

In another embodiment, Compounds of the Invention are compounds of Formula XI:

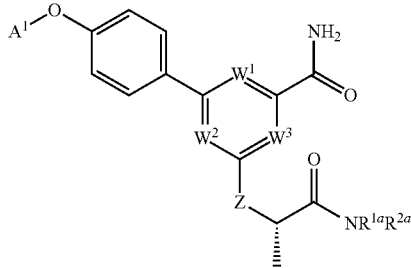

XI and the pharmaceutically acceptable salts, solvates, and prodrugs thereof, wherein $A^1$, $R^{1a}$, $R^{2a}$, $W^1$, $W^2$, $W^3$, and Z are as defined above in connection with Formula I.

In another embodiment, Compounds of the Invention are compounds of Formulae X or XI, wherein:
$W^1$ and $W^2$ are N and $W^3$ is CH; or
$W^1$ and $W^3$ are N and $W^2$ is CH; or
$W^2$ and $W^3$ are N and $W^1$ is CH;
$A^1$ is selected from the group consisting of optionally substituted phenyl and optionally substituted pyridyl;
Z is selected from the group consisting of —O— and —NH—;
$R^{1a}$ is selected from the group consisting of:
a) hydrogen;
b) alkyl;
c) (amino)alkyl;
d) (alkylamino)alkyl;
e) (dialkylamino)alkyl;
f) (carboxamido)alkyl; and
g) hydroxyalkyl; and
$R^{2a}$ is hydrogen; or $R^{1a}$ and $R^{2a}$ taken together with the nitrogen atom to which they are attached form an optionally substituted 5- or 6-membered heterocyclo, e.g., pyrrolidine, piperidine, piperazine, N-methylpiperazine, morpholine, and the pharmaceutically acceptable salts, solvates, and prodrugs thereof.

In another embodiment, Compounds of the Invention are compounds of Formulae X or XI, wherein $A^1$ is optionally substituted phenyl.

In another embodiment, Compounds of the Invention are compounds of Formulae X or XI, wherein Z is —NH—.

In another embodiment, Compounds of the Invention are compounds of Formulae X or XI, wherein Z is —O—.

In another embodiment, Compounds of the Invention are compounds of Formulae X or XI, wherein $R^{1a}$ and $R^{2a}$ are hydrogen.

In another embodiment, Compounds of the Invention are compounds of Formulae X or XI, wherein:
$W^1$ and $W^2$ are N and $W^3$ is CH;
$A^1$ is selected from the group consisting of optionally substituted phenyl and optionally substituted pyridyl;
Z is —O—; and
$R^{1a}$ and $R^{2a}$ are is hydrogen, and the pharmaceutically acceptable salts, solvates, and prodrugs thereof.

In another embodiment, Compounds of the Invention are compounds of Formula XIV:

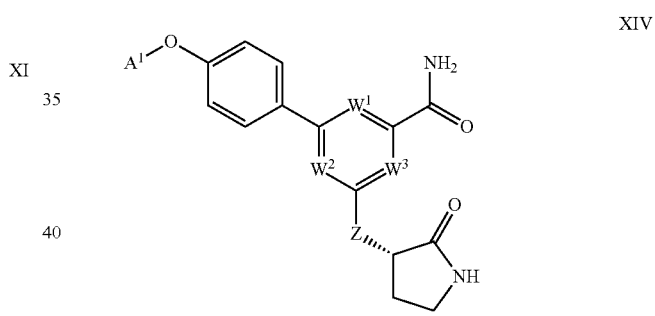

XIV and the pharmaceutically acceptable salts, solvates, and prodrugs thereof, wherein $A^1$, $W^1$, $W^2$, $W^3$, and Z are as defined above in connection with Formula I.

In another embodiment, Compounds Of the Invention are compounds of Formula XV:

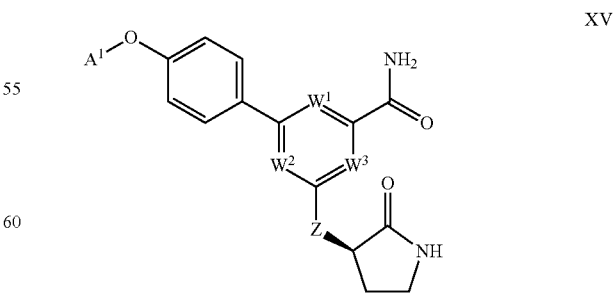

XV and the pharmaceutically acceptable salts, solvates, and prodrugs thereof, wherein $A^1$, $W^1$, $W^2$, $W^3$, and Z are as defined above in connection with Formula I.

In another embodiment, Compounds of the Invention are compounds of Formulae XIV or XV, wherein:

$W^1$ and $W^2$ are N and $W^3$ is CH; or
$W^1$ and $W^3$ are N and $W^2$ is CH; or
$W^2$ and $W^3$ are N and $W^1$ is CH;

$A^1$ is selected from the group consisting of optionally substituted phenyl and optionally substituted pyridyl; and Z is selected from the group consisting of —O— and —NH—, and the pharmaceutically acceptable salts, solvates, and prodrugs thereof.

In another embodiment, Compounds of the Invention are compounds of Formulae XIV or XV, wherein $A^1$ is optionally substituted phenyl.

In another embodiment, Compounds of the Invention are compounds of Formulae XIV or XV, wherein $A^1$ is optionally substituted pyridyl.

In another embodiment, Compounds of the Invention are compounds of Formulae XIV or XV, wherein Z is —NH—.

In another embodiment, Compounds of the Invention are compounds of Formulae XIV or XV, wherein Z is —O—.

In another embodiment, Compounds of the Invention are compounds of Formulae XIV or XV, wherein:

$W^1$ and $W^2$ are N and $W^3$ is CH;

$A^1$ is selected from the group consisting of optionally substituted phenyl and optionally substituted pyridyl; and Z is —NH—, and the pharmaceutically acceptable salts, solvates, and prodrugs thereof.

In another embodiment, Compounds of the Invention are compounds of any of Formulae I-XV, wherein $A^1$ is substituted pyridyl having one or two substituents or substituted phenyl having one, two, or three substituents.

In another embodiment, Compounds of the Invention are compounds of any of Formulae I-XV, wherein $A^1$ is substituted pyridyl having one or two substituents or substituted phenyl having one, two, or three substituents, wherein each substituent is independently selected from the group consisting of halo, cyano, hydroxy, amino, haloalkyl, alkoxy, haloalkoxy, and alkyl.

In another embodiment, Compounds of the Invention are compounds of any of Formulae I-XV, wherein $A^1$ is substituted pyridyl having one substituent or substituted phenyl having one or two substituents, wherein each substituent is independently selected from the group consisting of halo, cyano, hydroxy, amino, haloalkyl, alkoxy, haloalkoxy, and alkyl.

In another embodiment, Compounds of the Invention are compounds of any of Formulae I-XV, wherein $A^1$ is substituted pyridyl having one substituent or substituted phenyl having one or two substituents, wherein each substituent is independently selected from the group consisting of fluoro, chloro, cyano, $C_{1-4}$ haloalkyl, (e.g. $F_3C$—), $C_{1-4}$ haloalkoxy, (e.g., $F_3CO$—), $C_{1-4}$alkoxy, and $C_1$-$C_4$alkyl.

In another embodiment, Compounds of the Invention are compounds of TABLE 2, and the pharmaceutically acceptable salts, prodrugs, and solvates thereof.

TABLE 2

| Compound Example No. | Structure |
| --- | --- |
| 1 | 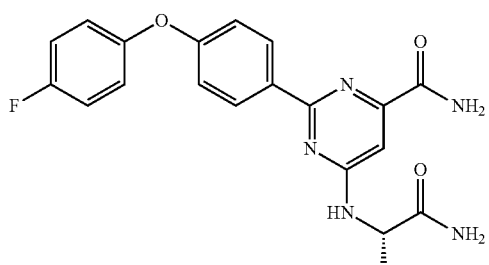 |
| 2 | 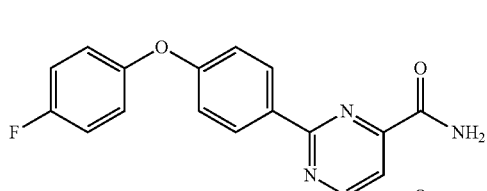 |

TABLE 2-continued

| Compound Example No. | Structure |
|---|---|
| 3 | 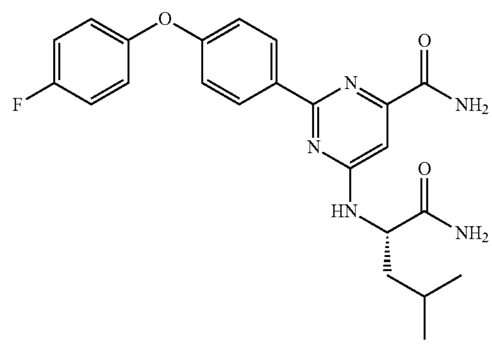 [SMILES: CC(C)C[C@H](Nc1cc(C(N)=O)nc(-c2ccc(Oc3ccc(F)cc3)cc2)n1)C(N)=O] |
| 4 | 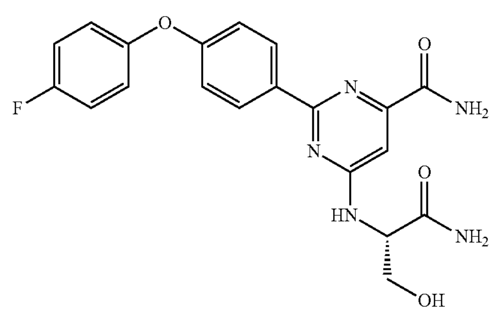 [SMILES: NC(=O)c1cc(N[C@@H](CO)C(N)=O)nc(-c2ccc(Oc3ccc(F)cc3)cc2)n1] |
| 5 | 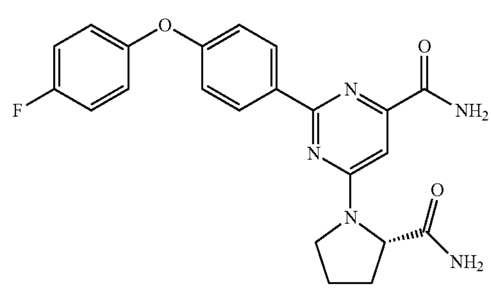 |
| 6 | 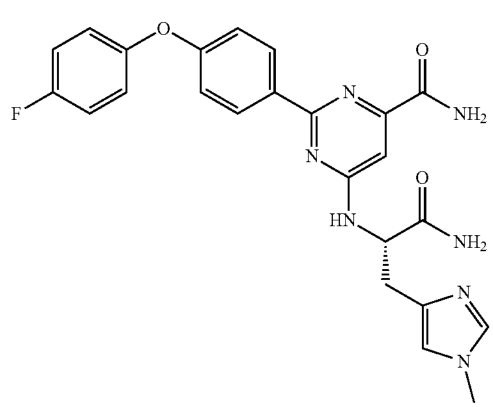 [SMILES: Cn1cnc(C[C@H](Nc2cc(C(N)=O)nc(-c3ccc(Oc4ccc(F)cc4)cc3)n2)C(N)=O)c1] |

TABLE 2-continued

| Compound Example No. | Structure |
|---|---|
| 7 | 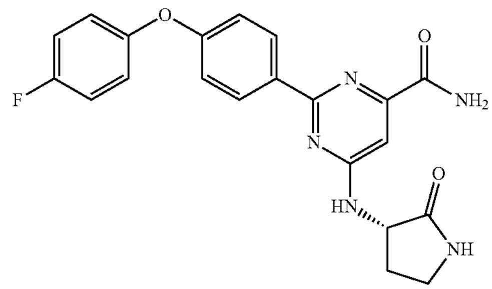 [SMILES: NC(=O)c1cc(N[C@H]2CCNC2=O)nc(-c2ccc(Oc3ccc(F)cc3)cc2)n1] |
| 8 | 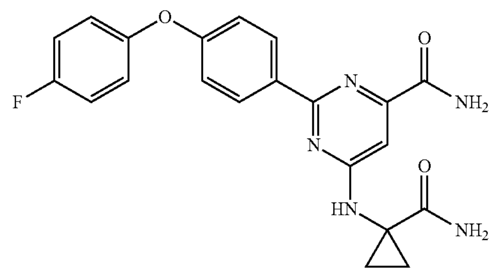 [SMILES: NC(=O)c1cc(NC2(C(N)=O)CC2)nc(-c2ccc(Oc3ccc(F)cc3)cc2)n1] |
| 9 | 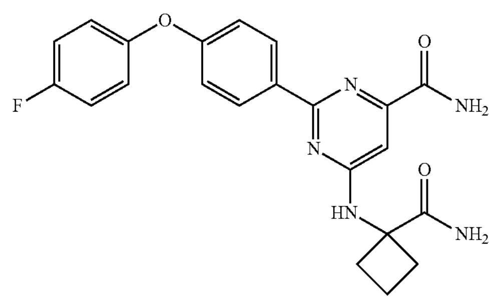 [SMILES: NC(=O)c1cc(NC2(C(N)=O)CCC2)nc(-c2ccc(Oc3ccc(F)cc3)cc2)n1] |
| 10 | 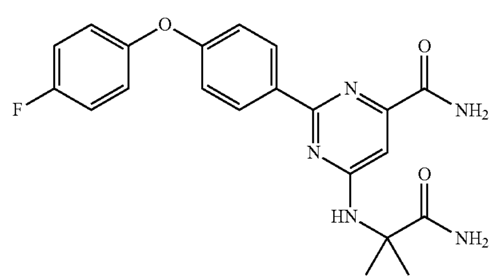 [SMILES: CC(C)(Nc1cc(C(N)=O)nc(-c2ccc(Oc3ccc(F)cc3)cc2)n1)C(N)=O] |
| 11 | 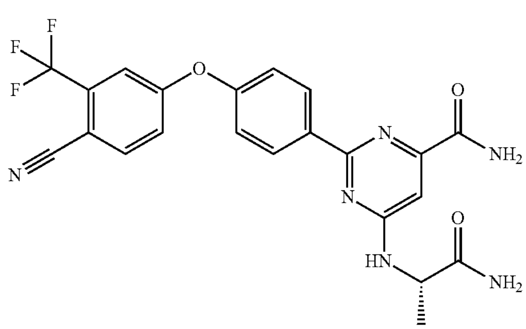 [SMILES: C[C@H](Nc1cc(C(N)=O)nc(-c2ccc(Oc3ccc(C#N)c(C(F)(F)F)c3)cc2)n1)C(N)=O] |

TABLE 2-continued

| Compound Example No. | Structure |
| --- | --- |
| 12 | 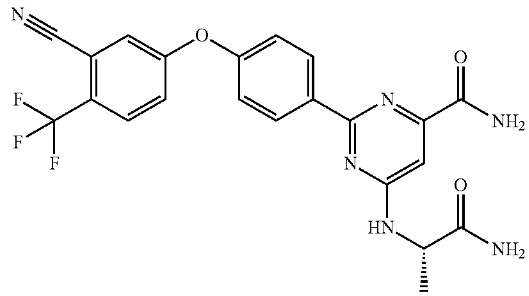 [SMILES: C[C@H](Nc1cc(C(N)=O)nc(-c2ccc(Oc3ccc(C(F)(F)F)c(C#N)c3)cc2)n1)C(N)=O] |
| 13 | 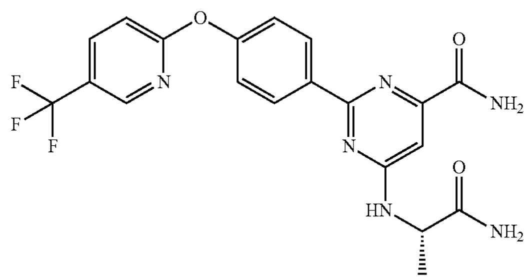 [SMILES: C[C@H](Nc1cc(C(N)=O)nc(-c2ccc(Oc3ccc(C(F)(F)F)cn3)cc2)n1)C(N)=O] |
| 14 | 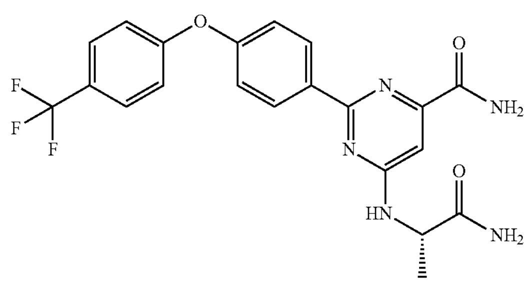 [SMILES: C[C@H](Nc1cc(C(N)=O)nc(-c2ccc(Oc3ccc(C(F)(F)F)cc3)cc2)n1)C(N)=O] |
| 15 | 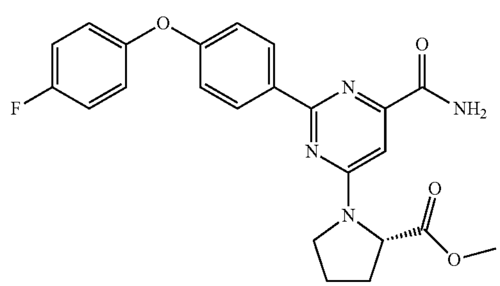 [SMILES: COC(=O)[C@@H]1CCCN1c1cc(C(N)=O)nc(-c2ccc(Oc3ccc(F)cc3)cc2)n1] |
| 16 | 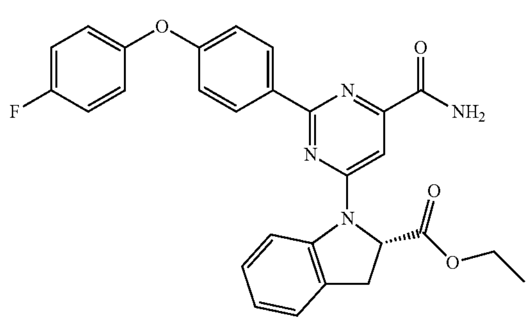 [SMILES: CCOC(=O)[C@@H]1Cc2ccccc2N1c1cc(C(N)=O)nc(-c2ccc(Oc3ccc(F)cc3)cc2)n1] |

TABLE 2-continued

| Compound Example No. | Structure |
|---|---|
| 17 | 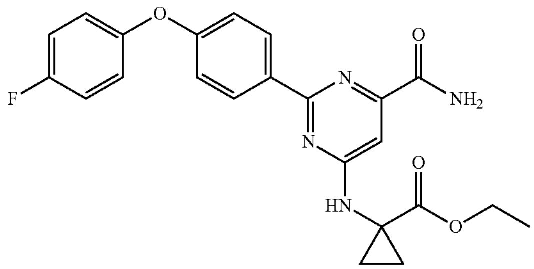 [SMILES: CCOC(=O)C1(Nc2cc(C(N)=O)nc(-c3ccc(Oc4ccc(F)cc4)cc3)n2)CC1] |
| 18 | 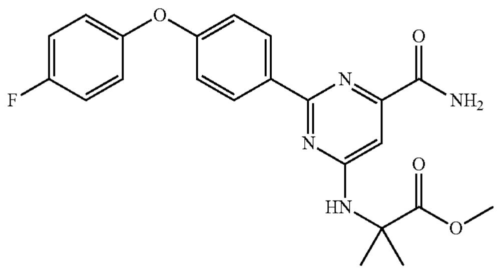 [SMILES: COC(=O)C(C)(C)Nc1cc(C(N)=O)nc(-c2ccc(Oc3ccc(F)cc3)cc2)n1] |
| 19 | 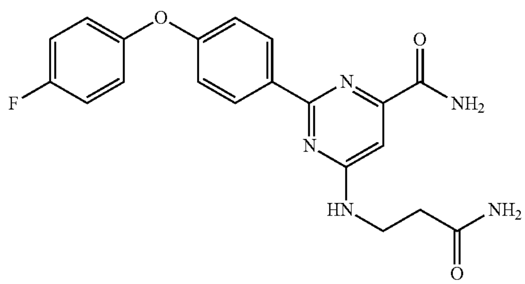 |
| 20 | 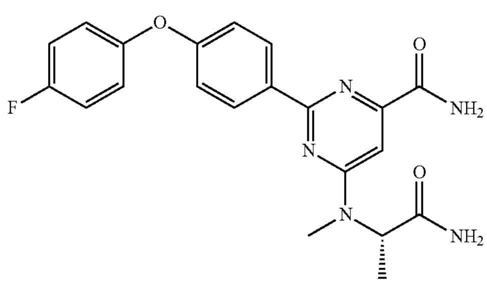 |
| 21 | 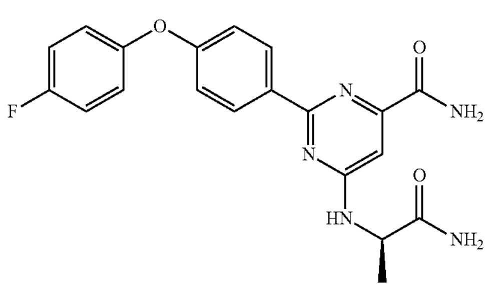 [SMILES: C[C@@H](Nc1cc(C(N)=O)nc(-c2ccc(Oc3ccc(F)cc3)cc2)n1)C(N)=O] |

TABLE 2-continued

| Compound Example No. | Structure |
|---|---|
| 22 | (structure) |
| 23 | (structure) |
| 24 | (structure) |
| 25 | (structure) |
| 26 | (structure) |

TABLE 2-continued

| Compound Example No. | Structure |
|---|---|
| 27 | 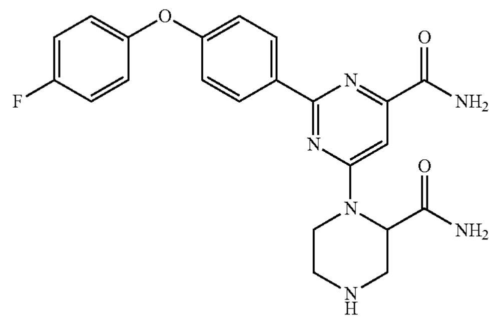 |
| 28 | 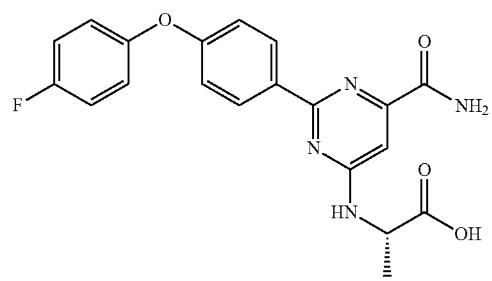 |
| 29 | 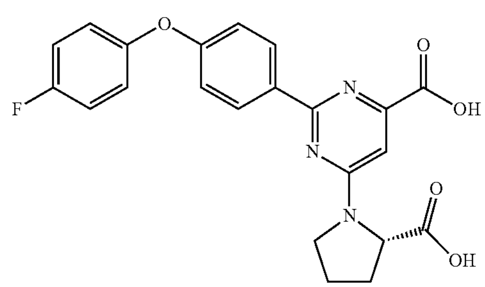 [SMILES: O=C(O)c1cc(N2CCC[C@H]2C(=O)O)nc(-c2ccc(Oc3ccc(F)cc3)cc2)n1] |
| 30 | 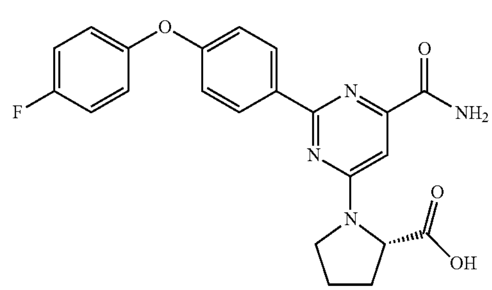 |
| 31 | 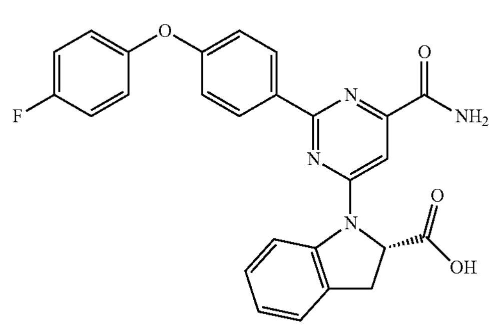 |

TABLE 2-continued
| Compound Example No. | Structure |
|---|---|
| 32 | 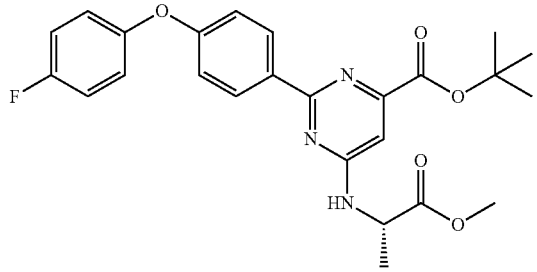 [SMILES: COC(=O)[C@H](C)Nc1cc(C(=O)OC(C)(C)C)nc(-c2ccc(Oc3ccc(F)cc3)cc2)n1] |
| 33 | 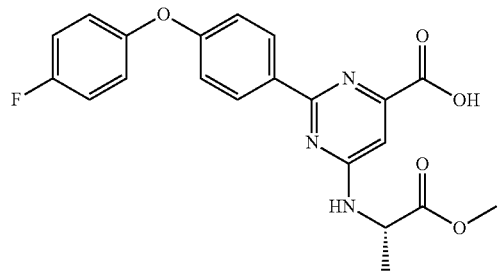 |
| 34 | 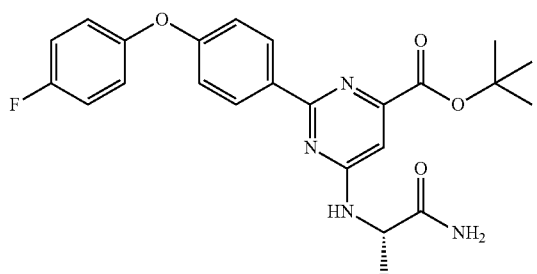 [SMILES: C[C@H](Nc1cc(C(=O)OC(C)(C)C)nc(-c2ccc(Oc3ccc(F)cc3)cc2)n1)C(N)=O] |
| 35 | 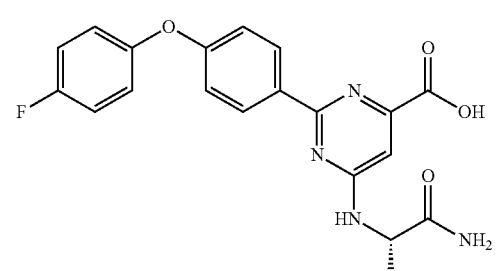 |
| 36 | 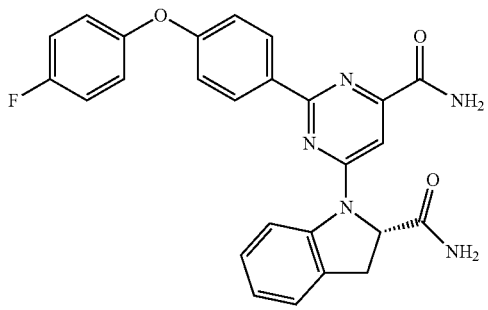 |

TABLE 2-continued

| Compound Example No. | Structure |
| --- | --- |
| 37 | 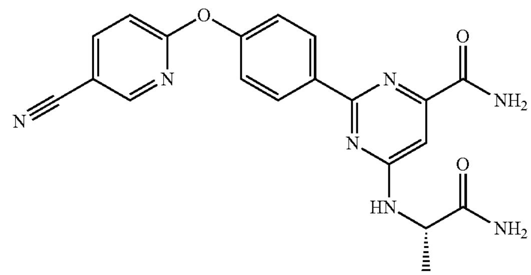 [SMILES: C[C@H](Nc1cc(C(N)=O)nc(-c2ccc(Oc3ccc(C#N)cn3)cc2)n1)C(N)=O] |
| 38 | 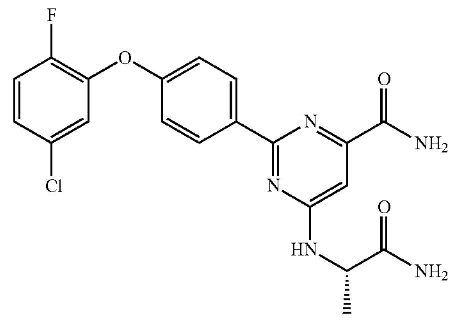 [SMILES: C[C@H](Nc1cc(C(N)=O)nc(-c2ccc(Oc3cc(Cl)ccc3F)cc2)n1)C(N)=O] |
| 39 | 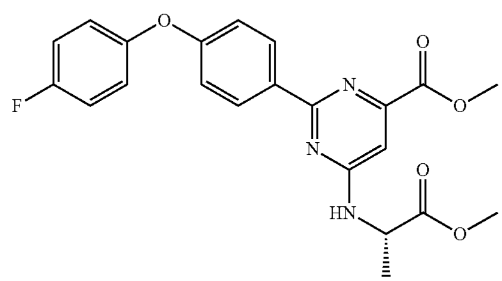 [SMILES: COC(=O)c1cc(N[C@@H](C)C(=O)OC)nc(-c2ccc(Oc3ccc(F)cc3)cc2)n1] |
| 40 | 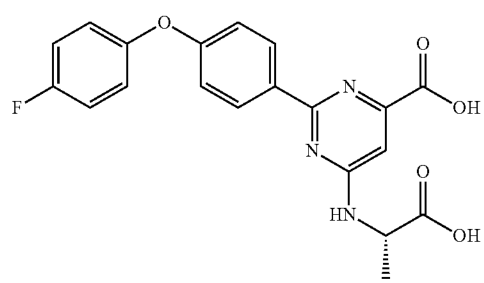 [SMILES: C[C@H](Nc1cc(C(=O)O)nc(-c2ccc(Oc3ccc(F)cc3)cc2)n1)C(=O)O] |
| 41 | 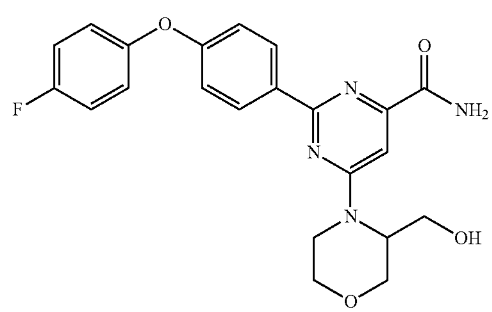 [SMILES: NC(=O)c1cc(N2CCOCC2CO)nc(-c2ccc(Oc3ccc(F)cc3)cc2)n1] |

TABLE 2-continued
| Compound Example No. | Structure |
|---|---|
| 42 | 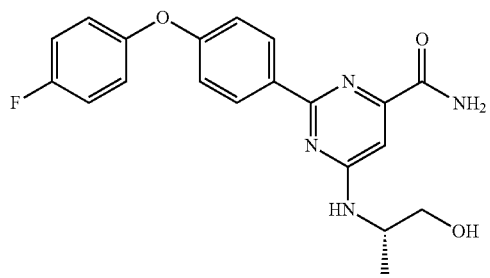 [SMILES: C[C@@H](CO)Nc1cc(C(N)=O)nc(-c2ccc(Oc3ccc(F)cc3)cc2)n1] |
| 43 | 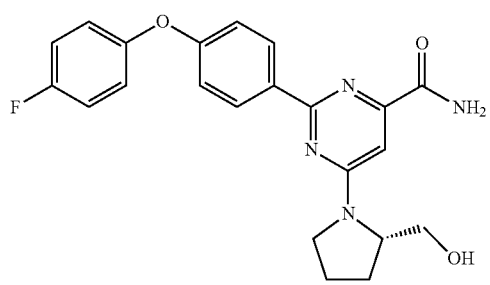 [SMILES: NC(=O)c1cc(N2CCC[C@H]2CO)nc(-c2ccc(Oc3ccc(F)cc3)cc2)n1] |
| 44 | 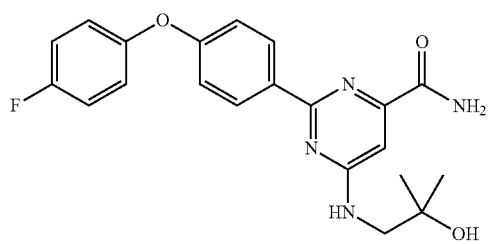 [SMILES: CC(C)(O)CNc1cc(C(N)=O)nc(-c2ccc(Oc3ccc(F)cc3)cc2)n1] |
| 45 | 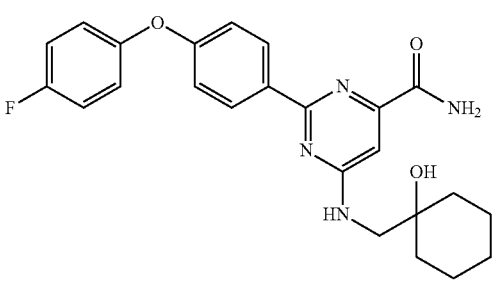 [SMILES: NC(=O)c1cc(NCC2(O)CCCCC2)nc(-c2ccc(Oc3ccc(F)cc3)cc2)n1] |
| 46 | 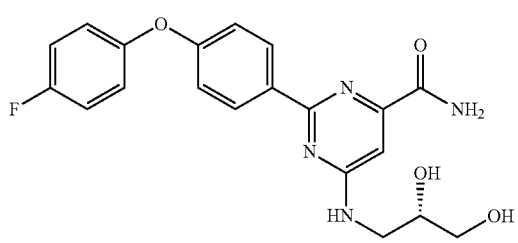 |

TABLE 2-continued

| Compound Example No. | Structure |
|---|---|
| 47 | 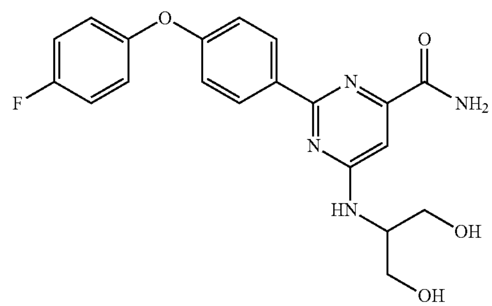 [SMILES: NC(=O)c1cc(NC(CO)CO)nc(-c2ccc(Oc3ccc(F)cc3)cc2)n1] |
| 48 | 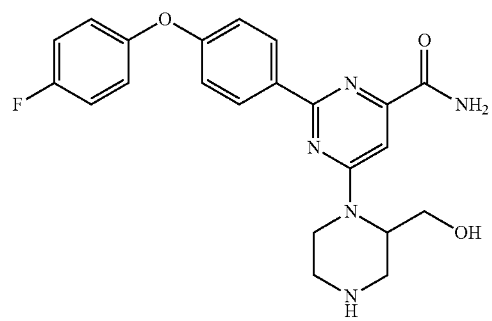 [SMILES: NC(=O)c1cc(N2CCNCC2CO)nc(-c2ccc(Oc3ccc(F)cc3)cc2)n1] |
| 49 | 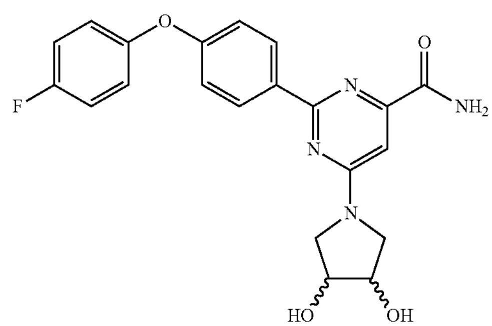 [SMILES: NC(=O)c1cc(N2CC(O)C(O)C2)nc(-c2ccc(Oc3ccc(F)cc3)cc2)n1] |
| 50 | 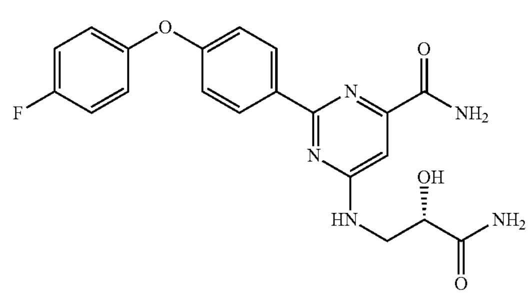 [SMILES: NC(=O)c1cc(NC[C@H](O)C(N)=O)nc(-c2ccc(Oc3ccc(F)cc3)cc2)n1] |
| 51 | 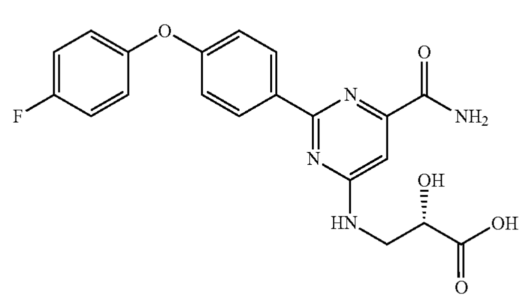 [SMILES: NC(=O)c1cc(NC[C@H](O)C(=O)O)nc(-c2ccc(Oc3ccc(F)cc3)cc2)n1] |

TABLE 2-continued

| Compound Example No. | Structure |
|---|---|
| 52 | 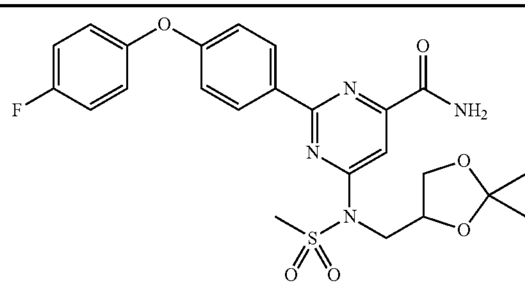 |
| 53 | 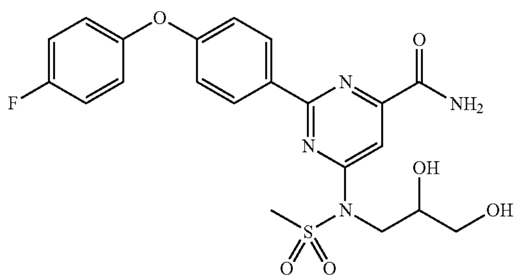 [SMILES: CS(=O)(=O)N(CC(O)CO)c1cc(C(N)=O)nc(-c2ccc(Oc3ccc(F)cc3)cc2)n1] |
| 54 | 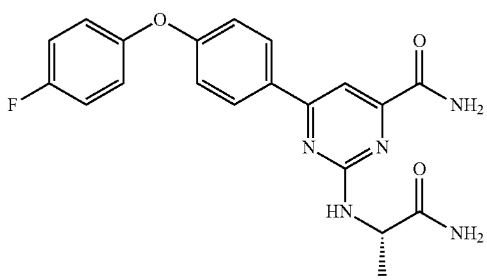 [SMILES: C[C@H](Nc1nc(C(N)=O)cc(-c2ccc(Oc3ccc(F)cc3)cc2)n1)C(N)=O] |
| 55 | 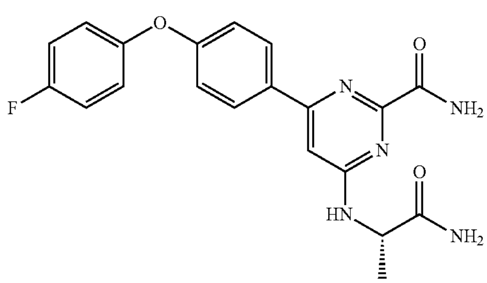 |
| 56 | 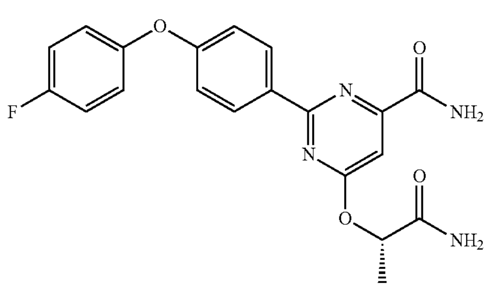 |

TABLE 2-continued

| Compound Example No. | Structure |
|---|---|
| 57 | 4-CF3-pyridin-2-yl-O-C6H4-[pyrimidine-4-carboxamide, 6-(NH-CH(CH3)-C(O)NH2)] |
| 58 | 3-CF3-pyridin-2-yl-O-C6H4-[pyrimidine-4-carboxamide, 6-(NH-CH(CH3)-C(O)NH2)] |
| 59 | 6-CF3-pyridin-2-yl-O-C6H4-[pyrimidine-4-carboxamide, 6-(NH-CH(CH3)-C(O)NH2)] |
| 60 | 6-CF3-pyridin-3-yl-O-C6H4-[pyrimidine-4-carboxamide, 6-(NH-CH(CH3)-C(O)NH2)] |
| 61 | 6-F-pyridin-2-yl-O-C6H4-[pyrimidine-4-carboxamide, 6-(NH-CH(CH3)-C(O)NH2)] |

TABLE 2-continued

| Compound Example No. | Structure |
|---|---|
| 62 | 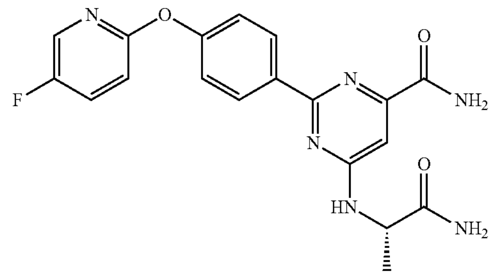 |
| 63 | 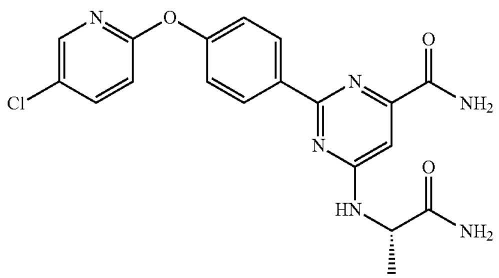 [SMILES: C[C@H](Nc1cc(C(N)=O)nc(-c2ccc(Oc3ccc(Cl)cn3)cc2)n1)C(N)=O] |
| 64 | 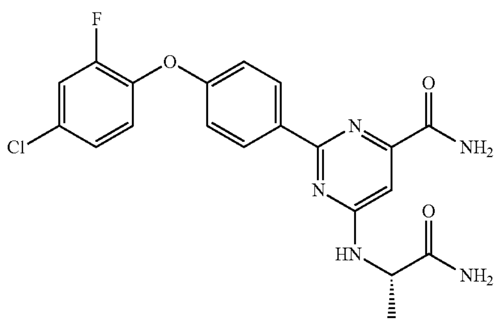 [SMILES: C[C@H](Nc1cc(C(N)=O)nc(-c2ccc(Oc3ccc(Cl)cc3F)cc2)n1)C(N)=O] |
| 65 | 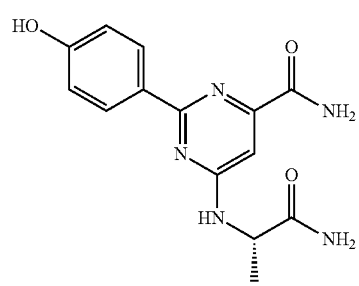 [SMILES: C[C@H](Nc1cc(C(N)=O)nc(-c2ccc(O)cc2)n1)C(N)=O] |
| 66 | 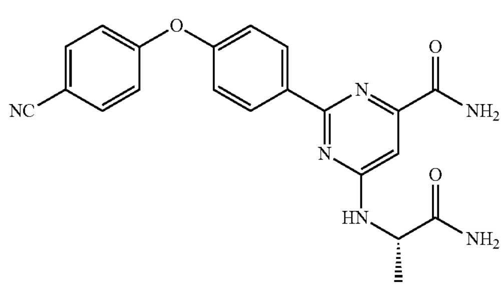 [SMILES: C[C@H](Nc1cc(C(N)=O)nc(-c2ccc(Oc3ccc(C#N)cc3)cc2)n1)C(N)=O] |

TABLE 2-continued
| Compound Example No. | Structure |
|---|---|
| 67 | 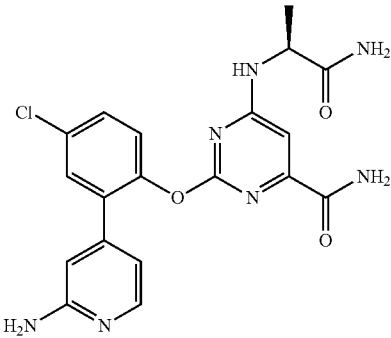 [SMILES: C[C@H](Nc1cc(C(N)=O)nc(Oc2ccc(Cl)cc2-c2ccnc(N)c2)n1)C(N)=O] |
| 68 | 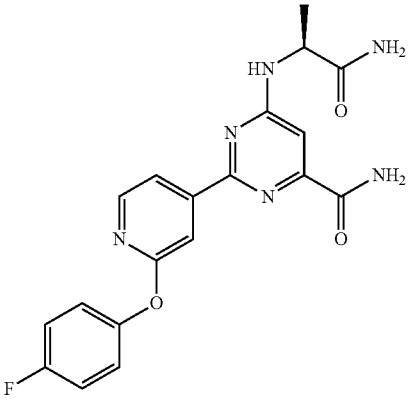 [SMILES: C[C@H](Nc1cc(C(N)=O)nc(-c2ccnc(Oc3ccc(F)cc3)c2)n1)C(N)=O] |
| 69 | 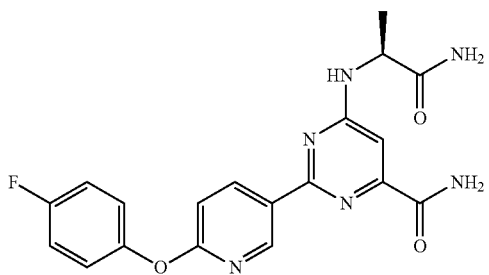 [SMILES: C[C@H](Nc1cc(C(N)=O)nc(-c2ccc(Oc3ccc(F)cc3)nc2)n1)C(N)=O] |
| 70 | 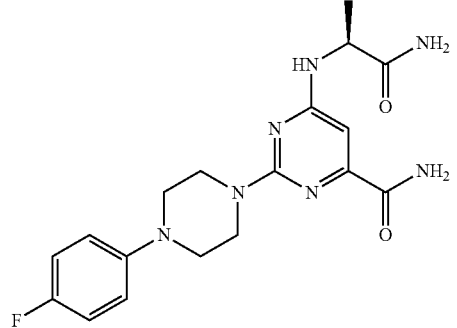 [SMILES: C[C@H](Nc1cc(C(N)=O)nc(N2CCN(c3ccc(F)cc3)CC2)n1)C(N)=O] |

TABLE 2-continued
| Compound Example No. | Structure |
|---|---|
| 71 | 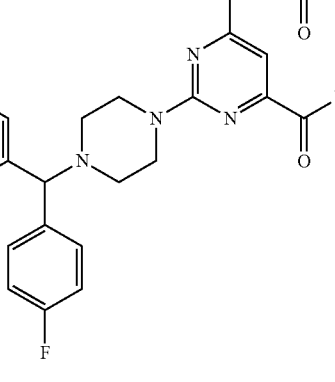 |
| 72 | 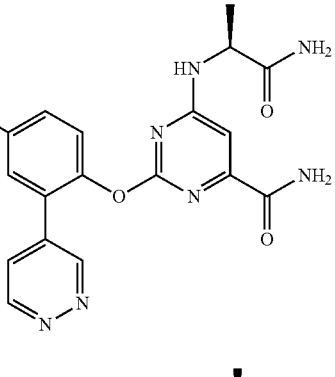 |
| 73 | 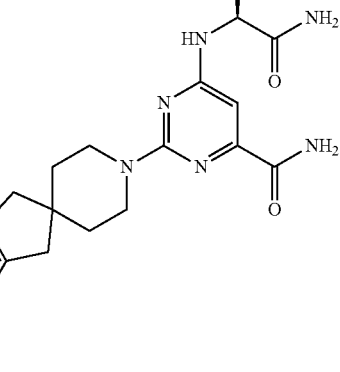 |
| 74 | 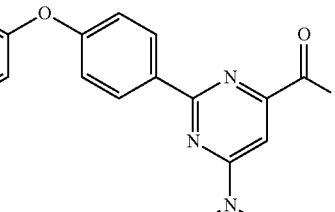 |

TABLE 2-continued

| Compound Example No. | Structure |
|---|---|
| 75 | 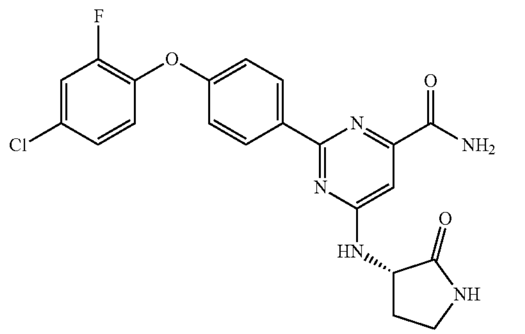 [SMILES: NC(=O)c1cc(N[C@H]2CCNC2=O)nc(-c2ccc(Oc3ccc(Cl)cc3F)cc2)n1] |
| 76 | 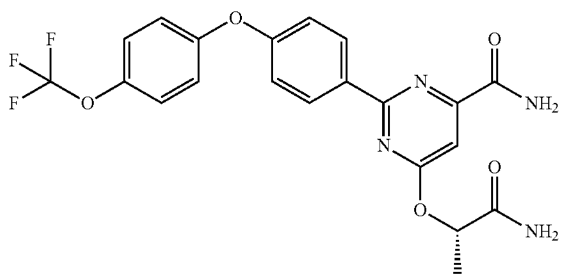 [SMILES: C[C@H](Oc1cc(C(N)=O)nc(-c2ccc(Oc3ccc(OC(F)(F)F)cc3)cc2)n1)C(N)=O] |
| 77 | 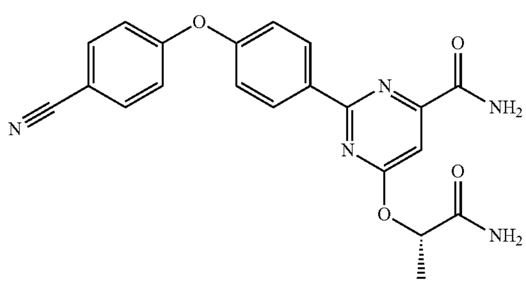 [SMILES: C[C@H](Oc1cc(C(N)=O)nc(-c2ccc(Oc3ccc(C#N)cc3)cc2)n1)C(N)=O] |
| 78 | 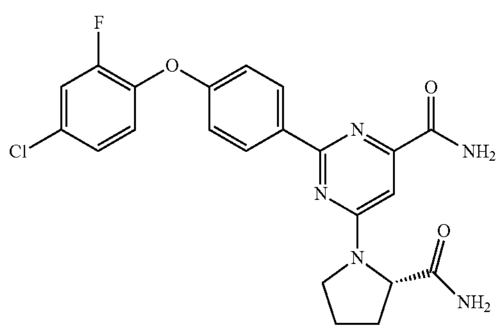 [SMILES: NC(=O)c1cc(N2CCC[C@H]2C(N)=O)nc(-c2ccc(Oc3ccc(Cl)cc3F)cc2)n1] |
| 79 | 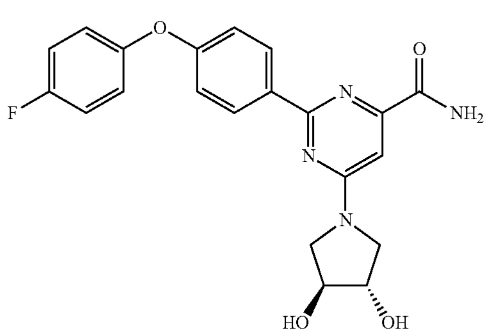 [SMILES: NC(=O)c1cc(N2C[C@H](O)[C@@H](O)C2)nc(-c2ccc(Oc3ccc(F)cc3)cc2)n1] |

TABLE 2-continued

| Compound Example No. | Structure |
|---|---|
| 80 | 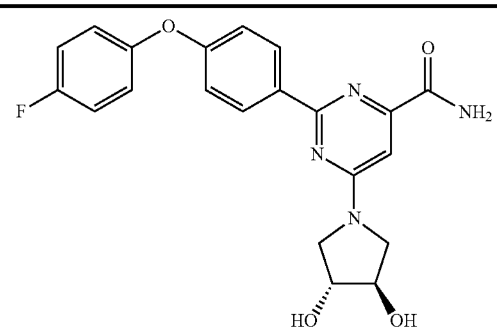 |
| 81 | 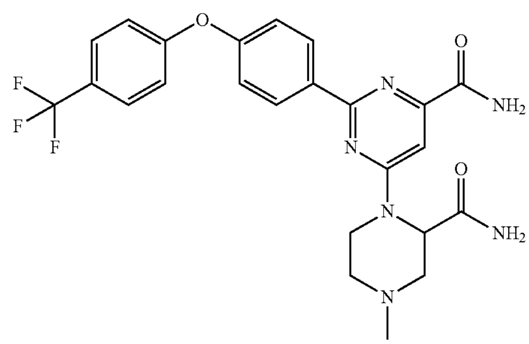 [SMILES: CN1CCN(c2cc(C(N)=O)nc(-c3ccc(Oc4ccc(C(F)(F)F)cc4)cc3)n2)C(C(N)=O)C1] |
| 82 | 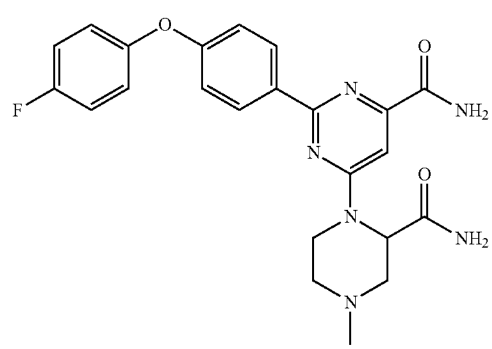 [SMILES: CN1CCN(c2cc(C(N)=O)nc(-c3ccc(Oc4ccc(F)cc4)cc3)n2)C(C(N)=O)C1] |
| 83 | 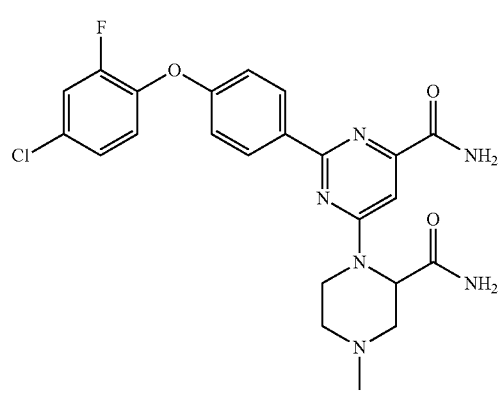 [SMILES: CN1CCN(c2cc(C(N)=O)nc(-c3ccc(Oc4ccc(Cl)cc4F)cc3)n2)C(C(N)=O)C1] |

TABLE 2-continued
| Compound Example No. | Structure |
|---|---|
| 84 | 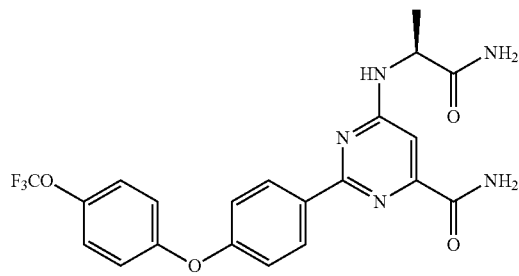 [SMILES: C[C@H](Nc1cc(C(N)=O)nc(-c2ccc(Oc3ccc(OC(F)(F)F)cc3)cc2)n1)C(N)=O] |
| 85 | 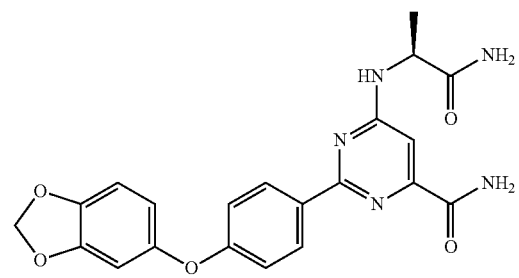 [SMILES: C[C@H](Nc1cc(C(N)=O)nc(-c2ccc(Oc3ccc4c(c3)OCO4)cc2)n1)C(N)=O] |
| 86 | 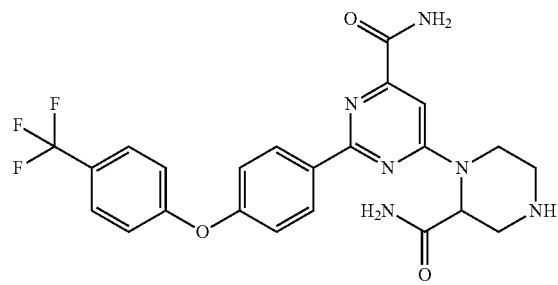 [SMILES: NC(=O)c1cc(N2CCNCC2C(N)=O)nc(-c2ccc(Oc3ccc(C(F)(F)F)cc3)cc2)n1] |
| 87 | 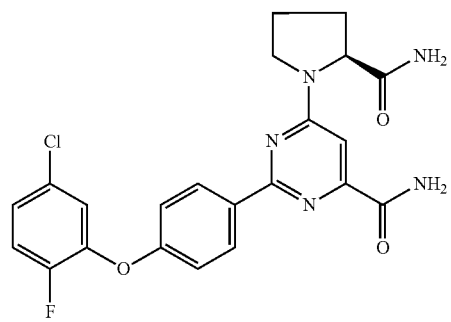 [SMILES: NC(=O)c1cc(N2CCC[C@H]2C(N)=O)nc(-c2ccc(Oc3cc(Cl)ccc3F)cc2)n1] |
| 88 | 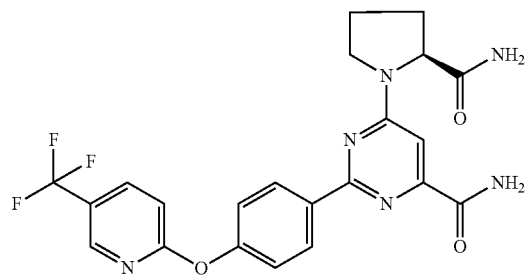 [SMILES: NC(=O)c1cc(N2CCC[C@H]2C(N)=O)nc(-c2ccc(Oc3ccc(C(F)(F)F)cn3)cc2)n1] |

TABLE 2-continued

| Compound Example No. | Structure |
|---|---|
| 89 | 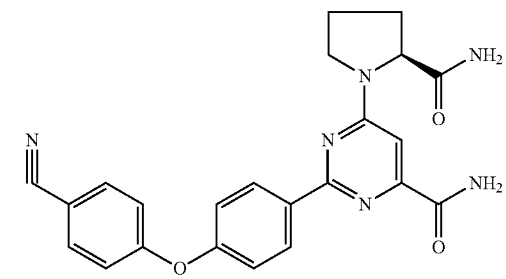 [SMILES: N#Cc1ccc(Oc2ccc(-c3nc(C(N)=O)cc(N4CCC[C@H]4C(N)=O)n3)cc2)cc1] |
| 90 | 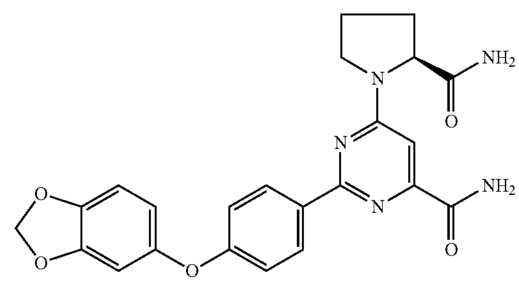 [SMILES: NC(=O)c1cc(N2CCC[C@H]2C(N)=O)nc(-c2ccc(Oc3ccc4c(c3)OCO4)cc2)n1] |
| 91 | 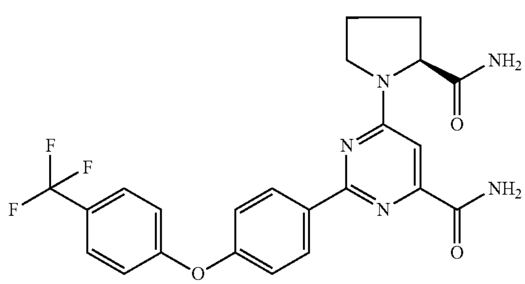 [SMILES: NC(=O)c1cc(N2CCC[C@H]2C(N)=O)nc(-c2ccc(Oc3ccc(C(F)(F)F)cc3)cc2)n1] |
| 92 | 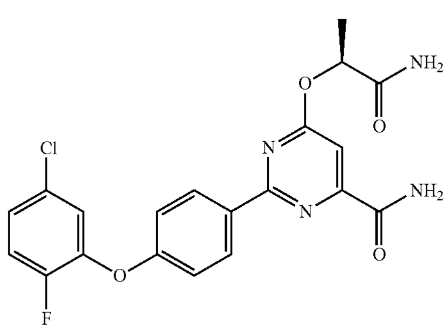 [SMILES: C[C@H](Oc1cc(C(N)=O)nc(-c2ccc(Oc3cc(Cl)ccc3F)cc2)n1)C(N)=O] |
| 93 | 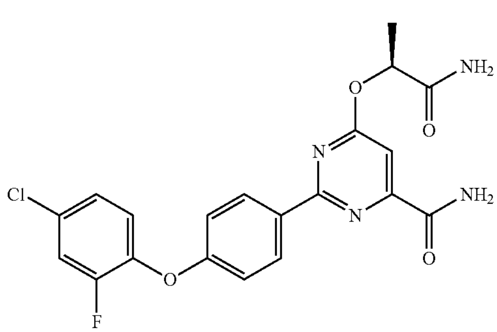 [SMILES: C[C@H](Oc1cc(C(N)=O)nc(-c2ccc(Oc3ccc(Cl)cc3F)cc2)n1)C(N)=O] |

TABLE 2-continued

| Compound Example No. | Structure |
|---|---|
| 94 | 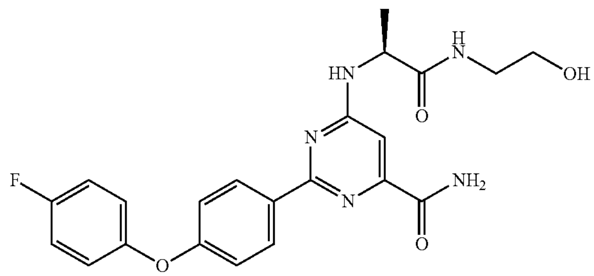 [SMILES: C[C@H](Nc1cc(C(N)=O)nc(-c2ccc(Oc3ccc(F)cc3)cc2)n1)C(=O)NCCO] |
| 95 | 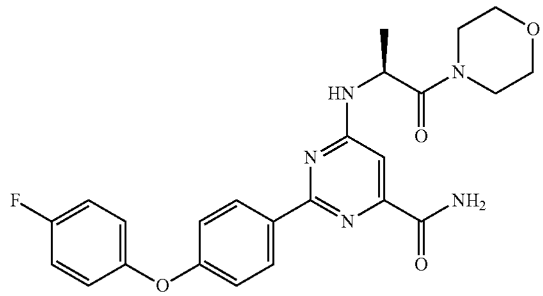 [SMILES: C[C@H](Nc1cc(C(N)=O)nc(-c2ccc(Oc3ccc(F)cc3)cc2)n1)C(=O)N1CCOCC1] |
| 96 | 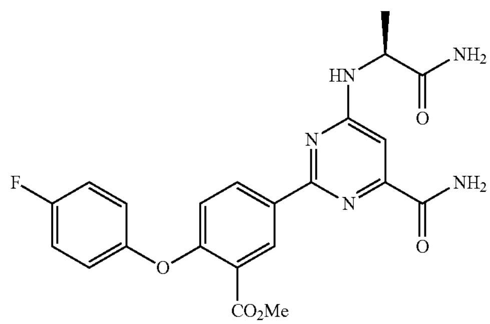 [SMILES: COC(=O)c1cc(-c2nc(N[C@@H](C)C(N)=O)cc(C(N)=O)n2)ccc1Oc1ccc(F)cc1] |
| 97 | 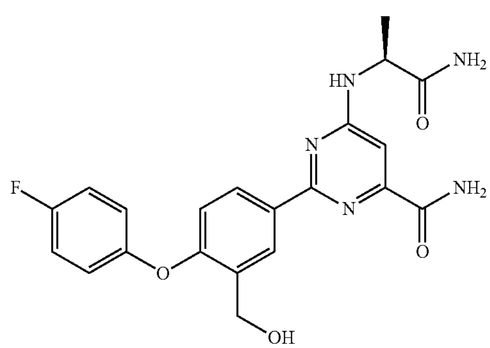 [SMILES: C[C@H](Nc1cc(C(N)=O)nc(-c2ccc(Oc3ccc(F)cc3)c(CO)c2)n1)C(N)=O] |
| 98 | 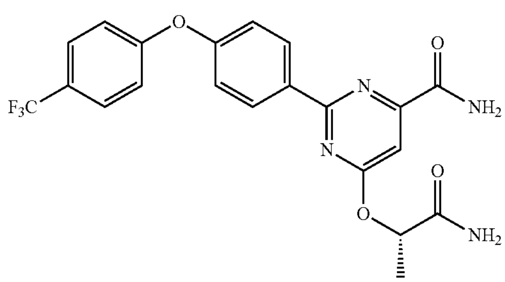 [SMILES: C[C@H](Oc1cc(C(N)=O)nc(-c2ccc(Oc3ccc(C(F)(F)F)cc3)cc2)n1)C(N)=O] |

TABLE 2-continued
| Compound Example No. | Structure |
|---|---|
| 99 | 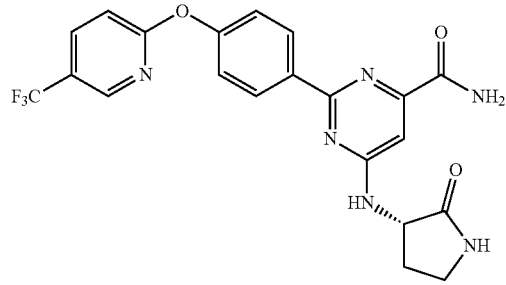 [SMILES: NC(=O)c1cc(N[C@H]2CCNC2=O)nc(-c2ccc(Oc3ccc(C(F)(F)F)cn3)cc2)n1] |
| 100 | 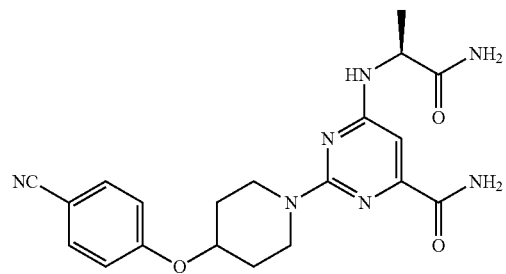 [SMILES: C[C@H](Nc1cc(C(N)=O)nc(N2CCC(Oc3ccc(C#N)cc3)CC2)n1)C(N)=O] |
| 101 | 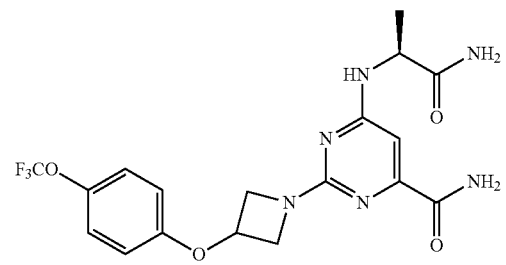 [SMILES: C[C@H](Nc1cc(C(N)=O)nc(N2CC(Oc3ccc(OC(F)(F)F)cc3)C2)n1)C(N)=O] |
| 102 | 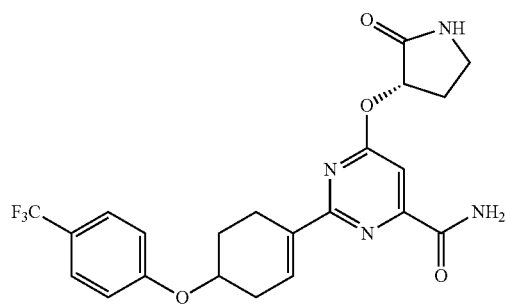 [SMILES: NC(=O)c1cc(O[C@H]2CCNC2=O)nc(C2=CCC(Oc3ccc(C(F)(F)F)cc3)CC2)n1] |
| 103 | 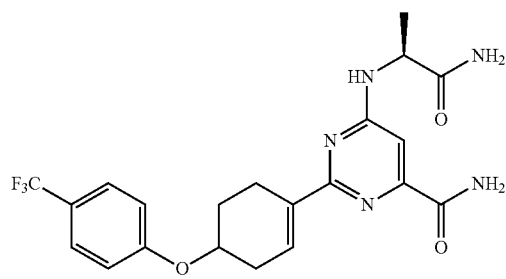 [SMILES: C[C@H](Nc1cc(C(N)=O)nc(C2=CCC(Oc3ccc(C(F)(F)F)cc3)CC2)n1)C(N)=O] |

The chemical names of the compound examples are provided in TABLE 3.

TABLE 3

| Compound Example No. | Chemical Name |
|---|---|
| 1 | (S)-6-((1-amino-1-oxopropan-2-yl)amino)-2-(4-(4-fluorophenoxy) phenyl)pyrimidine-4-carboxamide |
| 2 | 6-((2-amino-2-oxoethyl)amino)-2-(4-(4-fluorophenoxy)phenyl) pyrimidine-4-carboxamide |
| 3 | (S)-6-((1-amino-4-methyl-1-oxopentan-2-yl)amino)-2-(4-(4-fluorophenoxy)phenyl) pyrimidine-4-carboxamide |
| 4 | (S)-6-((1-amino-3-hydroxy-1-oxopropan-2-yl)amino)-2-(4-(4-fluorophenoxy)phenyl) pyrimidine-4-carboxamide |
| 5 | (S)-6-(2-carbamoylpyrrolidin-1-yl)-2-(4-(4-fluorophenoxy)phenyl) pyrimidine-4-carboxamide |
| 6 | (S)-6-((1-amino-3-(1-methyl-1H-imidazol-4-yl)-1-oxopropan-2-yl) amino)-2-(4-(4-fluorophenoxy)phenyl)pyrimidine-4-carboxamide |
| 7 | (S)-2-(4-(4-fluorophenoxy)phenyl)-6-((2-oxopyrrolidin-3-yl)amino) pyrimidine-4-carboxamide |
| 8 | 6-((1-carbamoylcyclopropyl)amino)-2-(4-(4-fluorophenoxy)phenyl) pyrimidine-4-carboxamide |
| 9 | 6-((1-carbamoylcyclobutyl)amino)-2-(4-(4-fluorophenoxy)phenyl) pyrimidine-4-carboxamide |
| 10 | 6-((1-amino-2-methyl-1-oxopropan-2-yl)amino)-2-(4-(4-fluorophenoxy)phenyl)pyrimidine-4-carboxamide |
| 11 | (S)-6-((1-amino-1-oxopropan-2-yl)amino)-2-(4-(4-cyano-3-(trifluoromethyl)phenoxy) phenyl)pyrimidine-4-carboxamide |
| 12 | (S)-6-((1-amino-1-oxopropan-2-yl)amino)-2-(4-(3-cyano-4-(trifluoromethyl)phenoxy)phenyl)pyrimidine-4-carboxamide |
| 13 | (S)-6-((1-amino-1-oxopropan-2-yl)amino)-2-(4-((5-(trifluoromethyl)pyridin-2-yl)oxy)phenyl)pyrimidine-4-carboxamide |
| 14 | (S)-6-((1-amino-1-oxopropan-2-yl)amino)-2-(4-(4-(trifluoromethyl)phenoxy)phenyl) pyrimidine-4-carboxamide |
| 15 | (S)-methyl 1-(6-carbamoyl-2-(4-(4-fluorophenoxy)phenyl)pyrimidin-4-yl)pyrrolidine-2-carboxylate |
| 16 | (S)-ethyl 1-(6-carbamoyl-2-(4-(4-fluorophenoxy)phenyl)pyrimidin-4-yl)indoline-2-carboxylate |
| 17 | ethyl 1-((6-carbamoyl-2-(4-(4-fluorophenoxy)phenyl)pyrimidin-4-yl)amino)cyclopropanecarboxylate |
| 18 | methyl 2-((6-carbamoyl-2-(4-(4-fluorophenoxy)phenyl)pyrimidin-4-yl)amino)-2-methylpropanoate |
| 19 | 6-((3-amino-3-oxopropyl)amino)-2-(4-(4-fluorophenoxy)phenyl)pyrimidine-4-carboxamide |
| 20 | (S)-6-((1-amino-1-oxopropan-2-yl)(methyl)amino)-2-(4-(4-fluorophenoxy)phenyl)pyrimidine-4-carboxamide |
| 21 | (R)-6-((1-amino-1-oxopropan-2-yl)amino)-2-(4-(4-fluorophenoxy)phenyl)pyrimidine-4-carboxamide |
| 22 | 6-((1-amino-1-oxopropan-2-yl)amino)-2-(4-(4-fluorophenoxy)phenyl)pyrimidine-4-carboxamide |
| 23 | 6-((4-amino-4-oxobutan-2-yl)amino)-2-(4-(4-fluorophenoxy)phenyl)pyrimidine-4-carboxamide |
| 24 | 6-(3-carbamoylpiperidin-1-yl)-2-(4-(4-fluorophenoxy)phenyl)pyrimidine-4-carboxamide |
| 25 | 4-(6-carbamoyl-2-(4-(4-fluorophenoxy)phenyl)pyrimidin-4-yl)morpholine-3-carboxamide |
| 26 | 4-(6-carbamoyl-2-(4-(4-fluorophenoxy)phenyl)pyrimidin-4-yl)morpholine-2-carboxamide |
| 27 | 6-(2-carbamoylpiperazin-1-yl)-2-(4-(4-fluorophenoxy)phenyl)pyrimidine-4-carboxamide |
| 28 | (S)-2-((6-carbamoyl-2-(4-(4-fluorophenoxy)phenyl)pyrimidin-4-yl)amino)propanoic acid |
| 29 | (S)-6-(2-carboxypyrrolidin-1-yl)-2-(4-(4-fluorophenoxy)phenyl)pyrimidine-4-carboxylic acid |
| 30 | (S)-1-(6-carbamoyl-2-(4-(4-fluorophenoxy)phenyl)pyrimidin-4-yl)pyrrolidine-2-carboxylic acid |
| 31 | (S)-1-(6-carbamoyl-2-(4-(4-fluorophenoxy)phenyl)pyrimidin-4-yl)indoline-2-carboxylic acid |
| 32 | (S)-tert-butyl 2-(4-(4-fluorophenoxy)phenyl)-6-((1-methoxy-1-oxopropan-2-yl)amino)pyrimidine-4-carboxylate |
| 33 | (S)-2-(4-(4-fluorophenoxy)phenyl)-6-((1-methoxy-1-oxopropan-2-yl)amino)pyrimidine-4-carboxylic acid |
| 34 | (S)-tert-butyl 6-((1-amino-1-oxopropan-2-yl)amino)-2-(4-(4-fluorophenoxy)phenyl)pyrimidine-4-carboxylate |
| 35 | (S)-6-((1-amino-1-oxopropan-2-yl)amino)-2-(4-(4-fluorophenoxy)phenyl)pyrimidine-4-carboxylic acid |

TABLE 3-continued

| Compound Example No. | Chemical Name |
|---|---|
| 36 | (S)-1-(6-carbamoyl-2-(4-(4-fluorophenoxy)phenyl)pyrimidin-4-yl)indoline-2-carboxamide |
| 37 | (S)-6-((1-amino-1-oxopropan-2-yl)amino)-2-(4-((5-cyanopyridin-2-yl)oxy)phenyl)pyrimidine-4-carboxamide |
| 38 | S)-6-((1-amino-1-oxopropan-2-yl)amino)-2-(4-(5-chloro-2-fluorophenoxy)phenyl)pyrimidine-4-carboxamide |
| 39 | (S)-methyl 2-(4-(4-fluorophenoxy)phenyl)-6-((1-methoxy-1-oxopropan-2-yl)amino)pyrimidine-4-carboxylate |
| 40 | (S)-6-((1-carboxyethyl)amino)-2-(4-(4-fluorophenoxy)phenyl)pyrimidine-4-carboxylic acid |
| 41 | 2-(4-(4-fluorophenoxy)phenyl)-6-(3-(hydroxymethyl)morpholino)pyrimidine-4-carboxamide |
| 42 | (S)-2-(4-(4-fluorophenoxy)phenyl)-6-((1-hydroxypropan-2-yl)amino)pyrimidine-4-carboxamide |
| 43 | (S)-2-(4-(4-fluorophenoxy)phenyl)-6-(2-(hydroxymethyl)pyrrolidin-1-yl)pyrimidine-4-carboxamide |
| 44 | 2-(4-(4-fluorophenoxy)phenyl)-6-((2-hydroxy-2-methylpropyl)amino)pyrimidine-4-carboxamide |
| 45 | 2-(4-(4-fluorophenoxy)phenyl)-6-(((1-hydroxycyclohexyl)methyl)amino)pyrimidine-4-carboxamide |
| 46 | (S)-6-((2,3-dihydroxypropyl)amino)-2-(4-(4-fluorophenoxy)phenyl)pyrimidine-4-carboxamide |
| 47 | 6-((1,3-dihydroxypropan-2-yl)amino)-2-(4-(4-fluorophenoxy)phenyl)pyrimidine-4-carboxamide |
| 48 | 2-(4-(4-fluorophenoxy)phenyl)-6-(2-(hydroxymethyl)piperazin-1-yl)pyrimidine-4-carboxamide |
| 49 | 6-(3,4-dihydroxypyrrolidin-1-yl)-2-(4-(4-fluorophenoxy)phenyl)pyrimidine-4-carboxamide |
| 50 | (S)-6-((3-amino-2-hydroxy-3-oxopropyl)amino)-2-(4-(4-fluorophenoxy)phenyl)pyrimidine-4-carboxamide |
| 51 | (S)-3-((6-carbamoyl-2-(4-(4-fluorophenoxy)phenyl)pyrimidin-4-yl)amino)-2-hydroxypropanoic acid |
| 52 | 6-(N-((2,2-dimethyl-1,3-dioxolan-4-yl)methyl)methylsulfonamido)-2-(4-(4-fluorophenoxy)phenyl)pyrimidine-4-carboxamide |
| 53 | 6-(N-(2,3-dihydroxypropyl)methylsulfonamido)-2-(4-(4-fluorophenoxy)phenyl)pyrimidine-4-carboxamide |
| 54 | (S)-2-((1-amino-1-oxopropan-2-yl)amino)-6-(4-(4-fluorophenoxy)phenyl)pyrimidine-4-carboxamide |
| 55 | (S)-4-((1-amino-1-oxopropan-2-yl)amino)-6-(4-(4-fluorophenoxy)phenyl)pyrimidine-2-carboxamide |
| 56 | (S)-6-((1-amino-1-oxopropan-2-yl)oxy)-2-(4-(4-fluorophenoxy)phenyl)pyrimidine-4-carboxamide |
| 57 | (S)-6-((1-amino-1-oxopropan-2-yl)amino)-2-(4-((4-trifluoromethyl)pyridine-2-yl)oxy)phenyl)pyrimidine-4-carboxamide |
| 58 | (S)-6-((1-amino-1-oxopropan-2-yl)amino)-2-(4-((3-trifluoromethyl)pyridine-2-yl)oxy)phenyl)pyrimidine-4-carboxamide |
| 59 | (S)-6-((1-amino-1-oxopropan-2-yl)amino)-2-(4-((6-trifluoromethyl)pyridine-2-yl)oxy)phenyl)pyrimidine-4-carboxamide |
| 60 | (S)-6-((1-amino-1-oxopropan-2-yl)amino)-2-(4-((6-trifluoromethyl)pyridine-3-yl)oxy)phenyl)pyrimidine-4-carboxamide |
| 61 | (S)-6-((1-amino-1-oxopropan-2-yl)amino)-2-(4-((6-fluoropyridine-2-yl)oxy)phenyl)pyrimidine-4-carboxamide |
| 62 | (S)-6-((1-amino-1-oxopropan-2-yl)amino)-2-(4-((5-fluoropyridine-2-yl)oxy)phenyl)pyrimidine-4-carboxamide |
| 63 | (S)-6-((1-amino-1-oxopropan-2-yl)amino)-2-(4-((5-chloropyridine-2-yl)oxy)phenyl)pyrimidine-4-carboxamide |
| 64 | (S)-6-((1-amino-1-oxopropan-2-yl)amino)-2-(4-(4-chloro-2-fluorophenoxy)phenyl)pyrimidine-4-carboxamide |
| 65 | 6-((S)-1-Carbamoyl-ethylamino)-2-(4-hydroxy-phenyl)-pyrimidine-4-carboxylic acid amide |
| 66 | 6-((S)-1-Carbamoyl-ethylamino)-2-[4-(4-cyano-phenoxy)-phenyl]-pyrimidine-4-carboxylic acid amide |
| 67 | (S)-6-((1-amino-1-oxopropan-2-yl)amino)-2-(2-(2-aminopyridin-4-yl)-4-chlorophenoxy)pyrimidine-4-carboxamide |
| 68 | (S)-6-((1-amino-1-oxopropan-2-yl)amino)-2-(2-(4-fluorophenoxy)pyridin-4-yl)pyrimidine-4-carboxamide |
| 69 | (S)-6-((1-amino-1-oxopropan-2-yl)amino)-2-(6-(4-fluorophenoxy)pyridin-3-yl)pyrimidine-4-carboxamide |
| 70 | (S)-6-((1-amino-1-oxopropan-2-yl)amino)-2-(4-(4-fluorophenyl)piperazin-1-yl)pyrimidine-4-carboxamide |
| 71 | (S)-6-((1-amino-1-oxopropan-2-yl)amino)-2-(4-(bis(4-fluorophenyl)methyl)piperazin-1-yl)pyrimidine-4-carboxamide |

TABLE 3-continued

| Compound Example No. | Chemical Name |
|---|---|
| 72 | (S)-6-((1-amino-1-oxopropan-2-yl)amino)-2-(2-(pyridazin-4-yl)-4-(trifluoromethyl)phenoxy)pyrimidine-4-carboxamide |
| 73 | (S)-6-((1-amino-1-oxopropan-2-yl)amino)-2-(1,3-dihydrospiro[indene-2,4'-piperidin]-1'-yl)pyrimidine-4-carboxamide |
| 74 | 6-(3-carbamoylpiperazin-1-yl)-2-(4-(4-fluorophenoxy)phenyl)pyrimidine-4-carboxamide |
| 75 | (S)-2-(4-(4-chloro-2-fluorophenoxy)phenyl)-6-((2-oxopyrrolidin-3-yl)amino)pyrimidine-4-carboxamide |
| 76 | (S)-6-((1-amino-1-oxopropan-2-yl)oxy)-2-(4-(4-(trifluoromethoxy)phenoxy)phenyl)pyrimidine-4-carboxamide |
| 77 | (S)-6-((1-amino-1-oxopropan-2-yl)oxy)-2-(4-(4-cyanophenoxy)phenyl)pyrimidine-4-carboxamide |
| 78 | (S)-6-(2-carbamoylpyrrolidin-1-yl)-2-(4-(4-chloro-2-fluorophenoxy)phenyl)pyrimidine-4-carboxamide |
| 79 | 6-((3S,4S)-3,4-dihydroxypyrrolidin-1-yl)-2-(4-(4-fluorophenoxy)phenyl)pyrimidine-4-carboxamide |
| 80 | 6-((3R,4R)-3,4-dihydroxypyrrolidin-1-yl)-2-(4-(4-fluorophenoxy)phenyl)pyrimidine-4-carboxamide |
| 81 | 6-(2-carbamoyl-4-methylpiperazin-1-yl)-2-(4-(4-(trifluoromethyl)phenoxy)phenyl)pyrimidine-4-carboxamide |
| 82 | 6-(2-carbamoyl-4-methylpiperazin-1-yl)-2-(4-(4-fluorophenoxy)phenyl)pyrimidine-4-carboxamide |
| 83 | 6-(2-carbamoyl-4-methylpiperazin-1-yl)-2-(4-(4-chloro-2-fluorophenoxy)phenyl)pyrimidine-4-carboxamide |
| 84 | (S)-6-((1-amino-1-oxopropan-2-yl)amino)-2-(4-(4-(trifluoromethoxy)phenoxy)phenyl)pyrimidine-4-carboxamide |
| 85 | (S)-6-((1-amino-1-oxopropan-2-yl)amino)-2-(4-(benzo[d][1,3]dioxol-5-yloxy)phenyl)pyrimidine-4-carboxamide |
| 86 | 6-(2-carbamoylpiperazin-1-yl)-2-(4-(4-(trifluoromethyl)phenoxy)phenyl)pyrimidine-4-carboxamide |
| 87 | (S)-6-(2-carbamoylpyrrolidin-1-yl)-2-(4-(5-chloro-2-fluorophenoxy)phenyl)pyrimidine-4-carboxamide |
| 88 | (S)-6-(2-carbamoylpyrrolidin-1-yl)-2-(4-((5-(trifluoromethyl)pyridin-2-yl)oxy)phenyl)pyrimidine-4-carboxamide |
| 89 | (S)-6-(2-carbamoylpyrrolidin-1-yl)-2-(4-(4-cyanophenoxy)phenyl)pyrimidine-4-carboxamide |
| 90 | (S)-2-(4-(benzo[d][1,3]dioxol-5-yloxy)phenyl)-6-(2-carbamoylpyrrolidin-1-yl)pyrimidine-4-carboxamide |
| 91 | (S)-6-(2-carbamoylpyrrolidin-1-yl)-2-(4-(4-(trifluoromethyl)phenoxy)phenyl)pyrimidine-4-carboxamide |
| 92 | (S)-6-((1-amino-1-oxopropan-2-yl)oxy)-2-(4-(5-chloro-2-fluorophenoxy)phenyl)pyrimidine-4-carboxamide |
| 93 | (S)-6-((1-amino-1-oxopropan-2-yl)oxy)-2-(4-(4-chloro-2-fluorophenoxy)phenyl)pyrimidine-4-carboxamide |
| 94 | (S)-2-(4-(4-fluorophenoxy)phenyl)-6-((1-((2-hydroxyethyl)amino)-1-oxopropan-2-yl)amino)pyrimidine-4-carboxamide |
| 95 | (S)-2-(4-(4-fluorophenoxy)phenyl)-6-((1-morpholino-1-oxopropan-2-yl)amino)pyrimidine-4-carboxamide |
| 96 | (S)-methyl 5-(4-((1-amino-1-oxopropan-2-yl)amino)-6-carbamoylpyrimidin-2-yl)-2-(4-fluorophenoxy)benzoate |
| 97 | (S)-6-((1-amino-1-oxopropan-2-yl)amino)-2-(4-(4-fluorophenoxy)-3-(hydroxymethyl)phenyl)pyrimidine-4-carboxamide |
| 98 | (S)-6-((1-amino-1-oxopropan-2-yl)oxy)-2-(4-(4-(trifluoromethyl) phenoxy)phenyl)pyrimidine-4-carboxamide |
| 99 | (S)-6-((2-oxopyrrolidin-3-yl)amino)-2-(4-((5-(trifluoromethyl) pyridin-2-yl)oxy)phenyl)pyrimidine-4-carboxamide |
| 100 | (S)-6-((1-amino-1-oxopropan-2-yl)amino)-2-(4-(4-cyanophenoxy) piperidin-1-yl)pyrimidine-4-carboxamide |
| 101 | (S)-6-((1-amino-1-oxopropan-2-yl)amino)-2-(3-(4-(trifluoromethoxy)phenoxy)azetidin-1-yl)pyrimidine-4-carboxamide |
| 102 | 6-(((S)-2-oxopyrrolidin-3-yl)oxy)-2-(4-(4-(trifluoromethyl) phenoxy)cyclohex-1-en-1-yl)pyrimidine-4-carboxamide |
| 103 | 6-(((S)-1-amino-1-oxopropan-2-yl)amino)-2-(4-(4-(trifluoromethyl) phenoxy)cyclohex-1-en-1-yl)pyrimidine-4-carboxamide |

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{1-10}$ alkyl group. In another embodiment, the alkyl group is chosen from a straight chain $C_{1-6}$ alkyl group. In another embodiment, the alkyl group is chosen from a branched chain $C_{1-6}$ alkyl group. In another embodiment, the alkyl group is chosen from a straight chain $C_{1-4}$ alkyl group. In another embodiment, the alkyl group is chosen from a branched chain $C_{1-4}$ alkyl group. In another embodiment, the alkyl group is chosen from a straight or branched chain $C_{2-4}$ alkyl group. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, decyl, and the like. Non-limiting exemplary $C_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —CH$_2$CH$_2$NO$_2$, —CH$_2$CH$_2$CO$_2$H, —CH$_2$CH$_2$SO$_2$CH$_3$, —CH$_2$CH$_2$COPh, —CH$_2$C$_6$H$_{11}$, and the like.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and the like.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkyl is substituted with two substituents. In another embodiment, the optionally substituted cycloalkyl is substituted with one substituent. Non-limiting exemplary optionally substituted cycloalkyl groups include:

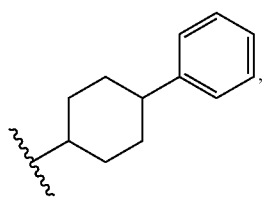

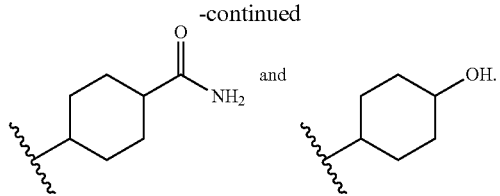

For the purpose of the present disclosure, the term "cycloalkenyl" as used by itself or part of another group refers to a partially unsaturated cycloalkyl group as defined above. In one embodiment, the cycloalkenyl has one carbon-to-carbon double bond. In another embodiment, the cycloalkenyl group is chosen from a $C_{4-8}$ cycloalkenyl group. Exemplary cycloalkenyl groups include cyclopentenyl, cyclohexenyl and the like.

For the purpose of the present disclosure, the term "optionally substituted cycloalkenyl" as used by itself or as part of another group means that the cycloalkenyl as defined above is either unsubstituted or substituted with one, two, or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkenyl is substituted with two substituents. In another embodiment, the optionally substituted cycloalkenyl is substituted with one substituent. In another embodiment, the cycloalkenyl is unsubstituted.

For the purpose of the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano: hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "(cycloalkyl)alkyl" as used by itself or as part of another group refers to an alkyl group substituted with at least one optionally substituted cycloalkyl group. Non-limiting exemplary (cycloalkyl)alkyl groups include:

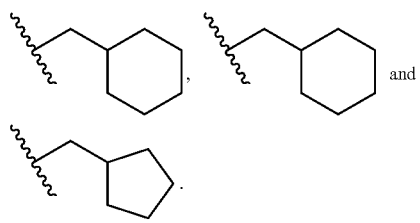

For the purpose of the present disclosure, the term "hydroxy(cycloalkyl)alkyl" as used by itself or as part of another group refers to (cycloalkyl)alkyl group substituted with at least one hydroxy group. The hydroxy group(s) can be at any available position. Non-limiting exemplary hydroxy(cycloalkyl)alkyl groups include:

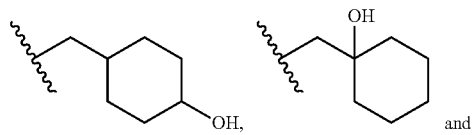

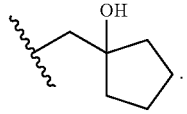

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —$SCH_3$, and —$SCH_2CH_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "heteroalkyl" as used by itself or part of another group refers to a stable straight or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. Non-limiting exemplary heteroalkyl groups include —$CH_2OCH_2CH_2OCH_3$, —$OCH_2CH_2OCH_2CH_2OCH_3$, —$CH_{-2}NHCH_2CH_2OCH_2$, —$OCH_2CH_2NH_2$, and —$NHCH_2CH_2N(H)CH_3$.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "aryl" as used by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, or (heteroaryl)alkyl. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-difluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Examples include

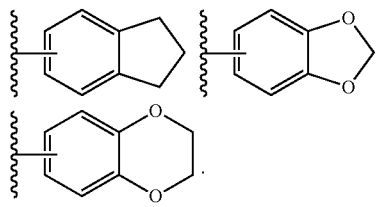

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "aralkyloxy" as used by itself or as part of another group refers to an aralkyl group attached to a terminal oxygen atom. A non-limiting exemplary aralkyloxy group is $PhCH_2O$—.

For the purpose of the present disclosure, the term "heteroaryl" or "heteroaromatic" refers to monocyclic and bicyclic aromatic ring systems having 5 to 14 ring atoms (i.e., $C_5$-$C_{14}$ heteroaryl) and 1, 2, 3, or 4 heteroatoms independently chosen from oxygen, nitrogen and sulfur. In one embodiment, the heteroaryl has three heteroatoms. In another embodiment, the heteroaryl has two heteroatoms. In another embodiment, the heteroaryl has one heteroatom. In one embodiment, the heteroaryl is a $C_5$ heteroaryl. In another embodiment, the heteroaryl is a $C_6$ heteroaryl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, pyrimidin-5-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide and the like.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted heteroaryl has one substituent. In one embodiment, the optionally substituted is an optionally substituted pyridyl, i.e., 2-, 3-, or 4-pyridyl. Any available carbon or nitrogen atom can be substituted. In another embodiment, the optionally substituted heteroaryl is an optionally substituted indole.

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) and at least one heteroatom. Each heteroatom is independently selected from the group consisting of oxygen, sulfur, including sulfoxide and sulfone, and/or nitrogen atoms, which can be quaternized. The term "heterocyclo" is meant to include cyclic ureido groups such as 2-imidazolidinone and cyclic amide groups such as β-lactam, γ-lactam, δ-lactam and ε-lactam. The term "heterocyclo" is also meant to include groups having fused optionally substituted aryl groups, e.g., indolinyl. In one embodiment, the heterocyclo group is chosen from a 5- or 6-membered cyclic group containing one ring and one or two oxygen and/or nitrogen atoms. The heterocyclo can be optionally linked to the rest of the molecule through a carbon or nitrogen atom. Non-limiting exemplary heterocyclo groups include 2-imidazolidinone, piperidinyl, morpholinyl, piperazinyl, pyrrolidinyl, and indolinyl.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (heteroaryl)

alkyl, and the like. Substitution may occur on any available carbon or nitrogen atom, and may form a spirocycle. Non-limiting exemplary optionally substituted heterocyclo groups include:

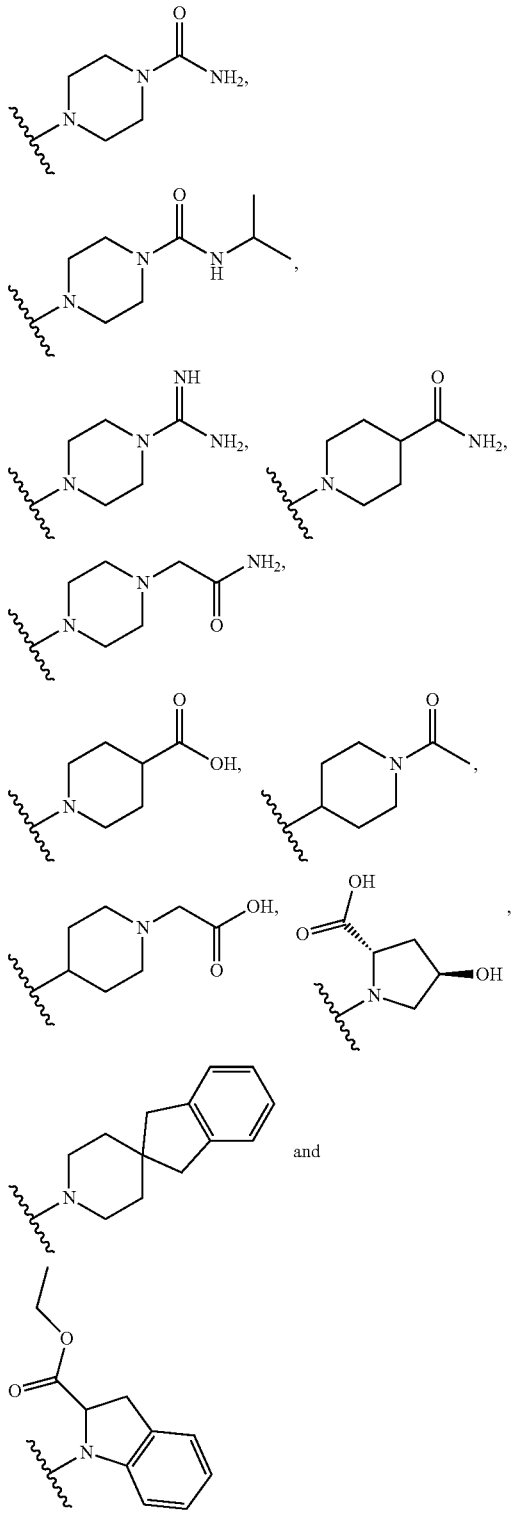

For the purpose of the present disclosure, the term "amino" as used by itself or as part of another group refers to —NH$_2$.

For the purpose of the present disclosure, the term "alkylamino" as used by itself or as part of another group refers to —NHR$^{15}$, wherein R$^{15}$ is alkyl.

For the purpose of the present disclosure, the term "dialkylamino" as used by itself or as part of another group refers to —NR$^{16a}$R$^{16b}$, wherein R$^{16a}$ and R$^{16b}$ are each independently alkyl or R$^{16a}$ and R$^{16b}$ are taken together to form a 3- to 8-membered optionally substituted heterocyclo.

For the purpose of the present disclosure, the term "hydroxyalkylamino" as used by itself or as part of another group refers to —NHR$^{17}$, wherein R$^{17}$ is hydroxyalkyl.

For the purpose of the present disclosure, the term "arylamino" as used by itself or as part of another group refers to —NR$^{18a}$R$^{18b}$, wherein R$^{18a}$ is optionally substituted aryl and R$^{18b}$ is hydrogen or alkyl.

For the purpose of the present disclosure, the term "cycloalkylamino" as used by itself or as part of another group refers to —NR$^{19a}$R$^{19b}$, wherein R$^{19a}$ is optionally substituted cycloalkyl and R$^{19b}$ is hydrogen or alkyl.

For the purpose of the present disclosure, the term "heteroarylamino" as used by itself or as part of another group refers to —NR$^{20a}$R$^{20b}$ wherein R$^{20a}$ is optionally substituted heteroaryl and R$^{20b}$ is hydrogen or alkyl.

For the purpose of the present disclosure, the term "heterocycloamino" as used by itself or as part of another group refers to —NR$^{21a}$R$^{21b}$ wherein R$^{21a}$ is optionally substituted heterocyclo and R$^{21b}$ is hydrogen or alkyl.

For the purpose of the present disclosure, the term "(amino)alkyl" as used by itself or as part of another group refers to an alkyl group substituted with an amino group. Non-limiting exemplary amino alkyl groups include —CH$_2$CH$_2$NH$_2$, —CH$_2$CH$_2$CH$_2$NH$_2$, —CH$_2$CH$_2$CH$_2$CH$_2$NH$_2$ and the like.

For the purpose of the present disclosure, the term "diaminoalkyl" as used by itself or as part of another group refers an alkyl group substituted with two amino groups. A non-limiting exemplary diaminoalkyl includes —CH$_2$CH(NH$_2$)CH$_2$CH$_2$NH$_2$.

For the purpose of the present disclosure, the term "(alkylamino)alkyl" as used by itself or as part of another group refers alkyl group substituted an alkylamino group. A non-limiting exemplary (alkylamino)alkyl group is —CH$_2$CH$_2$N(H)CH$_3$.

For the purpose of the present disclosure, the term "(dialkylamino)alkyl" as used by itself or as part of another group refers to an alkyl group substituted by a dialkylamino group. A non-limiting exemplary (dialkylamino)alkyl group is —CH$_2$CH$_2$N(CH$_3$)$_2$.

For the purpose of the present disclosure, the term "(cyano)alkyl" as used by itself or as part of another group refers to an alkyl group substituted with one or more cyano, e.g., —CN, groups. Non-limiting exemplary (cyano)alkyl groups include —CH$_2$CH$_2$CN, —CH$_2$CH$_2$CH$_2$CN, and —CH$_2$CH$_2$CH$_2$CH$_2$CN.

For the purpose of the present disclosure, the term "carboxamido" as used by itself or as part of another group refers to a radical of formula —C(=O)NR$^{24a}$R$^{24b}$, wherein R$^{24a}$ and R$^{24b}$ are each independently hydrogen, optionally substituted alkyl, optionally substituted aryl, or optionally substituted heteroaryl, or R$^{24a}$ and R$^{24b}$ taken together with the nitrogen to which they are attached from a 3- to 8-membered heterocyclo group. In one embodiment, R$^{24a}$ and R$^{24b}$ are each independently hydrogen or optionally substituted alkyl. Non-limiting exemplary carboxamido groups include —CONH$_2$, —CON(H)CH$_3$, CON(CH$_3$)$_2$, and CON(H)Ph.

For the purpose of the present disclosure, the term "(carboxamido)alkyl" as used by itself or as part of another group refers to an alkyl group with a carboxamido group. Non-limiting exemplary (carboxamido)alkyl groups include —$CH_2CONH_2$, —$C(H)CH_3$—$CONH_2$, and —$CH_2CON(H)CH_3$.

For the purpose of the present disclosure, the term "sulfonamido" as used by itself or as part of another group refers to a radical of the formula —$SO_2NR^{23a}R^{23b}$, wherein $R^{23a}$ and $R^{23b}$ are each independently hydrogen, optionally substituted alkyl, or optionally substituted aryl, or $R^{23a}$ and $R^{23b}$ taken together with the nitrogen to which they are attached from a 3- to 8-membered heterocyclo group. Non-limiting exemplary sulfonamido groups include —$SO_2NH_2$, —$SO_2N(H)CH_3$, and —$SO_2N(H)Ph$.

For the purpose of the present disclosure, the term "alkylcarbonyl" as used by itself or as part of another group refers to a carbonyl group, i.e., —$C(=O)$—, substituted by an alkyl group. A non-limiting exemplary alkylcarbonyl group is —$COCH_3$.

For the purpose of the present disclosure, the term "arylcarbonyl" as used by itself or as part of another group refers to a carbonyl group, i.e., —$C(=O)$—, substituted by an optionally substituted aryl group. A non-limiting exemplary arylcarbonyl group is —COPh.

For the purpose of the present disclosure, the term "alkylsulfonyl" as used by itself or as part of another group refers to a sulfonyl group, i.e., —$SO_2$—, substituted by any of the above-mentioned optionally substituted alkyl groups. A non-limiting exemplary alkylsulfonyl group is —$SO_2CH_3$.

For the purpose of the present disclosure, the term "arylsulfonyl" as used by itself or as part of another group refers to a sulfonyl group, i.e., —$SO_2$—, substituted by any of the above-mentioned optionally substituted aryl groups. A non-limiting exemplary arylsulfonyl group is —$SO_2Ph$.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —$CH_2CO_2H$.

For the purpose of the present disclosure, the term "alkoxycarbonyl" as used by itself or as part of another group refers to a carbonyl group, i.e., —$C(=O)$—, substituted by an alkoxy group. Non-limiting exemplary alkoxycarbonyl groups are —$CO_2Me$ and —$CO_2Et$.

For the purpose of the present disclosure, the term "aralkyl" as used by itself or as part of another group refers to an alkyl group substituted with one, two, or three optionally substituted aryl groups. In one embodiment, the aralkyl group is a $C_{1-4}$ alkyl substituted with one optionally substituted aryl group. Non-limiting exemplary aralkyl groups include benzyl, phenethyl, —$CHPh_2$, and —$CH(4-F-Ph)_2$.

For the purpose of the present disclosure, the term "ureido" as used by itself or as part of another group refers to a radical of the formula —$NR^{22a}$—$C(=O)$—$NR^{22b}R^{22c}$, wherein $R^{22a}$ is hydrogen, alkyl, or optionally substituted aryl, and $R^{22b}$ and $R^{22c}$ are each independently hydrogen, alkyl, or optionally substituted aryl, or $R^{22b}$ and $R^{22c}$ taken together with the nitrogen to which they are attached form a 4- to 8-membered heterocyclo group. Non-limiting exemplary ureido groups include —NH—$C(C=O)$—$NH_2$ and —NH—$C(C=O)$—$NHCH_3$.

For the purpose of the present disclosure, the term "guanidino" as used by itself or as part of another group refers to a radical of the formula —$NR^{25a}$—$C(=NR^{26})$—$NR^{25b}R^{25c}$, wherein $R^{25a}$, $R^{25b}$, and $R^{25c}$ are each independently hydrogen, alkyl, or optionally substituted aryl, and $R^{26}$ is hydrogen, alkyl, cyano, alkylsulfonyl, alkylcarbonyl, carboxamido, or sulfonamido. Non-limiting exemplary guanidino groups include —NH—C(C=NH)—$NH_2$, —NH—C(C=NCN)—$NH_2$, —NH—C(C=NH)—$NHCH_3$ and the like.

For the purpose of the present disclosure, the term "azido" as used by itself or as part of another group refers to a radical of the formula —$N_3$.

For the purpose of the present disclosure, the term "(heterocyclo)alkyl" as used by itself or as part of another group refers to an alkyl group substituted with one, two, or three optionally substituted heterocyclo groups. In one embodiment, the (heterocyclo)alkyl is a $C_{1-4}$ alkyl substituted with one optionally substituted heterocyclo group. Non-limiting exemplary (heterocyclo)alkyl groups include:

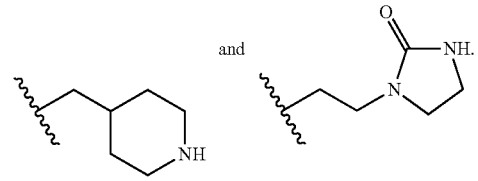 [SMILES: *CC1CCNCC1 ; "and" ; *CCN1CCNC1=O]

For the purpose of the present disclosure, the term "(heteroaryl)alkyl" as used by itself or as part of another group refers to an alkyl group substituted with one, two, or three optionally substituted heteroaryl groups. In one embodiment, the (heteroaryl)alkyl group is a $C_{1-4}$ alkyl substituted with one optionally substituted heteroaryl group. Non-limiting exemplary (heteroaryl)alkyl groups include:

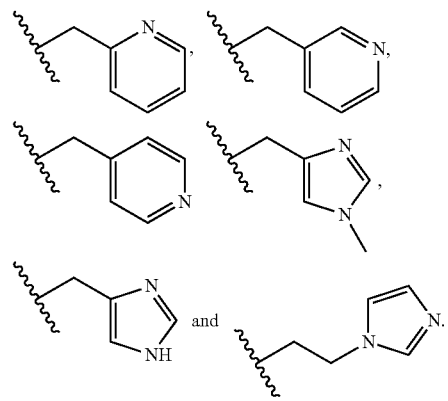

For the purpose of the present disclosure, the term "alkylcarbonylamino" as used by itself or as part of another group refers to an alkylcarbonyl group attached to an amino. A non-limiting exemplary alkylcarbonylamino group is —NH-$COCH_3$.

The present disclosure encompasses prodrugs of any of the disclosed compounds. As used herein, prodrugs are considered to be any covalently bonded carriers that release the active parent drug in vivo. In general, such prodrugs will be functional derivatives of Compounds of the Invention which will be readily convertible in vivo, e.g., by being metabolized, into the required Compound of the Invention. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984). Non-limiting examples of prodrugs include esters or amides of Compounds of the Invention having hydroxyalkyl or aminoalkyl as a substituent, and these can be prepared by reacting such parent compounds with anhydrides such as succinic anhydride.

The present disclosure encompasses any of the Compounds of the Invention being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, e.g., $^3H$, $^{11}C$, and $^{14}C$. Isotopically-labeled Compounds of the Invention can be prepared by methods known in the art.

The present disclosure encompasses $^3H$, $^{11}C$, or $^{14}C$ radiolabeled Compounds of the Invention and the use of any such compounds as radioligands for their ability to bind to the sodium channel. For example, one use of the labeled compounds of the present disclosure is the characterization of specific receptor binding. Another use of a labeled Compound of the Invention is an alternative to animal testing for the evaluation of structure-activity relationships. For example, the receptor assay can be performed at a fixed concentration of a labeled Compound of the Invention and at increasing concentrations of a test compound in a competition assay. For example, a tritiated Compound of the Invention can be prepared by introducing tritium into the particular compound, for example, by catalytic dehalogenation with tritium. This method may include reacting a suitably halogen-substituted precursor of the compound with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

Some of the Compounds of the Invention may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

The term "treat," "treating" or "treatment" is meant to encompass administering to a subject a compound of the present disclosure for the purposes of amelioration or cure, including preemptive and palliative treatment. In one embodiment, the term "treat," "treating" or "treatment" is meant to encompass administering to a subject a compound of the present disclosure for the purposes of amelioration or cure.

The term "about," as used herein in connection with a measured quantity, refers to the normal variations in that measured quantity, as expected by the skilled artisan making the measurement and exercising a level of care commensurate with the objective of measurement and the precision of the measuring equipment.

The present disclosure encompasses the preparation and use of salts of the Compounds of the Invention, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like.

Acid addition salts can be formed by mixing a solution of the particular Compound of the Invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The present disclosure encompasses the preparation and use of solvates of Compounds of the Invention. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Invention can be present as solvated forms with a pharmaceutically acceptable solvent, such as water, methanol, ethanol, and the like, and it is intended that the disclosure includes both solvated and unsolvated forms of Compounds of the Invention. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.* 603-604 (2001). A typical, non-limiting, process of preparing a solvate would involve dissolving a Compound of the Invention in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Since Compounds of the Invention are blockers of sodium ($Na^+$) channels, a number of diseases and conditions mediated by sodium ion influx can be treated by employing these compounds. The present disclosure is thus directed generally to a method for treating a disorder responsive to the blockade of sodium channels in an animal suffering from, or at risk of suffering from, said disorder, said method comprising administering to the animal an effective amount of one or more Compounds of the Invention.

The present disclosure is further directed to a method of modulating sodium channels in an animal in need thereof, said method comprising administering to the animal a modulating-effective amount of at least one Compound of the Invention.

More specifically, the present disclosure provides a method of treating stroke, neuronal damage resulting from head trauma, epilepsy, neuronal loss following global and focal ischemia, pain (e.g., acute pain, chronic pain, which includes but is not limited to neuropathic pain, postoperative pain, and inflammatory pain, or surgical pain), a neurodegenerative disorder (e.g., Alzheimer's disease, amyotrophic lateral sclerosis (ALS), or Parkinson's disease), migraine, manic depression, tinnitus, myotonia, a movement disorder, or cardiac arrhythmia, or providing local anesthesia. In one embodiment, the disclosure provides a method of treating pain. In another embodiment, the type of pain is chronic pain. In another embodiment, the type of pain is neuropathic pain. In another embodiment, the type of pain is postoperative pain. In another embodiment, the type of pain is inflammatory pain. In another embodiment, the type of pain is surgical pain. In another embodiment, the type of pain is acute pain. In another embodiment, the treatment of pain (e.g., chronic pain, such as neuropathic pain, postoperative pain, or inflammatory pain, acute pain or surgical pain) is preemptive. In another embodiment, the treatment of pain is palliative. In each instance, such method of treatment requires administering to an animal in need of such treatment an amount of a Compound of the Invention that is therapeutically effective in achieving said treatment. In one embodiment, the amount of such compound is the amount that is effective to block sodium channels in vitro. In one embodiment, the amount of such compound is the amount that is effective to block sodium channels in vivo.

Chronic pain includes, but is not limited to, inflammatory pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

Chronic somatic pain generally results from inflammatory responses to tissue injury such as nerve entrapment, surgical procedures, cancer or arthritis (Brower, *Nature Biotechnology* 18:387-391 (2000)).

The inflammatory process is a complex series of biochemical and cellular events activated in response to tissue injury or the presence of foreign substances (Levine, *Inflammatory Pain, In: Textbook of Pain*, Wall and Melzack eds., 3$^{rd}$ ed., 1994). Inflammation often occurs at the site of injured tissue, or foreign material, and contributes to the process of tissue repair and healing. The cardinal signs of inflammation include erythema (redness), heat, edema (swelling), pain and loss of function (ibid.). The majority of patients with inflammatory pain do not experience pain continually, but rather experience enhanced pain when the inflamed site is moved or touched. Inflammatory pain includes, but is not limited to, that associated with osteoarthritis and rheumatoid arthritis.

Chronic neuropathic pain is a heterogeneous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

Neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The present disclosure is also directed to the use of a Compound of the Invention in the manufacture of a medicament for treating a disorder responsive to the blockade of sodium channels (e.g., any of the disorders listed above) in an animal suffering from said disorder.

General Synthesis of Compounds

Compounds of the Invention are prepared using methods known to those skilled in the art in view of this disclosure. For example, compounds of Formula II can be prepared according to General Scheme 1.

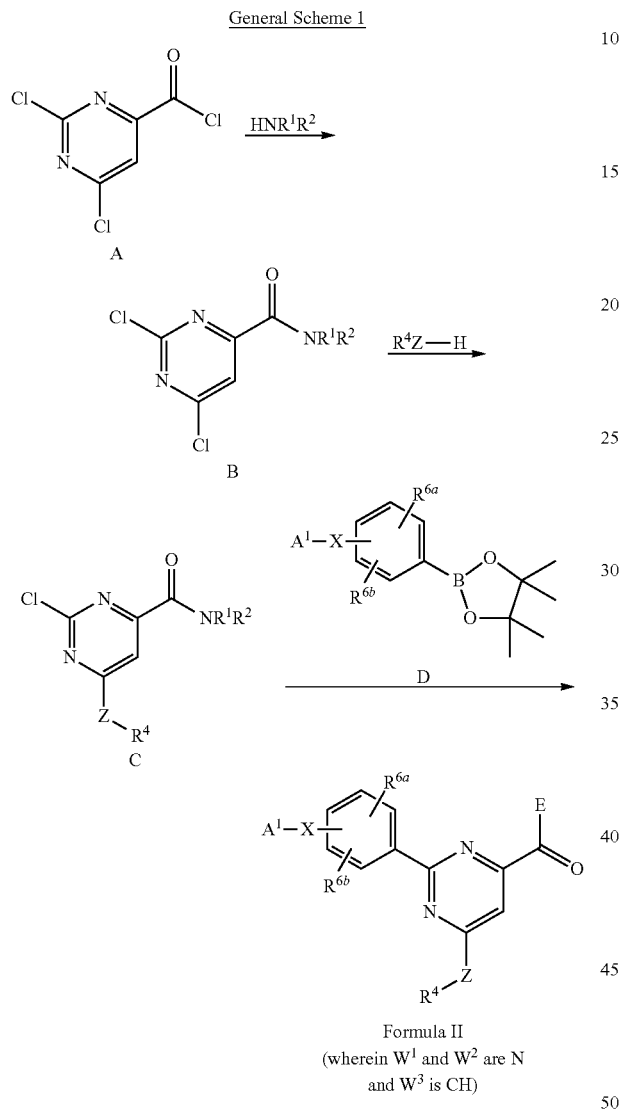

Briefly, 2,6-dichloropyrimidine-4-carbonyl chloride (compound A) is made to react with an amine, $HNR^1R^2$, to give a 2,6-dichloropyrimidine-4-carboxamide, compound B. Compound B is made to react with $R^4Z$—H, e.g., (S)-methyl 2-aminopropanoate, (S)-2-aminopropanamide, (S)-methyl 3-amino-2-hydroxypropanoate, (S)-ethyl 2-hydroxypropanoate, to give Compound C. Compound C is made to react with a dioxaborolane (compound D) to give a compound having Formula II wherein $W^1$ and $W^2$ are N and $W^3$ is CH. Compounds of Formula II wherein $W^1$ and $W^3$ are N and $W^2$ is CH are prepared in similar fashion starting from 4,6-dichloropyrimidine-2-carbonyl chloride, and compounds of Formula II wherein $W^2$ and $W^3$ are N and $W^1$ is CH are prepared in similar fashion starting from 2,4-dichloropyrimidine-6-carbonyl chloride. Compounds of Formula II wherein $A^2$ is optionally substituted cycloalkyl or optionally substituted cycloalkenyl are prepared in similar fashion starting from the appropriate dioxaborolane, e.g.,

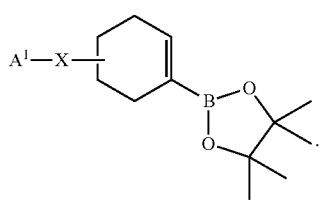

Compounds of Formula VIII can be prepared according to General Scheme 2:

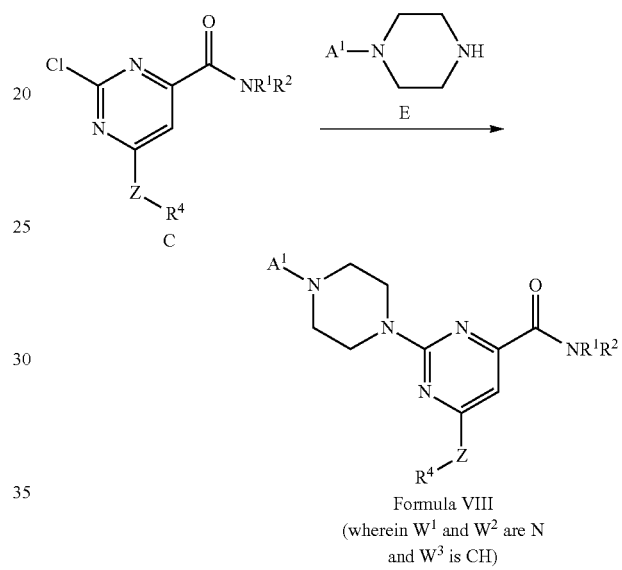

Briefly, Compound C (See General Scheme 1) is made to react with Compound E to give a compound having Formula VIII wherein $W^1$ and $W^2$ are N and $W^3$ is CH.

Compounds of Formula IX can be prepared according to General Scheme 3:

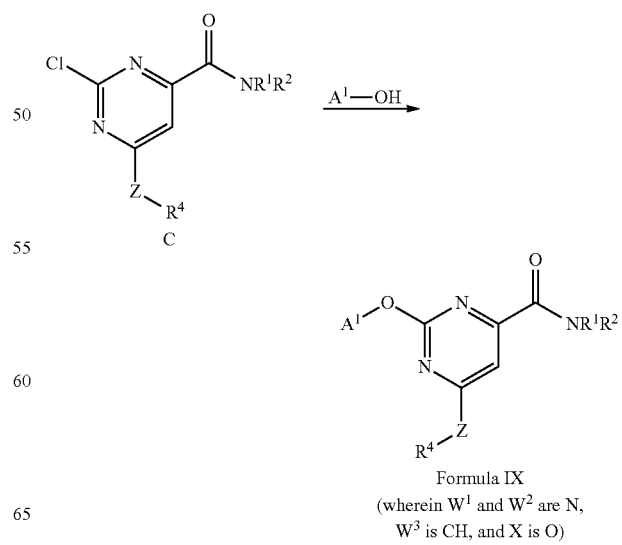

Briefly, Compound C (See General Scheme 1) is made to react with A¹OH to give a compound having Formula IX wherein $W^1$ and $W^2$ are N, $W^3$ is CH, and X is O.

Testing of Compounds

Compounds of the Invention were assessed by sodium mobilization and/or electrophysiological assays for sodium channel blocker activity. One aspect of the present disclosure is based on the use of the Compounds of the Invention as sodium channel blockers. Based upon this property, Compounds of the Invention are considered useful in treating a condition or disorder responsive to the blockade of sodium ion channels, e.g., stroke, neuronal damage resulting from head trauma, epilepsy, seizures, general epilepsy with febrile seizures, severe myoclonic epilepsy in infancy, neuronal loss following global and focal ischemia, migraine, familial primary erythromelalgia, paroxysmal extreme pain disorder, cerebellar atrophy, ataxia, dystonia, tremor, mental retardation, autism, a neurodegenerative disorder (e.g., Alzheimer's disease, amyotrophic lateral sclerosis (ALS), or Parkinson's disease), manic depression, tinnitus, myotonia, a movement disorder, cardiac arrhythmia, or providing local anesthesia. Compounds of the Invention are also expected to be effective in treating pain, e.g., acute pain, chronic pain, which includes but is not limited to, neuropathic pain, postoperative pain, and inflammatory pain, or surgical pain.

More specifically, the present disclosure is directed to Compounds of the Invention that are blockers of sodium channels. According to the present disclosure, those compounds having useful sodium channel blocking properties exhibit an $IC_{50}$ for $Na_v1.1$, $Na_v1.2$, $Na_v1.3$, $Na_v1.4$, $Na_v1.5$, $Na_v1.6$, $Na_v1.7$, $Na_v1.8$, and/or $Na_v1.9$ of about 100 μM or less, e.g., about 50 μM or less, about 25 μM or less, about 10 μM or less, about 5 μM or less, or about 1 μM or less, in sodium mobilization and/or electrophysiological assays. In certain embodiments, Compounds of the Invention exhibit an $IC_{50}$ for $Na_v1.7$ of 100 μM or less, about 50 μM or less, about 25 μM or less, about 10 μM or less, about 5 μM or less, about 1 μM or less, about 0.5 μM or less, about 0.1 μM or less, about 0.05 μM or less, or about 0.01 μM or less. Compounds of the Invention can be tested for their $Na^+$ channel blocking activity using methods known in the art and by the following fluorescence imaging and electrophysiological in vitro assays and/or in vivo assays.

In one embodiment, Compounds of the Invention demonstrate substantially no penetration across the CNS blood-brain barrier in a mammal. Such compounds are referred to as "peripherally restricted" as a means to designate their PNS versus CNS tissue selectivity.

In one embodiment, the PNS:CNS concentration ratio of a peripherally restricted Compound of the Invention is about 5:1, about 10:1, about 20:1, about 30:1; about 50:1; about 100:1, about 250:1, about 500:1, about 1000:1, about 5,000:1, about 10,000:1, or more. Compounds of the Invention can be tested for their ability to penetrate the central nervous system using in vitro and in vivo methods known in the art.

In Vitro Assay Protocols
FLIPR® Assays
Recombinant $Na_v1.7$ Cell Line:

In vitro assays were performed in a recombinant cell line expressing cDNA encoding the alpha subunit ($Na_v1.7$, SCN9a, PN1, NE) of human $Na_v1.7$ (Accession No. NM_002977). The cell line was provided by investigators at Yale University (Cummins et al, *J. Neurosci.* 18(23): 9607-9619 (1998)). For dominant selection of the $Na_v1.7$-expressing clones, the expression plasmid co-expressed the neomycin resistance gene. The cell line was constructed in the human embryonic kidney cell line, HEK293, under the influence of the CMV major late promoter, and stable clones were selected using limiting dilution cloning and antibiotic selection using the neomycin analogue, G418. Recombinant beta and gamma subunits were not introduced into this cell line. Additional cell lines expressing recombinant $Na_v1.7$ cloned from other species can also be used, alone or in combination with various beta subunits, gamma subunits or chaperones.

Non-recombinant Cell Lines Expressing Native $Na_v1.7$:

Alternatively, in vitro assays can be performed in a cell line expressing native, non-recombinant $Na_v1.7$, such as the ND7 mouse neuroblastoma X rat dorsal root ganglion (DRG) hybrid cell line ND7/23, available from the European Cell Culture Collection (Cat. No. 92090903, Salisbury, Wiltshire, United Kingdom). The assays can also be performed in other cell lines expressing native, non-recombinant $Na_v1.7$, from various species, or in cultures of fresh or preserved sensory neurons, such as dorsal root ganglion (DRG) cells, isolated from various species. Primary screens or counter-screens of other voltage-gated sodium channels can also be performed, and the cell lines can be constructed using methods known in the art, purchased from collaborators or commercial establishments, and they can express either recombinant or native channels. The primary counter-screen is for one of the central neuronal sodium channels, $Na_v1.2$ (rBIIa), expressed in HEK293 host cells (Ilyin et al., *Br. J. Pharmacol.* 144:801-812 (2005)). Pharmacological profiling for these counter-screens is carried out under conditions similar to the primary or alternative $Na_v1.7$ assays described below.

Cell Maintenance:

Unless otherwise noted, cell culture reagents were purchased from Mediatech of Herndon, Va. The recombinant $Na_v1.7$/HEK293 cells were routinely cultured in growth medium consisting of Dulbecco's minimum essential medium containing 10% fetal bovine serum (FBS, Hyclone, Thermo Fisher Scientific, Logan, Utah), 100 U/mL penicillin, 100 μg/mL streptomycin, 2-4 mM L-glutamine, and 500 mg/mL G418. For natural, non-recombinant cell lines, the selective antibiotic was omitted, and additional media formulations can be applied as needed.

Assay Buffer:

The assay buffer was formulated by removing 120 mL from a 1 L bottle of fresh, sterile $dH_2O$ (Mediatech, Herndon, Va.) and adding 100 mL of 10×HBSS that does not contain $Ca^{++}$ or $Mg^{++}$ (Gibco, Invitrogen, Grand Island, N.Y.) followed by 20 mL of 1.0 M Hepes, pH 7.3 (Fisher Scientific, BP299-100). The final buffer consisted of 20 mM Hepes, pH 7.3, 1.261 mM $CaCl_2$, 0.493 mM $MgCl_2$, 0.407 mM $Mg(SO)_4$, 5.33 mM KCl, 0.441 mM $KH_2PO_4$, 137 mM NaCl, 0.336 mM $Na_2HPO_4$ and 0.556 mM D-glucose (Hanks et al., *Proc. Soc. Exp. Biol. Med.* 71:196 (1949)), and the simple formulation was typically the basic buffer throughout the assay (i.e., all wash and addition steps).

CoroNa™ Green AM $Na^+$ Dye for Primary Fluorescence Assay:

The fluorescence indicator used in the primary fluorescence assay was the cell permeant version of CoroNa™ Green (Invitrogen, Molecular Probes, Eugene, Oreg.), a dye that emits light in the fluorescence range (Harootunian et al., *J. Biol. Chem.* 264(32):19458-19467 (1989)). The intensity of this emission, but not the wavelength range, is increased when the dye is exposed to $Na^+$ ions, which it can bind with partial selectivity. Cells expressing $Na_v1.7$ or other sodium channels were loaded with the CoroNa™ Green dye immediately in advance of the fluorescence assay, and then, after agonist stimulation, the mobilization of $Na^+$ ions was detected as the Na⁺ ions flowed from the extracellular fluid into the cytoplasm through the activated sodium channel pores. The dye was stored in the dark as a lyophilized powder, and then an aliquot was dissolved immediately before the cell loading procedure, according to the instructions of the manufacturer to a stock concentration of 10 mM in DMSO. It was then diluted in the assay buffer to a 4× concentrated working solution, so that the final concentration of dye in the cell loading buffer was 5 µM.

Membrane Potential Dye for Alternative Fluorescence Assays:

A fluorescence indicator that can be used in alternative fluorescence assays is the blue version membrane potential dye (MDS, Molecular Devices, Sunnyvale, Calif.), a dye that detects changes in molecules following a change in membrane potential. An increase in fluorescence is expected if agonist stimulation provokes a change in membrane potential. Cells expressing $Na_v1.7$ or other sodium channels are incubated with the membrane potential dye 30-60 minutes before the fluorescence assay. In the case of the KCl pre-stimulation version of the assay, the dye and all other components are washed out immediately before the assay, and the dye is then replaced. In the version lacking KCl pre-stimulation, the dye remains on the cells and is not washed out or replaced. The dye is stored in the dark as a lyophilized powder, and then an aliquot dissolved in assay buffer to form a 20×-concentrated stock solution that can be used for several weeks.

Agonists:

In the fluorescence assays, two agonists were used in combination, namely 1) veratridine; and 2) the venom from the yellow scorpion, *Leiurus quinquestriatus hebraeus*. Veratridine is an alkaloid small molecule that facilitates the capture of channel openings by inhibiting inactivation, and the scorpion venom is a natural preparation that includes peptide toxins selective for different subsets of voltage-gated sodium channels. These scorpion toxins inhibit the fast inactivation of their cognate target channels. Stock solutions of the agonists were prepared to 40 mM in DMSO (veratridine) and 1 mg/mL in $dH_2O$ (scorpion venom), and then diluted to make a 4× or 2× stock (depending on the particular assay) in assay buffer, the final concentration being 100 µM (veratridine) and 10 µg/mL (scorpion venom). Both of the agonists were purchased from Sigma Aldrich, St. Louis, Mo.

Test Compounds:

Test compounds were dissolved in DMSO to yield 10 mM stock solutions. The stock solutions were further diluted using DMSO in 1:3 serial dilution steps with 10 points (10,000 µM, 3.333 µM, 1.111 µM, 370 µM, 123 µM, 41 µM, 14 µM, 4.6 µM, 1.5 µM and 0.5 µM). The stock solutions were further diluted in assay buffer (1:125) as 4× stock serial dilutions with a DMSO concentration of 0.8% (final [DMSO], in the assay, from the compounds component=0.2%), so that the compounds' final concentrations in the assay were 20 µM, 6.7 µM, 2.2 µM, 0.74 µM, 0.25 µM and 0.08 µM, 0.03 µM, 0.01 µM, 0.003 µM and 0.001 µM. If a particular test article appeared to be especially potent, then the concentration curve was adjusted, e.g., to 10-fold lower concentrations, in order to perform the dose-response in a more relevant concentration range. Compound dilutions were added during the dye-loading and pre-stimulation step, and then again during the fluorescence assay, early in the kinetic read. Compound dilutions were added in duplicate rows across the middle 80 wells of the 96-well plate, whereas the fully stimulated and the fully inhibited controls (positive and negative) were located in the top 4 side wells and the bottom 4 side wells, respectively, on the left and right sides of the assay plate.

Data Analysis:

The data were analyzed according to methods known to those skilled in the art or using the GraphPad® Prism Program, version 4.0 or higher (available from GraphPad Software, San Diego, Calif.) to determine the $IC_{50}$ value for the test article. At least one standard reference compound was evaluated during each experiment.

FLIPR© or FLIPR$^{TETRA}$® Sodium Dye Assay with KCl and Test Article Pre-Incubation:

Cells were prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately fewer cells and less media. The plate was then incubated in growth media, with or without selective antibiotic, overnight at 37° C. at 5% $CO_2$, 95% humidity, in preparation for the assay. For counter-screens of other voltage-gated sodium channels, the procedure was very similar, though optimal densities of cells, media and subsequent assay components can be fine-tuned for the particular cell line or isoform.

The next day, at the start of the assay, the media was flicked from the cells and the wells were washed once with 50 µl/well assay buffer (1× Hank's balanced salt solution without sodium bicarbonate or phenol red, 20 mM Hepes, pH 7.3) and then pre-incubated with the test articles, CoroNa™ Green AM sodium dye (for cell loading) and KCl for re-polarization and synchronization of the channels in the entire population of cells. For this dye-loading and pre-stimulation step, the components were added as follows, immediately after the wash step: 1) first, the compound dilutions and controls were added as 4× concentrates in assay buffer at 50 µL/well; 2) CoroNa™ Green AM dye was diluted from the stock solution to 20 µM in assay buffer (4× concentrate) and added to the plate at 50 µL/well; and 3) finally, a solution of 180 mM KCl (2×) was prepared by diluting a 2M stock solution into assay buffer and the solution was added to the cells at 100 µl/well. The cells were incubated at 25° C. in the dark for 30 min. before their fluorescence was measured.

The plates containing dye-loaded cells were then flicked to remove the pre-incubation components and washed once with 100 µL/well assay buffer. A 100 µL/well aliquot of assay buffer was added back to the plate, and the real-time assay was commenced. The fluorescence of cells was measured using a fluorescence plate reader (FLIPR$^{TETRA}$® or FLIPR384®, MDS, Molecular Devices, Sunnyvale, Calif.) Samples were excited by either a laser or a PMT light source (Excitation wavelength=470-495 nM) and the emissions are filtered (Emission wavelength=515-575 nM). The additions of compound and the channel activators in this cell-based, medium-to-high throughput assay were performed on the fluorescence plate reader and the results (expressed as relative fluorescence units) were captured by means of camera shots every 1-3 sec., then displayed in real-time and stored. Generally, there was a 15 sec. base line, with camera shots taken every 1.5 sec., then the test compounds were added, then another 120 sec. baseline was conducted, with camera shots taken every 3 sec.; and finally, the agonist solution (containing veratridine and scorpion venom) was added. The amplitude of fluorescence increase, resulting from the binding of Na⁺ ions to the CoroNa™ Green dye, was captured for ~180 sec. thereafter. Results were expressed in relative fluorescence units (RFU) and can be determined by using the maximum signal during the latter part of the stimulation; or the maximum minus the minimum during the whole agonist stimulation period; or by taking the area under the curve for the whole stimulation period.

The assay can be performed as a screening assay as well with the test articles present in standard amounts (e.g., 10 μM) in only one or two wells of a multi-well plate during the primary screen. Hits in this screen were typically profiled more exhaustively (multiple times), subjected to dose-response or competition assays and tested in counter screens against other voltage-gated sodium channels or other biologically relevant target molecules.

FLIPR® or FLIPR$^{TETRA}$® Membrane Potential Assay with KCl and Test Article Pre-Incubation:

Cells are prepared by plating the recombinant HEK293 cells or other host cells expressing either recombinant or non-recombinant, native, Na$_v$1.7 alpha subunit, alone or in combination with various beta and gamma subunits at a density of 40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% $CO_2$, 95% humidity, in preparation for the assay (see, e.g., Benjamin et. al., *J. Biomol. Screen* 10(0:365-373 (2005)). For screens and counter-screens of other voltage-gated sodium channels, the assay protocol is similar, though optimal densities of cells, media and subsequent assay components can be fine-tuned for the particular cell line or sodium channel isoform being tested.

The next day, at the start of the assay, the media is flicked from the cells and the wells are washed once with 50 μL/well assay buffer (1× Hank's balanced salt solution without sodium bicarbonate or phenol red, 20 mM Hepes, pH 7.3) and then pre-incubated with the test articles, the membrane potential dye (for cell loading), and the KCl for re-polarization and synchronization of the channels in the entire population of cells. For this dye-loading and pre-stimulation step, the components are added as follows, immediately after the wash step: 1) first, the compound dilutions and controls are added as 4× concentrates in assay buffer at 50 μL/well; 2) membrane potential dye is diluted from the stock solution in assay buffer (4× concentrate) and added to the plate at 50 μL/well; and 3) finally, a solution of 180 mM KCl (2×) is prepared by diluting a 2M stock solution into assay buffer and the solution added to the cells at 100 μL/well. The cells are incubated at 37° C. in the dark for 30-60 min. before their fluorescence is measured.

The plates containing dye-loaded cells are then flicked to remove the pre-incubation components and washed once with 50 μL/well assay buffer. A 50 μL/well aliquot of membrane potential dye is added back to the plate, and the real-time assay is commenced. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first) and then the channel activators (later) in this are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well with the test articles present in standard amounts (e.g., 10 μM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

FLIPR® or FLIPR$^{TETRA}$® Sodium Dye Assay without KCl and Test Article Pre-Incubation:

Cells are prepared by plating the recombinant HEK293 cells or other host cells expressing either recombinant or non-recombinant, native, Na$_v$1.7 alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% $CO_2$, 95% humidity, in preparation for the assay. For counter-screens of other voltage-gated sodium channels, the procedure is very similar, though optimal densities of cells, media and subsequent assay components can be fine-tuned for the particular cell line or isoform.

The next day, at the start of the assay, the media is flicked from the cells and the wells washed once with 50 μL/well assay buffer (1× Hank's balanced salt solution without sodium bicarbonate or phenol red, 20 mM Hepes, pH 7.3). Membrane potential dye is then added to each well of the 96-well plate (50 μL/well), from a freshly diluted sample of the stock (now at 4× concentration) in the assay buffer. The cells are incubated at 37° C. in the dark for 30-60 min. before their fluorescence is measured.

In this standard membrane potential assay, the 96-well plate containing dye-loaded cells is then loaded directly onto the plate reader without aspirating the dye solution and without any further washing of the cells. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first, 50 μL/well from a 4× stock plate) and then the channel activators (later, 100 μL/well from a 2× stock solution) in this kinetic assay are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec.; and finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well, with the test articles present in standard amounts (e.g. 10 μM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

Electrophysiology Assay

Cells:

The $hNa_v1.7$ expressing HEK-293 cells were plated on 35 mm culture dishes pre-coated with poly-D-lysine in standard DMEM culture media (Mediatech, Inc., Herndon, Va.) and incubated in a 5% $CO_2$ incubator at 37° C. Cultured cells were used approximately 12-48 h after plating.

Electrophysiology:

On the day of experimentation, the 35 mm dish was placed on the stage of an inverted microscope equipped with a perfusion system that continuously perfuses the culture dish with fresh recording media. A gravity driven superfusion system was used to apply test solutions directly to the cell under evaluation. This system consists of an array of glass pipette glass connected to a motorized horizontal translator. The outlet of the shooter was positioned approximately 100 μm from the cell of interest.

Whole cell currents were recorded using the whole-cell patch clamp configuration using an Axopatch 200B amplifier (Axon Instruments, Foster City Calif.), 1322A A/D converter (Axon Instruments) and pClamp software (v. 8; Axon Instruments) and stored on a personal computer. Gigaseals were formed and the whole-cell configuration was established in voltage clamp mode, and membrane currents generated by $hNa_v1.7$ were recorded in gap-free mode. Borosilicate glass pipettes have resistance values between 1.5 and 2.0 MΩ when filled with pipette solution and series resistance (<5 MΩ) was compensated 75-80%. Signals were sampled at 50 kHz and low pass filtered at 3 kHz.

Voltage Protocols:

After establishing the whole-cell configuration in voltage clamp mode, two voltage protocols were run to establish: 1) the holding potential; and 2) the test potential for each cell.

Resting Block:

To determine a membrane potential at which the majority of channels are in the resting state, a standard steady-state inactivation (SSIN) protocol was run using 100 ms prepulses×10 mV depolarizing steps. The holding potential for testing resting block ($Vh_1$) was 20 mV more hyperpolarized than the first potential where inactivation is observed with the inactivation protocol.

From this holding potential a standard I-V protocol was run to determine the potential at which the maximal current (Imax) was elicited. This potential was the test potential (Vt).

The compound testing protocol was a series of 10 ms depolarizations from the $Vh_1$ (determined from the SSIN) to the Vt (determined from the I-V protocol) repeated every 10-15 seconds. After a stable baseline was established, a high concentration of a test compound (highest concentration solubility permits or that which provides ~50% block) was applied and block of the current assessed. Washout of the compound was attempted by superfusing with control solution once steady-state block was observed. The fractional response was calculated as follows:

$FR=I$(after drug)$/I$(control), where I is the peak current amplitude and was used for estimating resting block dissociation constant, $K_r$:

$K_r=[\text{drug}]*\{FR/(1-FR)\}$, where [drug] is the concentration of a drug.

Block of Inactivated Channels:

To assess the block of inactivated channels the holding potential was depolarized such that 20-50% of the current amplitude was reduced when pulsed to the same Vt as above. The magnitude of this depolarization depends upon the initial current amplitude and the rate of current loss due to slow inactivation. This was the second holding potential ($Vh_2$). The current reduction was recorded to determine the fraction of available channels at this potential (h).

$h=I@Vh_2/I$max.

At this membrane voltage a proportion of channels are in the inactivated state, and thus inhibition by a blocker includes interaction with both resting and inactivated channels.

To determine the potency of the test compound on inactivated channels, a series of currents were elicited by 10 ms voltage steps from $Vh_2$ to $V_t$ every 10-15 seconds. After establishing a stable baseline, the low concentration of the compound was applied. Multiple cumulative concentrations may have to be applied to identify a concentration that will block between 40-60% of the current. Washout was attempted to re-establish baseline. Fractional responses were measured with respect to a projected baseline to determine $K_{app}$.

$K_{app}=[\text{drug}]*\{FR/(1-FR)\}$, where [drug] is the concentration of a drug.

This $K_{app}$ value, along with the calculated $K_r$ and h values, were used to calculate the affinity of the compound for the inactivated channels ($K_i$) using the following equation:

$K_i=(1-h)/((1/K_{app})-(h/K_r))$.

Solutions and Chemicals:

For electrophysiological recordings the external solution was either standard, DMEM supplemented with 10 mM HEPES (pH adjusted to 7.34 with NaOH and the osmolarity adjusted to 320) or Tyrodes salt solution (Sigma, USA) supplemented with 10 mM HEPES (pH adjusted to 7.4 with NaOH; osmolarity=320). The internal pipette solution contained (in mM): NaCl (10), CsF (140), $CaCl_2$ (1), $MgCl_2$ (5), EGTA (11), HEPES (10: pH 7.4, 305 mOsm). Compounds were prepared first as a series of stock solutions in DMSO and then dissolved in external solution; DMSO content in final dilutions did not exceed 0.3%. At this concentration, DMSO did not affect sodium currents. Vehicle solution used to establish base line was also contacting 0.3% DMSO.

Data Analysis:

Data was analyzed off-line using Clampfit software (pClamp, v. 8; Axon Instruments) and graphed using GraphPad Prizm (v. 4.0 or higher) software.

In Vivo Assay for Pain

Compounds of the Invention can be tested for their antinociceptive activity in the formalin model as described in Hunskaar et al., *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period, mice are weighed and given either the compound of interest administered i.p. or p.o., or the appropriate volume of vehicle (for example, 10% Tween-80 or 0.9% saline, and other pharmaceutically acceptable vehicles) as control. Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value <0.05 is considered significant. Compounds are considered to be efficacious for treating acute and chronic pain if they have activity in blocking both the early and second phase of formalin-induced paw-licking activity.

In Vivo Assays for Inflammatory or Neuropathic Pain

Test Animals:

Each experiment uses rats weighing between 200-260 g at the start of the experiment. The rats are group-housed and have free access to food and water at all times, except prior to oral administration of a test compound when food is removed for 16 h before dosing. A control group acts as a comparison to rats treated with a Compound of the Invention. The control group is administered the carrier as used for the test compound. The volume of carrier administered to the control group is the same as the volume of carrier and test compound administered to the test group.

Inflammatory Pain:

To assess the actions of Compounds of the Invention on the treatment of inflammatory pain the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (Bartho et al., *Naunyn-Schmiedeberg's Archives of Pharmacol.* 342:666-670 (1990)). The left hind paw of each animal is administered a 50 µL intraplantar injection of 50% FCA. 24 hour post injection, the animal is assessed for response to noxious mechanical stimuli by determining the paw withdrawal threshold (PWT), or to noxious thermal stimuli by determining the paw withdrawal latency (PWL), as described below. Rats are then administered a single injection of either a test compound or 30 mg/Kg of a positive control compound (e.g., indomethacin). Responses to noxious mechanical or thermal stimuli are then determined 1, 3, 5 and 24 hours post administration (admin). Percentage reversal of hyperalgesia for each animal is defined as:

$$\% \text{ reversal} = \frac{\left[\begin{array}{l}(\text{post administration } PWT \text{ or } PWL) - \\ (\text{pre-administration } PWT \text{ or } PWL)\end{array}\right]}{\left[\begin{array}{l}(\text{baseline } PWT \text{ or } PWL) - \\ (\text{pre-administration } PWT \text{ or } PWL)\end{array}\right]} \times 100$$

Neuropathic Pain:

To assess the actions of the test compounds for the treatment of neuropathic pain the Seltzer model or the Chung model can be used.

In the Seltzer model, the partial sciatic nerve ligation model of neuropathic pain is used to produce neuropathic hyperalgesia in rats (Seltzer et al., *Pain* 43:205-218 (1990)). Partial ligation of the left sciatic nerve is performed under isoflurane/$O_2$ inhalation anesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{ reversal} = \frac{\left[\begin{array}{l}(\text{post administration } PWT) - \\ (\text{pre-administration } PWT)\end{array}\right]}{\left[\begin{array}{l}(\text{baseline } PWT) - \\ (\text{pre-administration } PWT)\end{array}\right]} \times 100$$

In the Chung model, the spinal nerve ligation (SNL) model of neuropathic pain is used to produce mechanical hyperalgesia, thermal hyperalgesia, and tactile allodynia in rats. Surgery is performed under isoflurane/$O_2$ inhalation anesthesia. Following induction of anesthesia a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is (are) isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is (are) not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Compound of the Invention for the left rear paw of the animal. The animals can also be assessed for response to noxious thermal stimuli or for tactile allodynia, as described below. The Chung model for neuropathic pain is described in Kim et al., *Pain* 50(3):355-363 (1992).

Tactile Allodynia:

Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia:

Representative Compounds of the Invention were tested in the SNL-induced mechanical hyperalgesia model in rats. Sensitivity to noxious mechanical stimuli was measured in animals using the paw pressure test to assess mechanical hyperalgesia. In rats, hind paw withdrawal thresholds ("PWT"), measured in grams, in response to a noxious mechanical stimulus were determined using an analgesymeter (Model 7200, commercially available from Ugo Basile of Italy), as described in Stein (*Biochemistry & Behavior* 31: 451-455 (1988)). The rat's paw was placed on a small platform, and weight was applied in a graded manner up to a maximum of 250 grams. The endpoint was taken as the weight at which the paw was completely withdrawn. PWT was determined once for each rat at each time point. PWT can be measured only in the injured paw, or in both the injured and non-injured paw. Rats were tested prior to surgery to determine a baseline, or normal, PWT. Rats were tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

Compound Example Nos. 84, 98, and 99 reduced SNL-induced mechanical hyperalgesia in rats when dosed orally at 100 mg/kg (vehicle: 0.5% methyl cellulose) one hour before testing.

In Vivo Assay for Anticonvulsant Activity

Compounds of the Invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

Pharmaceutical Compositions

Compounds of the Invention can be administered to a mammal in the form of a raw chemical without any other components present. Compounds of the Invention can also be administered to a mammal as part of a pharmaceutical composition containing the compound combined with a suitable pharmaceutically acceptable carrier. Such a carrier can be selected from pharmaceutically acceptable excipients and auxiliaries.

Pharmaceutical compositions within the scope of the present disclosure include all compositions where a Compound of the Invention is combined with one or more pharmaceutically acceptable carriers. In one embodiment, the Compound of the Invention is present in the composition in an amount that is effective to achieve its intended therapeutic purpose. While individual needs may vary, a determination of optimal ranges of effective amounts of each compound is within the skill of the art. Typically, a Compound of the Invention can be administered to a mammal, e.g., a human, orally at a dose of from about 0.0025 to about 1500 mg per kg body weight of the mammal, or an equivalent amount of a pharmaceutically acceptable salt, prodrug, or solvate thereof, per day to treat the particular disorder. A useful oral dose of a Compound of the Invention administered to a mammal is from about 0.0025 to about 50 mg per kg body weight of the mammal, or an equivalent amount of the pharmaceutically acceptable salt, prodrug, or solvate thereof. For intramuscular injection, the dose is typically about one-half of the oral dose.

A unit oral dose may comprise from about 0.01 mg to about 1 g of the Compound of the Invention, e.g., about 0.01 mg to about 500 mg, about 0.01 mg to about 250 mg, about 0.01 mg to about 100 mg, 0.01 mg to about 50 mg, e.g., about 0.1 mg to about 10 mg, of the compound. The unit dose can be administered one or more times daily, e.g., as one or more tablets or capsules, each containing from about 0.01 mg to about 1 g of the compound, or an equivalent amount of a pharmaceutically acceptable salt, prodrug or solvate thereof.

A pharmaceutical composition of the present disclosure can be administered to any animal that may experience the beneficial effects of a Compound of the Invention. Foremost among such animals are mammals, e.g., humans and companion animals, although the disclosure is not intended to be so limited.

A pharmaceutical composition of the present disclosure can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a pharmaceutical composition of the present disclosure can be administered orally and is formulated into tablets, dragees, capsules or an oral liquid preparation. In one embodiment, the oral formulation comprises extruded multiparticulates comprising the Compound of the Invention.

Alternatively, a pharmaceutical composition of the present disclosure can be administered rectally, and is formulated in suppositories.

Alternatively, a pharmaceutical composition of the present disclosure can be administered by injection.

Alternatively, a pharmaceutical composition of the present disclosure can be administered transdermally.

Alternatively, a pharmaceutical composition of the present disclosure can be administered by inhalation or by intranasal or transmucosal administration.

Alternatively, a pharmaceutical composition of the present disclosure can be administered by the intravaginal route.

A pharmaceutical composition of the present disclosure can contain from about 0.01 to 99 percent by weight, and preferably from about 0.25 to 75 percent by weight, of active compound(s).

A method of the present disclosure, such as a method for treating a disorder responsive to the blockade of sodium channels in an animal in need thereof, can further comprise administering a second therapeutic agent to the animal in combination with a Compound of the Invention. In one embodiment, the other therapeutic agent is administered in an effective amount.

Effective amounts of the other therapeutic agents are known to those skilled in the art. However, it is well within the skilled artisan's purview to determine the other therapeutic agent's optimal effective-amount range.

Compounds of the Invention (i.e., the first therapeutic agent) and the second therapeutic agent can act additively or, in one embodiment, synergistically. Alternatively, the second therapeutic agent can be used to treat a disorder or condition that is different from the disorder or condition for which the first therapeutic agent is being administered, and which disorder or condition may or may not be a condition or disorder as defined herein. In one embodiment, a Compound of the Invention is administered concurrently with a second therapeutic agent; for example, a single composition comprising both an effective amount of a Compound of the Invention and an effective amount of the second therapeutic agent can be administered. Accordingly, the present disclosure further provides a pharmaceutical composition comprising a combination of a Compound of the Invention, the second therapeutic agent, and a pharmaceutically acceptable carrier. Alternatively, a first pharmaceutical composition comprising an effective amount of a Compound of the Invention and a second pharmaceutical composition comprising an effective amount of the second therapeutic agent can be concurrently administered. In another embodiment, an effective amount of a Compound of the Invention is administered prior or subsequent to administration of an effective amount of the second therapeutic agent. In this embodiment, the Compound of the Invention is administered while the second therapeutic agent exerts its therapeutic effect, or the second therapeutic agent is administered while the Compound of the Invention exerts its therapeutic effect for treating a disorder or condition.

The second therapeutic agent can be an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol. II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox H inhibitors include, but are not limited to, rofecoxib, and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating stroke include, but are not limited to, anticoagulants such as heparin, agents that break up clots such as streptokinase or tissue plasminogen activator, agents that reduce swelling such as mannitol or corticosteroids, and acetylsalicylic acid.

Examples of useful therapeutic agents for treating a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating ALS include, but are not limited to, baclofen, neurotrophic factors, riluzole, tizanidine, benzodiazepines such as clonazepan and dantrolene.

Examples of useful therapeutic agents for treating cognitive disorders include, but are not limited to, agents for treating dementia such as tacrine; donepezil; ibuprofen; antipsychotic drugs such as thioridazine and haloperidol; and antidepressant drugs such as those given below.

Examples of useful therapeutic agents for treating a migraine include, but are not limited to, sumatriptan; methysergide; ergotamine; caffeine; and beta-blockers such as propranolol, verapamil, and divalproex.

Examples of useful therapeutic agents for treating vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating dyskinesia include, but are not limited to, reserpine and tetrabenazine.

Examples of useful therapeutic agents for treating depression include, but are not limited to, tricyclic antidepressants such as amitryptyline, amoxapine, bupropion, clomipramine, desipramine, doxepin, imipramine, maprotiline, nefazodone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

A pharmaceutical composition of the present disclosure is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

The following examples are illustrative, but not limiting, of the compounds, compositions, and methods of the present disclosure. Suitable modifications and adaptations of the variety of conditions and parameters normally encountered in clinical therapy and which are obvious to those skilled in the art in view of this disclosure are within the spirit and scope of the disclosure.

EXAMPLES

Example 1

Preparation of 2-fluoro-6-(4-(4,4,5,5-tetramethyl-1,3,2-dioxaborolan-2-yl)phenoxy)pyridine

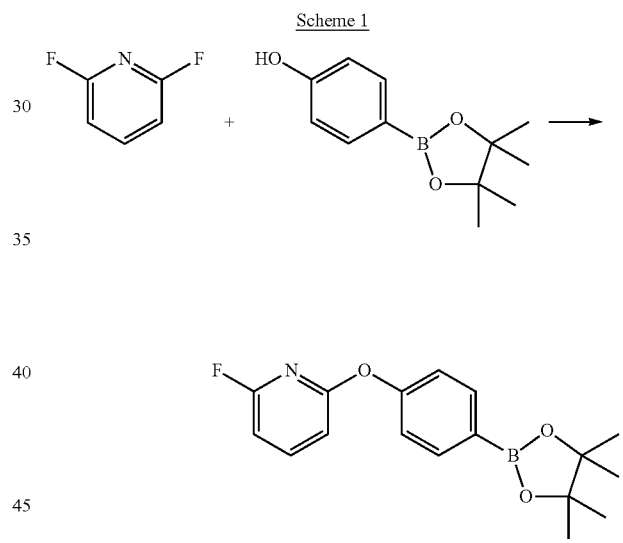

A sealed pressure glass vessel containing the mixture of 2,6-difluoropyridine (2.1 g, 18 mmol, Aldrich), 4-(4,4,5,5-tetramethyl-1,3,2-dixoaborolan-2-yl)phenol (4 g, 18 mmol), and $Cs_2CO_3$ (7 g, 21 mmol, Aldrich) in DMF (25 mL) was heated at 80° C. for 4 h. After cooling to room temperature, the mixture was diluted with brine (200 mL) and extracted with EtOAc (2×200 mL). The combined organic layers were dried over $Na_2SO_4$, filtered, and concentrated on a rotary evaporator. The residue was purified via silica gel chromatography (0-10% EtOAc in hexane) to give 2-fluoro-6-(4-(4,4,5,5-tetramethyl-1,3,2-dioxaborolan-2-yl)phenoxy)pyridine as viscous liquid (3.6 g, 63%). $^1$H NMR (400 MHz, $CDCl_3$): 7.87 (2H, d, J=8.8 Hz), 7.76 (1H, q, J=7.6 Hz), 7.15 (2H, d, J=8.8 Hz), 6.73 (1H, dd, J=1.6, 8 Hz), 6.63 (1H, dd, J=2.8, 8 Hz), 1.37 (12H, s). LC/MS: m/z=316 $[M+H]^+$. Unless otherwise indicated all $^1$H NMR chemical shifts reported herein are denoted by the delta (δ) scale.

The following dioxaborolanes where prepared in a similar manner:

5-fluoro-2-(4-(4,4,5,5-tetramethyl-1,3,2-dioxaborolan-2-yl)phenoxy)pyridine

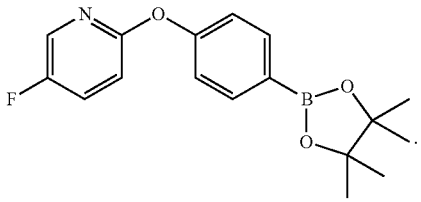 [SMILES: CC1(C)OB(c2ccc(Oc3ccc(F)cn3)cc2)OC1(C)C]

¹H NMR (400 MHz, CDCl₃): 8.02 (1H, m), 7.85 (2H, m), 7.42 (1H, m), 7.1 (2H, m), 6.9 (1H, m), 1.32 (12H, s). LC/MS: m/z=316 [M+H]⁺.

5-chloro-2-(4-(4,4,5,5-tetramethyl-1,3,2-dioxaborolan-2-yl)phenoxy)pyridine

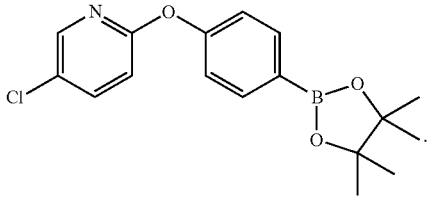 [SMILES: CC1(C)OB(c2ccc(Oc3ccc(Cl)cn3)cc2)OC1(C)C]

¹H NMR (400 MHz, CDCl₃): 8.06 (1H, d, J=2.8 Hz), 7.78 (2H, d, J=8.4 Hz), 7.56 (1H, dd, J=2.8, 8.8 Hz), 7.04 (2H, d, J=8.4 Hz), 6.81 (1H, d, J=8.8 Hz), 1.27 (12H, s). LC/MS: m/z=322 [M+H]⁺.

2-(4-(4,4,5,5-tetramethyl-1,3,2-dioxaborolan-2-yl)phenoxy)-6-(trifluoromethyl)pyridine

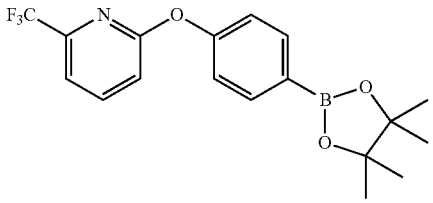 [SMILES: CC1(C)OB(c2ccc(Oc3cccc(C(F)(F)F)n3)cc2)OC1(C)C]

¹H NMR (400 MHz, CDCl₃): 7.87 (2H, d, J=8.8 Hz), 7.85 (1H, q, J=7.6 Hz), 7.41 (1H, d, J=7.6 Hz), 7.19 (2H, m), 7.05 (1H, d, J=8 Hz), 1.38 (12H, s). LC/MS: m/z=366 [M+H]⁺.

2-(4-(4,4,5,5-tetramethyl-1,3,2-dioxaborolan-2-yl)phenoxy)-4-(trifluoromethyl)pyridine

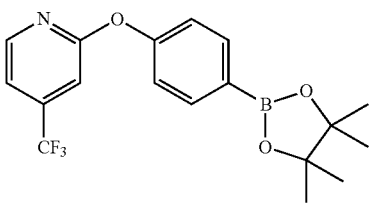 [SMILES: CC1(C)OB(c2ccc(Oc3cc(C(F)(F)F)ccn3)cc2)OC1(C)C]

¹H NMR (400 MHz, CDCl₃): 8.35 (1H, d, J=5.2 Hz), 7.90 (2H, m), 7.22 (1H, m), 7.16 (3H, m), 1.37 (12H, s). LC/MS: m/z=366 [M+H]⁺.

2-(4-(4,4,5,5-tetramethyl-1,3,2-dioxaborolan-2-yl)phenoxy)-3-(trifluoromethyl)pyridine

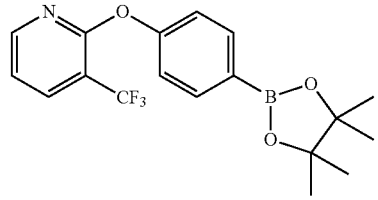 [SMILES: CC1(C)OB(c2ccc(Oc3ncccc3C(F)(F)F)cc2)OC1(C)C]

¹H NMR (400 MHz, CDCl₃): 8.30 (1H, d, J=4.8 Hz), 8.01 (1H, d, J=8 Hz), 7.90 (2H, d, J=8.4 Hz), 7.18 (2H, d, J=8.4 Hz), 7.11 (1H, dd, J=4.8, 7.2 Hz), 1.37 (12H, s). LC/MS: m/z=366 [M+H]⁺.

5-(4-(4,4,5,5-tetramethyl-1,3,2-dioxaborolan-2-yl)phenoxy)-2-(trifluoromethyl)pyridine

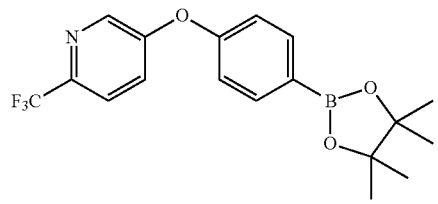 [SMILES: CC1(C)OB(c2ccc(Oc3ccc(C(F)(F)F)nc3)cc2)OC1(C)C]

¹H NMR (400 MHz, CDCl₃): 8.51 (1H, d, J=2.4 Hz), 7.88 (2H, d, J=8.8 Hz), 7.65 (1H, d, J=8.4 Hz), 7.37 (1H, dd, J=2.8, 8.8 Hz), 7.08 (2H, d, J=8.4 Hz), 1.38 (12H, s). LC/MS: m/z=388 [M+H]⁺.

Example 2

Preparation of (S)-6-((1-amino-1-oxopropan-2-yl)amino)-2-(4-(4-fluorophenoxy)phenyl)pyrimidine-4-carboxamide (Cpd No. 1)

Scheme 2

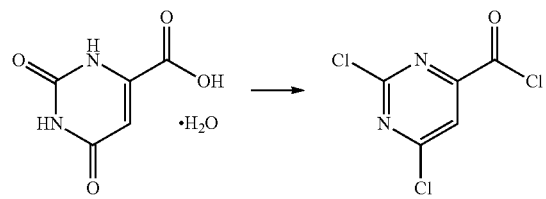

2,6-dichloropyrimidine-4-carbonyl chloride

A mixture of orotic acid mono hydrate (34.828 g, 200.0 mmol), phosphorus oxychloride (100 mL, 1092 mmol) and 20 drops of DMF were heated at 110° C. overnight. After cooling, the dark mixture was diluted with 500 mL hexanes and vigorously stirred. The hexane layer was decanted and quickly washed with water (1×100 mL) then brine (1×100 mL) and dried over MgSO₄. The organics were filtered and carefully evaporated in vacuo to give 2,6-dichloropyrimidine-4-carbonyl chloride as a light yellow liquid (26.13 g, 123.6 mmol, 62% yield). ¹H NMR (400 MHz, CDCl₃): 7.93 (1H, s).

Scheme 3

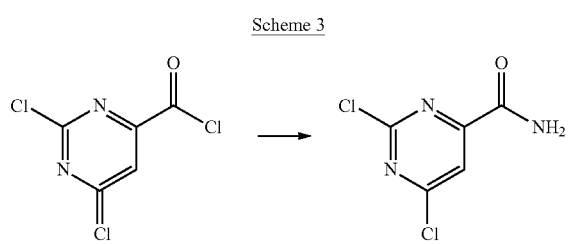

2,6-dichloropyrimidine-4-carboxamide

To a solution of 2,6-dichloropyrimidine-4-carbonyl chloride (26.13 g, 123.6 mmol) in Et$_2$O (500 mL) was added a mixture of 0.5M ammonia in dioxane (250 mL, 125 mmol) and iPr$_2$NEt (22 mL, 126 mmol) dropwise over approximately 50 minutes. After stirring overnight the reaction was concentrated in vacuo to a residue and chromatographed over silica gel with 10-50% EtOAc in hexanes. The product fractions were evaporated in vacuo, and the resulting solid residue triturated with 10 mL 10% EtOAc/hexanes and filtered to give 2,6-dichloropyrimidine-4-carboxamide as an orange crystalline solid (9.743 g, 50.74 mmol, 41% yield). LC/MS: m/z=192.2 [M+H]$^+$, $^1$H NMR (400 MHz, DMSO-d$_6$): 8.40 (1H, br s), 8.16 (1H, br s), 8.10 (1H, s).

Scheme 4

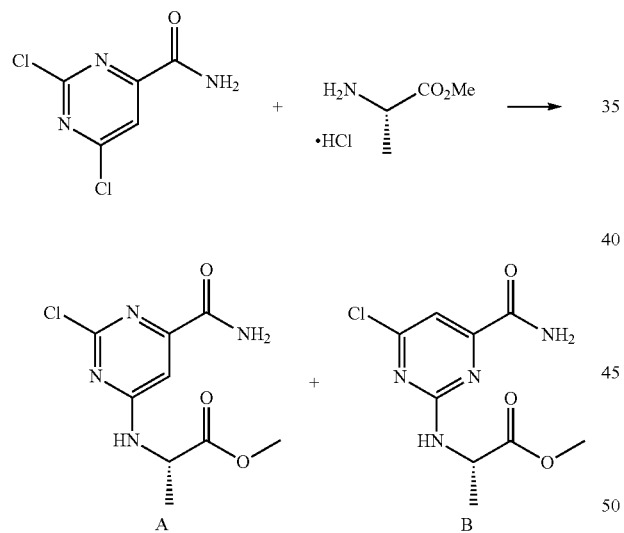

(S)-methyl 2-((6-carbamoyl-2-chloropyrimidin-4-yl)amino)propanoate (A) and (S)-methyl 2((4-carbamoyl-6-chloropyrimidin-2-yl)amino)propanoate (B)

To a mixture of 2,6-dichloropyrimidine-4-carboxamide (4.800 g, 25.00 mmol) in acetonitrile (100 mL) was added (S)-methyl 2-aminopropanoate hydrochloride (3.565 g, 25.54 mmol) and iPr$_2$NEt (9.60 mL, 55.11 mmol). The mixture was heated at 50° C. overnight then concentrated in vacuo. The residue was chromatographed over silica gel with 20-60% acetone in hexanes. Two isomers were obtained from the chromatography. The first isomer to elute was (S)-methyl 2-((6-carbamoyl-2-chloropyrimidin-4-yl)amino)propanoate (A) and the second to elute was (S)-methyl 2-((4-carbamoyl-6-chloropyrimidin-2-yl)amino)propanoate (B). Separately, the appropriate product fractions were evaporated in vacuo to give (S)-methyl 2-((6-carbamoyl-2-chloropyrimidin-4-yl)amino)propanoate (A) as a pale tan powder (5.133 g, 19.84 mmol, 79% yield). LC/MS: m/z=259.2 [M+H]$^+$ and (S)-methyl 2-((4-carbamoyl-6-chloropyrimidin-2-yl)amino)propanoate (B) as a tan powder (0.652 g, 2.52 mmol, 10% yield). LC/MS: m/z=259.2 [M+H]$^+$.

Scheme 5

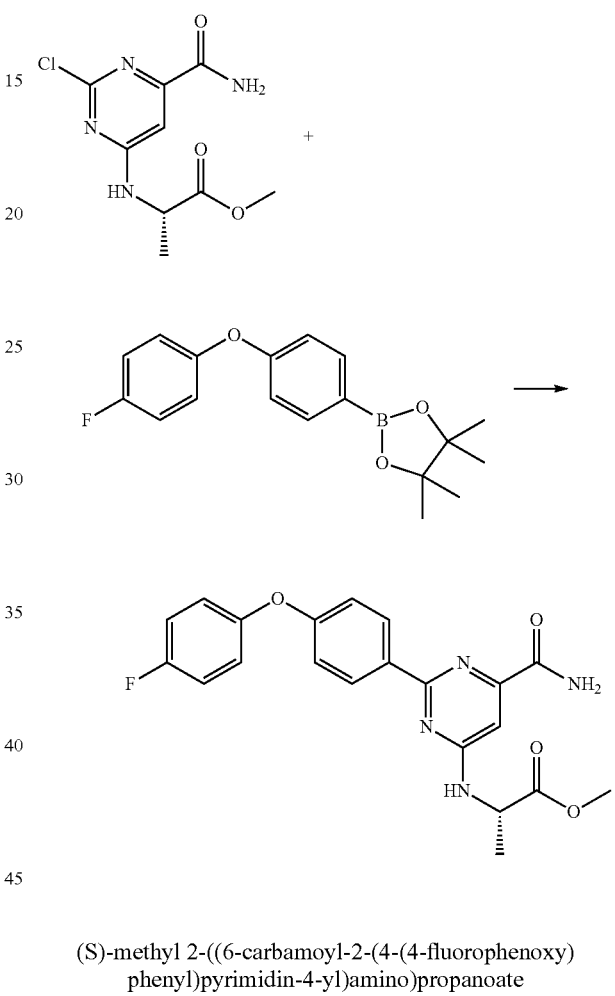

(S)-methyl 2-((6-carbamoyl-2-(4-(4-fluorophenoxy)phenyl)pyrimidin-4-yl)amino)propanoate To a suspension of (S)-methyl 2-((6-carbamoyl-2-chloropyrimidin-4-yl)amino)propanoate (5.133 g, 19.84 mmol) in dioxane (100 mL) was added 2-(4-(4-fluorophenoxy)phenyl)-4,4,5,5-tetramethyl-1,3,2-dioxaborolane (6.858 g, 21.83 mmol), 2M aqueous Na$_2$CO$_3$ (19.9 mL, 39.8 mmol) and PdCl$_2$(dppf) (0.809 g, 0.99 mmol). The reaction vessel was flushed with argon, sealed and heated at 100° C. overnight. After cooling, the reaction mixture was diluted with 500 mL EtOAc and washed with brine (3×100 mL). The organic layer was dried over Na$_2$SO$_4$, filtered and chromatographed over silica gel with 20-60% acetone in hexanes. The product fractions were isolated and evaporated in vacuo to give the product (S)-methyl 2-((6-carbamoyl-2-(4-(4-fluorophenoxy)phenyl)pyrimidin-4-yl)amino)propanoate as a yellow-orange solid (4.128 g, 10.05 mmol, 51% yield). LC/MS: m/z=411.2 [M+H]$^+$.

Scheme 6

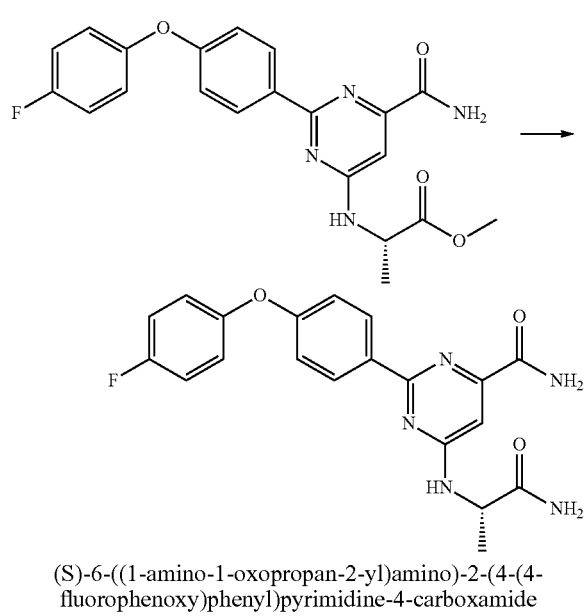

(S)-6-((1-amino-1-oxopropan-2-yl)amino)-2-(4-(4-fluorophenoxy)phenyl)pyrimidine-4-carboxamide A solution of (S)-methyl 2-((6-carbamoyl-2-(4-(4-fluorophenoxy)phenyl)pyrimidin-4-yl)amino)propanoate (4.128 g, 10.05 mmol) in 7M ammonia in methanol (100 mL, 700 mmol) was heated in a sealed tube for 3 days at 50° C. After cooling, the reaction mixture was evaporated in vacuo. The residue was triturated with 150 mL methanol and filtered to obtain the first batch of product. The filtrate was evaporated and chromatographed over silica gel with 50-100% acetone in hexanes. The product fractions were isolated and evaporated in vacuo. This residue was triturated with 40 mL methanol and filtered to give the second batch of product. The first and second batches of product were combined and triturated once more with 10 mL methanol, filtered and dried under vacuum at 50° C. to give (S)-6-((1-amino-1-oxopropan-2-yl)amino)-2-(4-(4-fluorophenoxy)phenyl)pyrimidine-4-carboxamide (Example 1) as a pale tan-gray powder (2.620 g, 6.63 mmol, 66% yield). LC/MS: m/z=396.2 [M+H]$^+$, $^1$H NMR (400 MHz, DMSO-d$_6$): 8.54 (2H, d, J=8.8 Hz), 8.27 (1H, s), 7.95 (1H, d, J=6.4 Hz), 7.74 (1H, s), 7.53 (1H, s), 7.31-7.24 (2H, m), 7.19-7.13 (2H, m), 7.08 (1H, s), 7.04-6.97 (3H, m), 4.60-4.51 (1H, m), 1.36 (3H, d, J=7.0 Hz).

Example 3

Preparation of 6-(2-carbamoylpiperazin-1-yl)-2-(4-(4-fluorophenoxy)phenyl)pyrimidine-4-carboxamide (Cpd No. 27)

Scheme 7

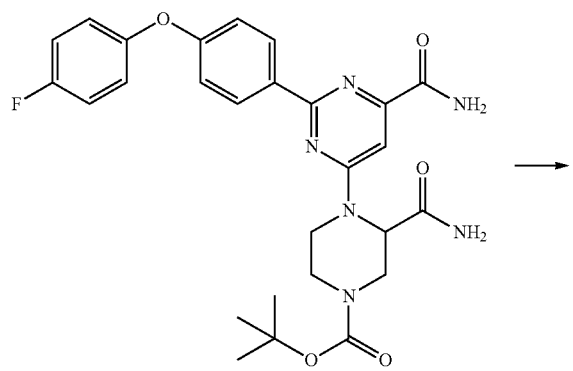

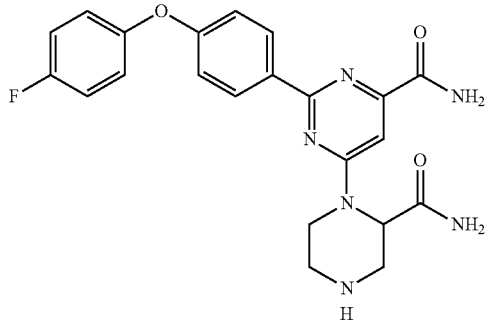

As To a milky suspension of the tert-butyl 3-carbamoyl-4-(6-carbamoyl-2-(4-(4-fluorophenoxy)phenyl)pyrimidin-4-yl)piperazine-1-carboxylate (0.363 g, 0.677 mmol) in dioxane (10 mL) was added 4M HCl in dioxane (2 mL, 8 mmol). After stirring for 3 days the reaction was concentrated in vacuo. The solid residue was partitioned between 10 mL EtOAc and 2 mL 2M aqueous Na$_2$CO$_3$ solution. The mixture was diluted with 25 mL EtOAc, 8 mL water and 25 mL brine. The organic layer was separated and the aqueous layer was extracted four times with 25 mL EtOAc. The combined organic layers were dried over MgSO4, filtered, and evaporated in vacuo. The residue was triturated with 2 mL 1:1 EtOAc/hexanes, filtered, and rinsed once with 2 mL 1:1 EtOAc/hexanes. The solid was dried under vacuum at 40° C. to give the product 6-(2-carbamoylpiperazin-1-yl)-2-(4-(4-fluorophenoxy)phenyl)pyrimidine-4-carboxamide as a pale tan powder (0.212 g, 0.486 mmol, 72% yield).

$^1$H NMR (400 MHz, CD$_3$OD): 8.50 (2H, d, J=9.0 Hz), 7.36 (1H, s), 7.19-7.08 (4H, m), 7.03 (2H, d, J=9.0 Hz), 5.32 (1H, br s), 4.14 (1H, br s), 3.62-3.47 (2H, m), 3.19-3.12 (1H, m), 3.08 (1H, dd, J=13.4 Hz, 5.0 Hz), 2.87 (1H, dt, J=12.7 Hz, 3.5 Hz). LC/MS: m/z=437.1 [M+H]$^+$.

Example 4

Preparation of (S)-2-((6-carbamoyl-2-(4-(4-fluorophenoxy)phenyl)pyrimidin-4-yl)amino)propanoic acid (Cpd No. 28)

Scheme 8

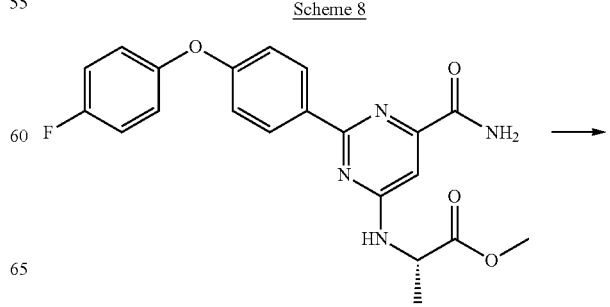

113
-continued

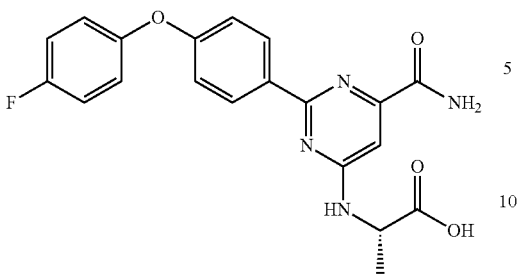

To a solution of the (S)-methyl 2-((6-carbamoyl-2-(4-(4-fluorophenoxy)phenyl)pyrimidin-4-yl)amino)propanoate (0.123 g, 0.300 mmol) in 5:1 THF/water (5 mL) was added LiOH.H$_2$O (0.025 g, 0.60 mmol). After stirring 3 days, the reaction was quenched with 1N aqueous HCl (0.60 mL). The mixture was evaporated in vacuo then chromatographed using reverse-phase HPLC with a 40-100% acetonitrile in water (+0.1% TFA) gradient. The product fractions were pooled and concentrated to give a solid suspension. After cooling, the solid precipitate was filtered, rinsed with water and dried under vacuum at 50° C. to give (S)-2-((6-carbamoyl-2-(4-(4-fluorophenoxy)phenyl)pyrimidin-4-yl)amino)propanoic acid as a white powder (0.049 g, 0.12 mmol, 41% yield). $^1$H NMR (400 MHz, DMSO-d$_6$): 12.57 (1H, s), 8.50 (2H, d, J=8.8 Hz), 8.29 (1H, s), 8.12 (1H, d, J=6.1 Hz), 7.76 (1H, s), 7.31-7.24 (2H, m), 7.18-7.12 (2H, m), 7.07 (1H, s), 7.03 (2H, d, J=8.8 Hz), 4.56 (1H, m), 1.44 (3H, d, J=7.5 Hz). LC/MS: m/z=397.1 [M+H]$^+$.

Example 5

Preparation of (S)-6-(2-carboxypyrrolidin-1-yl)-2-(4-(4-fluorophenoxy)phenyl)pyrimidine-4-carboxylic acid (A) (Cpd No. 29) and (S)-1-(6-carbamoyl-2-(4-(4-fluorophenoxy)phenyl)pyrimidin-4-yl)pyrrolidine-2-carboxylic acid (B) (Cpd No. 30)

Scheme 9

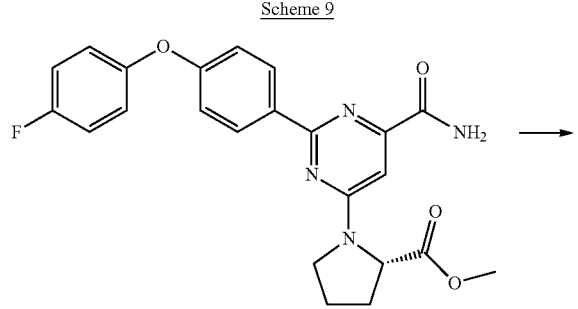

114
-continued

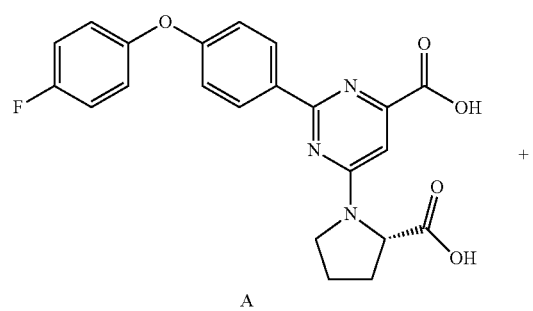

A

B

To a mixture of the (S)-methyl 1-(6-carbamoyl-2-(4-(4-fluorophenoxy)phenyl)pyrimidin-4-yl)pyrrolidine-2-carboxylate (0.439 g, 1.01 mmol) in 5:1 THF/water (10 mL) was added LiOH.H$_2$O (0.084 g, 2.00 mmol). After stirring 3 days the reaction was quenched with 1N aqueous HCl (2.00 mL). The mixture was evaporated in vacuo then chromatographed using reverse-phase HPCL with a 40-100% acetonitrile in water (+0.1% TFA) gradient. The first product to elute was the (S)-6-(2-carboxypyrrolidin-1-yl)-2-(4-(4-fluorophenoxy)phenyl)pyrimidine-4-carboxylic acid (A) followed by the (S)-1-(6-carbamoyl-2-(4-(4-fluorophenoxy)phenyl)pyrimidin-4-yl)pyrrolidine-2-carboxylic acid (B). Separately, product fractions for each product were pooled and concentrated to give solid suspensions. The solid precipitates were filtered, rinsed with water, and dried under vacuum at 50° C. to give (S)-6-(2-carboxypyrrolidin-1-yl)-2-(4-(4-fluorophenoxy)phenyl)pyrimidine-4-carboxylic acid (A) as a light tan powder (0.170 g, 0.402 mmol, 40% yield) and (S)-1-(6-carbamoyl-2-(4-(4-fluorophenoxy)phenyl)pyrimidin-4-yl)pyrrolidine-2-carboxylic acid (B) as an off-white powder (0.125 g, 0.296 g, 29% yield). (S)-6-(2-carboxypyrrolidin-1-yl)-2-(4-(4-fluorophenoxy)phenyl)pyrimidine-4-carboxylic acid (A): $^1$H NMR (400 MHz, DMSO-d$_6$): Exists as a ~80:20 ratio of rotamers: 13.71-12.30 (2H, br m), 8.43 (0.4H, d, J=8.8 Hz), 8.37 (1.6H, d, J=8.8 Hz), 7.32-7.24 (2H, m), 7.20-7.13 (2H, m), 7.09-6.99 (2.8H, m), 6.79 (0.2H, s), 4.62-4.55 (1H, m), 3.87-3.48 (2H, m), 2.38-2.29 (1H, m), 2.24-1.98 (3H, m). LC/MS: m/z=424.1 [M+H]$^+$. (S)-1-(6-carbamoyl-2-(4-(4-fluorophenoxy)phenyl)pyrimidin-4-yl)pyrrolidine-2-carboxylic acid (B): $^1$H NMR (400 MHz, DMSO-d$_6$): Exists as a 80:20 ratio of rotamers: 13.05 (0.2H, br s), 12.60 (0.8H, br s), 8.57 (0.4H, d, J=8.8 Hz), 8.51 (1.6H, d, J=8.8 Hz), 8.35 (1H, s), 7.81 (1H, s), 7.32-7.24 (2H, m), 7.20-7.13 (2H, m), 7.08-6.97 (2.8H, m), 6.79 (0.2H, s), 4.62-4.52 (1H, m), 3.86-3.72 (0.4H, m), 3.66-3.55 (1.6H, m), 2.40-2.28 (1H, m), 2.22-1.95 (3H, m). LC/MS: m/z=423.1 [M+H]$^+$.

Example 6

Preparation of S)-2-(4-(4-fluorophenoxy)phenyl)-6-((1-methoxy-1-oxopropan-2-yl)amino)pyrimidine-4-carboxylic acid trifluoroacetic acid salt

Scheme 10

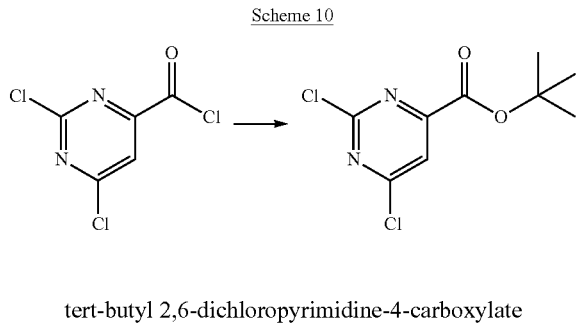

tert-butyl 2,6-dichloropyrimidine-4-carboxylate

To a solution of 2,6-dichloropyrimidine-4-carbonyl chloride (1.026 g, 4.85 mmol) in DCM (25 mL) was added iPr₂NEt (1.01 mL, 5.80 mmol) and t-butanol (0.51 mL, 5.3 mmol). The mixture was stirred overnight then pyridine (0.39 mL, 4.8 mmol) was added and the stirring continued over another night. The reaction mixture was evaporated in vacuo and the resulting residue was chromatographed over silica gel with 0-40% EtOAc in hexanes. The product fractions were evaporated in vacuo to give tert-butyl 2,6-dichloropyrimidine-4-carboxylate as a yellow-orange waxy solid (0.310 g, 1.24 mmol, 26% yield). $^1$H NMR (400 MHz, DMSO-$d_6$): 8.15 (1H, s), 1.56 (9H, s). LC/MS: m/z=271.1 [M+Na]$^+$.

Scheme 11

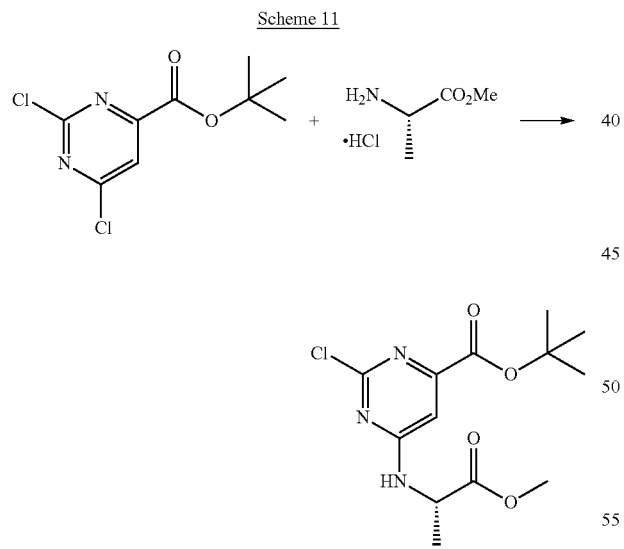

(S)-tert-butyl 2-chloro-6-((1-methoxy-1-oxopropan-2-yl)amino)pyrimidine-4-carboxylate To a mixture of tert-butyl 2,6-dichloropyrimidine-4-carboxylate (0.310 g, 1.24 mmol) in acetonitrile (5 mL) was added (S)-methyl 2-aminopropanoate hydrochloride (0.177 g, 1.27 mmol) and iPr₂NEt (0.48 mL, 2.8 mmol). The mixture was heated at 50° C. overnight then concentrated in vacuo. The residue was chromatographed over silica gel with 10-50% EtOAc in hexanes. The product fractions were evaporated in vacuo to yield (S)-tert-butyl 2-chloro-6-((1-methoxy-1-oxopropan-2-yl)amino)pyrimidine-4-carboxylate as a colorless glass (0.347 g, 1.10 mmol, 89% yield). $^1$H NMR (400 MHz, DMSO-$d_6$): 8.70 (1H, d, J=6.8 Hz), 7.12 (1H, s), 4.56-4.47 (1H, m), 3.65 (3H, s), 1.53 (9H, s), 1.39 (3H, d, J=7.2 Hz). LC/MS: m/z=316.2 [M+H]$^+$.

Scheme 12

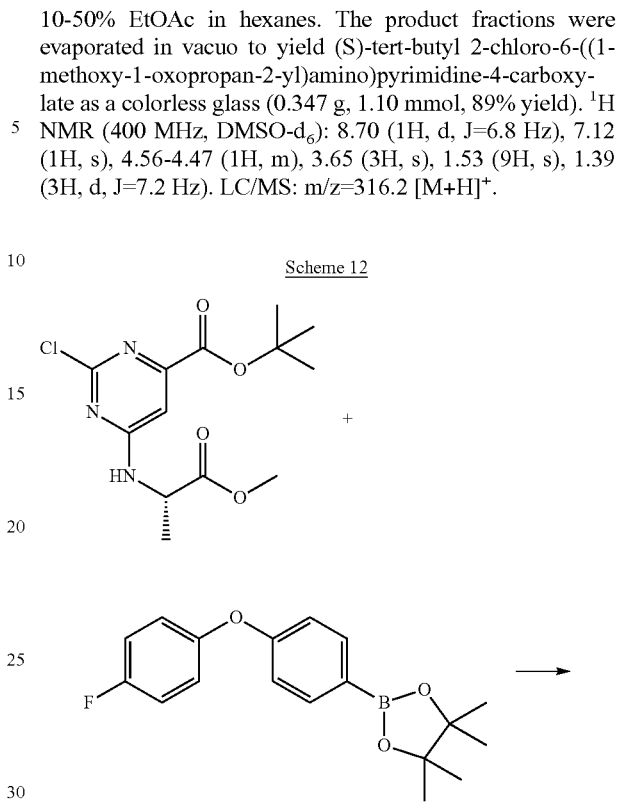

(S)-tert-butyl 2-(4-(4-fluorophenoxy)phenyl)-6-(1-methoxy-1-oxopropan-2-yl)amino)pyrimidine-4-carboxylate (Cpd No. 32)

To a mixture of the (S)-tert-butyl 2-chloro-6-((1-methoxy-1-oxopropan-2-yl)amino)pyrimidine-4-carboxylate (0.347 g, 1.10 mmol) in dioxane (10 mL) was added 2-(4-(4-fluorophenoxy)phenyl)-4,4,5,5-tetramethyl-1,3,2-dioxaborolane (0.348 g, 1.11 mmol), 2M aqueous Na₂CO₃ (1.10 mL, 2.20 mmol) and PdCl₂(dppf) (0.050 g, 0.061 mmol). The reaction vessel was flushed with argon, sealed, and heated at 80° C. for 2 days. After cooling, the reaction mixture was evaporated in vacuo and the residue chromatographed over silica gel with 10-40% EtOAc in hexanes. The product fractions were evaporated in vacuo to give (S)-tert-butyl 2-(4-(4-fluorophenoxy)phenyl)-6-((1-methoxy-1-oxopropan-2-yl)amino)pyrimidine-4-carboxylate as an off-white foam (0.316 g, 0.676 mmol, 61% yield). $^1$H NMR (400 MHz, DMSO-$d_6$): 8.31-8.25 (3H, m), 7.32-7.24 (2H, m), 7.19-7.14 (2H, m), 7.06 (2H, d, J=9.0 Hz), 7.04 (1H, s), 4.60-4.51 (1H, m), 3.63 (3H, s), 1.56 (9H, s), 1.44 (3H, d, J=7.2 Hz). LC/MS: m/z=468.2 [M+H]$^+$.

Scheme 13

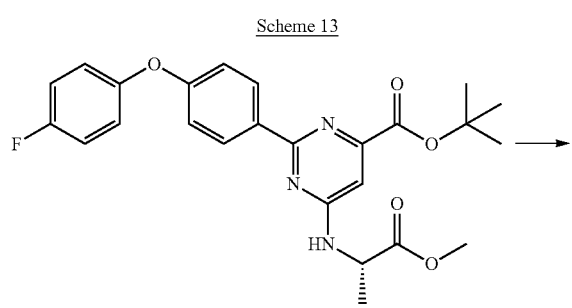

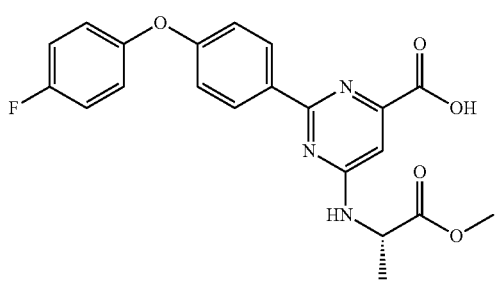

(S)-2-(4-(4-fluorophenoxy)phenyl)-6-((1-methoxy-1-oxopropan-2-yl)amino) pyrimidine-4-carboxylic acid trifluoroacetic acid salt (Cpd No. 33)

To a solution of the (S)-tert-butyl 2-(4-(4-fluorophenoxy)phenyl)-6-((1-methoxy-1-oxopropan-2-yl)amino)pyrimidine-4-carboxylate (0.312 g, 0.667 mmol) in DCM (10 mL) was added TFA (5 mL, 67 mmol). After stirring for 3 days the reaction was evaporated in vacuo and the residue triturated with hexanes, filtered and dried under a stream of nitrogen to give (S)-2-(4-(4-fluorophenoxy)phenyl)-6-((1-methoxy-1-oxopropan-2-yl)amino)pyrimidine-4-carboxylic acid as the trifluoroacetic acid salt as a cream-colored powder (0.326 g, 0.620 mmol, 93%). $^1$H NMR (400 MHz, DMSO-$d_6$): 8.36-8.26 (3H, m), 7.32-7.24 (2H, m), 7.20-7.13 (2H, m), 7.10-7.03 (3H, m), 4.60-4.52 (1H, m), 3.64 (3H, s), 1.45 (3H, d, J=7.2 Hz). LC/MS: m/z=412.1 [M+H]$^+$.

Example 7

Preparation of (S)-6-((1-amino-1-oxopropan-2-yl)amino)-2-(4-(4-fluorophenoxy)phenyl)pyrimidine-4-carboxylic acid (Cpd No. 35)

Scheme 14

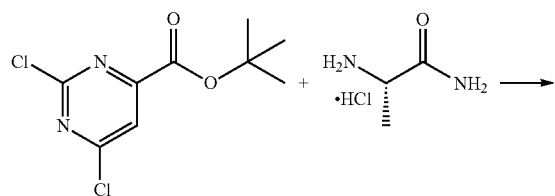

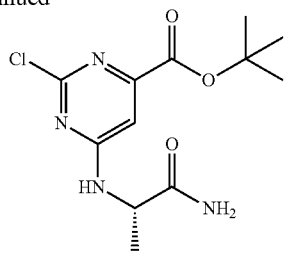

(S)-tert-butyl 6-((1-amino-1-oxopropan-2-yl)amino)-2-chloropyrimidine-4-carboxylate To a solution of the tert-butyl 2,6-dichloropyrimidine-4-carboxylate (0.626 g, 2.51 mmol) in acetonitrile (10 mL) was added (S)-2-aminopropanamide hydrochloride (0.319 g, 2.56 mmol) and iPr$_2$NEt (0.96 mL, 5.5 mmol). The mixture was heated at 50° C. for 6 h then concentrated in vacuo. The residue was chromatographed over silica gel using 50-100% EtOAc in hexanes. The product fractions were evaporated in vacuo to give (S)-tert-butyl 6-((1-amino-1-oxopropan-2-yl)amino)-2-chloropyrimidine-4-carboxylate as an off-white foam (0.628 g, 2.09 mmol, 83% yield). LC/MS: m/z=301.2 [M+H]$^+$.

Scheme 15

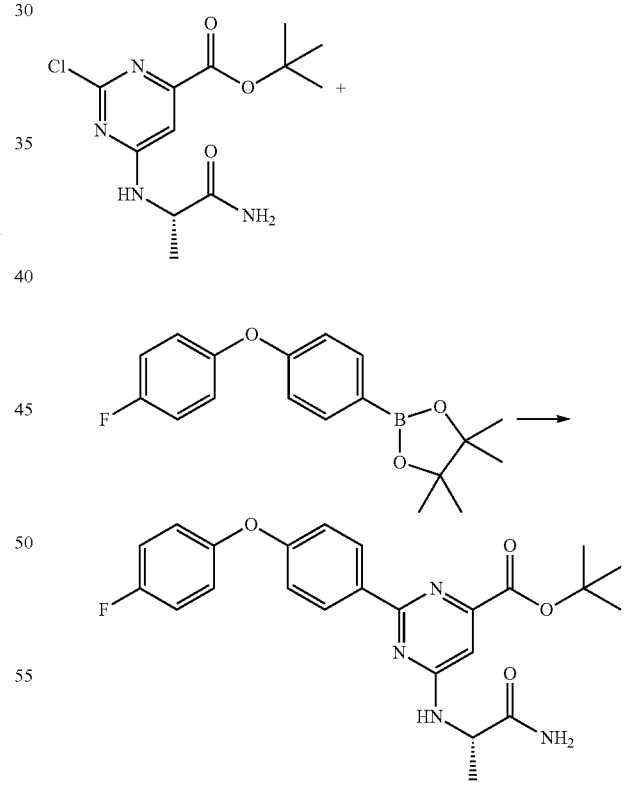

(S)-tert-butyl 6-((1-amino-1-oxopropan-2-yl)amino)-2-(4-(4-fluorophenoxy)phenyl)pyrimidine-4-carboxylate (Cpd No. 34)

To a mixture of (S)-tert-butyl 6-((1-amino-1-oxopropan-2-yl)amino)-2-chloropyrimidine-4-carboxylate (0.628 g, 2.09 mmol) in dioxane (10 mL) was added 2-(4-(4-fluorophenoxy)phenyl)-4,4,5,5-tetramethyl-1,3,2-dioxaborolane (0.791 g, 2.52 mmol), 2M aqueous Na$_2$CO$_3$ (2.1 mL, 4.2 mmol) and PdCl$_2$(dppf) (0.087 g, 0.11 mmol). The reaction vessel was flushed with argon, sealed and heated at 80° C. overnight. After cooling, the reaction mixture was evaporated in vacuo and the residue chromatographed over silica gel with 50-90% EtOAc in hexanes. The product fractions were evaporated in vacuo to give a residue which was triturated with 5 mL 1:1 EtOAc/hexanes. The solid was filtered off, rinsed twice with 2 mL 1:1 EtOAc/hexanes, and dried under vacuum to give (S)-tert-butyl 6-((1-amino-1-oxopropan-2-yl)-amino)-2-(4-(4-fluorophenoxy)phenyl)pyrimidine-4-carboxylate as a cream-colored powder (0.537 g, 1.19 mmol, 57% yield). $^1$H NMR (400 MHz, DMSO-d$_6$): 8.36 (2H, d, J=9.0 Hz), 7.97 (1H, d, J=6.6 Hz), 7.54 (1H, s), 7.31-7.24 (2H, m), 7.19-7.13 (2H, m), 7.09-6.99 (4H, m), 4.59-4.50 (1H, m), 1.55 (9H, s), 1.36 (3H, d, J=7.0 Hz). LC/MS: m/z=453.3 [M+H]$^+$.

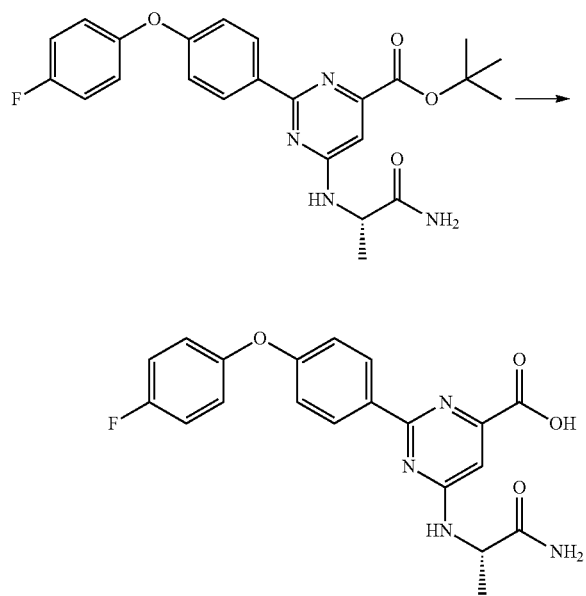

(S)-6-((1-amino-1-oxopropan-2-yl)amino)-2-(4-(4-fluorophenoxy)phenyl)pyrimidine-4-carboxylic acid To a suspension of the (S)-tert-butyl 6-((1-amino-1-oxopropan-2-yl)-amino)-2-(4-(4-fluorophenoxy)phenyl)pyrimidine-4-carboxylate (0.426 g, 0.941 mmol) in DCM (10 mL) was added TFA (5 mL, 67 mmol). After stirring overnight, the reaction was evaporated in vacuo and the residue triturated with 3 mL acetonitrile, filtered, rinsed once with 1 mL acetonitrile and dried under vacuum at 40° C. to give (S)-6-((1-amino-1-oxopropan-2-yl)amino)-2-(4-(4-fluorophenoxy)phenyl)pyrimidine-4-carboxylic acid as an off-white powder (0.343 g, 0.865 mmol, 92% yield). $^1$H NMR (400 MHz, DMSO-d$_6$): 8.40 (2H, d, J=8.8 Hz), 8.05 (1H, d, J=6.6 Hz), 7.56 (1H, s), 7.32-7.24 (2H, m), 7.19-7.14 (2H, m), 7.11 (1H, s), 7.07-7.01 (3H, m), 4.61-4.52 (1H, m), 1.37 (3H, d, J=7.0 Hz). LC/MS: m/z=397.1 [M+H]$^+$.

Example 8

Preparation of (S)-6-((1-amino-1-oxopropan-2-yl)amino)-2-(4-(4-(trifluoromethyl)phenoxy)phenyl)pyrimidine-4-carboxamide (Cpd No. 14)

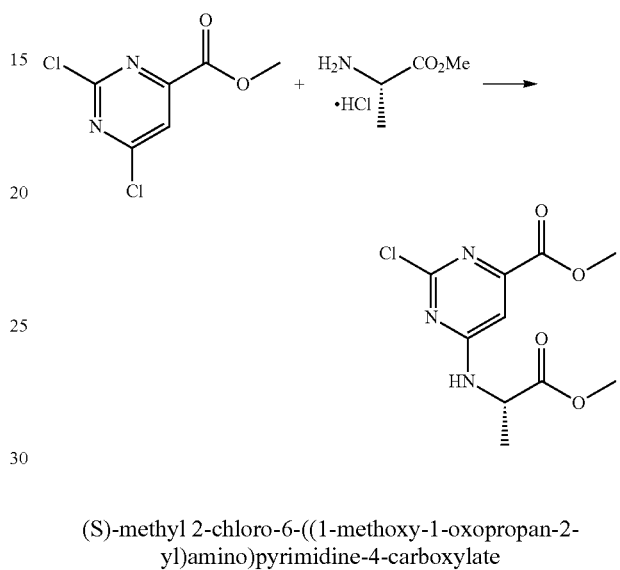

(S)-methyl 2-chloro-6-((1-methoxy-1-oxopropan-2-yl)amino)pyrimidine-4-carboxylate To a mixture of methyl 2,6-dichloropyrimidine-4-carboxylate (5.175 g, 25.00 mmol) in acetonitrile (100 mL) was added (S)-methyl 2-aminopropanoate hydrochloride (3.497 g, 25.05 mmol) and iPr$_2$NEt (9.6 mL, 55.1 mmol). The mixture was heated at 50° C. overnight then concentrated in vacuo. The residue was chromatographed over silica gel with 30-70% EtOAc in hexanes. The product fractions were evaporated in vacuo to yield (S)-methyl 2-chloro-6-((1-methoxy-1-oxopropan-2-yl)amino)pyrimidine-4-carboxylate as a thick yellow-orange oil (4.194 g, 15.33 mmol, 61% yield). LC/MS: m/z=274.2 [M+H]$^+$.

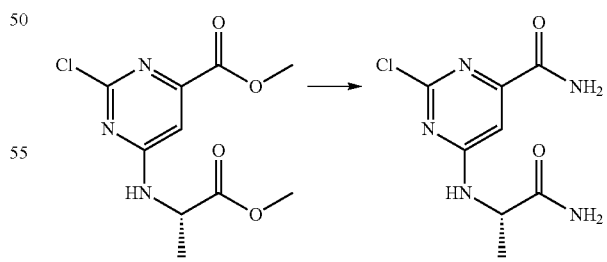

(S)-6-((1-amino-1-oxopropan-2-yl)amino)-2-chloropyrimidine-4-carboxamide

A solution of the (S)-methyl 2-chloro-6-((1-methoxy-1-oxopropan-2-yl)amino)pyrimidine-4-carboxylate (3.719 g, 13.59 mmol) in 7M ammonia in methanol (20 mL, 140 mmol)

was heated in a sealed tube for 3 days at 50° C. After cooling, the precipitated solid was filtered off and rinsed with MeOH (2×5 mL) then dried under vacuum at 40° C. to give (S)-6-(1-amino-1-oxopropan-2-yl)amino)-2-chloropyrimidine-4-carboxamide as a pale yellow powder (2.946 g, 12.09 mmol, 89% yield). LC/MS: m/z=244.2 [M+H]$^+$.

Scheme 19

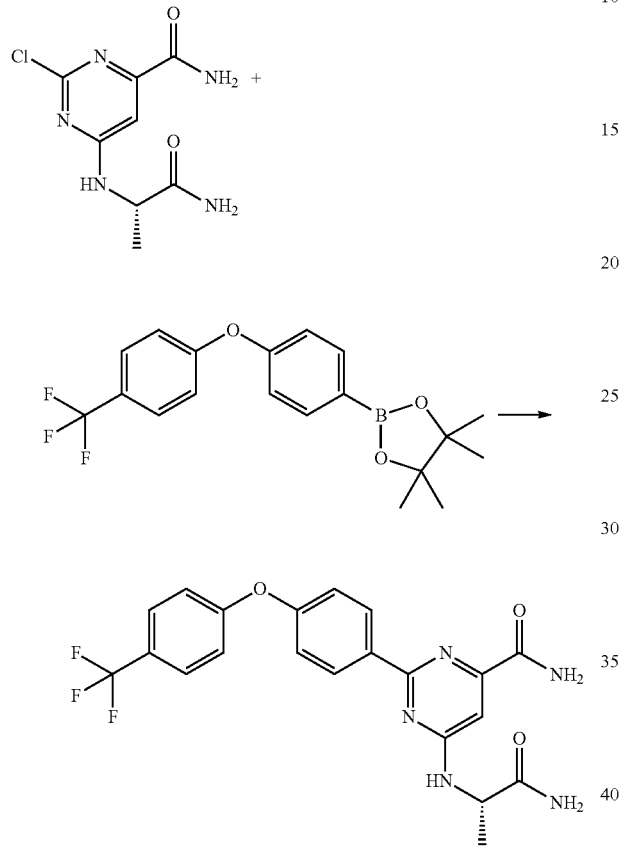

(S)-6-((1-amino-1-oxopropan-2-yl)amino)-2-(4-(4-(trifluoromethyl)phenoxy)phenyl)pyrimidine-4-carboxamide To a suspension of (S)-6-((1-amino-1-oxopropan-2-yl)amino)-2-chloropyrimidine-4-carboxamide (0.244 g, 1.00 mmol) in dioxane (5.0 mL) was added 4,4,5,5-tetramethyl-2-(4-(4-(trifluoromethyl)phenoxy)phenyl)-1,3,2-dioxaborolane (0.403 g, 1.11 mmol), 2M aqueous Na$_2$CO$_3$ (1.0 mL, 2.0 mmol) and PdCl$_2$(dppf) (0.044 g, 0.054 mmol). The reaction vessel was flushed with argon, sealed, and heated at 100° C. overnight. After cooling, the reaction mixture was evaporated in vacuo and the residue chromatographed over silica gel with 50-100% acetone in hexanes. The product fractions were evaporated in vacuo and the resulting solid triturated with 2 mL MeOH, filtered, and dried under vacuum at 42° C. to give (S)-6-((1-amino-1-oxopropan-2-yl)amino)-2-(4-(4-(trifluoromethyl)phenoxy)phenyl)pyrimidine-4-carboxamide as a cream-colored powder (0.283 g, 0.635 mmol, 64% yield). $^1$H NMR (400 MHz, DMSO-d$_6$): 8.61 (2H, d, J=8.8 Hz), 8.31 (1H, s), 7.98 (1H, d, J=6.4 Hz), 7.80-7.73 (3H, m), 7.55 (1H, s), 7.25-7.16 (4H, m), 7.11 (1H, s), 7.01 (1H, s), 4.62-4.53 (1H, m), 1.37 (3H, d, J=7.0 Hz). LC/MS: m/z=446.1 [M+H]$^+$.

Example 9

Preparation of (S)-6-((1-carboxyethyl)amino)-2-(4-(4-fluorophenoxy)phenyl)pyrimidine-4-carboxylic acid (Cpd No. 40)

Scheme 20

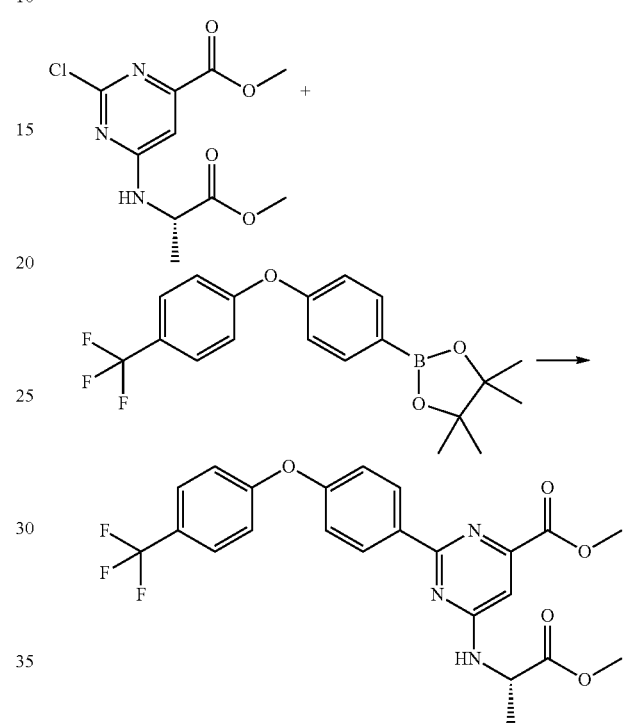

(S)-methyl 2-(4-(4-fluorophenoxy)phenyl)-6-((1-methoxy-1-oxopropan-2-yl)amino)pyrimidine-4-carboxylate (Cpd No. 39)

To a mixture of the (S)-methyl 2-chloro-6-((1-methoxy-1-oxopropan-2-yl)amino)pyrimidine-4-carboxylate (4.826 g, 17.63 mmol) in dioxane (100 mL) was added 2-(4-(4-fluorophenoxy)phenyl)-4,4,5,5-tetramethyl-1,3,2-dioxaborolane (6.651 g, 21.17 mmol), 2M aqueous Na$_2$CO$_3$ (17.6 mL, 35.2 mmol) and PdCl$_2$(dppf) (0.727 g, 0.89 mmol). The flask was flushed with argon, sealed, and heated on a 100° C. oil bath for 30 minutes. The flask ruptured. As much of the reaction mixture as possible was partitioned between methanol and hexanes. The hexanes were removed and the methanol layer was washed a second time. The methanol fraction was evaporated in vacuo and chromatographed over silica gel with 20-60% EtOAc in hexanes. The product fractions were isolated and evaporated in vacuo and chromatographed a second time over silica gel with 10-50% EtOAc in hexanes. The product fractions were evaporated in vacuo and the resulting solid triturated with 2 mL MeOH, filtered, rinsed once with 1 mL MeOH, and dried under vacuum at 40° C. to give (S)-methyl 2-(4-(4-fluorophenoxy)phenyl)-6-((1-methoxy-1-oxopropan-2-yl)amino)pyrimidine-4-carboxylate as a yellow powder (0.140 g, 0.329 mmol, 2% yield). $^1$H NMR (400 MHz, DMSO-d$_6$): 8.34-8.25 (3H, m), 7.31-7.24 (2H, m), 7.19-7.14 (2H, m), 7.10 (1H, s), 7.06 (2H, d, J=8.8 Hz), 4.60-4.52 (1H, m), 3.89 (3H, s), 3.64 (3H, s), 1.45 (3H, d, J=7.2 Hz). LC/MS: m/z=426.1 [M+H]$^+$.

Scheme 21

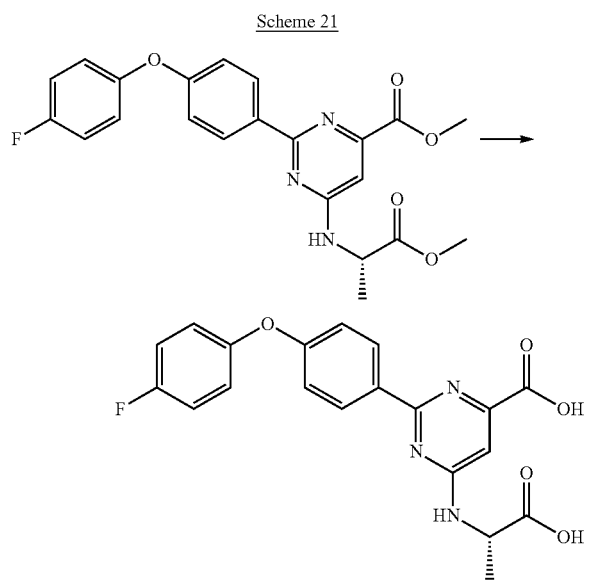

(S)-6-((1-carboxyethyl)amino)-2-(4-(4-fluorophenoxy)phenyl)pyrimidine-4-carboxylic acid To a solution of (S)-methyl 2-(4-(4-fluorophenoxy)phenyl)-6-(1-methoxy-1-oxopropan-2-yl)amino)pyrimidine-4-carboxylate (0.125 g, 0.294 mmol) in 5:1 THF/water (5 mL) portionwise over 2 days was add LiOH.H$_2$O (0.030 g, 0.71 mmol). After the final addition the reaction was stirred for 2 h then diluted with 5 mL water and neutralized with 0.70 mL 1N aqueous HCl solution. The resulting solid was filtered, dried under vacuum at 40° C., triturated with 2 mL 20% EtOAc in hexanes then hexanes, filtered, and dried under vacuum at 40° C. to give (S)-6-((1-carboxyethyl)amino)-2-(4-(4-fluorophenoxy)phenyl)pyrimidine-4-carboxylic acid as a pale tan powder (0.094 g, 0.24 mmol, 81%). $^1$H NMR (400 MHz, DMSO-d$_6$): 13.21 (1H, br s), 12.63 (1H, br s), 8.37 (2H, d, J=9.0 Hz), 8.16 (1H, d, J=6.6 Hz), 7.31-7.24 (2H, m), 7.19-7.13 (2H, m), 7.08 (1H, s), 7.05 (2H, d, J=9.0 Hz), 4.57-4.47 (1H, m), 1.44 (3H, d, J=7.2 Hz). LC/MS: m/z=398.0 [M+H]$^+$.

Example 10

Preparation of 2-(4-(4-fluorophenoxy)phenyl)-6-(3-(hydroxymethyl)morpholino) pyrimidine-4-carboxamide (Cpd No. 41)

Scheme 22

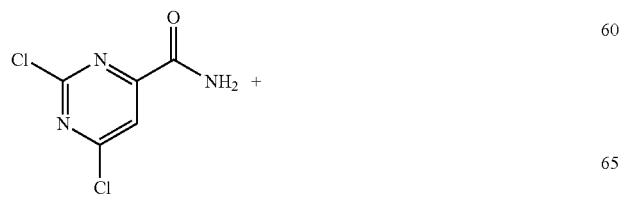

2-chloro-6-(3-(hydroxymethyl)morpholino)pyrimidine-4-carboxamide

To a mixture of 2,6-dichloropyrimidine-4-carboxamide (0.384 g, 2.00 mmol) in acetonitrile (10 mL) was added morpholin-3-ylmethanol hydrochloride (0.310 g, 2.02 mmol) and iPr$_2$NEt (0.77 mL, 4.4 mmol). The mixture was heated at 50° C. overnight then concentrated in vacuo. The residue was chromatographed over silica gel with 25-75% acetone in hexanes. The product fractions were evaporated in vacuo to yield 2-chloro-6-(3-(hydroxymethyl)morpholino)pyrimidine-4-carboxamide as a pale tan solid (0.501 g, 1.84 mmol, 92% yield). LC/MS: m/z=273.2 [M+H]$^+$.

Scheme 23

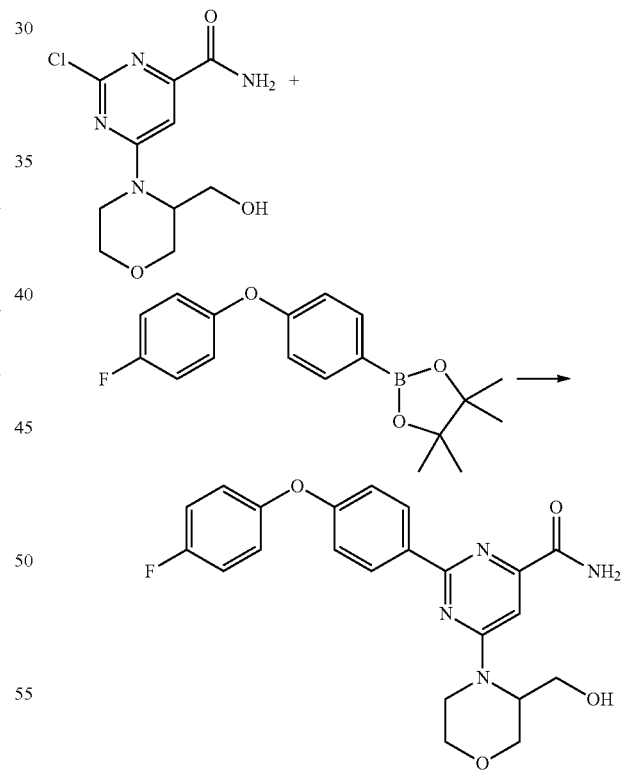

2-(4-(4-fluorophenoxy)phenyl)-6-(3-(hydroxymethyl)morpholino)pyrimidine-4-carboxamide To a mixture of the 2-chloro-6-(3-(hydroxymethyl)morpholino)pyrimidine-4-carboxamide (0.501 g, 1.84 mmol) in dioxane (10 mL) was added 2-(4-(4-fluorophenoxy)phenyl)-4,4,5,5-tetramethyl-1,3,2-dioxaborolane (0.637 g, 2.03 mmol), 2M aqueous Na$_2$CO$_3$ (1.8 mL, 3.6 mmol), and PdCl$_2$(dppf) (0.078 g, 0.096 mmol). The reaction vessel was flushed with argon, sealed, and heated at 100° C. overnight. After cooling, the reaction mixture was evaporated in vacuo and the residue chromatographed over silica gel with 25-75% acetone in hexanes. The product fractions that were less than 97% isomerically pure were evaporated in vacuo and the resulting solid triturated with 3 mL acetone, filtered and rinsed with 1 mL acetone. This solid was then combined with the fractions from the chromatography that were greater than 97% isomerically pure. This combined material was triturated with 5 mL acetone, filtered, and rinsed once with 5 mL acetone. The solid was dried under vacuum at 40° C. to yield 2-(4-(4-fluorophenoxy)phenyl)-6-(3-(hydroxymethyl)morpholino)pyrimidine-4-carboxamide as an off-white powder (0.384 g, 0.905 mmol, 49% yield). $^1$H NMR (400 MHz, DMSO-d$_6$): 8.54 (2H, d, J=8.8 Hz), 8.35 (1H, s), 7.80 (1H, s), 7.31-7.24 (2H, m), 7.22 (1H, s), 7.19-7.13 (2H, m), 7.04 (2H, d, J=9.0 Hz), 4.99 (1H, t, J=5.7 Hz), 4.60 (1H, very broad s), 4.14 (1H, very broad s), 4.04 (1H, d, J=11.4 Hz), 3.94 (1H, dd, J=11.6 Hz, 3.5 Hz), 3.76-3.68 (1H, m), 3.59-3.43 (3H, m), 3.25-3.13 (1H, m). LC/MS: m/z=425.1 [M+H]$^+$.

Example 11

Preparation of 2-(4-(4-fluorophenoxy)phenyl)-6-(2-(hydroxymethyl)piperazin-1-yl)pyrimidine-4-carboxamide (Cpd No. 48)

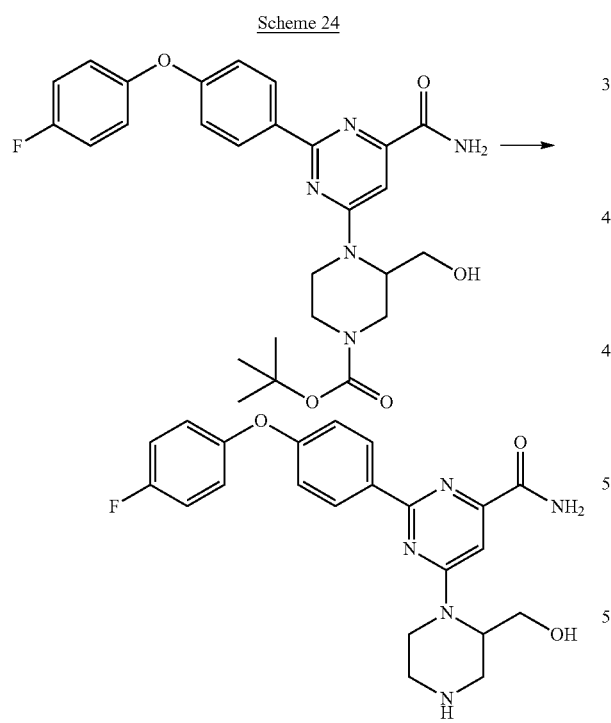

Scheme 24

To a solution of the tert-butyl 4-(6-carbamoyl-2-(4-(4-fluorophenoxy)phenyl)pyrimidin-4-yl)-3-(hydroxymethyl)piperazine-1-carboxylate (0.848 g, 1.62 mmol) in dioxane (25 mL) was added 4M HCl in dioxane (5 mL, 20 mmol). After stirring overnight the reaction was concentrated in vacuo. The residue was triturated with 10 mL acetonitrile, filtered, and rinsed with 10 mL acetonitrile. The solid was then successively suspended and filtered three times from warm acetonitrile. The solid residue was then partitioned between 10 mL EtOAc and 2 mL 2M aqueous Na$_2$CO$_3$ solution. The mixture was diluted with 50 mL EtOAc and 25 mL water, the organic layer was removed and the aqueous emulsion was washed once more with 50 mL EtOAc. The aqueous emulsion was filtered off and rinsed with water. The resulting pasty solid was triturated with 2 mL acetonitrile, filtered, rinsed once with 1 mL acetonitrile, and dried under vacuum to give 2-(4-(4-fluorophenoxy)phenyl)-6-(2-(hydroxymethyl)piperazin-1-yl)pyrimidine-4-carboxamide as a pale tan powder (0.198 g, 0.468 mmol, 29% yield). $^1$H NMR (400 MHz, DMSO-d$_6$): 8.52 (2H, d, J=8.8 Hz), 8.32 (1H, s), 7.78 (1H, s), 7.31-7.24 (2H, m), 7.22-7.12 (3H, m), 7.04 (2H, d, J=8.8 Hz), 4.85 (1H, s), 4.79-4.60 (1H, very broad s), 3.83-3.74 (1H, m), 3.56 (1H, br s), 3.17-3.09 (1H, m), 3.05-2.94 (2H, m), 2.73-2.65 (1H, m), 2.63-2.54 (1H, m), 2.49-2.32 (2H, m). LC/MS: m/z=424.2 [M+H]$^+$.

Example 12

Preparation of 6-(3,4-dihydroxypyrrolidin-1-yl)-2-(4-(4-fluorophenoxy)phenyl)pyrimidine-4-carboxamide (Cpd No. 49)

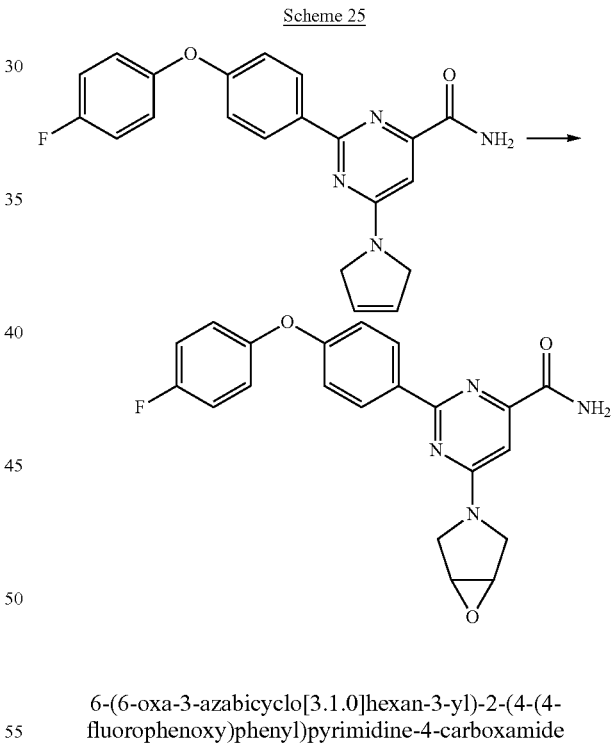

Scheme 25

6-(6-oxa-3-azabicyclo[3.1.0]hexan-3-yl)-2-(4-(4-fluorophenoxy)phenyl)pyrimidine-4-carboxamide To a suspension of the 6-(2,5-dihydro-1H-pyrrol-1-yl)-2-(4-(4-fluorophenoxy)phenyl)pyrimidine-4-carboxamide (0.333 g, 0.885 mmol) in DCM (25 mL) was added mCPBA (0.201 g, 0.897 mmol, 77% solid). After 2 h, more mCPBA was added (0.198 g, 0.883 mmol, 77% solid). After stirring overnight, more mCPBA was added (0.202 g, 0.901 mmol, 77% solid) and the reaction was heated to reflux. After 5 h, more mCPBA was added (0.200 g, 0.892 mmol, 77% solid). After 2 h, more mCPBA was added (0.202 g, 0.901 mmol, 77% solid) and refluxing was continued overnight. When cooled, the reaction mixture was diluted with 100 mL DCM, washed twice with 25 mL saturated aqueous NaHCO₃ solution, and once with 25 mL brine. The organic layers were dried over MgSO4, filtered, and evaporated to a residue. The residue was chromatographed over silica gel with 25-75% acetone in hexanes. The product fractions were evaporated in vacuo and the resulting solid triturated with 1 mL acetone, filtered, rinsed once with 0.5 mL acetone and dried under vacuum at 40° C. to give 6-(6-oxa-3-azabicyclo[3.1.0]hexan-3-yl)-2-(4-(4-fluorophenoxy)phenyl)pyrimidine-4-carboxamide as an off-white powder (0.052 g, 0.13 mmol, 15% yield). LC/MS: m/z=393.2 [M+H]⁺.

Scheme 26

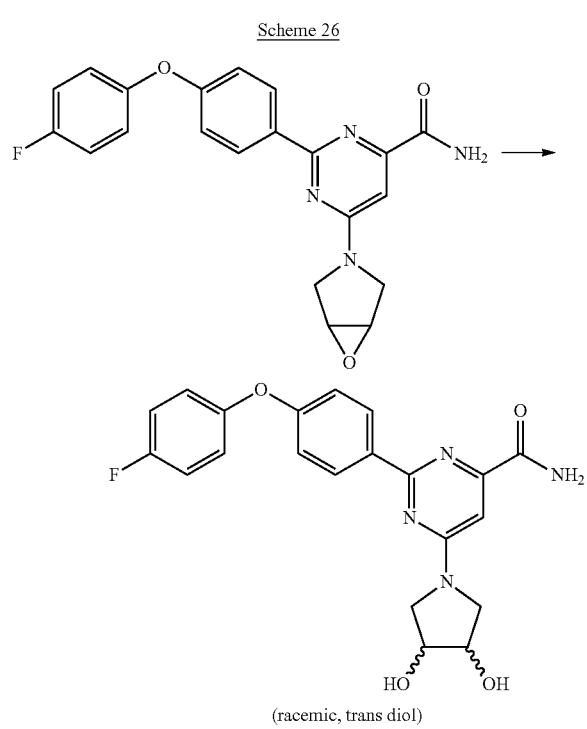

6-(3,4-dihydroxypyrrolidin-1-yl)-2-(4-(4-fluorophenoxy)phenyl)pyrimidine-4-carboxamide To a suspension of the 6-(6-oxa-3-azabicyclo[3.1.0]hexan-3-yl)-2-(4-(4-fluorophenoxy)phenyl)pyrimidine-4-carboxamide (0.050 g, 0.13 mmol) in THF (5 mL) and water (1 mL) was added a 60% HClO₄ solution (0.1 mL). After stirring overnight, the reaction was heated at 50° C. for 2 days. After the reaction cooled it was quenched with solid NaHCO₃ and evaporated in vacuo. The residue was chromatographed over silica gel with 50-100% acetone in hexanes. The product fractions were evaporated and the resulting residue dissolved in 1 mL acetonitrile with warming. Upon cooling a solid formed. The solid was filtered and rinsed once with 1 mL acetonitrile. The remaining solid was suspended in 1 mL warm acetonitrile, filtered and air-dried to give 6-(3,4-dihydroxypyrrolidin-1-yl)-2-(4-(4-fluorophenoxy)phenyl)pyrimidine-4-carboxamide as a fine crystalline powder (0.009 g, 0.02 mmol, 17%). ¹H NMR (400 MHz, DMSO-d₆): 8.55 (2H, d, J=8.8 Hz), 8.34 (1H, d, J=2.4 Hz), 7.88 (1H, d, J=2.4 Hz), 7.31-7.24 (2H, m), 7.19-7.13 (2H, m), 7.05 (2H, d, J=9.0 Hz), 6.90 (1H, s), 5.29 (1H, d, J=3.7 Hz), 5.22 (1H, d, J=3.3 Hz), 4.14-4.10 (1H, m), 4.09-4.05 (1H, m), 3.76-3.63 (3H, m), 3.35-3.30 (1H, m). LC/MS: m/z=411.1 [M+H]⁺.

Example 13

Preparation of (S)-6-((3-amino-2-hydroxy-3-oxopropyl)amino)-2-(4-(4-fluorophenoxy)phenyl)pyrimidine-4-carboxamide (Cpd No. 50)

Scheme 27

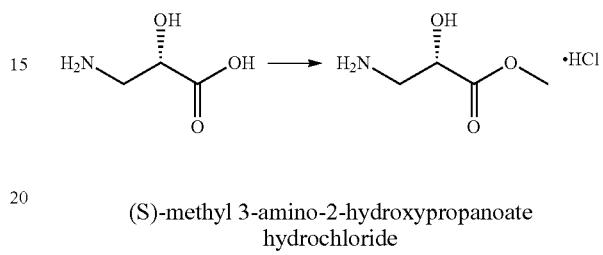

(S)-methyl 3-amino-2-hydroxypropanoate hydrochloride

To an ice-cooled suspension of (S)-3-amino-2-hydroxypropanoic acid (0.904 g) in MeOH (15 mL) was added SOCl₂ (2.0 mL, 27 mmol) over ~2.5 minutes. After the addition the reaction was allowed to warm to room temperature. After stirring overnight, the reaction was evaporated in vacuo. MeOH was added and the mixture evaporated in vacuo a second time to yield the product (S)-methyl 3-amino-2-hydroxypropanoate hydrochloride as a colorless oil. ¹H NMR (400 MHz, DMSO-d₆): 8.16 (3H, s), 6.36 (1H, s), 4.38 (1H, br d, J=8.3 Hz), 3.68 (3H, s), 3.10 (1H, dd, J=12.9 Hz, 3.7 Hz), 2.90 (1H, dd, J=12.9 Hz, 8.6 Hz).

Scheme 28

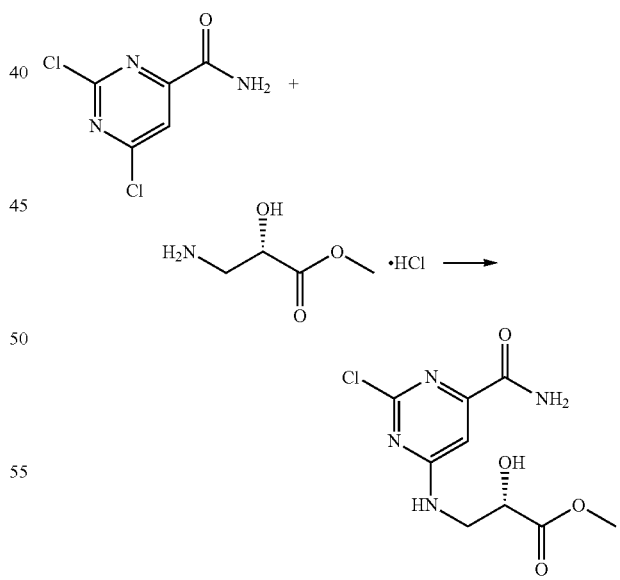

(S)-methyl 3-((6-carbamoyl-2-chloropyrimidin-4-yl)amino)-2-hydroxypropanoate

To a mixture of the (S)-methyl 3-amino-2-hydroxypropanoate hydrochloride (0.333 g, 2.14 mmol) in acetonitrile (10 mL) was added 2,6-dichloropyrimidine-4-carboxamide (0.385 g, 2.01 mmol) and iPr₂NEt (0.77 mL, 4.4 mmol). The mixture was heated at 50° C. overnight then cooled. The precipitated solid was filtered off, rinsed once with 2 mL acetonitrile, and air-dried to give (S)-methyl 3-((6-carbamoyl-2-chloropyrimidin-4-yl)amino)-2-hydroxypropanoate as a pale peach-colored powder (0.421 g, 1.53 mmol, 76% yield). LC/MS: m/z=275.1 [M+H]⁺.

Scheme 29

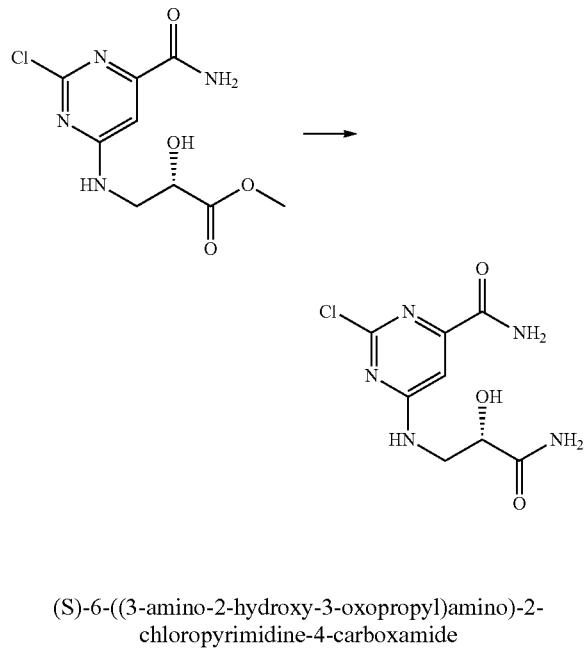

(S)-6-((3-amino-2-hydroxy-3-oxopropyl)amino)-2-chloropyrimidine-4-carboxamide

A mixture of the (S)-methyl 3-((6-carbamoyl-2-chloropyrimidin-4-yl)amino)-2-hydroxypropanoate (0.421 g, 1.53 mmol) and 7M ammonia in MeOH (10 mL, 70 mmol) were heated in a sealed tube at 50° C. overnight. The precipitated solid was filtered off from the warm reaction mixture, rinsed once with 5 mL MeOH, and air-dried to give (S)-6-((3-amino-2-hydroxy-3-oxopropyl)amino)-2-chloropyrimidine-4-carboxamide as a light tan powder (0.372 g, 1.43 mmol, 94% yield). LC/MS: m/z=260.1 [M+H]⁺.

Scheme 30

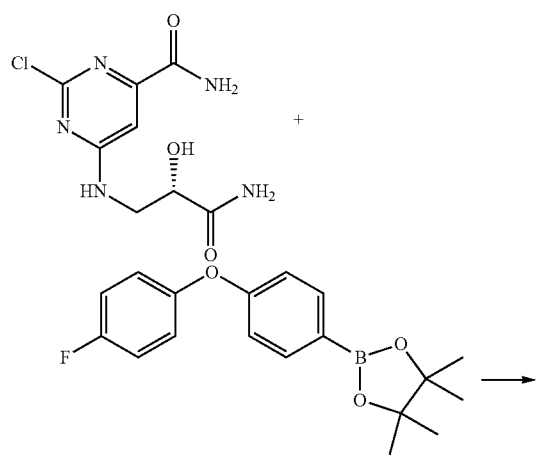

-continued

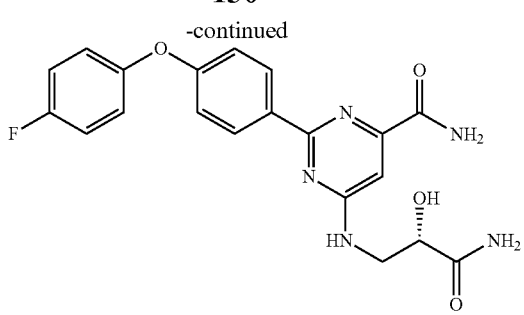

(S)-6-((3-amino-2-hydroxy-3-oxopropyl)amino)-2-(4-(4-fluorophenoxy)phenyl)pyrimidine-4-carboxamide To a mixture of the (S)-6-((3-amino-2-hydroxy-3-oxopropyl)amino)-2-chloropyrimidine-4-carboxamide (0.372 g, 1.43 mmol) in dioxane (10 mL) was added 2-(4-(4-fluorophenoxy)phenyl)-4,4,5,5-tetramethyl-1,3,2-dioxaborolane (0.494 g, 1.57 mmol), 2M aqueous Na₂CO₃ (1.45 mL, 2.90 mmol), and PdCl₂(dppf) (0.063 g, 0.077 mmol). The reaction vessel was flushed with argon, sealed, and heated at 100° C. overnight. After cooling, the reaction mixture was evaporated in vacuo and the residue triturated with 25 mL acetone. The insoluble solid was filtered off and washed successively with water, MeOH, 1N aqueous HCl, water, and MeOH. The solid was then dissolved in 3 mL DMSO with warming and diluted with 15 mL MeOH. Upon standing the solution deposited a solid that was filtered and rinsed twice with 5 mL MeOH and once with 2:1 acetonitrile/DMSO. The remaining solid was purified by reverse-phase chromatography using a 40-70% acetonitrile in water (+0.1% TFA) gradient. The product fractions were pooled and lyophilized to give (S)-6-(3-amino-2-hydroxy-3-oxopropyl)amino)-2-(4-(4-fluorophenoxy)phenyl)pyrimidine-4-carboxamide as a cream-colored powder (0.115 g, 0.280 mmol, 20% yield). ¹H NMR (400 MHz, DMSO-d₆): 8.54 (2H, d, J=8.1 Hz), 8.26 (1H, s), 7.91-7.84 (1H, m), 7.73 (1H, s), 7.33-7.23 (4H, m), 7.19-7.13 (2H, m), 7.08-7.01 (3H, m), 5.78 (1H, br s), 4.14-4.07 (1H, m), 3.92-3.83 (1H, m), 3.53-3.45 (1H, m). LC/MS: m/z=412.0 [M+H]⁺.

Example 14

Preparation of (S)-3-((6-carbamoyl-2-(4-(4-fluorophenoxy)phenyl)pyrimidin-4-yl)amino)-2-hydroxypropanoic acid (Cpd No. 51)

Scheme 31

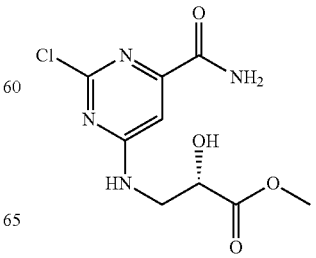

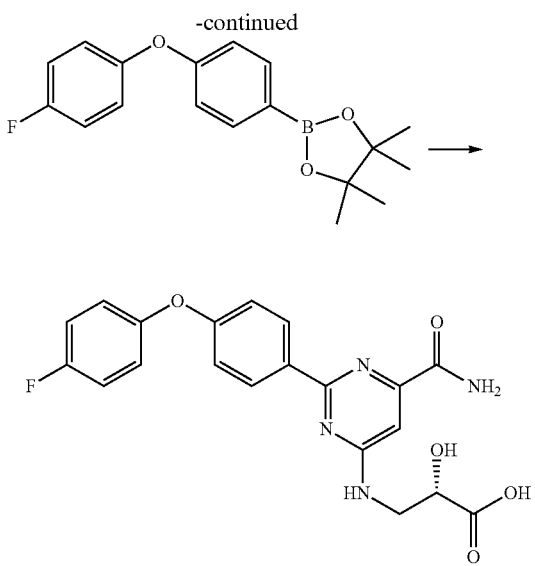

To a mixture of the (S)-methyl 3-((6-carbamoyl-2-chloropyrimidin-4-yl)amino)-2-hydroxypropanoate (0.408 g, 1.49 mmol) in dioxane (10 mL) was added 2-(4-(4-fluorophenoxy)phenyl)-4,4,5,5-tetramethyl-1,3,2-dioxaborolane (0.517 g, 1.65 mmol), 2M aqueous $Na_2CO_3$ (1.50 mL, 3.00 mmol) and $PdCl_2(dppf)$ (0.066 g, 0.081 mmol). The reaction vessel was flushed with argon, sealed and heated at 100° C. overnight. After cooling, the reaction mixture was diluted with acetone and decanted. Water was added to the insoluble residue to make a suspension. The solid was filtered, washed successively with water, acetone, 1N aqueous HCl then MeOH. The solid was dried under vacuum at 40° C. to give the product (S)-3-((6-carbamoyl-2-(4-(4-fluorophenoxy)phenyl)pyrimidin-4-yl)amino)-2-hydroxypropanoic acid as a light tan powder (0.053 g, 0.13 mmol, 9% yield). $^1$H NMR (400 MHz, DMSO-$d_6$): 12.61 (1H, s), 8.53 (2H, d, J=8.3 Hz), 8.27 (1H, s), 7.99-7.93 (1H, s), 7.73 (1H, s), 7.31-7.24 (2H, m), 7.19-7.13 (2H, m), 7.08-7.01 (3H, m), 5.60 (1H, s), 4.26 (1H, s), 3.90-3.80 (1H, s), 3.64-3.54 (1H, m). LC/MS: m/z=413.1 [M+H]$^+$.

Example 15

Preparation of 6-(N-(2,3-dihydroxypropyl)methylsulfonamido)-2-(4-(4-fluorophenoxy)phenyl)pyrimidine-4-carboxamide (Cpd No. 53)

Scheme 32

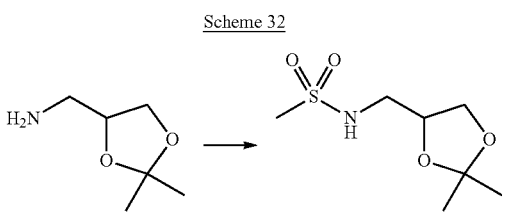

N-((2,2-dimethyl-1,3-dioxolan-4-yl)methyl)methanesulfonamide

To a solution of the (2,2-dimethyl-1,3-dioxolan-4-yl)methanamine (4.616 g, 35.19 mmol) in diethylether (100 mL) was added pyridine (2.90 mL, 35.9 mmol). A solution of methanesulfonyl chloride (2.75 mL, 35.4 mmol) in diethylether (50 mL) was added to the amine solution over 30 minutes. After stirring for 2 h, the reaction was washed once with 25 mL water then twice with 25 mL brine. The organic layer was separated, dried over MgSO4, filtered, and evaporated to a residue. The residue was chromatographed over silica gel with 0-100% EtOAc in hexanes. The product fractions were evaporated in vacuo to give N-((2,2-dimethyl-1,3-dioxolan-4-yl)methyl)methanesulfonamide as a near-colorless oil (0.875 g, 4.18 mmol, 12% yield). $^1$H NMR (400 MHz, DMSO-$d_6$): 7.17 (1H, t, J=6.4 Hz), 4.13-4.06 (1H, m), 3.98 (1H, dd, J=8.3 Hz, 6.4 Hz), 3.66 (1H, dd, J=8.3 Hz, 5.7 Hz), 3.09-2.98 (2H, m), 2.91 (3H, s), 1.33 (3H, s), 1.26 (3H, s).

Scheme 33

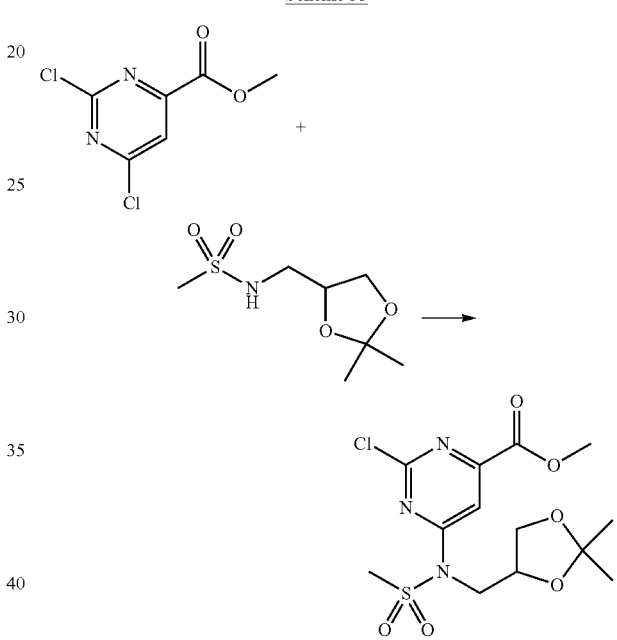

methyl 2-chloro-6-(N-((2,2-dimethyl-1,3-dioxolan-4-yl)methyl)methylsulfonamido)pyrimidine-4-carboxylate To a solution of N-((2,2-dimethyl-1,3-dioxolan-4-yl)methyl)methane sulfonamide (0.875 g, 4.18 mmol) in DMF (25 mL) was added 60% NaH in mineral oil (0.193 g, 4.83 mmol). After 10 minutes, methyl 2,6-dichloropyrimidine-4-carboxylate (0.871 g, 4.21 mmol) was added. After stirring for 30 minutes, the reaction mixture was diluted into 100 mL water and extracted three times with 50 mL EtOAc. The combined organic layers were washed once with 25 mL brine, dried over MgSO4, filtered, and evaporated to a residue. The residue was chromatographed over silica gel with 30-60% EtOAc in hexanes. The product fractions were concentrated in vacuo. After sitting overnight a crystalline solid formed. The solid was decanted and dried under vacuum to give methyl 2-chloro-6-(N-((2,2-dimethyl-1,3-dioxolan-4-yl)methyl)methylsulfonamido)pyrimidine-4-carboxylate as a cream-colored powder (0.911 g, 2.40 mmol, 57% yield). LC/MS: m/z=380.2 [M+H]$^+$.

Scheme 34

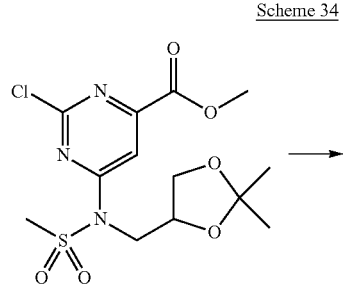

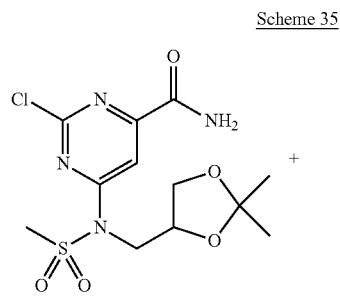

2-chloro-6-(N-((2,2-dimethyl-1,3-dioxolan-4-yl)methyl)methylsulfonamido) pyrimidine-4-carboxamide To a mixture of methyl 2-chloro-6-(N-((2,2-dimethyl-1,3-dioxolan-4-yl)methyl)methylsulfonamido)pyrimidine-4-carboxylate (0.911 g, 2.40 mmol) in MeOH (10 mL) was added 7M ammonia in MeOH (10 mL, 70 mmol). It started as a suspension, then dissolved, and then gave a precipitate. After 3 h the solid was filtered, rinsed once with 5 mL MeOH and air-dried to give the product 2-chloro-6-(N-((2,2-dimethyl-1,3-dioxolan-4-yl)methyl)methylsulfonamido)pyrimidine-4-carboxamide as a white powder (0.715 g, 1.96 mmol, 82% yield). LC/MS: m/z=365.2 [M+H]$^+$.

Scheme 35

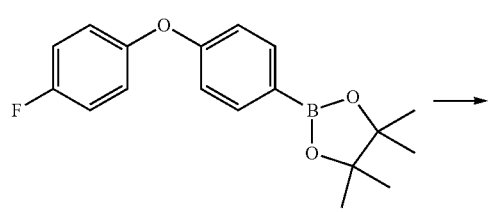

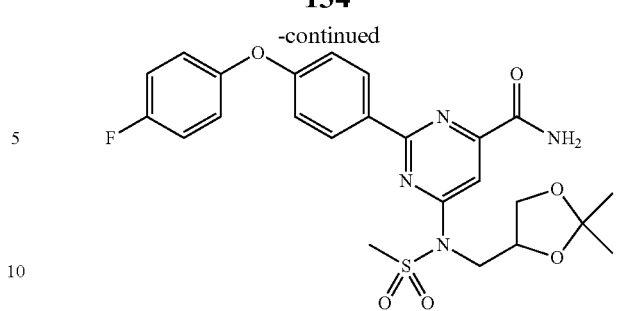

6-(N-((2,2-dimethyl-1,3-dioxolan-4-yl)methyl)methylsulfonamido)-2-(4-(4-fluorophenoxy)phenyl)pyrimidine-4-carboxamide (Cpd No. 52)

To a mixture of 2-chloro-6-(N-((2,2-dimethyl-1,3-dioxolan-4-yl)methyl)methylsulfonamido)pyrimidine-4-carboxamide (0.365 g, 1.00 mmol) in dioxane (5 mL) was added 2-(4-(4-fluorophenoxy)phenyl)-4,4,5,5-tetramethyl-1,3,2-dioxaborolane (0.379 g, 1.21 mmol), 2M aqueous Na$_2$CO$_3$ (1.0 mL, 2.0 mmol), and PdCl$_2$(dppf) (0.046 g, 0.056 mmol). The reaction vessel was flushed with argon, sealed, and heated at 80° C. overnight. After cooling, the reaction mixture was evaporated in vacuo to a residue. The residue was chromatographed over silica gel with 30-80% EtOAc in hexanes. The product fractions were evaporated to a residue and triturated with 5 mL 1:1 EtOAc/hexanes. The solid was filtered off, rinsed twice with 1 mL 1:1 EtOAc/hexanes, and dried under vacuum at 40° C. to give 6-(N-((2,2-dimethyl-1,3-dioxolan-4-yl)methyl)methylsulfonamido)-2-(4-(4-fluorophenoxy)phenyl)pyrimidine-4-carboxamide as a tan-orange powder (0.416 g, 0.805 mmol, 80% yield). $^1$H NMR (400 MHz, DMSO-d$_6$): 8.61-8.55 (3H, m), 8.01 (1H, s), 7.94-7.91 (1H, m), 7.33-7.26 (2H, m), 7.23-7.17 (2H, m), 7.10 (2H, d, J=9.0 Hz), 4.44-4.37 (1H, m), 4.35-4.28 (1H, m), 4.22-4.15 (1H, m), 4.07 (1H, dd, J=8.8 Hz, 6.6 Hz), 3.81 (1H, dd, J=8.6 Hz, 5.3 Hz), 3.52 (3H, s), 1.35 (3H, s), 1.23 (3H, s). LC/MS: m/z=517.2 [M+H]$^+$.

Scheme 36

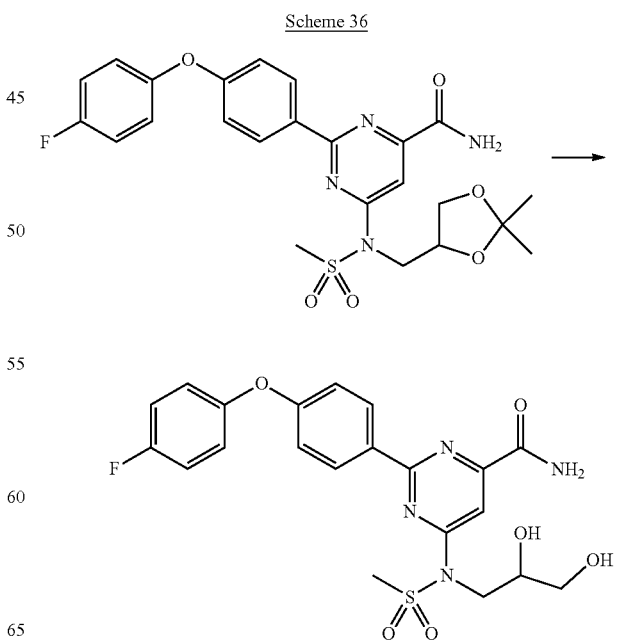

6-(N-(2,3-dihydroxypropyl)methylsulfonamido)-2-fluorophenoxy)phenyl)pyrimidine-4-carboxamide To a suspension of 6-(N-((2,2-dimethyl-1,3-dioxolan-4-yl)methyl)methyl sulfonamido)-2-(4-(4-fluorophenoxy)phenyl)pyrimidine-4-carboxamide (0.308 g, 0.596 g) in 85:15 DCM/MeOH (5 mL) was added 4M HCl in dioxane (1.0 mL). After 1 hour, water (0.5 mL) was added and a solid formed. After 1 hour, the solid was filtered and washed successively twice with 2 mL DCM, twice with 1 mL MeOH, once with 3 mL MeOH, and twice with 1 mL DCM. The solid was dried under vacuum at 40° C. to give 6-(N-(2,3-dihydroxypropyl)methylsulfonamido)-2-(4-(4-fluorophenoxy)phenyl)pyrimidine-4-carboxamide as a white powder (0.200 g, 0.420 mmol, 70% yield). $^1$H NMR (400 MHz, DMSO-d$_6$): 8.63-8.54 (3H, m), 8.01 (1H, s), 7.84 (1H, s), 7.33-7.26 (2H, m), 7.23-7.17 (2H, m), 7.09 (2H, d, J=8.8 Hz), 5.08 (1H, d, J=5.5 Hz), 4.80 (1H, t, J=5.7 Hz), 4.31-4.24 (1H, m), 4.05-3.96 (1H, m), 3.86-3.77 (1H, m), 3.54 (3H, s), 3.45-3.35 (2H, m). LC/MS: m/z=477.1 [M+H]$^+$.

Example 16

Preparation of (S)-2-((1-amino-1-oxopropan-2-yl)amino)-6-(4-(4-fluorophenoxy)phenyl)pyrimidine-4-carboxamide (Cpd No. 54)

Scheme 37

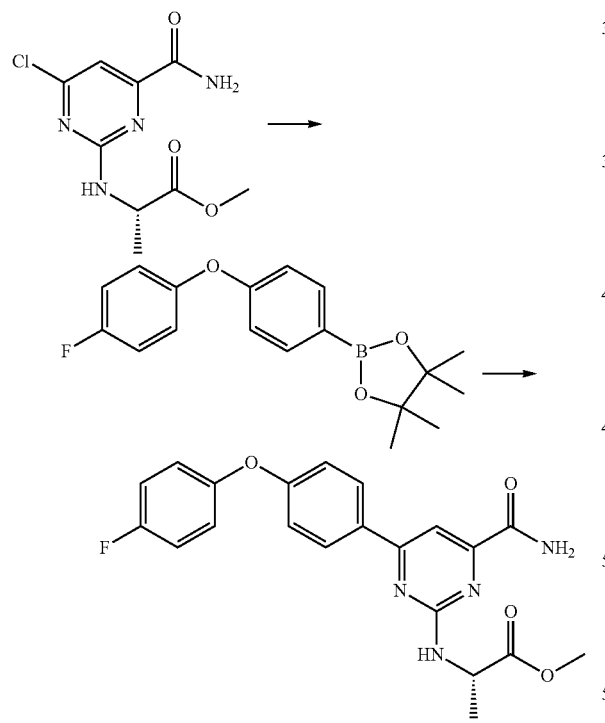

(S)-methyl 2-((4-carbamoyl-6-(4-(4-fluorophenoxy)phenyl)pyrimidin-2-yl)amino)propanoate To a mixture of (S)-methyl 2-((4-carbamoyl-6-chloropyrimidin-2-yl)amino)propanoate (0.642 g, 2.48 mmol) in dioxane (12.5 mL) was added 2-(4-(4-fluorophenoxy)phenyl)-4,4,5,5-tetramethyl-1,3,2-dioxaborolane (0.861 g, 2.74 mmol), 2M aqueous Na$_2$CO$_3$ (2.50 mL, 5.00 mmol), and PdCl$_2$(dppf) (0.105 g, 0.129 mmol). The reaction vessel was flushed with argon, sealed, and heated at 80° C. for 5 h. After cooling, the reaction mixture was evaporated in vacuo and the residue chromatographed over silica gel with 20-60% acetone in hexanes. The product fractions were evaporated in vacuo to give (S)-methyl 2-((4-carbamoyl-6-(4-(4-fluorophenoxy)phenyl)pyrimidin-2-yl)amino)propanoate as a tan-yellow glass (0.911 g, 2.22 mmol, 89% yield). LC/MS: m/z=411.2 [M+H]$^+$.

Scheme 38

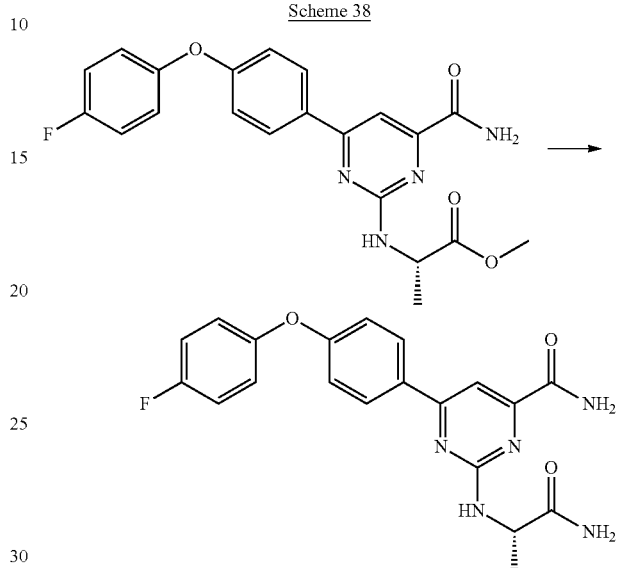

(S)-2-((1-amino-1-oxopropan-2-yl)amino)-6-(4-(4-fluorophenoxy)phenyl)pyrimidine-4-carboxamide A solution of (S)-methyl 2-((4-carbamoyl-6-(4-(4-fluorophenoxy)phenyl)pyrimidin-2-yl)amino)propanoate (0.911 g, 2.22 mmol) in 7M ammonia in methanol (20 mL, 140 mmol) was heated in a sealed tube for 4 days at 50° C. After cooling, the reaction mixture was evaporated in vacuo and the residue chromatographed over silica gel with 50-100% acetone in hexanes. The product fractions were evaporated in vacuo and the resulting solid triturated with 10 mL 1:1 acetone/hexanes. The solid was filtered, rinsed once with 5 mL 1:1 acetone/hexanes, and dried under vacuum at 40° C. to give (S)-2-((1-amino-1-oxopropan-2-yl)amino)-6-(4-(4-fluorophenoxy)phenyl)pyrimidine-4-carboxamide as a white powder (0.713 g, 1.80 mmol, 81% yield). $^1$H NMR (400 MHz, CD$_3$OD): 8.20 (2H, d, J=8.8 Hz), 7.76 (1H, s), 7.21-7.08 (4H, m), 7.06 (2H, d, J=8.8 Hz), 4.47 (1H, br s), 1.54 (3H, d, J=7.2 Hz). LC/MS: m/z=396.1 [M+H]$^+$.

Example 17

Preparation of (S)-4-((1-amino-1-oxopropan-2-yl)amino)-6-(4-(4-fluorophenoxy)phenyl)pyrimidine-2-carboxamide (Cpd No. 55)

Scheme 39

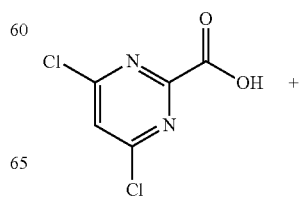

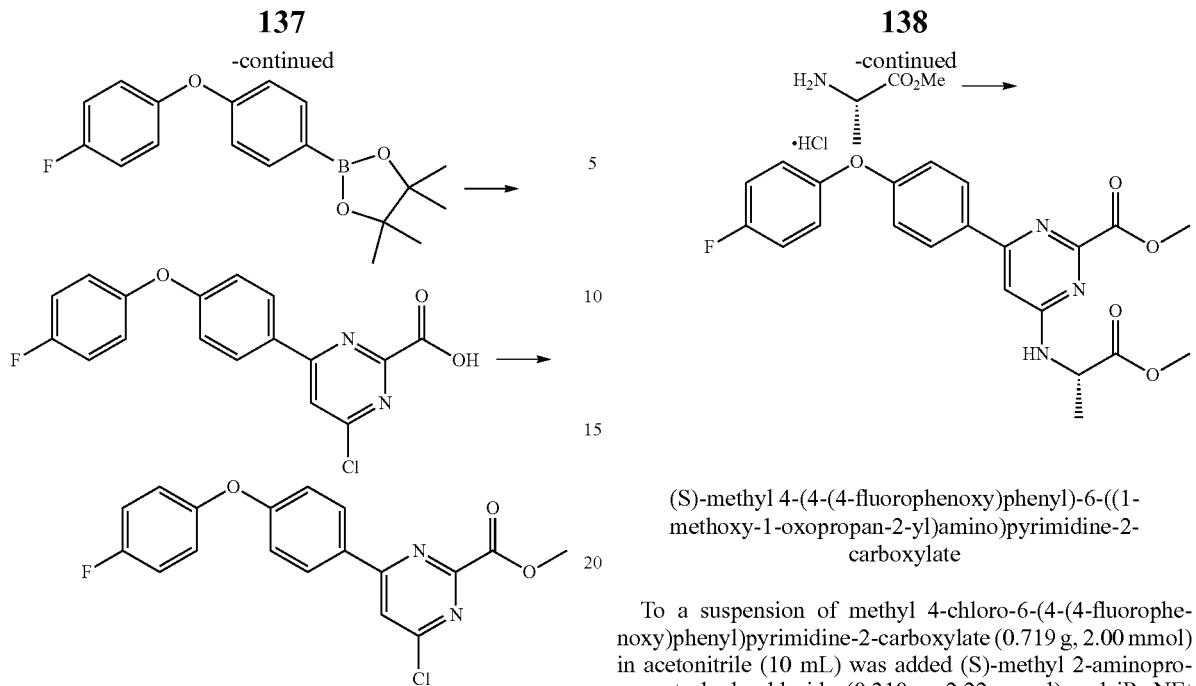

Methyl 4-chloro-6-(4-(4-fluorophenoxy)phenyl)pyrimidine-2-carboxylate

To a mixture of 4,6-dichloropyrimidine-2-carboxylic acid (1.931 g, 10.01 mmol) in dioxane (50 mL) was added 2-(4-(4-fluorophenoxy)phenyl)-4,4,5,5-tetramethyl-1,3,2-dioxaborolane (3.459 g, 11.01 mmol), 2M aqueous $Na_2CO_3$ (10.0 mL, 20.0 mmol), and $PdCl_2(dppf)$ (0.413 g, 0.506 mmol). The reaction vessel was flushed with argon, sealed, and heated at 100° C. for 5 h. After cooling, the reaction was partitioned between 100 mL EtOAc and 50 mL water. Some solid formed and was filtered off. The organic layers were separated and washed once more with 25 mL brine which caused more solid to form. The organic layer and the filtered solids were re-combined and evaporated in vacuo. To this residue was added MeOH (100 mL) and concentrated $H_2SO_4$ (1 mL). The mixture was heated at reflux for 2 h then cooled and quenched by addition of solid $NaHCO_3$. The mixture was evaporated in vacuo and the residue chromatographed over silica gel with 5-30% EtOAc/hexanes. The product fractions were evaporated and the residue triturated with 10 mL 1:1 EtOAc/hexanes. The solid was filtered, rinsed twice with 2 mL 1:1 EtOAc/hexanes and air-dried to give methyl 4-chloro-6-(4-(4-fluorophenoxy)phenyl)pyrimidine-2-carboxylate as a white powder (1.240 g, 3.46 mmol, 35% yield). LC/MS: m/z=359.2 [M+H]$^+$.

Scheme 40

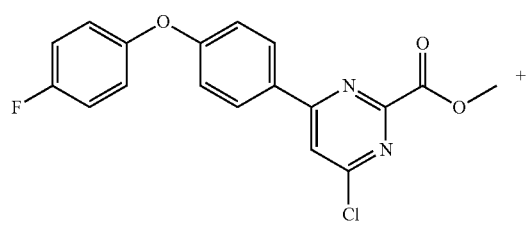

(S)-methyl 4-(4-(4-fluorophenoxy)phenyl)-6-((1-methoxy-1-oxopropan-2-yl)amino)pyrimidine-2-carboxylate To a suspension of methyl 4-chloro-6-(4-(4-fluorophenoxy)phenyl)pyrimidine-2-carboxylate (0.719 g, 2.00 mmol) in acetonitrile (10 mL) was added (S)-methyl 2-aminopropanoate hydrochloride (0.310 g, 2.22 mmol) and $iPr_2NEt$ (0.77 mL, 4.4 mmol). The mixture was heated at 50° C. for 2 h than 80° C. for 6 days. The mixture was evaporated in vacuo and the residue chromatographed over silica gel with 20-60% EtOAc/hexanes. The product fractions were evaporated in vacuo to give (S)-methyl 4-(4-(4-fluorophenoxy)phenyl)-6-((1-methoxy-1-oxopropan-2-yl)amino)pyrimidine-2-carboxylate as a pale tan oil (0.479 g, 1.13 mmol, 56% yield). LC/MS: m/z=426.2 [M+H]$^+$.

Scheme 41

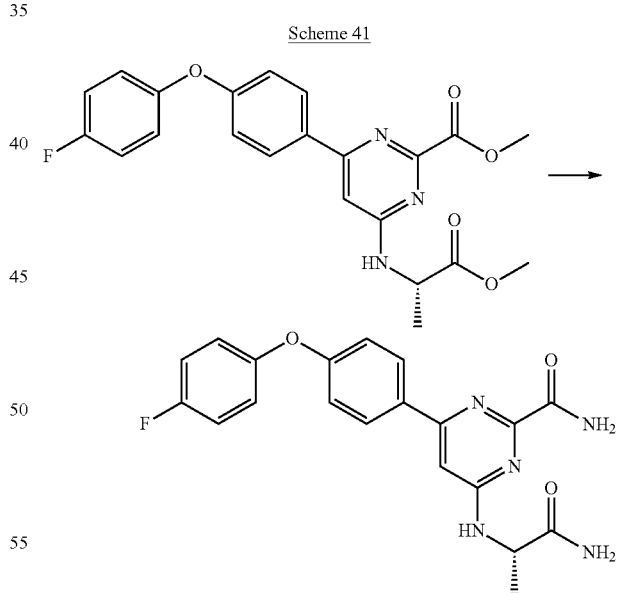

(S)-4-((1-amino-1-oxopropan-2-yl)amino)-6-(4-(4-fluorophenoxy)phenyl)pyrimidine-2-carboxamide A solution of (S)-methyl 4-(4-(4-fluorophenoxy)phenyl)-6-((1-methoxy-1-oxopropan-2-yl)amino)pyrimidine-2-carboxylate (0.479 g, 1.13 mmol) in 7M ammonia in methanol (70 mmol) was heated in a sealed tube overnight at 50° C. After cooling, the reaction mixture was evaporated in vacuo.

The residue was triturated with 5 mL 1:1 acetone/hexanes, filtered, rinsed once with 5 mL 1:1 acetone/hexanes and dried under vacuum at 40° C. to give (S)-4-((1-amino-1-oxopropan-2-yl)amino)-6-(4-(4-fluorophenoxy)phenyl)pyrimidine-2-carboxamide as a white powder (0.344 g, 0.870 mmol, 77% yield). $^1$H NMR (400 MHz, DMSO-d$_6$): 8.08 (2H, br d, J=6.6 Hz), 8.01 (1H, s), 7.77 (1H, br d, J=6.8 Hz), 7.66 (1H, s), 7.55 (1H, s), 7.32-7.24 (2H, m), 7.21-7.14 (2H, m), 7.13-7.04 (4H, m), 4.69-4.58 (1H, m), 1.33 (3H, d, J=6.8 Hz). LC/MS: m/z=396.1 [M+H]$^+$.

Example 18

Preparation of (S)-6-((1-amino-1-oxopropan-2-yl)oxy)-2-(4-(4-fluorophenoxy)phenyl)pyrimidine-4-carboxamide (Cpd No. 56)

warm up slowly and after 2 h was quenched with 2 mL 10% citric acid solution. The reaction mixture was partitioned between 50 mL EtOAc and 25 mL brine and the organic fraction dried over MgSO4, filtered and concentrated in vacuo. The residue was dissolved in dioxane (10 mL) and 2-(4-(4-fluorophenoxy)phenyl)-4,4,5,5-tetramethyl-1,3,2-dioxaborolane (0.691 g, 2.20 mmol), 2M aqueous Na$_2$CO$_3$ (2.0 mL, 4.0 mmol), and PdCl$_2$(dppf) (0.091 g, 0.11 mmol) were added. The reaction vessel was flushed with argon, sealed, and heated at 100° C. overnight. After cooling, the reaction mixture was evaporated in vacuo and the residue chromatographed over silica gel with 10-50% acetone in hexanes. The product fractions were evaporated in vacuo to give (S)-ethyl 2-((6-carbamoyl-2-(4-(4-fluorophenoxy)phenyl)pyrimidin-4-yl)oxy)propanoate as a pale tan oil (0.762 g, 1.79 mmol, 90% yield). LC/MS: m/z=426.2 [M+H]$^+$.

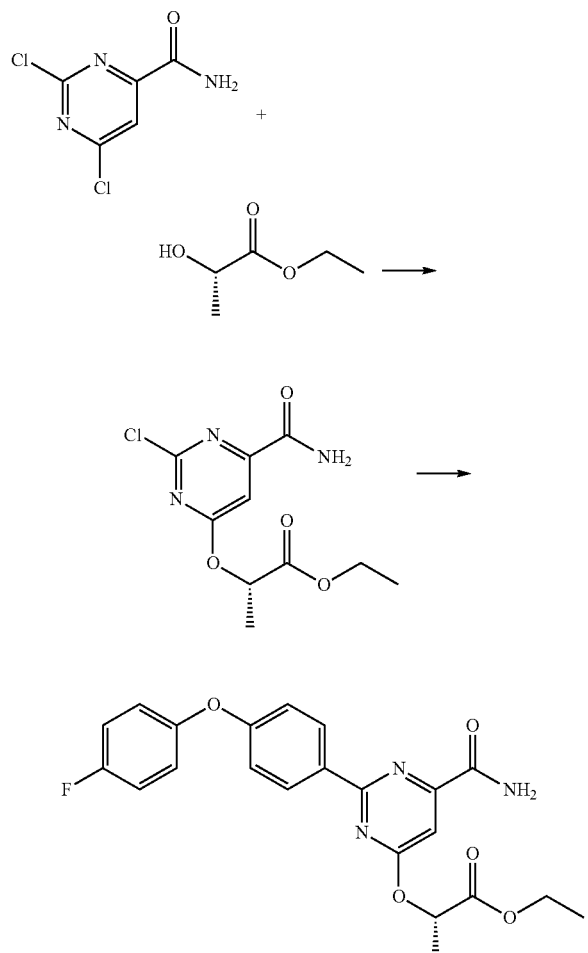

(S)-Ethyl 2-((6-carbamoyl-2-(4-(4-fluorophenoxy)phenyl)pyrimidin-4-yl)oxy)propanoate To a solution of 2,6-dichloropyrimidine-4-carboxamide (0.385 g, 2.01 mmol) in THF (10 mL) was added (S)-ethyl 2-hydroxypropanoate (0.26 mL, 2.3 mmol). The mixture was cooled on a dry-ice acetone bath and 60% NaH in mineral oil (0.094 g, 2.4 mmol) was added. The reaction was allowed to

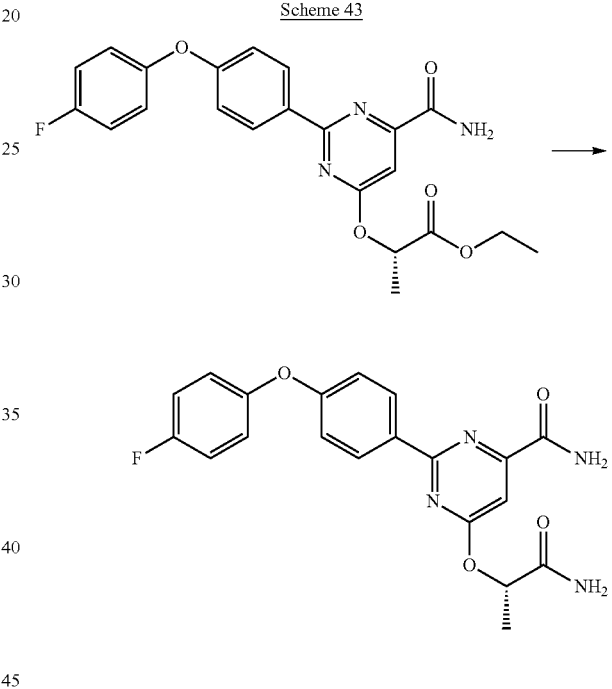

(S)-6-((1-amino-1-oxopropan-2-yl)oxy)-2-(4-(4-fluorophenoxy)phenyl)pyrimidine-4-carboxamide A solution of (S)-ethyl 2-((6-carbamoyl-2-(4-(4-fluorophenoxy)phenyl)pyrimidin-4-yl)oxy)propanoate (0.762 g, 1.79 mmol) in 7M ammonia in methanol (10 mL, 70 mmol) was heated in a sealed tube overnight at 50° C. After cooling, the reaction mixture was evaporated in vacuo and the residue chromatographed over silica gel with 25-100% acetone in hexanes. The product fractions were evaporated in vacuo and the residue triturated with 5 mL MeOH. The solid was filtered and rinsed again with 2 mL MeOH. The MeOH filtrate and washings were evaporated in vacuo and triturated with 2 mL MeOH, filtered, and rinsed again with 1 mL MeOH. The first and second batches of solid were combined and dried under vacuum at 40° C. to give (S)-6-((1-amino-1-oxopropan-2-yl)oxy)-2-(4-(4-fluorophenoxy)phenyl)pyrimidine-4-carboxamide as a white powder (0.220 g, 0.555 mmol, 31% yield). $^1$H NMR (400 MHz, DMSO-d$_6$): 8.59 (2H, d, J=8.8 Hz), 8.50 (1H, s), 7.96 (1H, s), 7.69 (1H, s), 7.33-7.25 (2H, m), 7.24

(1H, s), 7.23-7.15 (3H, m), 7.06 (2H, d, J=8.8 Hz), 5.36 (1H, q, J=6.8 Hz), 1.52 (3H, d, J=7.0 Hz). LC/MS: m/z=397.0 [M+H]$^+$.

Example 19

Preparation of (S)-6-((1-amino-1-oxopropan-2-yl)amino)-2-(4-((4-trifluoromethyl)pyridine-2-yl)oxy)phenyl)pyrimidine-4-carboxamide (Cpd No. 57)

Scheme 44

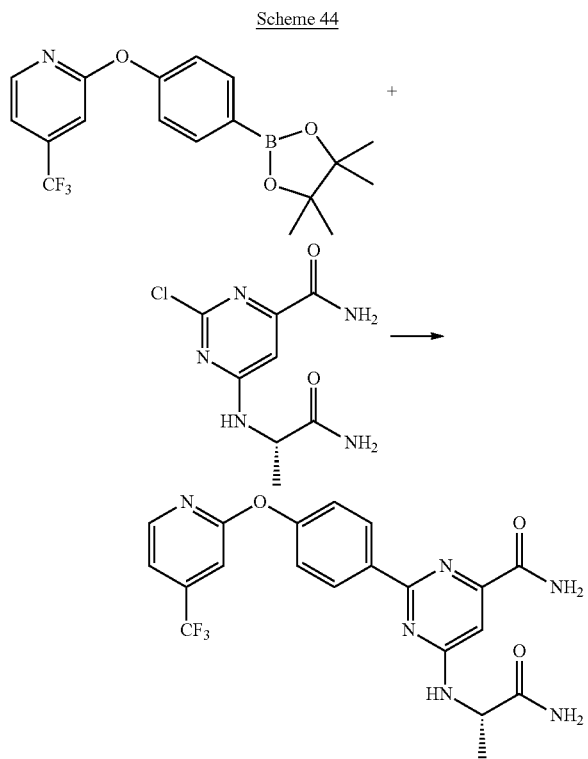

A sealed glass vial containing a mixture of 2-(4-(4,4,5,5-tetramethyl-1,3,2-dioxaborolan-2-yl)phenoxy)-4-(trifluoromethyl)pyridine (182 mg, 0.5 mmol), 6-(1-carbamoyl-ethylamino)-2-chloro-pyrimidine-4-carboxylic acid amide (122 mg, 0.5 mmol), PdCl$_2$(PPh$_3$)$_2$ (28 mg, 0.04 mmol, Aldrich), Cs$_2$CO$_3$ (325 mg, 1 mmol, Aldrich) in a mixed solvent of ethylene glycol dimethyl ether (1 mL), water (1 mL) and ethanol (0.5 mL) was heated at 100° C. for 2 h. After cooling to room temperature, the mixture was diluted with brine (2 mL) and extracted with EtOAc (2×25 mL). The combined organic layers were dried over Na$_2$SO$_4$, filtered, and concentrated on a rotary evaporator. The residue was purified via silica chromatography (0-10% MeOH/CH$_2$Cl$_2$) to give (S)-6-((1-amino-1-oxopropan-2-yl)amino)-2-(4-(4-trifluoromethyl)pyridine-2-yl)oxy)phenyl)pyrimidine-4-carboxamide as white solid, which was further triturated with methanol and dried under vacuum (59 mg, 26%). $^1$H NMR (400 MHz, DMSO-d$_6$): 8.60 (2H, d, J=8.8 Hz), 8.44 (1H, d, J=5.2 Hz), 8.32 (1H, br), 7.98 (1H, d, J=6.8 Hz), 7.74 (1H, bs), 7.57-7.52 (3H, m), 7.27 (2H, d, J=6.4 Hz), 7.13 (1H, s), 7.02 (1H, bs), 4.59 (1H, m), 1.38 (3H, d, J=7.2 Hz). LC/MS: m/z=447 [M+H]$^+$.

Example 20

Preparation of 6-((S)-1-Carbamoyl-ethylamino)-2-(4-hydroxy-phenyl)-pyrimidine-4-carboxylic acid amide (Cpd No. 65)

Scheme 45

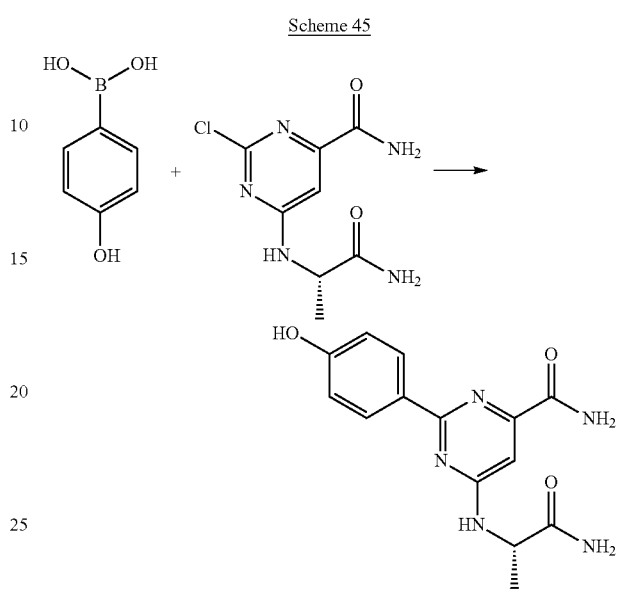

A 100 mL round-bottom flask was charged with 4-hydroxyphenyl boronic acid (1 g, 7.25 mmol), 6-((S)-1-carbamoyl-ethylamino)-2-chloro-pyrimidine-4-carboxylic acid amide (7.25 mmol, 1.76 g), PdCl$_2$(PPh$_3$)$_2$ (Aldrich, 0.5 mmol, 0.3562 g), Na$_2$CO$_3$ (7.25 mL, 2M aqueous solution), and dioxane (5 mL). The flask was purged with nitrogen and heated to 100° C. for 16 h at which time the reaction was complete. The reaction mixture was concentrated under reduced pressure. The residue was suspended in 50% MeOH in DCM, filtered by vacuum, and the filter cake was discarded. The filtrate was concentrated under reduced pressure and was suspended in DCM, stirred for one hour, and filtered by vacuum filtration to provide the title compound as a light brown powder (2 g, 91%). $^1$H NMR (CD$_3$OD) 8.25-8.09 (m, 2H), 7.09-6.92 (m, 1H), 6.82-6.70 (m, 2H), 4.62-4.40 (m, 1H), 1.49-1.31 (m, 3H). LC/MS: m/z 301[M+H]$^+$.

Example 21

Preparation of 6-((S)-1-Carbamoyl-ethylamino)-2-[4-(4-cyano-phenoxy)-phenyl]-pyrimidine-4-carboxylic acid amide (Cpd No. 66)

Scheme 46

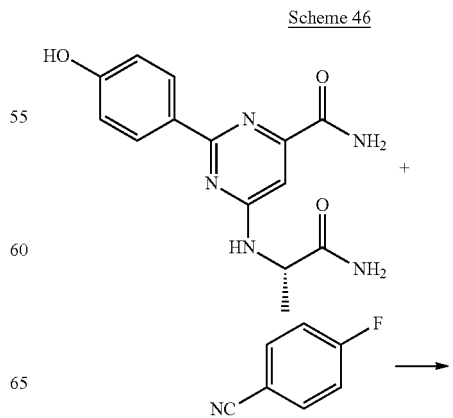

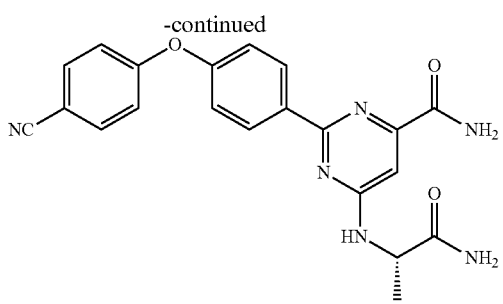

A 50-mL vial with a screw-top septum was charged with 6-((S)-1-carbamoyl-ethylamino)-2-(4-hydroxy-phenyl)-pyrimidine-4-carboxylic acid amide (100 mg, 0.3 mmol), 4-fluorobenzo-nitrile (40 mg, 0.3 mmol), potassium carbonate (92 mg, 0.7 mmol), and N,N-dimethylformamide (5 mL). The flask was purged with nitrogen and heated to 100° C. for 16 h at which time the reaction was complete. The mixture was then diluted with 20 mL water and extracted with 2×20 mL EtOAc. The combined organic layers were dried over sodium sulfate and concentrated under vacuum. The residue was dissolved in 20% methanol/chloroform and passed through a short plug of silica gel. The fractions containing the desired material were concentrated and suspended in a solution of 20% EtOAc/hexane. The suspension was filtered by vacuum and air was allowed to pass over the cake for one hour. The cake was then transferred to a scintillation vial, powdered, and heated under vacuum for one hour to provide the title compound as a white solid (44 mg, 33%). $^1$H NMR (DMSO-$d_6$): 8.66-8.59 (m, 2H), 8.35-8.28 (s, 1H), 8.02-7.95 (m, 1H), 7.91-7.84 (m, 2H), 7.79-7.70 (s, 1H), 7.59-7.51 (s, 1H), 7.25-7.15 (m, 4H), 7.14-7.08 (s, 1H), 7.05-6.97 (s, 1H), 4.64-4.49 (m, 1H), 1.43-1.31 (m, 3H). LC/MS: m/z 402[M+H]$^+$.

Example 22

Preparation of (S)-6-((1-amino-1-oxopropan-2-yl)amino)-2-(2-(2-aminopyridin-4-yl)-4-chlorophenoxy)pyrimidine-4-carboxamide (Cpd No. 67)

Scheme 47

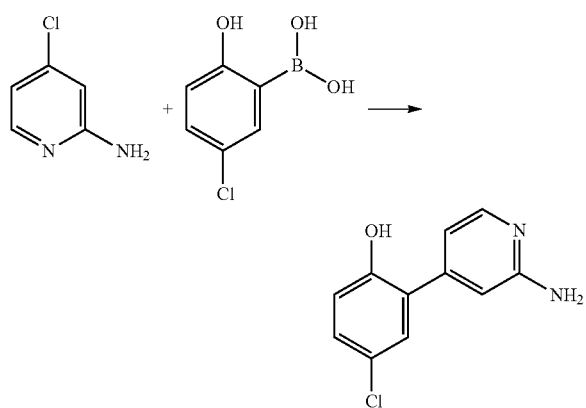

2-(2-aminopyridin-4-yl)-4-chlorophenol

A mixture of 4-chloro-2-aminopyridine (1.28 g, 10 mmol), boronic acid (1.72 g, 10 mmol), Na$_2$CO$_3$ (3.18 g, 30 mmol) and Pd(PPh$_3$)$_2$Cl$_2$ in DME/EtOH/H$_2$O (4 mL/2 mL/4 mL) was purged with Ar for one minute, then stirred at 100° C. for 14 hrs. The reaction mixture was cooled to 0° C., its pH was adjusted to 5 using 6N HCl, and diluted with EtOAc. The organic layer was isolated, dried over MgSO4, and concentrated under vacuum. The residue was subjected to silica gel flash chromatography using dichloromethane/methanol as the eluent to give 2-(2-aminopyridin-4-yl)-4-chlorophenol as a yellowish solid (1.8 g, yield 82%). LC/MS: m/z=221 [M+H]$^+$, (m/z+H) 221.

Scheme 48

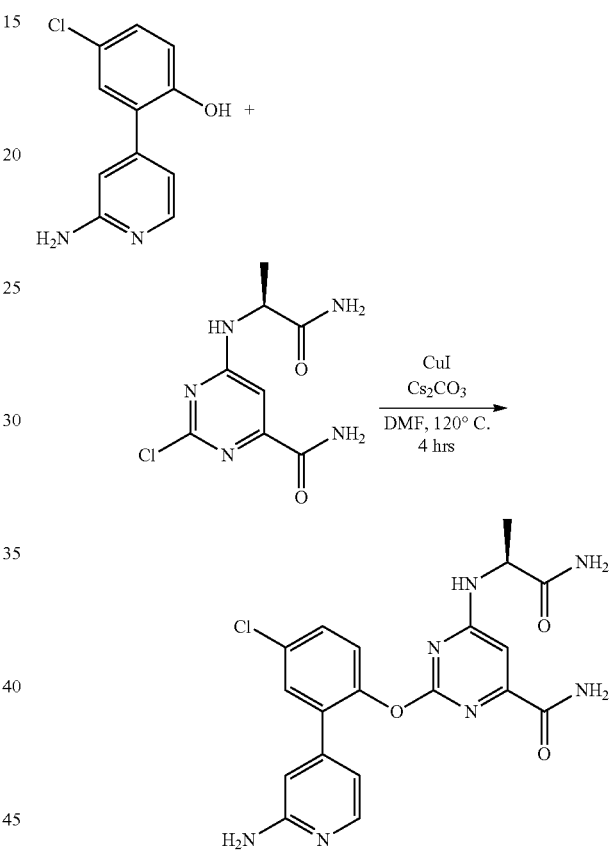

(S)-6-((1-amino-1-oxopropan-2-yl)amino)-2-(2-(2-aminopyridin-4-yl)-4-chlorophenoxy)pyrimidine-4-carboxamide A mixture of 2-(2-aminopyridin-4-yl)-4-chlorophenol (110 mg, 0.5 mmol), (S)-6-((1-amino-1-oxopropan-2-yl)amino)-2-chloropyrimidine-4-carboxamide (122 mg, 0.5 mmol), CuI (10 mg, 0.05 mmol) and Cs$_2$CO$_3$ (191 mg, 0.5 mmol) in DMF (3 mL) was stirred at 120° C. for 4 hrs. The reaction mixture was cooled to room temperature, worked up with dichloromethane and subjected to flash chromatography (DCM/methanol) to give (S)-6-((1-amino-1-oxopropan-2-yl)amino)-2-(2-(2-aminopyridin-4-yl)-4-chlorophenoxy)pyrimidine-4-carboxamide as a white solid (189 mg, yield 85%). $^1$H NMR (CD$_3$OD): 7.82-8.05 (1H, br), 7.6 (2H, m), 7.40 (2H, m), 6.80 (1H, m), 6.60 (2H, m), 4.23-4.10 (1H, m), 1.35 (3'-1, d, J=7.0 Hz). LC/MS: m/z=428 [M+H]$^+$.

Example 23

Preparation of 2-(pyridazin-4-yl)-4-(trifluoromethyl)phenol

Scheme 49

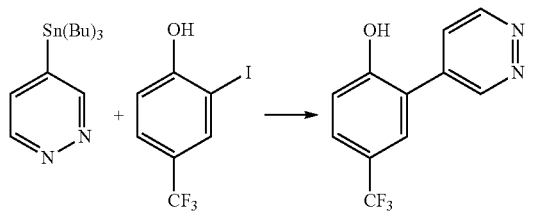

To a solution of 2-iodo-4-trifluoromethylphenol (2.6 g, 9.0 mmol) in DMF were added 4-(tributylstannyl)pyrazine (3.5 g, 9.49 mmol) and CsF (2.73 g, 18 mmol). The reaction mixture was stirred for 5 minutes, then Pd(PPh$_3$)$_4$ (0.52 g, 0.45 mmol) and CuI (178 mg, 0.94 mmol) were added. After purging with Ar for 1 minute, the mixture was stirred under Ar for 14 h at 45° C. The reaction was worked up with EtOAc. Removal of EtOAc followed by silica gel flash chromatography using dichloromethane/methanol as the eluent gave 2-(pyridazin-4-yl)-4-(trifluoromethyl)phenol as a slightly pink solid (1.08 g, yield 50%). LC/MS: m/z=241 [M+H]$^+$.

Example 24

Preparation of (S)-6-((1-amino-1-oxopropan-2-yl)amino)-2-(2-(4-fluorophenoxy)pyridin-4-yl)pyrimidine-4-carboxamide (Cpd No. 68)

Scheme 50

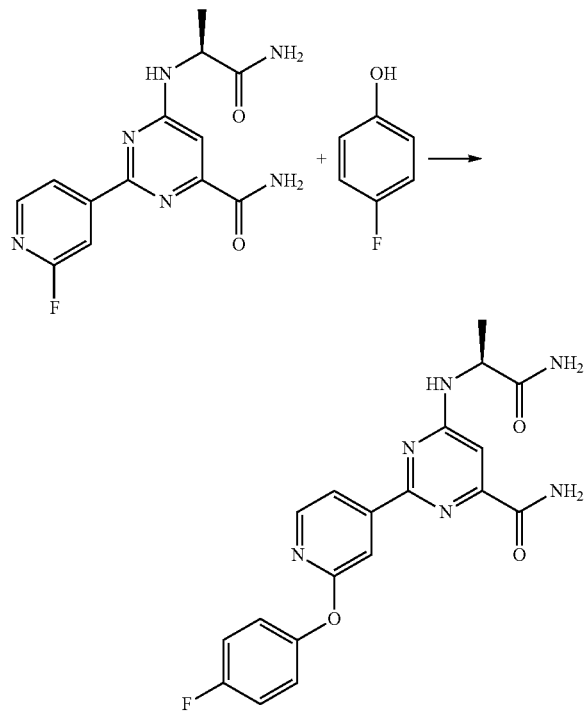

A mixture of (S)-6-((1-amino-1-oxopropan-2-yl)amino)-2-(2-fluoropyridin-4-yl)pyrimidine-4-carboxamide (60 mg, 0.2 mmol), 4-fluorophenol (40 mg, 0.2 mmol) and Cs$_2$CO$_3$ (76 mg, 0.2 mmol) in DMF (1 mL) was placed in a microwave reaction vial and heated in a microwave oven at 160° C. for 20 minutes. The reaction was worked up with DCM then dried and evaporated. The residue was subjected to C18 flash chromatography using acetonitrile/H$_2$O/0.1 TFA as the eluent and neutralized to give (S)-6-((1-amino-1-oxopropan-2-yl)amino)-2-(2-(4-fluorophenoxy)pyridin-4-yl)pyrimidine-4-carboxamide as white solid (40 mg, yield 50%). $^1$H NMR (CD$_3$OD): 7.90-8.21 (3H, m), 6.90-7.2 (5H, m), 4.4 (1H, m), 1.35 (3H, d, J=7.0 Hz). LC/MS: m/z=398 [M+H]$^+$.

Example 25

Preparation of (S)-6-((1-amino-1-oxopropan-2-yl)amino)-2-(6-(4-fluorophenoxy)pyridin-3-yl)pyrimidine-4-carboxamide (Cpd No. 69)

Scheme 51

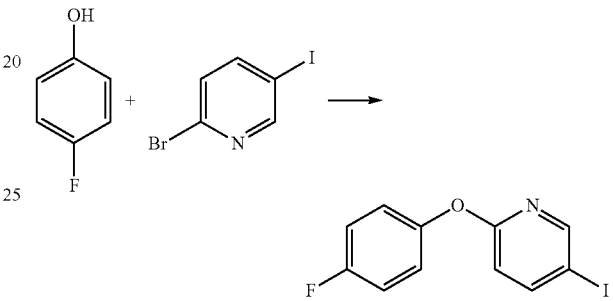

2-(4-fluoro-phenoxy)-5-iodo-pyridine

A mixture of 4-fluorophenol (1.12 g, 10 mmol), 2-bromo-5-iodopyridine (2.84 g, 10 mmol) and Cs$_2$CO$_3$ (3.83 g, 10 mmol) in DMF was stirred at 120° C. for 4 hrs. The reaction was worked up with EtOAc to give 2-(4-fluoro-phenoxy)-5-iodo-pyridine which was used for next step without further purification (crude yield 100%, yellowish solid). LC/MS: m/z=317 [M+H]$^+$.

Scheme 52

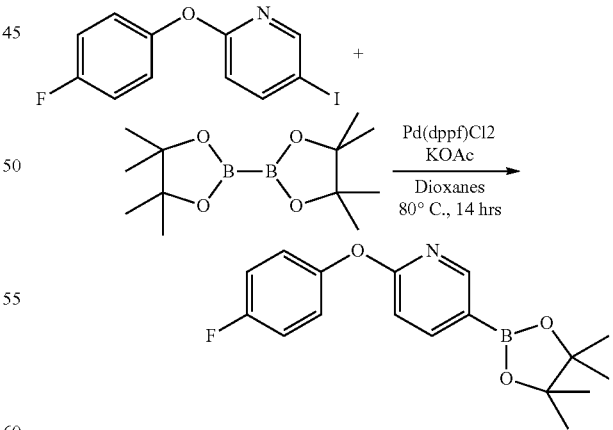

2-(4-fluoro-phenoxy)-5-(4,4,5,5-tetramethyl-[1,3,2]dioxaborolan-2-yl)-pyridine

A mixture of 2-(4-fluoro-phenoxy)-5-iodo-pyridine (6.75 g, 21.3 mmol), pinacol diborane (5.42 g, 21.3 mmol), KOAc (6.26 g, 64 mmol) and Pd(dppf)Cl$_2$ (0.82 g, 1 mmol) in dioxanes was purged with Ar for 2 minutes. The mixture was stirred under Ar for 14 hrs and worked up with EtOAc. Removal of EtOAc followed by silica gel flash chromatography (Hexanes/EtOAc) gave 2-(4-fluoro-phenoxy)-5-(4,4,5,5-tetramethyl-[1,3,2]dioxaborolan-2-yl)-pyridine as a colorless solid (4.5 g, yield 67%). LC/MS: m/z=317 [M+H]$^+$

Example 26

Preparation of (S)-6-((1-amino-1-oxopropan-2-yl)amino)-2-(4-(4-fluorophenyl)piperazin-1-yl)pyrimidine-4-carboxamide (Cpd No. 70)

Scheme 53

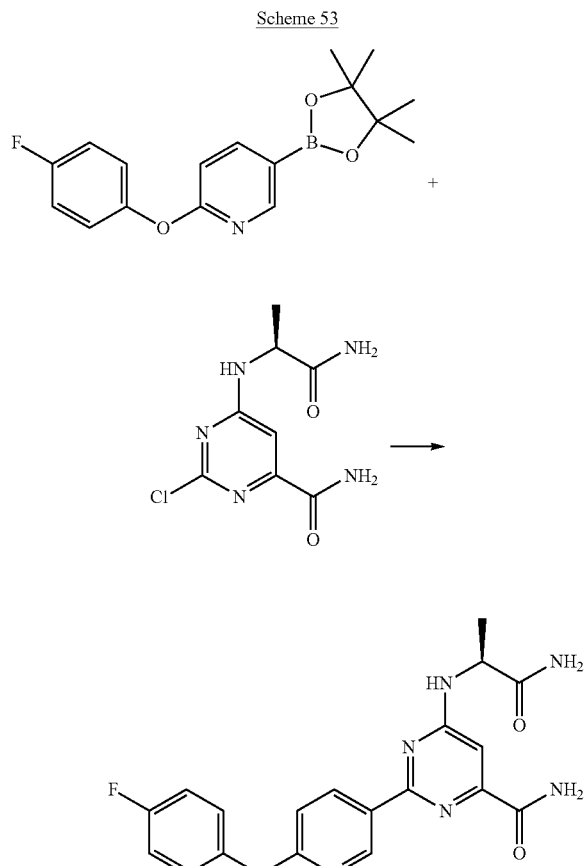

(S)-6-((1-amino-1-oxopropan-2-yl)amino)-2-(6-(4-fluorophenoxy)pyridin-3-yl)pyrimidine-4-carboxamide A mixture of 2-(4-fluorophenoxy)-5-(4,4,5,5-tetramethyl-[1,3,2]dioxaborolan-2-yl)pyridine (158 mg, 0.5 mmol), (S)-6-((1-amino-1-oxopropan-2-yl)amino)-2-chloropyrimidine-4-carboxamide (121 mg, 0.5 mmol), Na$_2$CO$_3$ (2 M, 1 mL, 2 mmol) and Pd(PPh$_3$)$_2$Cl$_2$ (20 mg, 0.025 mmol) in DME/EtOH/H$_2$O (2 mL/1 mL/2 mL) was purged with Ar for one minute, then stirred at 100° C. for 14 hrs. The reaction mixture was then worked up with DCM. The DCM was isolated, dried over MgSO$_4$, and removed under vacuum. The residue was subjected to silica gel flash chromatography using dichloromethane/methanol as the eluent to give (S)-6-((1-amino-1-oxopropan-2-yl)amino)-2-(6-(4-fluorophenoxy)pyridin-3-yl)pyrimidine-4-carboxamide as a gray solid (100 mg, yield 50%). NMR (DMSO-d$_6$): 9.3 (1H, s), 8.9 (1H, m), 8.3 (1H, s), 8.05 (1H, m), 7.75 (1H, s), 7.5 (1H, s), 7.2-7.4 (4H, m), 6.95-7.15 (2H, m), 6.80 (1H, s), 4.5 (1H, m), 1.35 (3H, d, J=7.0 Hz). LC/MS: m/z=398 [M+H]$^+$.

Scheme 54

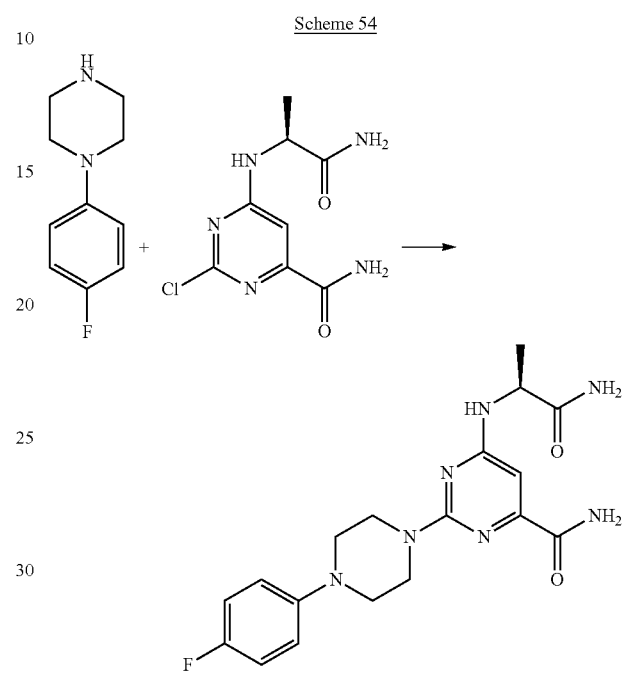

A mixture of 1-(4-fluorophenyl)piperazine (112 mg, 0.62 mmol), (S)-6-((1-amino-1-oxopropan-2-yl)amino)-2-chloropyrimidine-4-carboxamide (150 mg, 0.62 mmol) and Cs$_2$CO$_3$ (235 mg, 0.62 mmol) in DMF (3.0 mL) was stirred at 100° C. for 14 hrs. The reaction was worked up with EtOAc and purified by silica gel flash chromatography (DCM/methanol) to give (S)-6-((1-amino-1-oxopropan-2-yl)amino)-2-(4-(4-fluorophenyl)piperazin-1-yl)pyrimidine-4-carboxamide as a white solid (193 mg, 80%). $^1$H NMR (CD$_3$OD): 6.90-7.1 (4H, m), 6.55 (1H, s), 4.3 (1H, m), 3.98 (4H, m), 3.10 (4H, m), 1.40 (3H, d, J=7.0 Hz). LC/MS: m/z=388 [M+H]$^+$.

Example 27

Preparation of (S)-6-(2-carbamoylpyrrolidin-1-yl)-2-(4-(4-chloro-2-fluorophenoxy)phenyl)pyrimidine-4-carboxamide (Cpd. No. 78)

Scheme 55

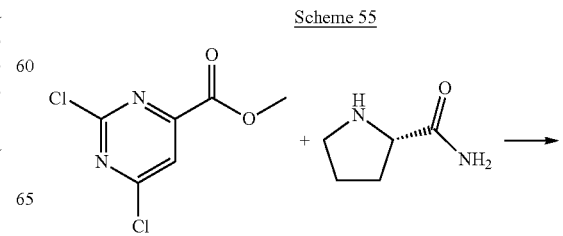

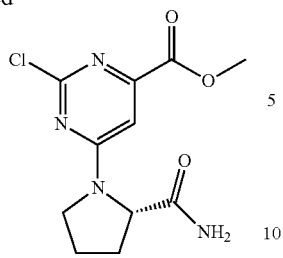

(S)-methyl 6-(2-carbamoylpyrrolidin-1-yl)-2-chloro-pyrimidine-4-carboxylate

To a mixture of methyl 2,6-dichloropyrimidine-4-carboxylate (2.074 g, 10.02 mmol) in acetonitrile (50 mL) was added (S)-pyrrolidine-2-carboxamide (1.150 g, 10.07 mmol) and iPr$_2$NEt (1.92 mL, 11.02 mmol). The mixture was heated at 50° C. overnight and then filtered while still warm. The filter cake was washed with acetonitrile (1×10 mL) then dried under vacuum at 40° C. to give a first batch of (S)-methyl 6-(2-carbamoylpyrrolidin-1-yl)-2-chloropyrimidine-4-carboxylate as a tan solid (0.671 g, 2.36 mmol, 24% yield). The filtrate and washes were evaporated in vacuo and triturated with warm acetonitrile (10 mL). The solid was filtered, washed with acetonitrile (2×5 mL), and dried under vacuum at 40° C. to give a second batch of (S)-methyl 6-(2-carbamoylpyrrolidin-1-yl)-2-chloropyrimidine-4-carboxylate as a solid (0.849 g, 2.98 mmol, 30% yield). LC/MS: m/z=285.1 [M+H]$^+$.

Scheme 56

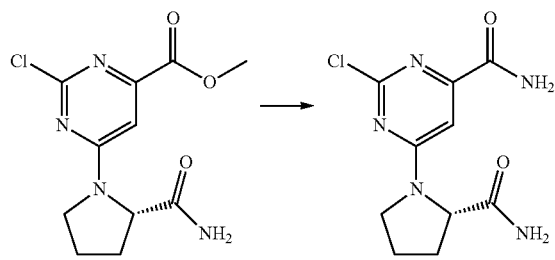

(S)-6-(2-carbamoylpyrrolidin-1-yl)-2-chloropyrimidine-4-carboxamide

A mixture of (S)-methyl 6-(2-carbamoylpyrrolidin-1-yl)-2-chloropyrimidine-4-carboxylate (0.849 g, 2.98 mmol) in 7M ammonia in MeOH (5.0 mL) was stirred at ambient temperature overnight and then filtered. The filter cake was washed with methanol (1×2 mL)) and dried under vacuum at 40° C. to give (S)-6-(2-carbamoylpyrrolidin-1-yl)-2-chloropyrimidine-4-carboxamide as a white powder (0.611 g, 2.27 mmol, 76% yield). LC/MS: m/z=270.2 [M+H]$^+$.

Scheme 57

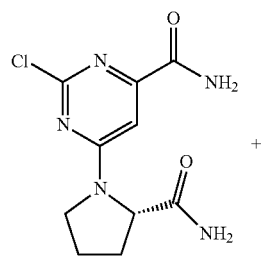

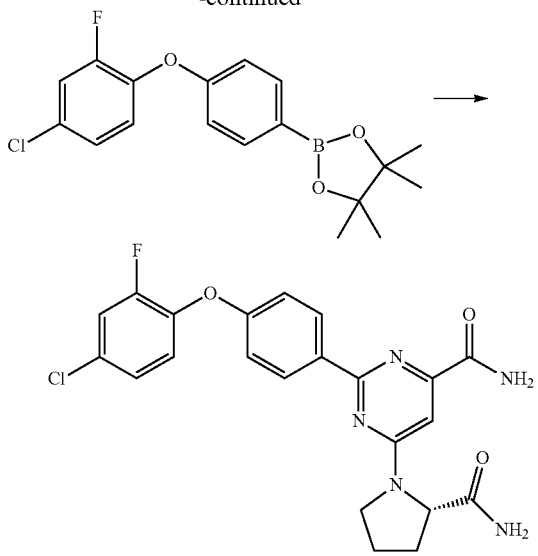

(S)-6-(2-carbamoylpyrrolidin-1-yl)-2-(4-(4-chloro-2-fluorophenoxy)phenyl)pyrimidine-4-carboxamide To a mixture of (S)-6-(2-carbamoylpyrrolidin-1-yl)-2-chloropyrimidine-4-carboxamide (0.272 g, 1.01 mmol) in dioxane (5 mL) was added 2-(4-(4-chloro-2-fluorophenoxy)phenyl)-4,4,5,5-tetramethyl-1,3,2-dioxaborolane (0.387 g, 1.11 mmol), 2M aqueous Na$_2$CO$_3$ (1.0 mL, 2.0 mmol) and PdCl$_2$(dppf) (0.044 g, 0.054 mmol). The reaction vessel was flushed with argon, sealed, and heated at 100° C. overnight. After cooling, the reaction mixture was evaporated in vacuo and the residue chromatographed over silica gel with 25-100% acetone in hexanes. The product fractions were evaporated in vacuo and the residue further chromatographed using reverse-phase chromatography with a 40-70% acetonitrile in water (+0.1% TFA) gradient. The product fractions were pooled and lyophilized. The residue was triturated with acetonitrile (3 mL). The solid was filtered off, washed with acetonitrile (1×1 mL), and dried under vacuum at 40° C. to give (S)-6-(2-carbamoylpyrrolidin-1-yl)-2-(4-(4-chloro-2-fluorophenoxy)phenyl)pyrimidine-4-carboxamide as an off-white powder (0.152 g, 0.333 mmol, 33% yield). $^1$H NMR (400 MHz, DMSO-d$_6$): Exists as a ~70:30 ratio of rotamers: 8.60-8.52 (2H, m), 8.35 (1H, s), 7.80 (1H, s), 7.73-7.67 (1.3H, m), 7.51 (0.7H, s), 7.38-7.28 (2H, m), 7.23 (0.3H, s), 7.09 (0.6H, d, J=8.3 Hz), 7.04 (1.4H, d, J=8.8 Hz), 7.00-6.94 (1.4H, m), 6.77 (0.3H, s), 4.58-4.52 (0.7H, m), 4.33-4.27 (0.3H, m), 3.90-3.81 (0.3H, m), 3.79-3.70 (0.3H, m), 3.70-3.62 (0.7H, m), 3.56-3.47 (0.7H, m), 2.38-2.17 (1H, m), 2.11-1.91 (3H, m). LC/MS: m/z=456.1 [M+H]$^+$.

Example 28

Preparation of 6-((3S,4S)-3,4-dihydroxypyrrolidin-1-yl)-2-(4-(4-fluorophenoxy)phenyl)pyrimidine-4-carboxamide (Cpd No. 79)

Scheme 58

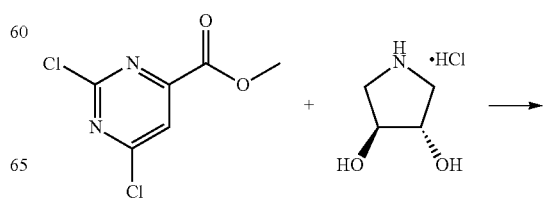

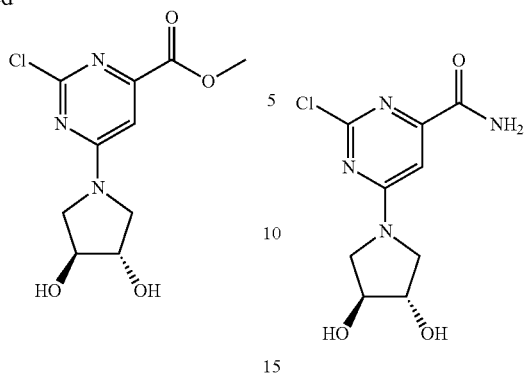

Methyl 2-chloro-6-((3S,4S)-3,4-dihydroxypyrrolidin-1-yl)pyrimidine-4-carboxylate A mixture of the (3S,4S)-pyrrolidine-3,4-diol hydrochloride (0.773 g, 5.54 mmol), methyl 2,6-dichloropyrimidine-4-carboxylate (1.038 g, 5.01 mmol), and iPr$_2$NEt (2.00 mL, 11.5 mmol) in acetonitrile (25 mL) was heated at 50° C. for 3 h. The reaction mixture was evaporated in vacuo and the residue chromatographed over silica gel with 25-75% acetone in hexanes. The product fractions were evaporated in vacuo to give methyl 2-chloro-6-((3S,4S)-3,4-dihydroxypyrrolidin-1-yl)pyrimidine-4-carboxylate as a light tan powder (1.132 g, 4.14 mmol, 83% yield). LC/MS: m/z=274.2 [M+H]$^+$.

Scheme 59

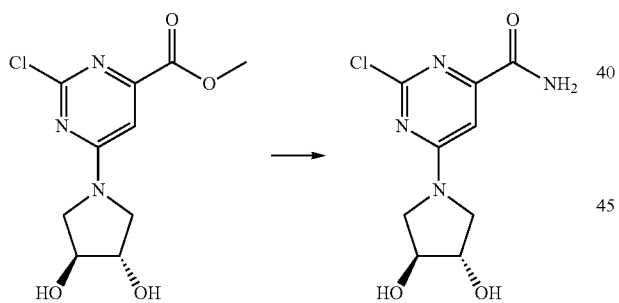

2-Chloro-6-((3S,4S)-3,4-dihydroxypyrrolidin-1-yl)pyrimidine-4-carboxamide

A solution of methyl 2-chloro-6-((3S,4S)-3,4-dihydroxypyrrolidin-1-yl)pyrimidine-4-carboxylate (1.132 g, 4.14 mmol) in 7M ammonia in MeOH (12 mL) was allowed to sit at ambient temperature overnight. The reaction mixture was evaporated in vacuo and the residue was taken up in EtOAc (10 mL). The residue first dissolved then quickly precipitated a solid. After cooling back down to ambient temperature the precipitated solid was filtered off then dried under vacuum at 40° C. to give 2-chloro-6-((3S,4S)-3,4-dihydroxypyrrolidin-1-yl)pyrimidine-4-carboxamide as a tan powder (0.969 g, 3.75 mmol, 91% yield). LC/MS: m/z=259.2 [M+H]$^+$.

Scheme 60

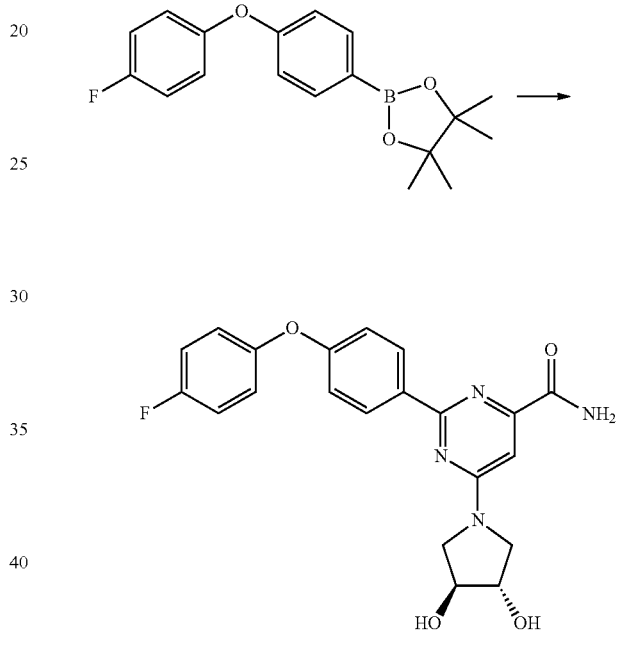

6-((3S,4S)-3,4-dihydroxypyrrolidin-1-yl)-2-(4-(4-fluorophenoxy)phenyl)pyrimidine-4-carboxamide To a mixture of 2-chloro-6-((3S,4S)-3,4-dihydroxypyrrolidin-1-yl)pyrimidine-4-carboxamide (0.261 g, 1.01 mmol) in dioxane (5 mL) was added 2-(4-(4-fluorophenoxy)phenyl)-4,4,5,5-tetramethyl-1,3,2-dioxaborolane (0.349 g, 1.11 mmol), 2M aqueous Na$_2$CO$_3$ (1.0 mL, 2.0 mmol) and PdCl$_2$(dppf) (0.045 g, 0.055 mmol). The reaction vessel was flushed with argon, sealed, and heated at 100° C. overnight. After cooling, the reaction mixture was evaporated in vacuo and the residue chromatographed over silica gel with 50-100% acetone in hexanes. The product fractions were evaporated in vacuo and the residue triturated with acetonitrile (2 mL). The solid was filtered, rinsed with acetonitrile (1×1 mL), and dried under vacuum at 40° C. to give 6-((3S,4S)-3,4-dihydroxypyrrolidin-1-yl)-2-(4-(4-fluorophenoxy)phenyl)pyrimidine-4-carboxamide as a cream-colored powder (0.307 g, 0.748 mmol, 74% yield). $^1$H NMR (400 MHz, DMSO-d$_6$): 8.55 (2H, d, J=8.6 Hz), 8.33 (1H, s), 7.79 (1H, s), 7.32-7.24 (2H, m), 7.20-7.13 (2H, m), 7.05 (2H, d, J=8.8 Hz), 6.90 (1H, s), 5.29 (1H, d, J=3.3 Hz), 5.21 (1H, d, J=3.3 Hz), 4.15-4.09 (1H, m), 4.09-4.05 (1H, m), 3.77-3.62 (3H, m), 3.35-3.30 (1H, m). LC/MS: m/z=411.1 [M+H]⁺.

Example 29

Preparation of 6-(2-carbamoyl-4-methylpiperazin-1-yl)-2-(4-(4-(trifluoromethyl)phenoxy)phenyl)pyrimidine-4-carboxamide (Cpd No. 81)

Scheme 61

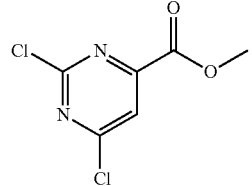

+

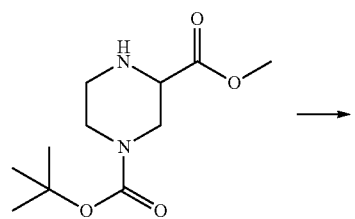

→

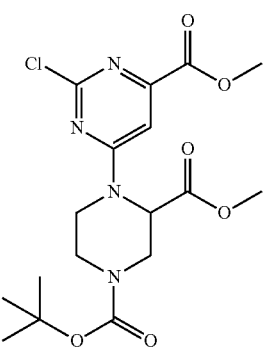

1-tert-butyl 3-methyl 4-(2-chloro-6-(methoxycarbonyl)pyrimidin-4-yl)piperazine-1,3-dicarboxylate A mixture of 1-tert-butyl 3-methyl piperazine-1,3-dicarboxylate (5.133 g, 21.01 mmol), methyl 2,6-dichloropyrimidine-4-carboxylate (4.354 g, 21.03 mmol), and iPr₂NEt (4.0 mL, 23.0 mmol) in acetonitrile (50 mL) was heated at 50° C. for 4 h. After cooling, the reaction mixture was evaporated in vacuo and the residue chromatographed over silica gel with 20-70% EtOAc in hexanes. The product fractions were evaporated in vacuo to give 1-tert-butyl 3-methyl 4-(2-chloro-6-(methoxycarbonyl)pyrimidin-4-yl)piperazine-1,3-dicarboxylate as a very pale yellow powder (6.626 g, 15.97 mmol, 76% yield). LC/MS: m/z=415.2 [M+H]⁺.

Scheme 62

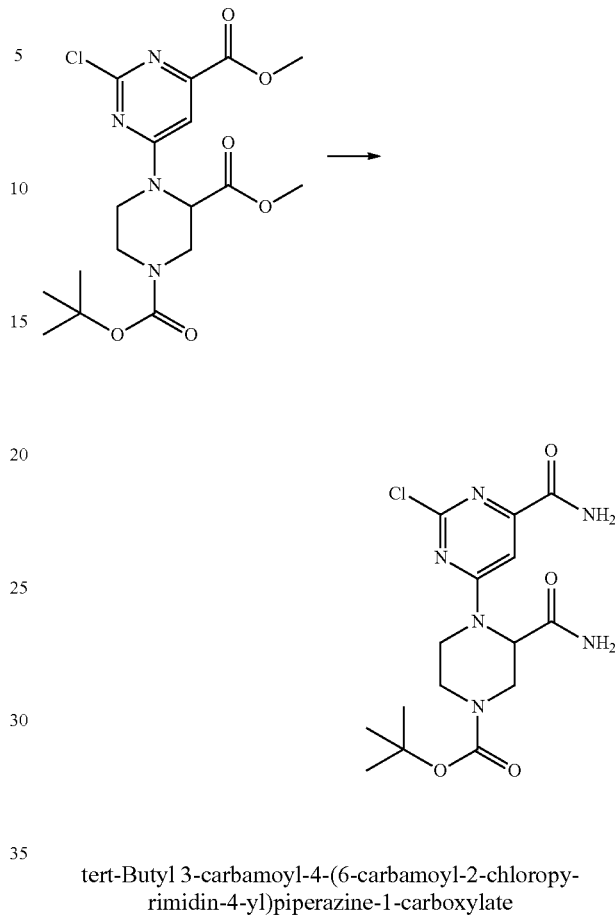

tert-Butyl 3-carbamoyl-4-(6-carbamoyl-2-chloropyrimidin-4-yl)piperazine-1-carboxylate A mixture of the 1-tert-butyl 3-methyl 4-(2-chloro-6-(methoxycarbonyl)pyrimidin-4-yl)piperazine-1,3-dicarboxylate (6.626 g, 15.97 mmol) in 7M ammonia in MeOH (25 mL, 175 mmol) was heated in a sealed tube at 50° C. for 3 days. The reaction mixture was evaporated in vacuo and chromatographed over silica gel with 25-75% acetone in hexanes. The product fractions were evaporated in vacuo to give the product tert-butyl 3-carbamoyl-4-(6-carbamoyl-2-chloropyrimidin-4-yl)piperazine-1-carboxylate as a cream-colored powder (4.744 g, 12.33 mmol, 77% yield). LC/MS: m/z=385.0 [M+H]⁺.

Scheme 63

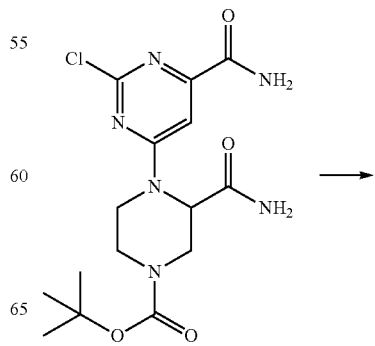

→

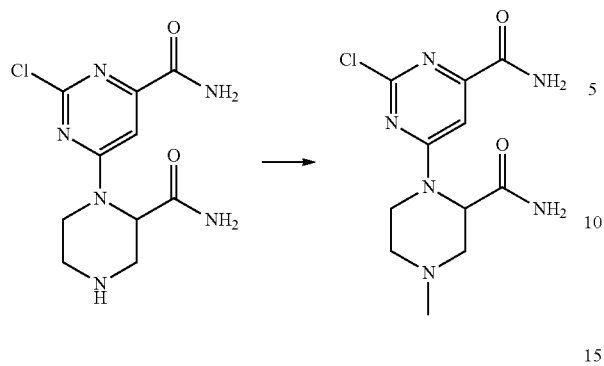

6-(2-Carbamoyl-4-methylpiperazin-1-yl)-2-chloro-pyrimidine-4-carboxamide

To a solution of tert-butyl 3-carbamoyl-4-(6-carbamoyl-2-chloropyrimidin-4-yl)piperazine-1-carboxylate (4.744 g, 12.33 mmol) in dioxane (25 mL) was added 4M HCl in dioxane (5.0 mL, 20.0 mmol). After stirring overnight the reaction was diluted with additional dioxane (25 mL) and 4M HCl in dioxane (5.0 mL, 20.0 mmol). After 5 h, MeOH (10 mL) was added. After stirring overnight more MeOH (10 mL) was added. After stirring one more night the reaction was evaporated in vacuo to give crude 6-(2-carbamoylpiperazin-1-yl)-2-chloropyrimidine-4-carboxamide hydrochloride. The crude hydrochloride salt was suspended in THF (50 mL). To this was added iPr$_2$NEt (7.10 mL, 40.8 mmol) and methyl iodide (0.85 mL, 13.7 mmol). The reaction vessel was sealed and heated at 70° C. for 5 h. The reaction mixture was cooled and partitioned between EtOAc (100 mL) and water (50 mL). The organics were isolated and saved. 1N aqueous NaOH was added to the aqueous layer then it was extracted with EtOAc (100 mL). These organics were also isolated and saved. Once more, 1N aqueous NaOH was added to the aqueous layer then it was extracted with EtOAc (100 mL). The organics were isolated and combined with the other batches of organic extracts. The combined organics were dried over Na$_2$SO$_4$, filtered, and evaporated in vacuo. The solid residue was triturated with MeOH (5 mL), filtered, and washed with MeOH (1×2 mL). The solid was dried under vacuum at 40° C. to give 6-(2-carbamoyl-4-methylpiperazin-1-yl)-2-chloropyrimidine-4-carboxamide as a cream-colored powder (0.924 g, 3.09 mmol, 25% yield). LC/MS: m/z=299.1 [M+H]$^+$.

Scheme 64

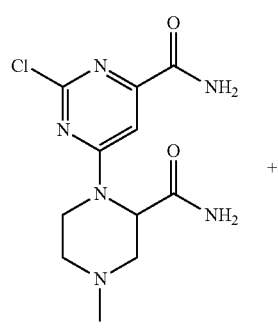

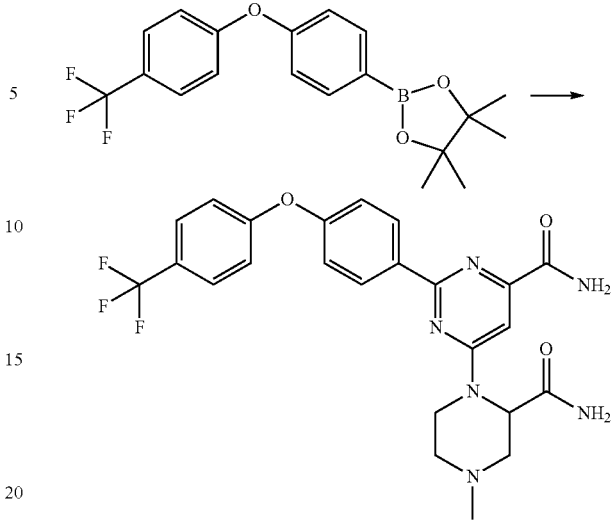

6-(2-Carbamoyl-4-methylpiperazin-1-yl)-2-(4-(4-(trifluoromethyl)phenoxy)phenyl)pyrimidine-4-carboxamide To a mixture of 6-(2-carbamoyl-4-methylpiperazin-1-yl)-2-chloropyrimidine-4-carboxamide (0.300 g, 1.00 mmol) in dioxane (5 mL) was added 4,4,5,5-tetramethyl-2-(4-(4-(trifluoromethyl)phenoxy)phenyl)-1,3,2-dioxaborolane (0.404 g, 1.11 mmol), 2M aqueous Na$_2$CO$_3$ (1.0 mL, 2.0 mmol) and PdCl$_2$(dppf) (0.046 g, 0.056 mmol). The reaction vessel was flushed with argon, sealed and heated at 100° C. overnight. After cooling, the reaction mixture was evaporated in vacuo and the residue chromatographed over silica gel with 0-20% MeOH in acetone. The product fractions were evaporated in vacuo and the residue triturated with 1:1 acetonitrile/MeOH (5 mL). The solid was filtered, washed with MeOH (1×1 mL), and acetonitrile (1×1 mL). An additional batch of material was obtained by evaporation of the filtrates, trituration of the residue with 1:1 acetonitrile/MeOH (2 mL) and washing the solid with MeOH (1×0.5 mL) then acetonitrile (1×0.5 mL). The combined solids were dried under vacuum at 40° C. to give 6-(2-carbamoyl-4-methylpiperazin-1-yl)-2-(4-(4-(trifluoromethyl)phenoxy)phenyl)pyrimidine-4-carboxamide as a very pale tan powder (0.271 g, 0.541 mmol, 54% yield). $^1$H NMR (400 MHz, CD$_3$OD): 8.57 (2H, d, J=9.0 Hz), 7.71 (2H, d, J=8.6 Hz), 7.39 (1H, s), 7.21 (2H, d, J=8.6 Hz), 7.16 (2H, d, J=9.0 Hz), 5.68-5.23 (1H, br), 4.49-3.93 (1H, br), 3.65-3.54 (1H, m), 3.51-3.43 (1H, m), 3.00-2.93 (1H, m), 2.40 (1H, dd, J=12.1 Hz, 4.6 Hz), 2.34 (3H, s), 2.21 (1H, dt, J=11.8 Hz, 3.5 Hz). LC/MS: m/z=501.1 [M+H]$^+$.

Example 30

Preparation of (S)-6-((1-amino-1-oxopropan-2-yl)amino)-2-(4-(4-(trifluoromethoxy)phenoxy)phenyl)pyrimidine-4-carboxamide (Cpd No. 84)

Scheme 65

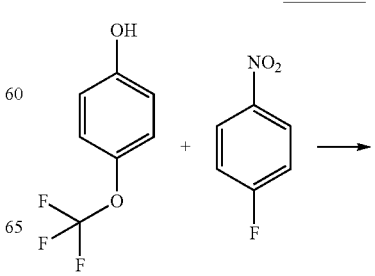

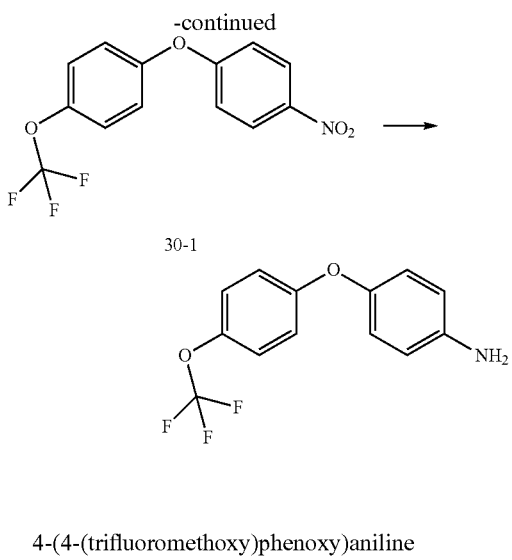

4-(4-(trifluoromethoxy)phenoxy)aniline

In a 150 mL round bottom flask 10.26 g of 4-trifluoromethoxyphenol (57.6 mmol) and 1 equivalent 4-fluoronitrobenzene (8.1 g, 57.6 mmol)) were dissolved in 50 mL DMF. Then, 2 equivalents of potassium carbonate (15.9 g, 115.2 mmol) were added to the solution and the mixture heated to 100° C. for 16 h. When the reaction was complete, the precipitate was collected by vacuum filtration and washed with ethyl acetate. The filtrate was concentrated under reduced pressure to a residue and then diluted with 200 mL ethyl acetate. The organic layer was washed with 2×200 mL water, dried over sodium sulfate, and concentrated under vacuum. The residue was passed through a short plug of silica gel using 100% ethyl acetate as the eluent. The filtrate was concentrated under vacuum. LC/MS showed that Compound 30-1 was present.

In a 500-mL round bottom flask, Compound 30-1 was dissolved in 100 mL MeOH. To the solution was added 50 mg of 10% Pd/C and cooled in a brine/ice bath. Solid NaBH$_4$ (4 g) was added portion-wise while keeping the temperature under 20° C. in a brine/ice cooling bath. LC/MS and TLC showed the reaction was complete after adding the NaBH$_4$. The reaction mixture was filtered through a pad of celite and the filtrate washed with MeOH. The filtrate was concentrated under vacuum and the dark brown 4-(4-(trifluoromethoxy)phenoxy)aniline was used as-is for the next reaction.

Scheme 66

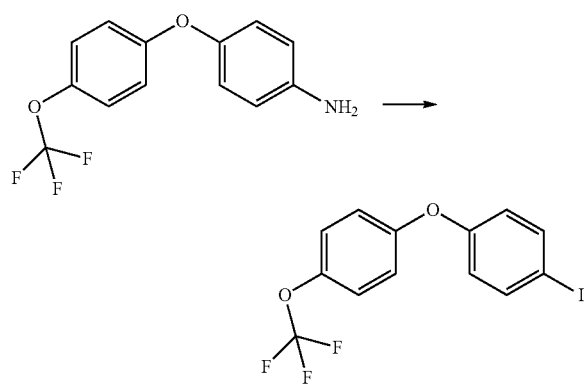

1-iodo-4-(4-(trifluoromethoxy)phenoxy)benzene

In a 300 mL round bottom flask, 6.92 g (25.63 mmol) 4-(4-(trifluoromethoxy)phenoxy)aniline was dissolved in 40 mL DME and cooled to 0° C. in a brine/ice bath. Using a dropping funnel, 10 equivalents aqueous H$_2$SO$_4$ (10N aqueous) were slowly added to the DME solution, immediately creating a salt suspension. The suspension was stirred at 0° C. for 10 minutes. Then, a solution of 1.5 equivalents sodium nitrite (2.65 g, 38.45 mmol) in 20 mL water was dropped slowly into the suspension while keeping the temperature below 5° C. After adding the sodium nitrite, the mixture was stirred at 0° C. for 30 minutes. Then, an aqueous solution of 3 equivalents sodium iodide was dropped slowly into the mixture. LC/MS showed the reaction was complete. The reaction mixture was diluted with 400 mL EtOAc and washed with 700 mL water and then 700 mL 1M sodium bisulfate. The organic layer was dried over sodium sulfate and concentrated under reduced pressure. The residue was then chromatographed by combiflash using a 330 gram silica column and a gradient of EtOAc (15% max) in hexane to provide 6.53 g of 1-iodo-4-(4-(trifluoromethoxy)-phenoxy)benzene (67%, white solid). m/z 380, $^1$H NMR (CHCl$_3$): 7.67-7.61 (m, 2H), 7.23-7.16 (m, 2H), 7.04-6.97 (m, 2H), 6.81-6.75 (m, 2H).

Scheme 67

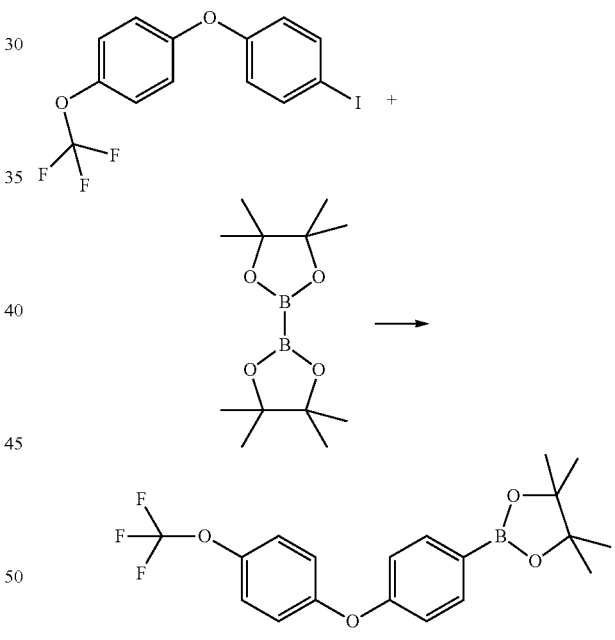

4,4,5,5-tetramethyl-2-(4-(4-(trifluoromethoxy)phenoxy)phenyl)-1,3,2-dioxaborolane In a 100 mL round bottom flask 1-iodo-4-(4-(trifluoromethoxy)-phenoxy)benzene (2.53 g, 6.66 mmol) was dissolved in 10 mL DMF and treated with 1.1 equivalents of bis-borolane (1.86 g, 7.3 mmol), 3 equivalents of potassium acetate (1.96 g, 19.98 mmol), and 0.07 equivalents PdCl$_2$dppf*CH$_2$Cl$_2$ (381 mg, 0.466 mmol). The flask was purged with nitrogen and heated for 10 h at 90° C., at which time the reaction was complete. The reaction mixture was diluted with 300 mL EtOAc and filtered by vacuum. The filtrate was washed with 2×300 mL water. The organic layer was dried over sodium sulfate and concentrated. The residue was chromatographed by combiflash using a 330 gram silica column and a gradient of ethyl acetate (5% max) in hexane to provide 905 mg (36% yield) of 4,4,5,5-tetramethyl-2-(4-(4-(trifluoromethoxy)phenoxy)phenyl)-1,3,2-dioxaborolane as a light brown oil. m/z 380, $^1$H NMR (CHCl$_3$): 7.83-7.77 (m, 2H), 7.22-7.15 (m, 2H), 7.05-6.95 (m, 4H), 1.36-1.32 (s, 12H).

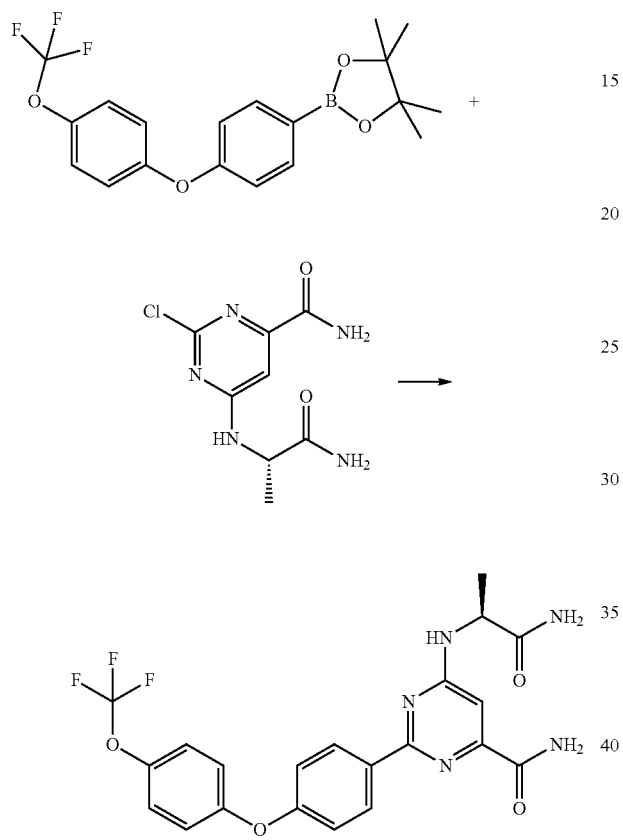

(S)-6-((1-amino-1-oxopropan-2-yl)amino)-2-(4-(4-(trifluoromethoxy)phenoxy)phenyl)pyrimidine-4-carboxamide A 50-mL vial with a screw-top septum was charged with 200 mg of 4,4,5,5-tetramethyl-2-(4-(4-(trifluoromethoxy)phenoxy)phenyl)-1,3,2-dioxaborolane, 1 equivalent (S)-6-((1-amino-1-oxopropan-2-yl)amino)-2-chloropyrimidine-4-carboxamide (129 mg, 0.53 mmol), 1.5 mL 2M aqueous Na$_2$CO$_3$, 0.07 equivalents PdCl$_2$(PPh$_3$)$_2$ (28 mg, 0.04 mmol), and 8 mL dioxane. The vial was purged with nitrogen and heated to 10° C. for 6 h, at which time the reaction was complete. The mixture was diluted with 100 mL EtOAc and washed two times with 100 mL water. The organic layer was dried over sodium sulfate and concentrated under reduced pressure. The residue was chromatographed by combiflash using a 40-gram silica column with a gradient EtOAc (100% max) in hexane to provide 76 mg (31% yield) of (S)-6-((1-amino-1-oxopropan-2-yl)amino)-2-(4-(4-(trifluoromethoxy)phenoxy)phenyl)pyrimidine-4-carboxamide as a white solid. m/z 461, $^1$H NMR (CD$_3$OD): 8.56-8.49 (m, 2H), 7.35-7.27 (m, 2H), 7.17-7.11 (m, 3H), 7.09-7.02 (m, 2H), 4.64-4.49 (m, 1H), 4.56-1.49 (m, 3H).

Example 31

Preparation of (S)-6-((1-amino-1-oxopropan-2-yl)amino)-2-(4-(benzo[d][1,3]dioxol-5-yloxy)phenyl)pyrimidine-4-carboxamide (Cpd No. 85)

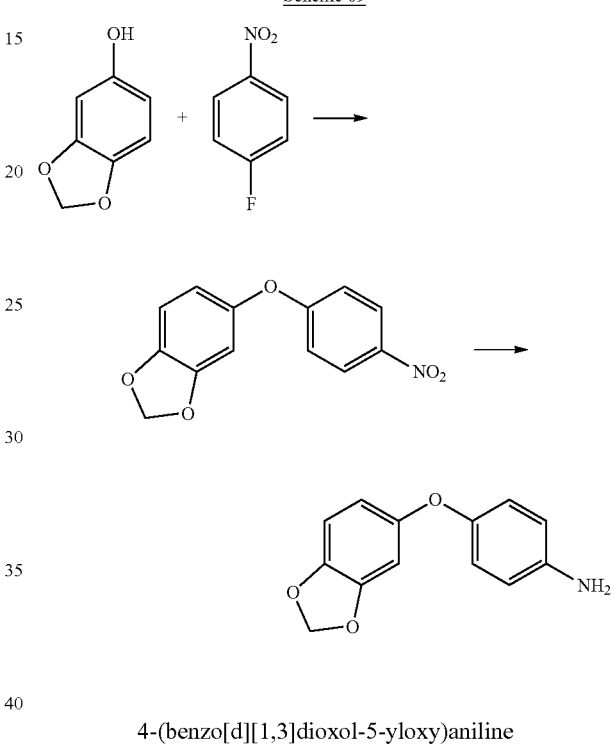

4-(benzo[d][1,3]dioxol-5-yloxy)aniline

In a 150 mL round bottom flask 7.95 g of sesamol (57.6 mmol) and 1 equivalent 4-fluoronitrobenzene (8.1 g, 57.6 mmol)) were dissolved in 50 mL DMF.

Then, 2 equivalents of potassium carbonate (15.9 g, 115.2 mmol) were added to the solution and the mixture heated to 100° C. for 16 h. When the reaction was complete, the precipitate was collected by vacuum filtration and washed with ethyl acetate. The filtrate was concentrated under reduced pressure to a residue and then diluted with 200 mL ethyl acetate. The organic layer was washed with 2×200 mL water, dried over sodium sulfate, and concentrated under reduced pressure. The residue was passed through a short plug of silica gel using 100% ethyl acetate as the eluent. The filtrate was concentrated under reduced pressure. In a 500-mL round bottom flask, the residue was dissolved in 100 mL MeOH. To the solution was added 50 mg of 10% Pd/C and cooled in a brine/ice bath. Solid NaBH$_4$ (4 g) was added portion-wise while keeping the temperature under 20° C. in a brine/ice cooling bath. LC/MS and TLC showed the reaction was complete after adding the NaBH$_4$. The reaction mixture was filtered through a pad of celite and the filtrate washed with MeOH. The filtrate was concentrated under reduced pressure and the dark brown residue was used without purification for the next reaction.

Scheme 70

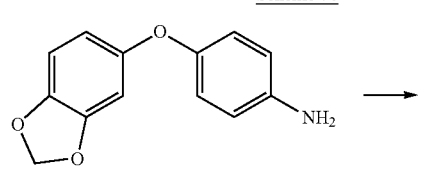

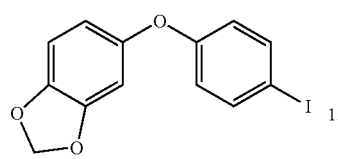

5-(4-iodophenoxy)benzo[d][1,3]dioxole

In a 300 mL round bottom flask, 5.28 g (22.96 mmol) 4-(benzo[d][1,3]dioxol-5-yloxy)aniline was dissolved in 40 mL DME and cooled to 0° C. in a brine/ice bath. Using a dropping funnel, 10 equivalents aqueous H$_2$SO$_4$ (10N aqueous) were slowly added to the DME solution, immediately creating a salt suspension. The suspension was stirred at 0° C. for 10 minutes. Then, a solution of 1.5 equivalents sodium nitrite (2.38 g, 34.45 mmol) in 20 mL water was dropped slowly into the suspension while keeping the temperature below 5° C. After adding the sodium nitrite, the mixture was stirred at 0° C. for 30 minutes. Then, a 30 mL aqueous solution of sodium iodide (10.32 g, 68.88 mmol) was dropped slowly into the mixture. LC/MS showed the reaction was complete. The mixture was diluted with 400 mL EtOAc and washed with 700 mL water and then 700 mL 1M sodium bisulfite. The organic layer was dried over sodium sulfate and concentrated under reduced pressure. The residue was then chromatographed by combiflash using a 330 gram silica column and a gradient of EtOAc (15% max) in hexane to provide 6 g of 5-(4-iodophenoxy)benzo[d][1,3]dioxole (77%, light brown oil). m/z 340, $^1$H NMR (CHCl$_3$): 7.61-7.54 (m, 2H), 6.79-6.68 (m, 3H), 6.58-6.53 (m, 1H), 6.51-6.45 (m, 1H), 6.00-5.96 (s, 2H).

Scheme 71

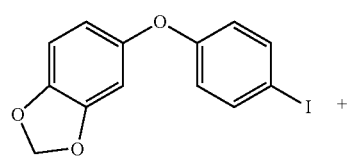

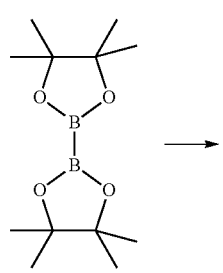

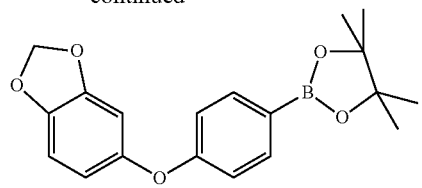

2-(4-(benzo[d][1,3]dioxol-5-yloxy)phenyl)-4,4,5,5-tetramethyl-1,3,2-dioxaborolane In a 100 mL round bottom flask 5-(4-iodophenoxy)benzo[d][1,3]dioxole (3 g, 8.82 mmol) was dissolved in 10 mL DMF and treated with 1.1 equivalents of bis-borolane (2.46 g, 9.7 mmol), 3 equivalents of potassium acetate (2.6 g, 26.46 mmol), and 0.07 equivalents of PdCl$_2$dppf*CH$_2$Cl$_2$ (503 mg, 0.616 mmol). The flask was purged with nitrogen and heated for 10 h at 90° C., at which time the reaction was complete. The reaction mixture was diluted with 300 mL EtOAc and filtered. The filtrate was washed with 2×300 mL water. The organic layer was dried over sodium sulfate and concentrated. The residue was chromatographed by combiflash using a 330 gram silica column and a gradient of ethyl acetate (5% max) in hexane to provide 905 mg (30% yield) of 2-(4-(benzo[d][1,3]dioxol-5-yloxy)phenyl)-4,4,5,5-tetramethyl-1,3,2-dioxaborolane as a light brown oil. m/z 340, $^1$H NMR (CHCl$_3$): 7.78-7.71 (m, 2H), 6.96-6.89 (m, 2H), 6.79-6.72 (m, 1H), 6.60-6.55 (m, 1H), 6.53-6.47 (m, 1H), 5.60-5.95 (s, 2H), 1.36-1.29 (s, 12H)

Scheme 72

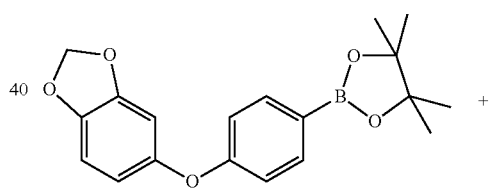

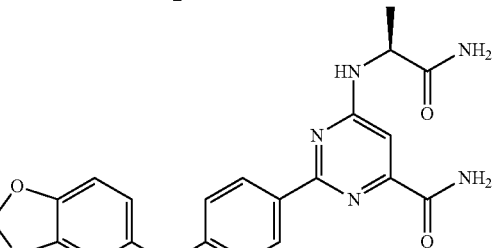

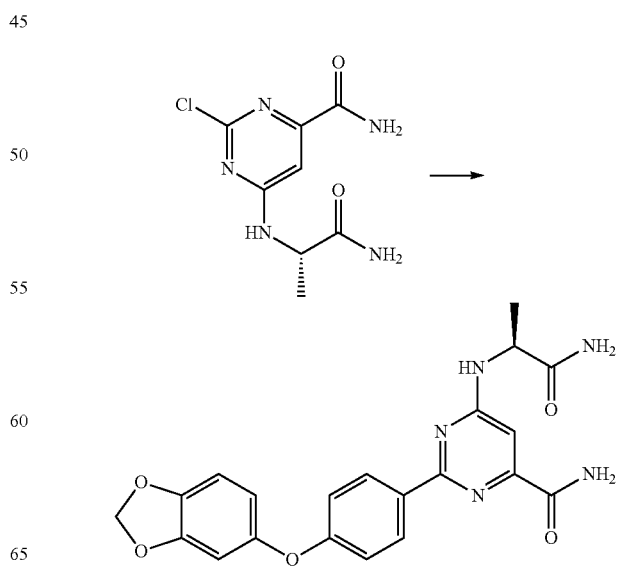

(S)-6-((1-amino-1-oxopropan-2-yl)amino)-2-(4-(benzo[d][1,3]dioxol-5-yloxy)phenyl)pyrimidine-4-carboxamide A 50-mL vial with a screw-top septum was charged with 200 mg of 2-(4-(benzo[d][1,3]dioxol-5-yloxy)phenyl)-4,4,5,5-tetramethyl-1,3,2-dioxaborolane, 1 equivalent of (S)-6-((1-amino-1-oxopropan-2-yl)amino)-2-chloropyrimidine-4-carboxamide (1.53 mg, 0.59 mmol), 1.5 mL 2M aqueous Na$_2$CO$_3$, 0.07 equivalents of PdCl$_2$(PPh$_3$)$_2$ (28 mg, 0.04 mmol), and 8 mL dioxane. The vial was purged with nitrogen and heated to 100° C. for 6 h, at which time the reaction was complete. The mixture was diluted with 100 mL EtOAc and washed two times with 100 mL water. The organic layer was dried over sodium sulfate and concentrated under reduced pressure. The residue was chromatographed by combiflash using a 40-gram silica column with a gradient EtOAc (100% max) in hexane to provide 108 mg (43% yield) of S)-6-((1-amino-1-oxopropan-2-yl)amino)-2-(4-(benzo[d][1,3]dioxol-5-yloxy)phenyl)pyrimidine-4-carboxamide as a white solid. m/z 421, $^1$H NMR (CD$_3$OD): 8.51-8.41 (m, 2H), 7.14-7.07 (s, 1H), 7.01-6.93 (m, 2H), 6.86-6.78 (m, 1H), 6.64-6.60 (m, 1H), 6.57-6.50 (m, 1H), 6.01-5.95 (s, 2H), 4.61-4.49 (m, 1H), 1.56-1.48 (m, 3H).

Example 32

Preparation of (S)-2-(4-(4-fluorophenoxy)phenyl)-6-((1-((2-hydroxyethyl)amino)-1-oxopropan-2-yl)amino)pyrimidine-4-carboxamide (Cpd No. 94)

Scheme 73

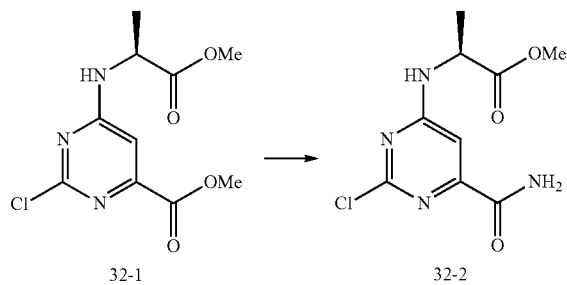

Compound 32-1 (273 mg, 1 mmol) was suspended in 5 mL of 7N NH$_3$ in methanol and stirred at room temperature for 14 h. The solvent was removed and the residual solid was washed with cold methanol. The solid was dried to give pure compound 32-2 as a white solid (240 mg, yield 93%). LC/MS: m/z=259 [M+H]$^+$.

Scheme 74

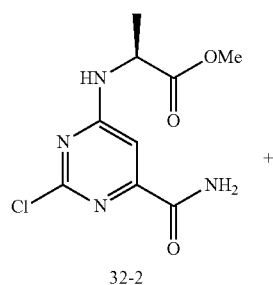

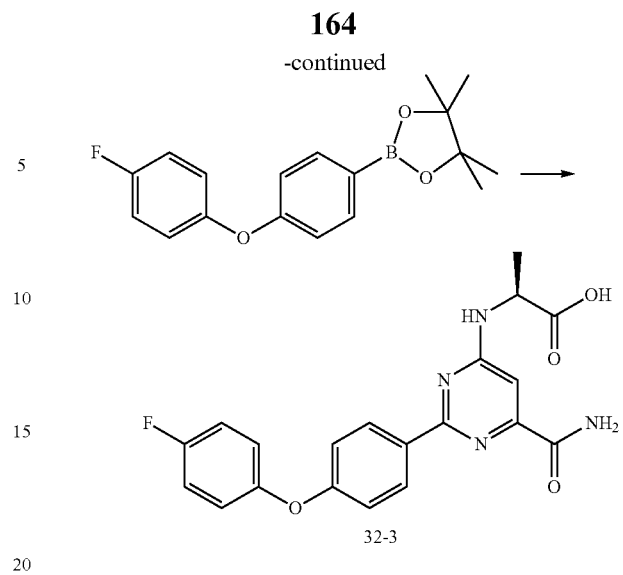

A mixture of 2-(4-(4-fluorophenoxy)phenyl)-4,4,5,5-tetramethyl-1,3,2-dioxaborolane (314 mg, 1 mmol), Compound 32-2 (258 mg, 1 mmol), Pd(dppf)Cl$_2$ (42 mg, 0.05 mmol), Na$_2$CO$_3$ (318 mg, 3 mmol) in DME/EtOH/H$_2$O (4 mL/2 mL/4 mL) was purged with argon for 1 minute and then heated at 100° C. under argon atmosphere for 14 h. The mixture was cooled with an ice bath and its pH was adjusted to 5 using 6N HCl, then extracted extensively with DCM. The DCM layer was combined and dried over MgSO$_4$. Removal of DCM and the residue was used for the next step without purification. Crude yield 100%. (LC/MS: m/z=397 [M+H]$^+$.

Scheme 75

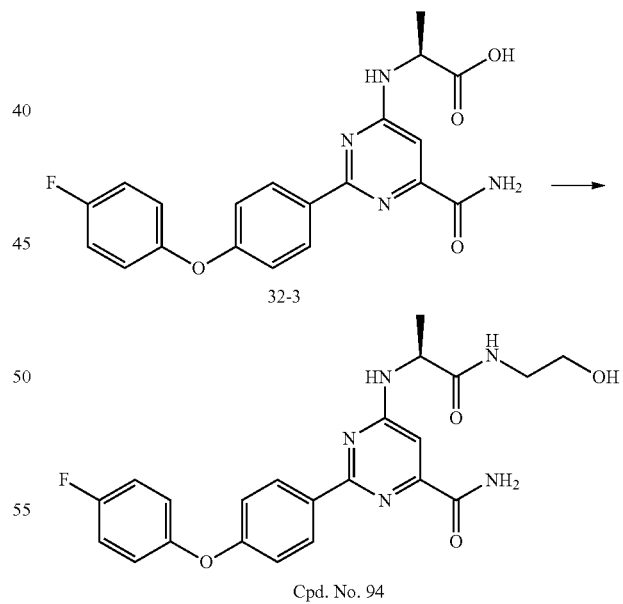

To a mixture of compound 32-3 (277 mg, 0.7 mmol) and EDC (192 mg, 0.84 mmol) in DCM (4 mL) at room temperature was added DIEA (0.24 mL, 1.4 mmol). After 2 minutes 2-aminoethanol (0.042 mL, 8.4 mmol) was added and the reaction mixture was stirred at room temperature for 14 h. The reaction was worked up with EtOAc. The crude product was subjected to flash column chromatography (DCM/MeOH) to give (S)-2-(4-(4-fluorophenoxy)phenyl)-6-((1-((2-hydroxyethyl)amino)-1-oxopropan-2-yl)amino)pyrimidine-4-carboxamide as a white solid (184 mg, 60%). $^1$H NMR (CD$_3$OD): 8.40 (m, 2H), 6.95-7.20 (m, 7H), 4.50 (m, 1H), 3.40-3.55 (m, 2H), 3.20 (m, 2H), 1.50 (d, J=7.20 Hz, 3H). LC/MS: m/z=440 [M+H]$^+$.

Example 33

Preparation of (S)-6-(1-amino-1-oxopropan-2-yl)amino)-2-(4-(4-fluorophenoxy)-3-(hydroxymethyl)phenyl)pyrimidine-4-carboxamide (Cpd No. 97)

Scheme 76

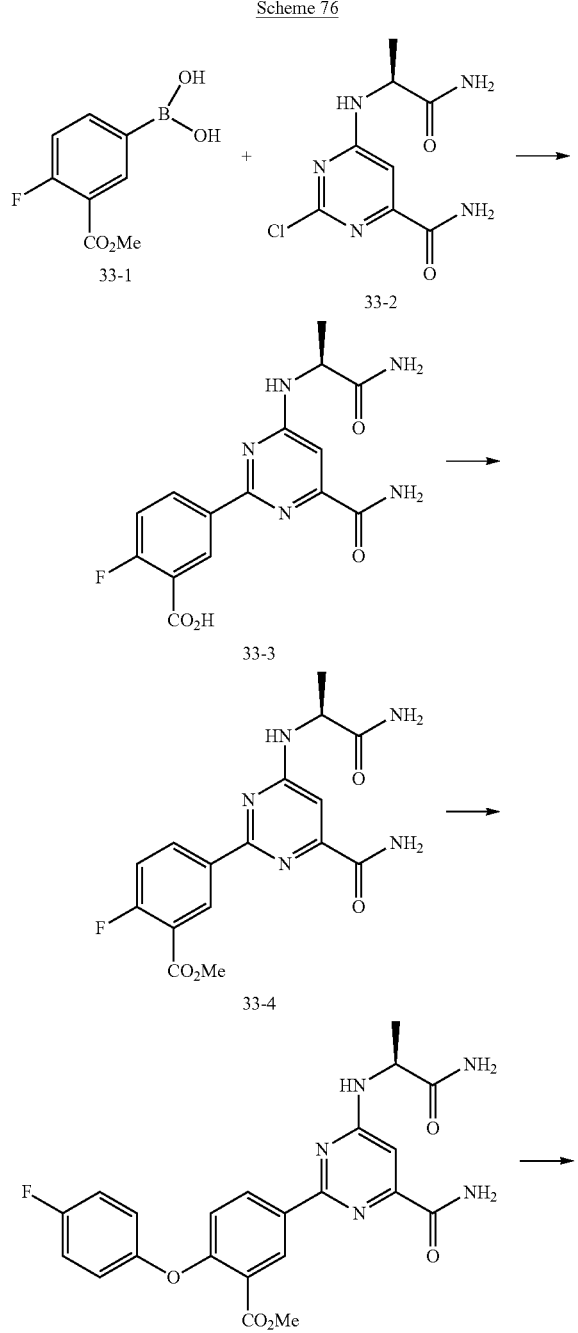

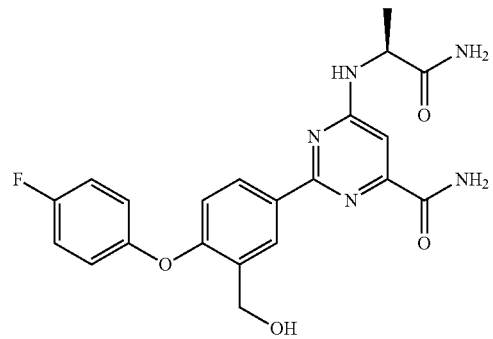

To a mixture of (4-fluoro-3-methoxycarbonylphenyl)boronic acid (compound 33-1) (198 mg, 1 mmol), compound 33-2 (243 mg, 1 mmol), PdCl$_2$(PPh$_3$)$_2$ (56 mg, 0.08 mmol) and Cs$_2$CO$_3$ (652 mg, 2 mmol) in a vial was added DME (2 mL), H$_2$O (2 mL) and ethyl alcohol (1 mL). The vial was then blanked with Argon, sealed, and heated at 80° C. for 3 h. After cooling to room temperature, the reaction mixture was acidified to pH 1.3 with diluted aqueous HCl solution. The precipitate that formed was collected, washed with water, and dried at 50° C. under vacuum for 12 h to provide compound 3. To a mixture of compound 33-3, HOBT (1 mmol), N-(3-dimethylaminopropyl)-N'-ethylcarbodiimde HCl (191 mg, 1 mmol) and proton sponge (214 mg, 1 mmol) in CH$_2$Cl$_2$ (5 mL) at room temperature were added MeOH (41 μL, 1 mmol). The reaction was stirred at room temperature for 2 h. The resulting mixture was poured onto a silica gel column and purified via chromatography with a gradient of 0 to 20% EtOAc in hexane to provide compound 33-4 (120 mg, 0.33 mmol). To a mixture of compound 33-4 (120 mg, 0.33 mmol), 4-fluorophenol (37 mg, 0.33 mmol), and Cs$_2$CO$_3$ (108 mg, 0.33 mmol) was added DMF(1 mL). The mixture was heated at 65° C. for four days. After cooling to room temperature the mixture was purified via silica gel chromatography with 0 to 10% MeOH in CH$_2$Cl$_2$ to provide (S)-methyl 5-(4-((1-amino-1-oxopropan-2-yl)amino)-6-carbamoylpyrimidin-2-yl)-2-(4-fluorophenoxy)benzoate (60 mg, 0.13 mmol). $^1$H NMR (400 MHz, DMSO-d$_6$): 8.92 (1H, d, J=2.4 Hz), 8.72 (1H, d, J=8.4 Hz), 8.32 (1H, s), 8.05 (1H, d, J=7.2 Hz), 7.80 (1H, s), 7.59 (1H, s), 7.28 (2H, m), 7.15 (1H, s), 7.11 (2H, m), 7.03 (2H, m), 4.56 (1H, m), 3.82 (3H, s), 1.42 (3H, d, J=6.8 Hz). LC/MS: m/z=454[M+H]$^+$.

To a solution of (S)-methyl 5-(4-((1-amino-1-oxopropan-2-yl)amino)-6-carbamoylpyrimidin-2-yl)-2-(4-fluorophenoxy)benzoate (50 mg, 0.11 mmol) in ethyl alcohol (1 mL) at room temperature was added NaBH$_4$ (21 mg, 0.55 mmol). The mixture was stirred at room temperature for 2 h and quenched with addition of MeOH. The mixture was poured onto silica gel and purified via chromatography with 0 to 20% MeOH in CH$_2$CH$_2$ to provide (S)-6-(1-amino-1-oxopropan-2-yl)amino)-2-(4-(4-fluorophenoxy)-3-(hydroxymethyl)phenyl)pyrimidine-4-carboxamide (30 mg, 0.07 mmol) as white solid. $^1$H NMR (400 MHz, DMSO-d$_6$): 8.57 (1H, d, J=2 Hz), 8.27 (1H, dd, J=2.4, 8.8 Hz), 7.05-6.94 (5H, m), 6.70 (1H, d, J=8.4 Hz), 4.68 (2H, s), 4.50 (1H, s), 1.42 (3H, d, J=7.2 Hz). LC/MS: m/z=426 [M+H]$^+$.

Example 34

The compounds of EXAMPLE 34 were prepared using the methodology described in EXAMPLES 1-33.

6-((2-amino-2-oxoethyl)amino)-2-(4-(4-fluorophenoxy)phenyl)pyrimidine-4-carboxamide (Cpd No. 2)

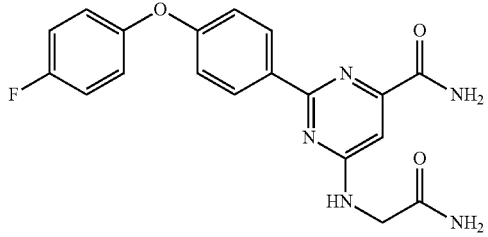 [SMILES: NC(=O)CNc1cc(C(N)=O)nc(-c2ccc(Oc3ccc(F)cc3)cc2)n1]

LC/MS: m/z=382.2 [M+H]⁺, ¹H NMR (400 MHz, DMSO-d₆): 8.52 (2H, d, J=9.0 Hz), 8.28 (1H, s), 8.05 (1H, d, J=5.7 Hz), 7.75 (1H, s), 7.50 (1H, s), 7.31-7.24 (2H, m), 7.19-7.13 (2H, m), 7.09 (1H, s), 7.07 (1H, s), 7.03 (2H, d, J=8.8 Hz), 4.01 (2H, d, J=5.3 Hz).

(S)-6-((1-amino-4-methyl-1-oxopentan-2-yl)amino)-2-(4-(4-fluorophenoxy)phenyl)pyrimidine-4-carboxamide (Cpd No. 3)

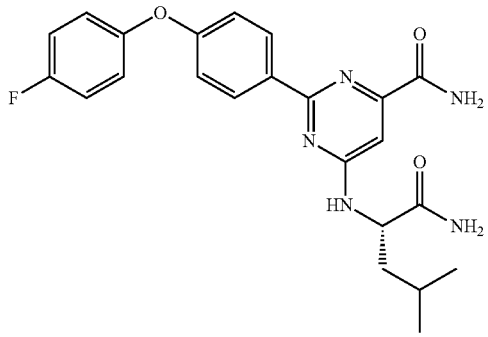 [SMILES: CC(C)C[C@H](Nc1cc(C(N)=O)nc(-c2ccc(Oc3ccc(F)cc3)cc2)n1)C(N)=O]

LC/MS: m/z=438.2 [M+H]⁺, ¹H NMR (400 MHz, DMSO-d₆): 8.55 (2H, d, J=8.8 Hz), 8.26 (1H, s), 7.88 (1H, d, J=7.5 Hz), 7.73 (1H, s), 7.56 (1H, s), 7.31-7.24 (2H, m), 7.19-7.13 (2H, m), 7.08 (1H, s), 7.04-6.98 (3H, m), 4.65-4.57 (1H, m), 1.78-1.66 (1H, m), 1.63-1.54 (2H, m), 0.94 (3H, d, J=6.6 Hz), 0.88 (3H, d, J=6.6 Hz).

(S)-6-((1-amino-3-hydroxy-1-oxopropan-2-yl)amino)-2-(4-(4-fluorophenoxy)phenyl)pyrimidine-4-carboxamide (Cpd No. 4)

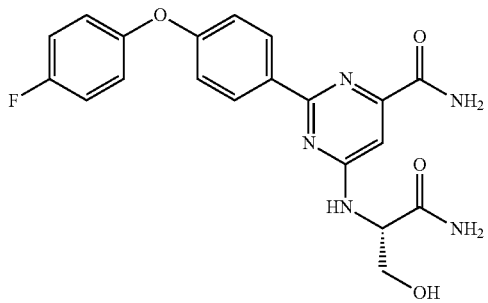 [SMILES: NC(=O)c1cc(N[C@@H](CO)C(N)=O)nc(-c2ccc(Oc3ccc(F)cc3)cc2)n1]

LC/MS: m/z=412.2 [M+H]⁺, ¹H NMR (400 MHz, DMSO-d₆): 8.53 (2H, d, J=8.6 Hz), 8.27 (1H, s), 7.89 (1H, d, J=7.0 Hz), 7.74 (1H, s), 7.49 (1H, s), 7.31-7.24 (2H, m), 7.19-7.13 (3H, m), 7.10 (1H, s), 7.02 (2H, d, J=8.8 Hz), 5.00 (1H, t, J=5.3 Hz), 4.69-4.62 (1H, m), 3.73 (2H, t, J=5.7 Hz).

(S)-6-(2-carbamoylpyrrolidin-1-yl)-2-(4-(4-fluorophenoxy)phenyl)pyrimidine-4-carboxamide (Cpd No. 5)

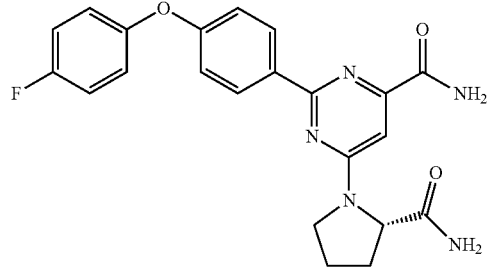 [SMILES: NC(=O)c1cc(N2CCC[C@H]2C(N)=O)nc(-c2ccc(Oc3ccc(F)cc3)cc2)n1]

LC/MS: m/z=422.2 [M+H]⁺, NMR (400 MHz, DMSO-d₆): Exists as a ~70:30 ratio of species 8.60-8.51 (2H, m), 8.35 (1H, s), 7.80 (1H, s), 7.72 (0.3H, s), 7.52 (0.7H, s), 7.33-7.22 (2.3H, m), 7.20-7.13 (2H, m), 7.08-6.95 (3.4H, m), 6.77 (0.3H, s), 4.59-4.52 (0.7H, m), 4.33-4.27 (0.3H, m), 3.91-3.82 (0.3H, m), 3.80-3.71 (0.3H, m), 3.70-3.62 (0.7H, m), 3.56-3.46 (0.7H, m), 2.28-2.17 (0.7H, m), 2.11-1.91 (3.3H, m).

(S)-6-((1-amino-3-(1-methyl-1H-imidazol-4-yl)-1-oxopropan-2-yl)amino)-2-(4-(4-fluorophenoxy)phenyl)pyrimidine-4-carboxamide (Cpd No. 6)

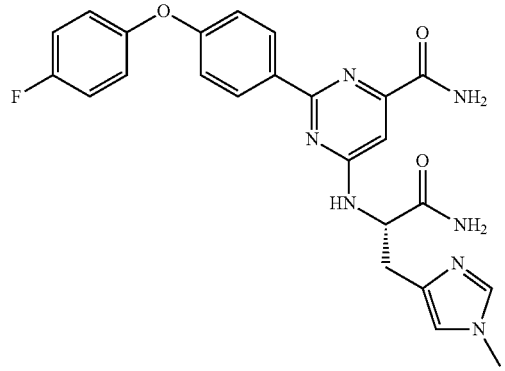 [SMILES: Cn1cnc(C[C@H](Nc2cc(C(N)=O)nc(-c3ccc(Oc4ccc(F)cc4)cc3)n2)C(N)=O)c1]

LC/MS: m/z=476.2 [M+H]⁺, ¹H NMR (400 MHz, DMSO-d₆): 8.55 (2H, d, J=8.6 Hz), 8.27 (1H, s), 7.95 (1H, d, J=7.0 Hz), 7.73 (1H, s), 7.63-7.57 (2H, m), 7.32-7.25 (2H, m), 7.19-7.14 (2H, m), 7.06 (1H, s), 7.05 (1H, s), 7.01 (2H, d, J=8.8 Hz), 6.94 (1H, s), 4.83-4.76 (1H, m), 3.57 (3H, s), 3.03-2.96 (1H, m), 2.91-2.83 (1H, m).

(S)-2-(4-(4-fluorophenoxy)phenyl)-6-(2-oxopyrrolidin-3-yl)amino)pyrimidine-4-carboxamide (Cpd No. 7)

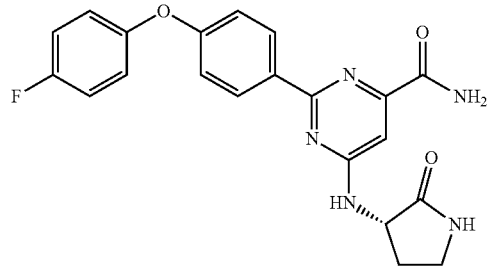 [SMILES: NC(=O)c1cc(N[C@H]2CCNC2=O)nc(-c2ccc(Oc3ccc(F)cc3)cc2)n1]

LC/MS: m/z=408.2 [M+H]+, 1H NMR (400 MHz, DMSO-d6): 8.52 (2H, d, J=8.8 Hz), 8.29 (1H, s), 8.08 (1H, d, J=7.0 Hz), 7.96 (1H, s), 7.76 (1H, s), 7.32-7.24 (2H, m), 7.20-7.13 (2H, m), 7.05 (1H, s), 7.03 (2H, d, J=8.8 Hz), 4.77-4.67 (1H, m), 3.33-3.23 (2H, m), 2.58-2.43 (1H, m, overlaps with DMSO peak), 2.06-1.92 (1H, m).

6-((1-carbamoylcyclopropyl)amino)-2-(4-(4-fluorophenoxy)phenyl)pyrimidine-4-carboxamide (Cpd No. 8)

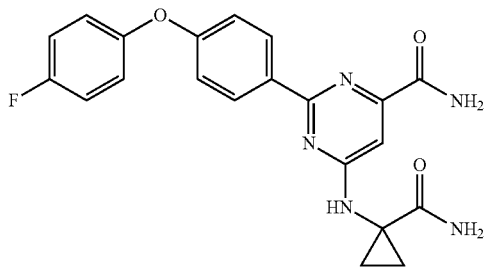 [SMILES: NC(=O)c1cc(NC2(C(N)=O)CC2)nc(-c2ccc(Oc3ccc(F)cc3)cc2)n1]

LC/MS: m/z=408.2 [M+H]+, 1H NMR (400 MHz, DMSO-d6): Exists as a ~1:1 ratio of conformers: 8.51 (2H, d, J=9.0 Hz), 8.39-8.23 (2H, m), 7.84 (0.5H, s), 7.75 (0.5H, s), 7.46 (0.5H, s), 7.34-7.23 (2.5H, m), 7.21-7.12 (2.5H, s), 7.04 (2H, d, J=8.8 Hz), 7.01 (0.5H, s), 6.98-6.90 (1H, m), 1.43 (2H, br s), 1.09-0.90 (2H, m).

6-((1-carbamoylcyclobutyl)amino)-2-(4-(4-fluorophenoxy)phenyl)pyrimidine-4-carboxamide (Cpd No. 9)

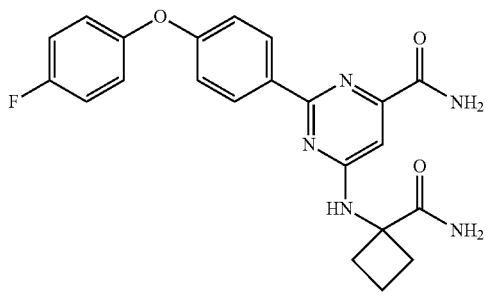 [SMILES: NC(=O)c1cc(NC2(C(N)=O)CCC2)nc(-c2ccc(Oc3ccc(F)cc3)cc2)n1]

LC/MS: m/z=422.2 [M+H]+, 1H NMR (400 MHz, DMSO-d6): 8.47 (2H, d, J=8.8 Hz), 8.35-8.25 (2H, m), 7.74 (1H, s), 7.31-7.23 (2H, m), 7.19-7.11 (2H, m), 7.06 (2H, s apparent), 6.99 (2H, d, J=8.8 Hz), 6.73 (1H, s), 2.72-2.62 (2H, m), 2.17-2.07 (2H, m), 1.96-1.85 (2H, m).

6-((1-amino-2-methyl-1-oxopropan-2-yl)amino)-2-(4-(4-fluorophenoxy)phenyl)pyrimidine-4-carboxamide (Cpd No. 10)

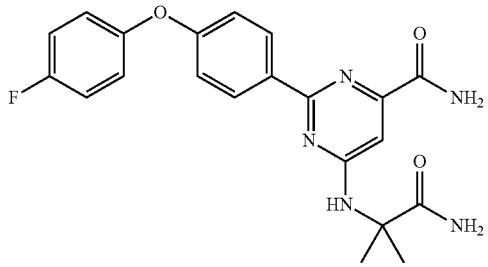 [SMILES: CC(C)(Nc1cc(C(N)=O)nc(-c2ccc(Oc3ccc(F)cc3)cc2)n1)C(N)=O]

LC/MS: m/z=410.2 [M+H]+, 1H NMR (400 MHz, DMSO-d6): 8.49 (2H, d, J=8.8 Hz), 8.27 (1H, s), 7.86 (1H, s), 7.72 (1H, s), 7.31-7.24 (2H, m), 7.19-7.11 (3H, m), 7.06 (1H, s), 6.99 (2H, d, J=8.8 Hz), 6.78 (1H, s), 1.48 (6H, s).

(S)-6-((1-amino-1-oxopropan-2-yl)amino)-2-(4-(4-cyano-3-(trifluoromethyl)phenoxy)phenyl)pyrimidine-4-carboxamide (Cpd No. 11)

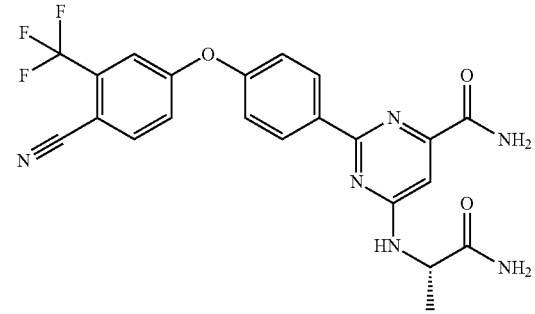 [SMILES: C[C@H](Nc1cc(C(N)=O)nc(-c2ccc(Oc3ccc(C#N)c(C(F)(F)F)c3)cc2)n1)C(N)=O]

LC/MS: m/z=471.1 [M+H]+, 1H NMR (400 MHz, DMSO-d6): 8.66 (2H, d, J=8.8 Hz), 8.34 (1H, s), 8.17 (1H, d, J=8.8 Hz), 8.01 (1H, d, J=6.6 Hz), 7.76 (1H, s), 7.61 (1H, d, J=2.2 Hz), 7.56 (1H, s), 7.41 (1H, dd, J=8.6, 2.4 Hz), 7.30 (2H, d, J=8.8 Hz), 7.31 (1H, s), 7.02 (1H, s), 4.63-4.54 (1H, m), 1.38 (3H, d, J=7.0 Hz).

(S)-6-((1-amino-1-oxopropan-2-yl)amino)-2-(4-(3-cyano-4-(trifluoromethyl)phenoxy)phenyl)pyrimidine-4-carboxamide (Cpd No. 12)

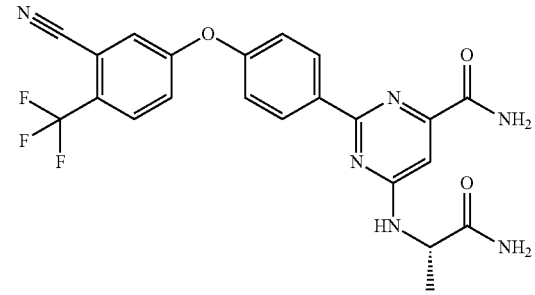 [SMILES: C[C@H](Nc1cc(C(N)=O)nc(-c2ccc(Oc3ccc(C(F)(F)F)c(C#N)c3)cc2)n1)C(N)=O]

LC/MS: m/z=471.1 [M+H]+, 1H NMR (400 MHz, DMSO-d6): 8.65 (2H, d, J=8.8 Hz), 8.33 (1H, s), 8.04-7.97 (2H, m), 7.92 (1H, d, J=2.2 Hz), 7.75 (1H, s), 7.55 (1H, s), 7.46 (1H, dd, J=8.8, 1.8 Hz), 7.27 (2H, d, J=8.8 Hz), 7.12 (1H, s), 7.01 (1H, s), 4.62-4.53 (1H, m), 1.38 (3H, d, J=7.0 Hz).

(S)-6-((1-amino-1-oxopropan-2-yl)amino)-2-(4-((5-(trifluoromethyl)pyridin-2-yl)oxy)phenyl)pyrimidine-4-carboxamide (Cpd No. 13)

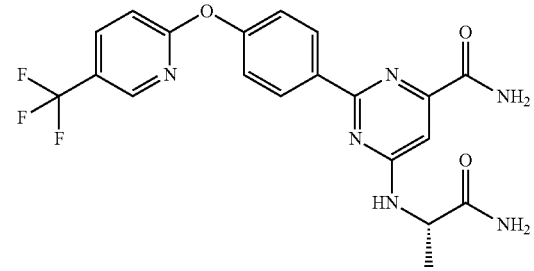

LC/MS: m/z=447.1 [M+H]⁺, ¹H NMR (400 MHz, DMSO-d₆): 8.63-8.58 (3H, m), 8.33 (1H, s), 8.27 (1H, dd, J=8.8, 2.6 Hz), 7.99 (1H, J=6.6 Hz), 7.75 (1H, s), 7.56 (1H, s), 7.32-7.26 (3H, m), 7.12 (1H, s), 7.02 (1H, s), 4.63-4.54 (1H, m), 1.38 (3H, d, J=7.0 Hz).

(S)-methyl 1-(6-carbamoyl-2-(4-(4-fluorophenoxy)phenyl)pyrimidin-4-yl)pyrrolidine-2-carboxylate (Cpd No. 15)

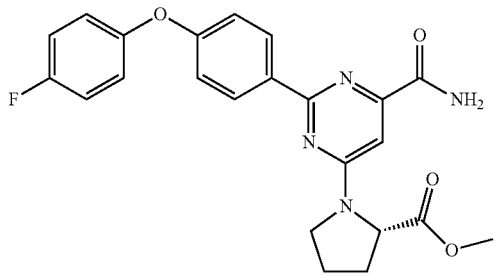

¹H NMR (400 MHz, DMSO-d₆): Exists as a ~90:10 ratio of rotamers: 8.57 (0.2H, d, J=7.9 Hz), 8.45 (1.8H, d, J=8.8 Hz), 8.36 (1H, s), 7.82 (1H, s), 7.32-7.24 (2H, m), 7.20-7.14 (2H, m), 7.07-7.01 (2.9H, m), 6.77 (0.1H, s), 4.76-4.70 (0.1H, m), 4.66-4.61 (0.9H, m), 3.72-3.57 (5H, m), 2.40-2.30 (1H, m), 2.12-1.97 (3H, m). LC/MS: m/z=437.2 [M+H]⁺.

(S)-ethyl 1-(6-carbamoyl-2-(4-(4-fluorophenoxy)phenyl)pyrimidin-4-yl) indoline-2-carboxylate (Cpd No. 16)

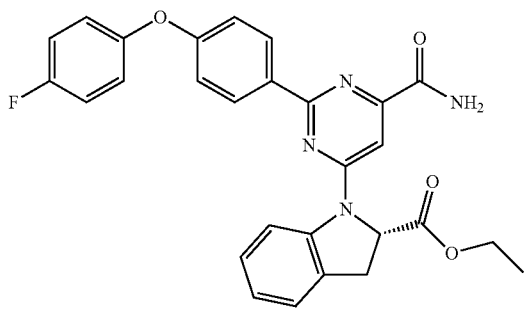 [SMILES: CCOC(=O)[C@@H]1Cc2ccccc2N1c1cc(C(N)=O)nc(-c2ccc(Oc3ccc(F)cc3)cc2)n1]

¹H NMR (400 MHz, CD₃OD): 8.55-8.50 (2H, m), 8.03 (1H, br s), 7.65 (1H, br s), 7.37-7.30 (2H, m), 7.22-7.11 (4H, m), 7.10-7.07 (3H, m), 5.37 (1H, dd, J=11.0 Hz, 3.7 Hz), 4.27-4.18 (2H, m), 3.72 (1H, dd, J=16.2 Hz, 11.4 Hz), 3.31-3.24 (1H, m), 1.24 (3H, t, J=7.0 Hz). LC/MS: m/z=499.1 [M+H]⁺.

Ethyl 1-((6-carbamoyl-2-(4-(4-fluorophenoxy)phenyl)pyrimidin-4-yl)amino)cyclopropanecarboxylate (Cpd No. 17)

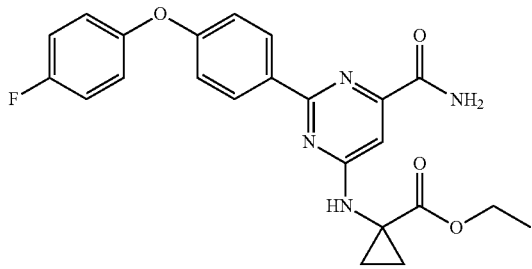 [SMILES: CCOC(=O)C1(Nc2cc(C(N)=O)nc(-c3ccc(Oc4ccc(F)cc4)cc3)n2)CC1]

¹H NMR (400 MHz, DMSO-d₆): 8.54-8.40 (3H, m), 8.39-8.29 (1H, m), 7.87-7.75 (1H, m), 7.32-7.24 (2H, m), 7.21-7.13 (2H, m), 7.07-6.99 (2.7H, m), 6.90 (0.3H, s), 4.13-3.99 (2H, m), 1.62-1.50 (2H, m), 1.30-1.05 (3H, m), 1.04-0.98 (2H, m). LC/MS: m/z=437.1 [M+H]⁺.

methyl 2-((6-carbamoyl-2-(4-(4-fluorophenoxy)phenyl)pyrimidin-4-yl)amino)-2-methylpropanoate (Cpd No. 18)

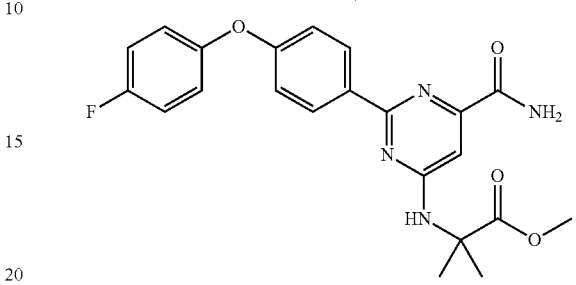

¹H NMR (400 MHz, DMSO-d₆): 8.43 (2H, d, J=9.0 Hz), 8.29 (1H, s), 8.19 (1H, s), 7.75 (1H, s), 7.32-7.24 (2H, m), 7.20-7.14 (2H, m), 7.05-7.00 (3H, m), 3.50 (3H, s), 1.53 (6H, s). LC/MS: m/z=425.2 [M+H]⁺.

6-((3-amino-3-oxopropyl)amino)-2-(4-(4-fluorophenoxy)phenyl)pyrimidine-4-carboxamide (Cpd No. 19)

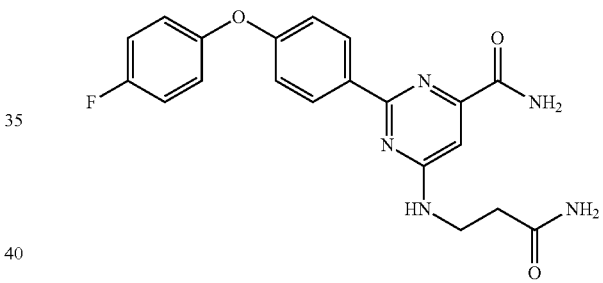

¹H NMR (400 MHz, DMSO-d₆): 8.53 (2H, d, J=8.6 Hz), 8.25 (1H, s), 7.90-7.84 (1H, m), 7.72 (1H, s), 7.36 (1H, s), 7.31-7.24 (2H, m), 7.19-7.12 (2H, m), 7.04 (2H, d, J=8.8 Hz), 6.98 (1H, s), 6.87 (1H, s), 3.70-3.59 (2H, m), 2.72 (2H, t, J=6.6 Hz). LC/MS: m/z=396.1 [M+H]⁺.

(S)-6-(((1-amino-1-oxopropan-2-yl)(methyl)amino)-2-(4-(4-fluorophenoxy)phenyl)pyrimidine-4-carboxamide (Cpd No. 20)

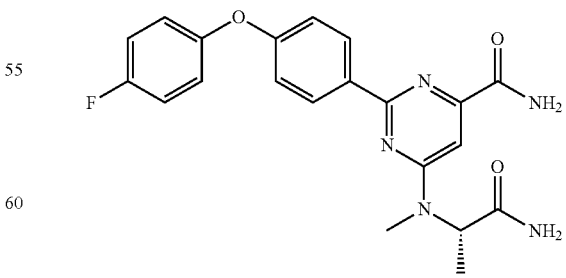

¹H NMR (400 MHz, DMSO-d₆): 8.56 (2H, d, J=9.0 Hz), 8.35 (1H, d, J=2.2 Hz), 7.80 (1H, d, J=2.2 Hz), 7.40 (1H, br s), 7.31-7.24 (2H, m), 7.19-7.13 (2H, m), 7.11 (1H, s), 7.07 (1H, br s), 7.03 (2H, d, J=8.8 Hz), 5.39 (1H, br s), 3.05 (3H, br s), 1.40 (3H, d, J=7.2 Hz). LC/MS: m/z=410.1 [M+H]⁺.

(R)-6-((1-amino-1-oxopropan-2-yl)amino)-2-(4-(4-fluorophenoxy)phenyl)pyrimidine-4-carboxamide (Cpd No. 21)

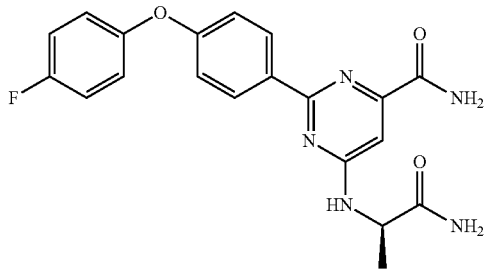 [SMILES: C[C@@H](Nc1cc(C(N)=O)nc(-c2ccc(Oc3ccc(F)cc3)cc2)n1)C(N)=O]

¹H NMR (400 MHz, DMSO-d₆): 8.54 (2H, d, J=8.8 Hz), 8.27 (1H, s), 7.94 (1H, d, J=6.4 Hz), 7.73 (1H, s), 7.53 (1H, s), 7.32-7.24 (2H, m), 7.20-7.12 (2H, m), 7.08 (1H, s), 7.06-6.97 (3H, m), 4.61-4.50 (1H, m), 1.36 (3H, d, J=7.0 Hz). LC/MS: m/z=396.1 [M+H]⁺.

6-((1-amino-1-oxopropan-2-yl)amino)-2-(4-(4-fluorophenoxy)phenyl)pyrimidine-4-carboxamide (Cpd No. 22)

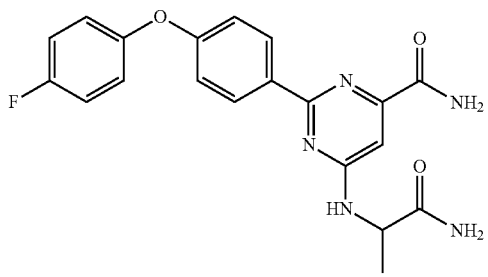 [SMILES: CC(Nc1cc(C(N)=O)nc(-c2ccc(Oc3ccc(F)cc3)cc2)n1)C(N)=O]

¹H NMR (400 MHz, DMSO-d₆): 8.54 (2H, d, J=8.8 Hz), 8.27 (1H, s), 7.95 (1H, d, J=5.9 Hz), 7.74 (1H, s), 7.53 (1H, s), 7.32-7.23 (2H, m), 7.19-7.12 (2H, m), 7.08 (1H, s), 7.05-6.97 (3H, m), 4.60-4.51 (1H, m), 1.36 (3H, d, J=7.2 Hz). LC/MS: m/z=396.1 [M+H]⁺.

6-((4-amino-4-oxobutan-2-yl)amino)-2-(4-(4-fluorophenoxy)phenyl)pyrimidine-4-carboxamide (Cpd No. 23)

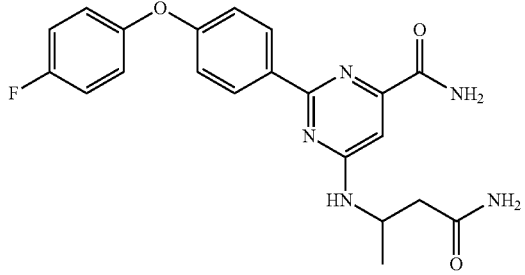

¹H NMR (400 MHz, DMSO-d₆): 8.52 (2H, d, J=8.8 Hz), 8.25 (1H, s), 7.75-7.66 (2H, m), 7.36 (1H, s), 7.31-7.24 (2H, m), 7.19-7.12 (2H, m), 7.04 (2H, d, J=9.0 Hz), 6.95 (1H, s), 6.85 (1H, s), 4.63-4.51 (1H, m), 2.48-2.42 (1H, m), 2.29-2.20 (1H, m), 1.21 (3H, d, J=6.4 Hz). LC/MS: m/z=410.1 [M+H]⁺.

6-(3-carbamoylpiperidin-1-yl)-2-(4-(4-fluorophenoxy)phenyl)pyrimidine-4-carboxamide (Cpd No. 24)

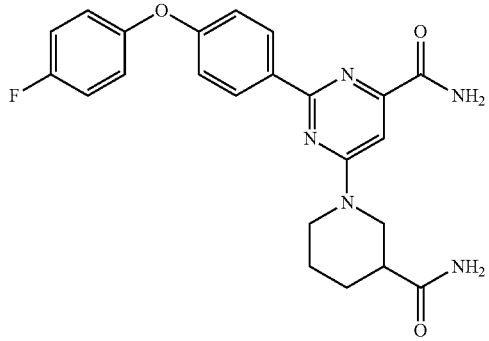 [SMILES: NC(=O)c1cc(N2CCCC(C(N)=O)C2)nc(-c2ccc(Oc3ccc(F)cc3)cc2)n1]

¹H NMR (400 MHz, DMSO-d₆): 8.52 (2H, d, J=8.6 Hz), 8.33 (1H, s), 7.79 (1H, s), 7.45 (1H, s), 7.32-7.21 (3H, m), 7.19-7.12 (2H, m), 7.05 (2H, d, J=8.8 Hz), 6.93 (1H, s), 4.45 (2H, br s), 3.19-3.00 (2H, m), 2.39-2.29 (1H, m), 1.97-1.88 (1H, m), 1.83-1.62 (2H, m), 1.51-1.37 (1H, m). LC/MS: m/z=436.2 [M+H]⁺.

4-(6-carbamoyl-2-(4-(4-fluorophenoxy)phenyl)pyrimidin-4-yl)morpholine-3-carboxamide (Cpd No. 25)

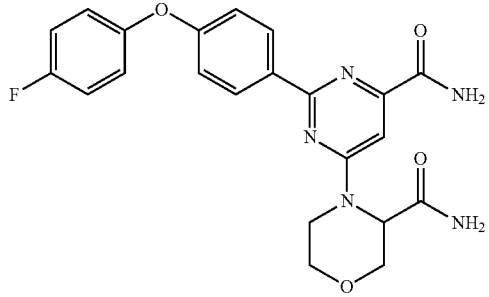 [SMILES: NC(=O)c1cc(N2CCOCC2C(N)=O)nc(-c2ccc(Oc3ccc(F)cc3)cc2)n1]

¹H NMR (400 MHz, DMSO-d₆): 8.54 (2H, d, J=8.1 Hz), 8.37 (1H, s), 7.82 (1H, s), 7.58 (1H, s), 7.32-7.20 (3H, m), 7.20-7.13 (3H, m), 7.04 (2H, d, J=8.3 Hz), 5.25 (0.5H, br s), 4.62 (0.5H, br s), 4.34 (1H, d, J=12.0 Hz), 4.00-4.93 (1H, m), 3.84 (1H, br s), 3.74 (1H, dd, J=11.8 Hz, 3.9 Hz), 3.59-3.45 (2H, m). LC/MS: m/z=438.1 [M+H]⁺.

4-(6-carbamoyl-2-(4-(4-fluorophenoxy)phenyl)pyrimidin-4-yl)morpholine-2-carboxamide (Cpd No. 26)

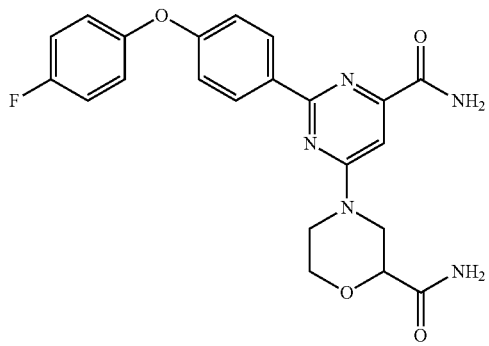 [SMILES: NC(=O)c1cc(N2CCOC(C(N)=O)C2)nc(-c2ccc(Oc3ccc(F)cc3)cc2)n1]

¹H NMR (400 MHz, DMSO-d₆): 8.53 (2H, d, J=9.0 Hz), 8.37 (1H, s), 7.83 (1H, s), 7.44 (1H, s), 7.40 (1H, s), 7.31-7.24 (2H, m), 7.23 (1H, s), 7.19-7.13 (2H, m), 7.07 (2H, d, J=8.8 Hz), 4.60 (1H, very broad s), 4.28 (1H, br s), 4.05-3.98 (2H, m), 3.66 (1H, dt, J=11.2 Hz, 2.6 Hz), 3.30-3.20 (1H, m), 3.19-3.05 (1H, m). LC/MS: m/z=438.1 [M+H]⁺.

(S)-1-(6-carbamoyl-2-(4-(4-fluorophenoxy)phenyl) pyrimidin-4-yl)indoline-2-carboxylic acid (Cpd No. 31)

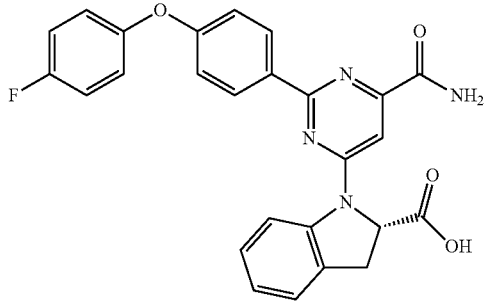

¹H NMR (400 MHz, DMSO-d₆): 13.29 (1H, br s), 8.61 (2H, d, J=9.0 Hz), 8.49 (1H, s), 7.95 (1H, s), 7.38-7.26 (5H, m), 7.25-7.16 (2.5H, m), 7.16-7.08 (2.5H, m), 7.08-7.02 (1H, m), 5.32 (1H, dd, J=11.2 Hz, 3.1 Hz), 3.69 (1H, dd, J=16.7 Hz, 11.2 Hz), 3.25 (1H, d, J=17.1 Hz). LC/MS: m/z=471.3 [M±H]⁺.

(S)-1-(6-carbamoyl-2-(4-(4-fluorophenoxy)phenyl) pyrimidin-4-yl)indoline-2-carboxamide (Cpd No. 36)

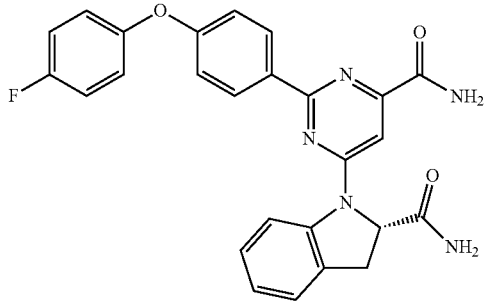 [SMILES: NC(=O)c1cc(N2c3ccccc3C[C@H]2C(N)=O)nc(-c2ccc(Oc3ccc(F)cc3)cc2)n1]

¹H NMR (400 MHz, DMSO-d₆): 8.6 (2H, d, J=9.0 Hz), 8.47 (1H, s), 7.93 (1H, s), 7.88 (1H, s), 7.42-7.25 (6H, m), 7.25-7.16 (2.5H, m), 7.16-7.06 (2.5H, m), 7.03 (1H, t, J=7.2 Hz), 5.12 (1H, br d, J=8.6 Hz), 3.72-3.61 (1H, m), 3.16-6.08 (1H, m). LC/MS: m/z=470.2 [M+H]⁺.

(S)-6-((1-amino-1-oxopropan-2-yl)amino)-2-(4-((5-cyanopyridin-2-yl)oxy)phenyl)pyrimidine-4-carboxamide (Cpd No. 37)

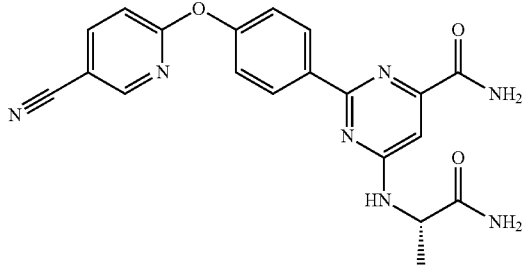 [SMILES: C[C@H](Nc1cc(C(N)=O)nc(-c2ccc(Oc3ccc(C#N)cn3)cc2)n1)C(N)=O]

¹H NMR (400 MHz, DMSO-d₆): 8.68 (1H, d, J=2.0 Hz), 8.61 (2H, d, J=8.8 Hz), 8.35 (1H, dd, J=8.8 Hz, 2.4 Hz), 8.32 (1H, s), 7.99 (1H, d, J=6.6 Hz), 7.75 (1H, s), 7.56 (1H, s), 7.32-7.26 (3H, m), 7.12 (1H, s), 7.01 (1H, s), 4.63-4.54 (1H, m), 1.38 (3H, d, J=7.0 Hz). LC/MS: m/z=404.1 [M+H]⁺.

(S)-6-((1-amino-1-oxopropan-2-yl)amino)-2-(4-(5-chloro-2-fluorophenoxy)phenyl)pyrimidine-4-carboxamide (Cpd No. 38)

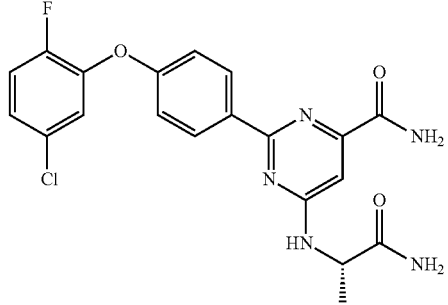

¹H NMR (400 MHz, DMSO-d₆): 8.56 (2H, d, J=8.8 Hz), 8.28 (1H, s), 7.96 (1H, d, J=6.1 Hz), 7.74 (1H, s), 7.56-7.47 (2H, m), 7.38-7.33 (2H, m), 7.12-7.06 (3H, m), 6.99 (1H, s), 4.60-4.51 (1H, m), 1.37 (3H, d, J=7.0 Hz). LC/MS: m/z=430.0 [M+H]⁺.

(S)-2-(4-(4-fluorophenoxy)phenyl)-6-(1-hydroxypropan-2-yl)amino) pyrimidine-4-carboxamide (Cpd No. 42)

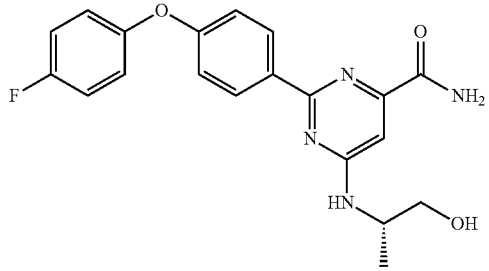 [SMILES: C[C@@H](CO)Nc1cc(C(N)=O)nc(-c2ccc(Oc3ccc(F)cc3)cc2)n1]

¹H NMR (400 MHz, DMSO-d₆): 8.51 (2H, d, J=8.1 Hz), 8.25 (1H, s), 7.72 (1H, s), 7.66-7.59 (1H, m), 7.32-7.23 (2H, m), 7.19-7.12 (2H, m), 7.04 (2H, d, J=8.1 Hz), 6.98 (1H, s), 4.84-4.77 (1H, m), 4.34-4.23 (1H, m), 3.57-3.47 (1H, m), 3.44-3.36 (1H, m), 1.18 (3H, d, J=6.6 Hz). LC/MS: m/z=383.2 [M+H]⁺.

(S)-2-(4-(4-fluorophenoxy)phenyl)-6-(2-(hydroxymethyl)pyrrolidin-1-yl)pyrimidine-4-carboxamide (Cpd No. 43)

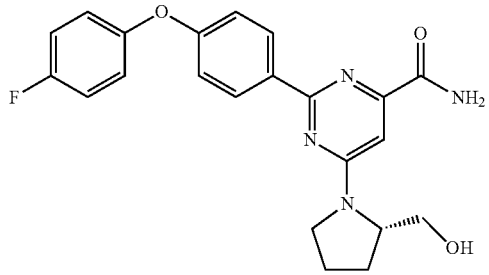 [SMILES: NC(=O)c1cc(N2CCC[C@H]2CO)nc(-c2ccc(Oc3ccc(F)cc3)cc2)n1]

¹H NMR (400 MHz, DMSO-d₆): 8.58-8.52 (2H, m), 8.33 (1H, s), 7.79 (1H, s), 7.33-7.25 (2H, m), 7.21-7.13 (2H, m), 7.11 (0.4H, br s), 7.07-7.02 (2H, m), 6.98 (0.6H, br s), 5.02 (0.4H, br s), 4.82 (0.6H, br s), 4.39 (0.6H, br s), 3.98 (0.4H, br s), 3.73 (1H, br s), 3.68-3.39 (2H, m), 3.41-3.30 (1H, m), 2.14-1.89 (4H, m). LC/MS: m/z=409.2 [M+H]⁺.

2-(4-(4-fluorophenoxy)phenyl)-6-((2-hydroxy-2-methylpropyl)amino) pyrimidine-4-carboxamide (Cpd No. 44)

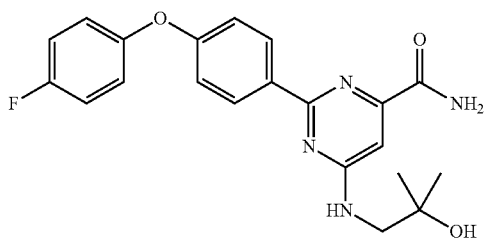 [SMILES: CC(C)(O)CNc1cc(C(N)=O)nc(-c2ccc(Oc3ccc(F)cc3)cc2)n1]

¹H NMR (400 MHz, DMSO-d₆): 8.51 (2H, d, J=9.0 Hz), 8.24 (1H, s), 7.76-7.69 (2H, m), 7.31-7.24 (2H, m), 7.18-7.12 (2H, m), 7.11 (1H, s), 7.04 (2H, d, J=9.0 Hz), 4.61 (1H, s), 3.48 (2H, d, J=5.7 Hz), 1.14 (6H, s). LC/MS: m/z=397.2 [M+H]⁺.

2-(4-(4-fluorophenoxy)phenyl)-6-(((1-hydroxycyclohexyl)methyl)amino) pyrimidine-4-carboxamide (Cpd No. 45)

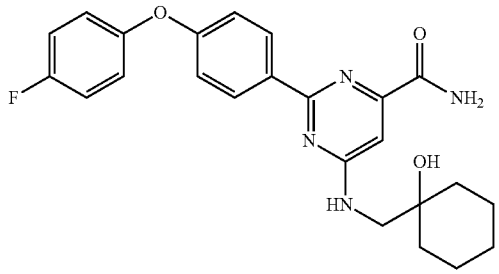 [SMILES: NC(=O)c1cc(NCC2(O)CCCCC2)nc(-c2ccc(Oc3ccc(F)cc3)cc2)n1]

¹H NMR (400 MHz, DMSO-d₆): 8.51 (2H, d, J=8.8 Hz), 8.24 (1H, s), 7.74-7.67 (2H, m), 7.31-7.24 (2H, m), 7.19-7.13 (2H, m), 7.11 (1H, s), 7.04 (2H, d, J=9.0 Hz), 4.39 (1H, s), 3.51 (2H, d, J=5.7 Hz), 1.62-1.33 (9H, m), 1.26-1.14 (1H, m). LC/MS: m/z=437.3 [M+H]⁺.

(S)-6-((2,3-dihydroxypropyl)amino)-2-(4-(4-fluorophenoxy)phenyl)pyrimidine-4-carboxamide (Cpd No. 46)

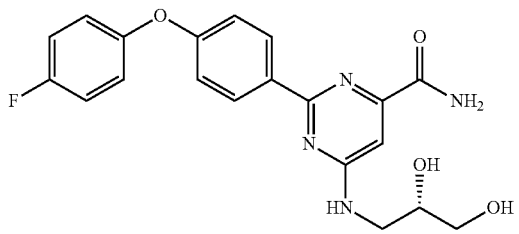 [SMILES: NC(=O)c1cc(NC[C@H](O)CO)nc(-c2ccc(Oc3ccc(F)cc3)cc2)n1]

¹H NMR (400 MHz, CD₃OD): 8.50 (2H, d, J=8.8 Hz), 7.21-7.08 (5H, m), 7.05 (2H, d, J=9.0 Hz), 3.99-3.90 (1H, m), 3.86-3.75 (1H, m), 3.66-3.55 (3H, m). LC/MS: m/z=399.1 [M+H]⁺.

6-((1,3-dihydroxypropan-2-yl)amino)-2-(4-(4-fluorophenoxy)phenyl)pyrimidine-4-carboxamide (Cpd No. 47)

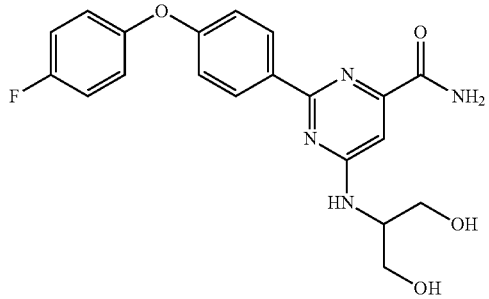 [SMILES: NC(=O)c1cc(NC(CO)CO)nc(-c2ccc(Oc3ccc(F)cc3)cc2)n1]

¹H NMR (400 MHz, DMSO-d₆): 8.52 (2H, d, J=8.8 Hz), 8.25 (1H, s), 7.71 (1H, s), 7.61 (1H, d, J=7.7 Hz), 7.32-7.24 (2H, m), 7.20-7.12 (2H, m), 7.08-7.01 (3H, m), 4.84-4.70 (2H, m), 4.32-4.21 (1H, m), 3.62-3.51 (4H, m). LC/MS: m/z=399.1 [M+H]⁺.

(S)-6-((1-amino-1-oxopropan-2-yl)amino)-2-(4-((3-trifluoromethyl)pyridine-2-yl)oxy)phenyl)pyrimidine-4-carboxamide (Cpd No. 58)

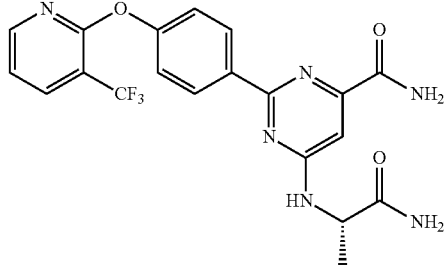 [SMILES: C[C@H](Nc1cc(C(N)=O)nc(-c2ccc(Oc3ncccc3C(F)(F)F)cc2)n1)C(N)=O]

¹H NMR (400 MHz, DMSO-d₆): 8.59 (2H, d, J=8.8 Hz), 8.42 (1H, d, J=4.8 Hz), 8.32 (1H, br), 8.30 (1H, bs), 7.98 (1H, d, J=6.8 Hz), 7.74 (1H, bs), 7.56 (1H, bs), 7.38 (1H, dd, J=5.6, 6.8 Hz), 7.24 (2H, d, J=8.8 Hz), 7.13 (1H, s), 7.02 (1H, bs), 4.59 (1H, m), 1.38 (3H, d, J=7.2 Hz). LC/MS: m/z=447 [M+H]⁺.

(S)-6-((1-amino-1-oxopropan-2-yl)amino)-2-(4-((6-trifluoromethyl)pyridine-2-yl)oxy)phenyl)pyrimidine-4-carboxamide (Cpd No. 59)

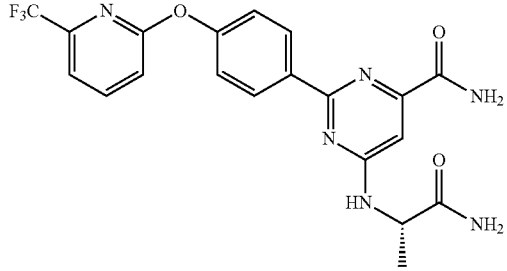 [SMILES: C[C@H](Nc1cc(C(N)=O)nc(-c2ccc(Oc3cccc(C(F)(F)F)n3)cc2)n1)C(N)=O]

¹H NMR (400 MHz, DMSO-d₆): 8.62 (2H, d, J=8.8 Hz), 8.34 (1H, br), 8.10 (1H, t, J=8 Hz), 7.98 (1H, d, J=6.8 Hz), 7.74 (1H, bs), 7.68 (1H, d, J=7.2 Hz) 7.57 (1H, bs), 7.40 (1H, d, J=8.4 Hz), 7.28 (2H, d, J=8.8 Hz), 7.13 (1H, s), 7.02 (1H, bs), 4.59 (1H, m), 1.38 (3H, d, J=7.2 Hz). LC/MS: m/z=447 [M+H]⁺.

(S)-6-((1-amino-1-oxopropan-2-yl)amino)-2-(4-((6-trifluoromethyl)pyridine-3-yl)oxy)phenyl)pyrimidine-4-carboxamide (Cpd No. 60)

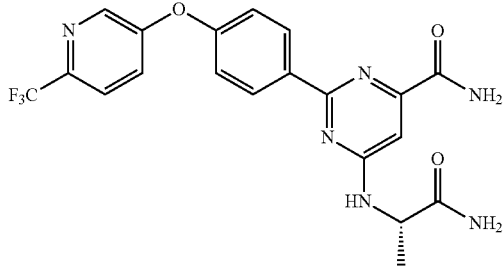 [SMILES: C[C@H](Nc1cc(C(N)=O)nc(-c2ccc(Oc3ccc(C(F)(F)F)nc3)cc2)n1)C(N)=O]

¹H NMR (400 MHz, DMSO-d₆): 8.64 (2H, d, J=8.8 Hz), 8.62 (1H, d, J=2.8 Hz), 8.33 (1H, br), 7.99 (1H, d, J=6.8 Hz), 7.93 (1H, d, J=8.8 Hz), 7.76 (1H, bs), 7.64 (1H, dd, J=8, 2.4 Hz) 7.55 (1H, bs), 7.27 (2H, d, J=8.8 Hz), 7.13 (1H, s), 7.02 (1H, bs), 4.59 (1H, m), 1.38 (3H, d, J=7.2 Hz). LC/MS: m/z=447 [M+H]⁺.

(S)-6-((1-amino-1-oxopropan-2-yl)amino)-2-(4-((6-fluoropyridine-2-yl)oxy)phenyl)pyrimidine-4-carboxamide (Cpd No. 61)

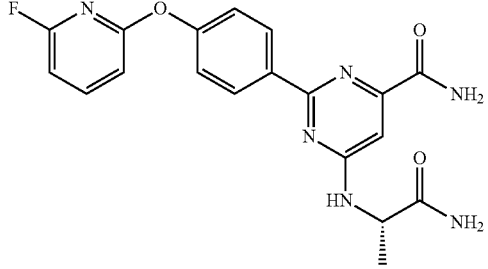 [SMILES: C[C@H](Nc1cc(C(N)=O)nc(-c2ccc(Oc3cccc(F)n3)cc2)n1)C(N)=O]

¹H NMR (400 MHz, DMSO-d₆): 8.60 (2H, d, J=8.8 Hz), 8.32 (1H, br), 8.05 (1H, q, J=8.4 Hz), 7.99 (1H, d, J=7.6 Hz), 7.75 (1H, bs), 7.55 (1H, bs), 7.25 (2H, d, J=8.8 Hz), 7.13 (1H, s), 7.02 (1H, bs), 7.00 (1H, dd, J=7.6, 1.2 Hz), 6.93 (1H, dd, J=8, 2.4 Hz), 4.59 (1H, m), 1.38 (3H, d, J=7.2 Hz). LC/MS: m/z=397 [M+H]⁺.

(S)-6-((1-amino-1-oxopropan-2-yl)amino)-2-(4-((5-fluoropyridine-2-yl)oxy)phenyl)pyrimidine-4-carboxamide (Cpd No. 62)

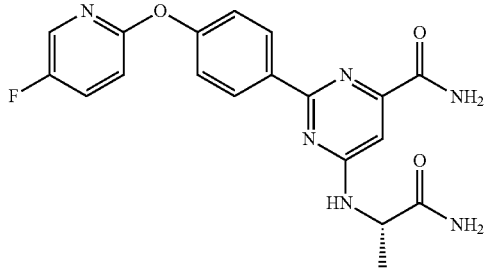 [SMILES: C[C@H](Nc1cc(C(N)=O)nc(-c2ccc(Oc3ccc(F)cn3)cc2)n1)C(N)=O]

¹H NMR (400 MHz, DMSO-d₆): 8.57 (2H, d, J=8.8 Hz), 8.30 (1H, br), 8.20 (1H, d, J=3.2 Hz), 7.97 (1H, d, J=6.4 Hz), 7.87 (1H, dt, J=2.8, 7.6 Hz), 7.75 (1H, bs), 7.55 (1H, bs), 7.19 (1H, d, J=8.8 Hz), 7.18 (2H, d, J=8.8 Hz), 7.11 (1H, s), 7.02 (1H, bs), 4.59 (1H, m), 1.38 (3H, d, J=7.2 Hz). LC/MS: m/z=397 [M+H]⁺.

(S)-6-((1-amino-1-oxopropan-2-yl)amino)-2-(4-((5-chloropyridine-2-yl)oxy)phenyl)pyrimidine-4-carboxamide (Cpd No. 63)

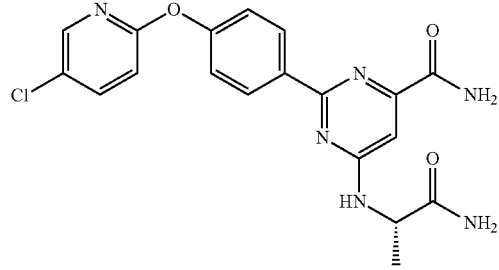 [SMILES: C[C@H](Nc1cc(C(N)=O)nc(-c2ccc(Oc3ccc(Cl)cn3)cc2)n1)C(N)=O]

¹H NMR (400 MHz, DMSO-d₆): 8.57 (2H, d, J=8.8 Hz), 8.31 (1H, br), 8.25 (1H, d, J=2.8 Hz), 8.00 (1H, dd, J=8.8, 2.8 Hz), 7.97 (1H, d, J=6.4 Hz), 7.74 (1H, bs), 7.55 (1H, bs), 7.21 (2H, d, J=8.8 Hz), 7.16 (1H, d, J=8.8 Hz), 7.11 (1H, s), 7.02 (1H, bs), 4.59 (1H, m), 1.38 (3H, d, J=7.2 Hz). LC/MS: m/z=413 [M+H]⁺.

(S)-6-((1-amino-1-oxopropan-2-yl)amino)-2-(4-(4-chloro-2-fluorophenoxy)phenyl)pyrimidine-4-carboxamide (Cpd No. 64)

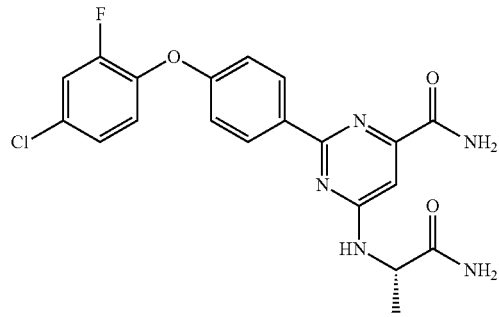 [SMILES: C[C@H](Nc1cc(C(N)=O)nc(-c2ccc(Oc3ccc(Cl)cc3F)cc2)n1)C(N)=O]

¹H NMR (400 MHz, DMSO-d₆): 8.55 (2H, d, J=8.8 Hz), 8.28 (1H, br), 7.96 (1H, d, J=6.0 Hz), 7.74 (1H, bs), 7.69 (1H, dd, J=11, 2.0 Hz), 7.54 (1H, bs), 7.35 (1H, dt, J=8.4, 2.4 Hz), 7.30 (1H, t, J=8.8 Hz), 7.09 (1H, bs), 7.05 (2H, d, J=8.8 Hz), 7.00 (1H, bs), 4.57 (1H, m), 1.38 (3H, d, J=7.2 Hz). LC/MS: m/z=430 [M+H]⁺.

(S)-6-((1-amino-1-oxopropan-2-yl)amino)-2-(4-(bis(4-fluorophenyl)methyl)piperazin-1-yl)pyrimidine-4-carboxamide (Cpd No. 71)

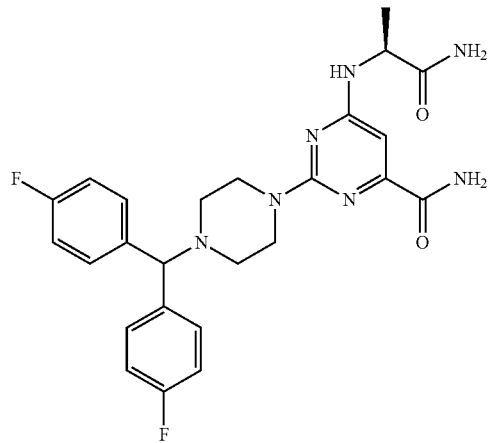 [SMILES: C[C@H](Nc1cc(C(N)=O)nc(N2CCN(C(c3ccc(F)cc3)c3ccc(F)cc3)CC2)n1)C(N)=O]

¹H NMR (CD₃OD): 7.20-7.4 (4H, m), 6.85-6.95 (4H, m), 6.40 (1H, s), 4.2 (2H, m), 3.65-3.79 (4H, m), 2.15-2.35 (4H, m), 1.40 (3H, d, J=7.0 Hz). LC/MS: m/z=496 [M+H]⁺.

(S)-6-((1-amino-1-oxopropan-2-yl)amino)-2-(2-(pyridazin-4-yl)-4-(trifluoromethyl)phenoxy)pyrimidine-4-carboxamide (Cpd No. 72)

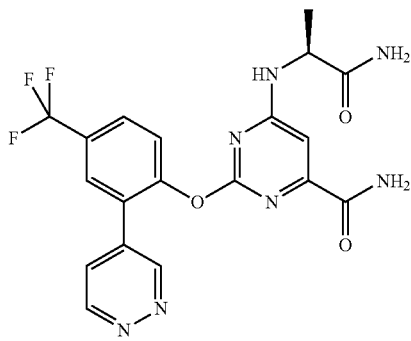 [SMILES: C[C@H](Nc1cc(C(N)=O)nc(Oc2ccc(C(F)(F)F)cc2-c2ccnnc2)n1)C(N)=O]

¹H NMR (CD₃OD): 9.09-9.51 (2H, m), 7.82-8.05 (3H, m), 7.4 (1H, m), 6.80 (1H, s), 4.0 (1H, m), 1.35 (3H, d, J=7.0 Hz). LC/MS: m/z=448 [M+H]⁺.

(S)-6-((1-amino-1-oxopropan-2-yl)amino)-2-(1,3-dihydrospiro[indene-2,4'-piperidin]-1'-yl)pyrimidine-4-carboxamide (Cpd. No. 73)

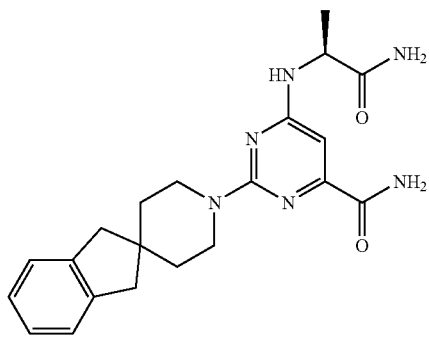 [SMILES: C[C@H](Nc1cc(C(N)=O)nc(N2CCC3(CC2)Cc2ccccc2C3)n1)C(N)=O]

¹H NMR (CD₃OD): 6.95-7.20 (m, 4H), 6.35 (1H, s), 4.6 (2H, m), 4.2 (1H, m), 2.95 (2H, m), 2.88 (m, 2H), 2.10 (2H, m), 1.70 (2H, m), 1.40 (2H, m), 1.28 (3H, d, J=7.0 Hz). LC/MS: m/z=395 [M+H]⁺.

6-(3-carbamoylpiperazin-1-yl)-2-(4-(4-fluorophenoxy)phenyl)pyrimidine-4-carboxamide (Cpd. No. 74)

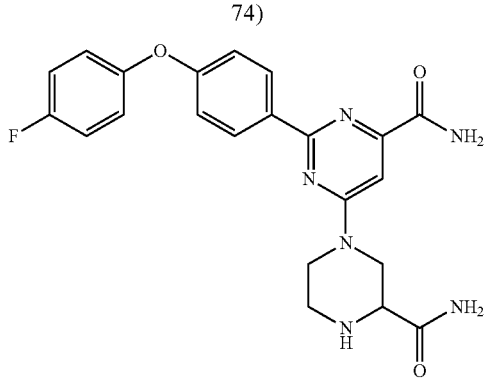

¹H NMR (400 MHz, DMSO-d₆): 8.53 (2H, d, J=9.0 Hz), 8.34 (1H, d, J=2.0 Hz), 7.80 (1H, d, J=2.2 Hz), 7.45 (1H, s), 7.31-7.24 (2H, m), 7.24-7.20 (2H, m), 7.19-7.12 (2H, m), 7.05 (2H, d, J=9.0 Hz), 5.02-3.71 (2H, br), 3.27 (3H, br s), 3.02-2.94 (1H, br m), 2.78-2.65 (2H, br m). LC/MS: m/z=437.1 [M+H]⁺.

(S)-2-(4-(4-chloro-2-fluorophenoxy)phenyl)-6-((2-oxopyrrolidin-3-yl)amino)pyrimidine-4-carboxamide (Cpd No. 75)

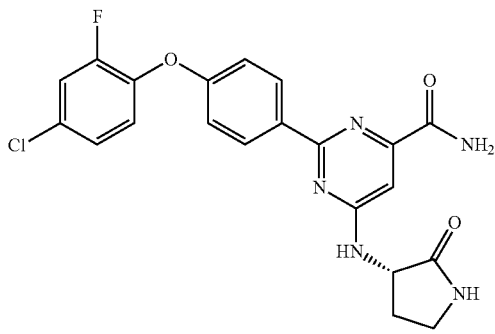 [SMILES: NC(=O)c1cc(N[C@H]2CCNC2=O)nc(-c2ccc(Oc3ccc(Cl)cc3F)cc2)n1]

¹H NMR (400 MHz, DMSO-d₆): 8.52 (2H, d, J=9.0 Hz), 8.29 (1H, s), 8.09 (1H, d, J=7.2 Hz), 7.96 (1H, s), 7.75 (1H, s), 7.70 (1H, dd, J=11.0 Hz, 2.2 Hz), 7.38-7.28 (2H, m), 7.09-7.03 (3H, m), 4.75 (1H, m), 3.32-3.23 (2H, m), 2.57-2.46 (1H, m, overlaps with DMSO peak), 2.06-1.93 (1H, m). LC/MS: m/z=442.0 [M+H]⁺.

(S)-6-((1-amino-1-oxopropan-2-yl)oxy)-2-(4-(4-(trifluoromethoxy)phenoxy)phenyl)pyrimidine-4-carboxamide (Cpd No. 76)

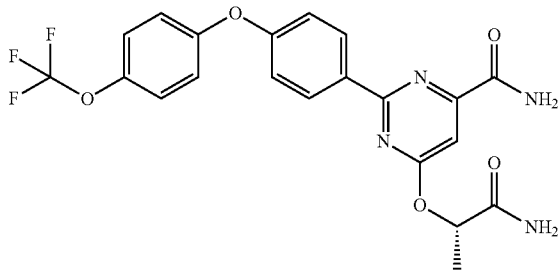 [SMILES: C[C@H](Oc1cc(C(N)=O)nc(-c2ccc(Oc3ccc(OC(F)(F)F)cc3)cc2)n1)C(N)=O]

¹H NMR (400 MHz, DMSO-d₆): 8.62 (2H, d, J=9.0 Hz), 8.51 (1H, s), 7.97 (1H, s), 7.70 (1H, s), 7.47-7.42 (2H, m), 7.26 (1H, s), 7.25-7.19 (3H, m), 7.14 (2H, d, J=9.0 Hz), 5.38 (1H, q, J=6.8 Hz), 1.53 (3H, d, J=6.8 Hz). LC/MS: m/z=463.0 [M+H]⁺.

(S)-6-((1-amino-1-oxopropan-2-yl)oxy)-2-(4-(4-cyanophenoxy)phenyl)pyrimidine-4-carboxamide (Cpd No. 77)

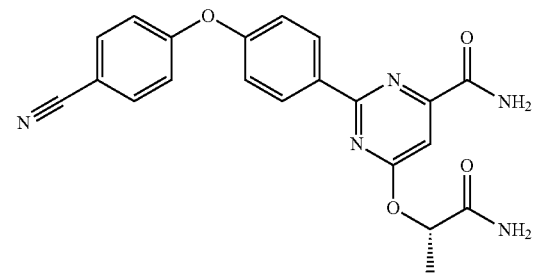 [SMILES: C[C@H](Oc1cc(C(N)=O)nc(-c2ccc(Oc3ccc(C#N)cc3)cc2)n1)C(N)=O]

¹H NMR (400 MHz, DMSO-d₆): 8.67 (2H, d, J=9.0 Hz), 8.55 (1H, s), 7.98 (1H, s), 7.89 (2H, d, J=9.0 Hz), 7.71 (1H, s), 7.28 (1H, s), 7.25 (2H, d, J=8.8 Hz), 7.24-7.19 (3H, m), 5.39 (1H, q, J=6.8 Hz), 1.53 (3H, d, J=6.8 Hz). LC/MS: m/z=404.1 [M+H]⁺.

6-((3R,4R)-3,4-dihydroxypyrrolidin-1-yl)-2-(4-(4-fluorophenoxy)phenyl)pyrimidine-4-carboxamide (Cpd No. 80)

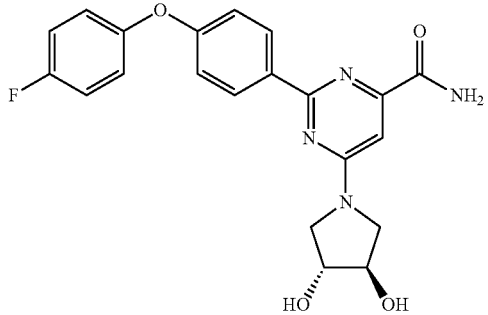 [SMILES: NC(=O)c1cc(N2C[C@@H](O)[C@H](O)C2)nc(-c2ccc(Oc3ccc(F)cc3)cc2)n1]

¹H NMR (400 MHz, DMSO-d₆): 8.55 (2H, d, J=9.0 Hz), 8.33 (1H, d, J=2.2 Hz), 7.79 (1H, d, J=2.2 Hz), 7.31-7.24 (2H, m), 7.19-7.13 (2H, m), 7.05 (2H, d, J=9.0 Hz), 6.90 (1H, s), 5.29 (1H, d, J=3.5 Hz), 5.21 (1H, d, J=3.5 Hz), 4.14-4.09 (1H, m), 4.09-4.04 (1H, m), 3.76-3.62 (3H, m), 3.35-3.30 (1H, m). LC/MS: m/z=411.1 [M+H]⁺.

6-(2-carbamoyl-4-methylpiperazin-1-yl)-2-(4-(4-fluorophenoxy)phenyl)pyrimidine-4-carboxamide (Cpd No. 82)

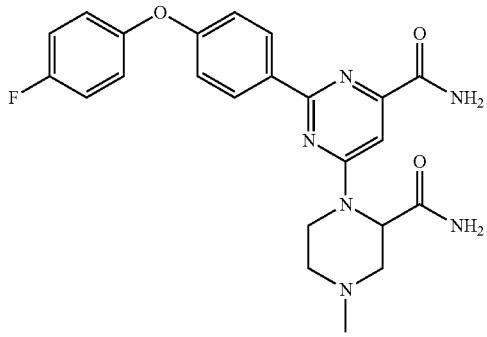 [SMILES: CN1CCN(c2cc(C(N)=O)nc(-c3ccc(Oc4ccc(F)cc4)cc3)n2)C(C(N)=O)C1]

¹H NMR (400 MHz, CD₃OD): 8.49 (2H, d, J=8.8 Hz), 7.37 (1H, s), 7.19-7.08 (4H, m), 7.03 (2H, d, J=9.0 Hz), 5.65-5.24 (1H, br), 4.48-3.95 (1H, br), 3.64-3.53 (1H, m), 3.50-3.42 (1H, m), 2.99-2.92 (1H, m), 2.40 (1H, dd, J=12.1 Hz, 4.8 Hz), 2.33 (3H, s), 2.20 (1H, dt, J=11.6 Hz, 3.5 Hz). LC/MS: m/z=451.2 [M+H]⁺.

6-(2-carbamoyl-4-methylpiperazin-1-yl)-2-(4-(4-chloro-2-fluorophenoxy)phenyl)pyrimidine-4-carboxamide (Cpd No. 83)

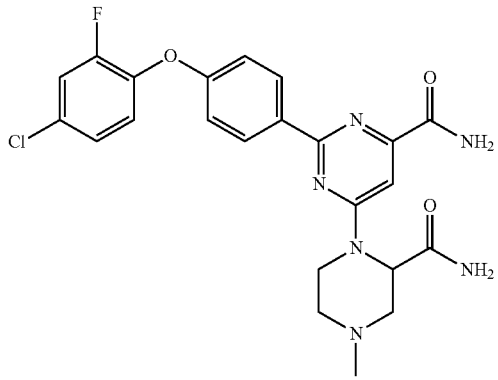 [SMILES: CN1CCN(c2cc(C(N)=O)nc(-c3ccc(Oc4ccc(Cl)cc4F)cc3)n2)C(C(N)=O)C1]

¹H NMR (400 MHz, CD₃OD): 8.50 (2H, d, J=9.0 Hz), 7.42 (1H, dd, J=10.5 Hz, 2.4 Hz), 7.37 (1H, s), 7.29-7.18 (2H, m), 7.04 (2H, d, J=8.8 Hz), 5.64-5.22 (1H, br), 4.50-3.92 (1H, br), 3.65-3.53 (1H, m), 3.50-3.41 (1H, m), 2.99-2.92 (1H, m), 2.40 (1H, dd, J=11.8 Hz, 4.8 Hz), 2.33 (3H, s), 2.20 (1H, dt, J=11.6 Hz, 3.5 Hz). LC/MS: m/z=485.1 [M+H]⁺.

6-(2-carbamoylpiperazin-1-yl)-2-(4-(4-(trifluoromethyl)phenoxy)phenyl)pyrimidine-4-carboxamide (Cpd No. 86)

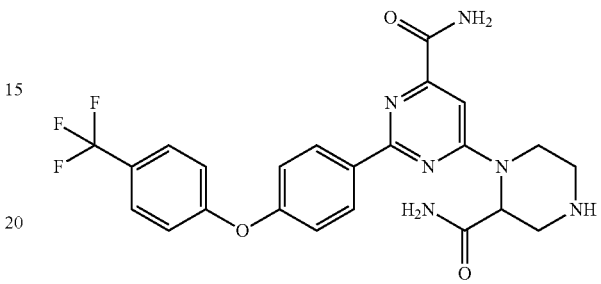

¹H NMR (CD₃OD): 8.45 (m, 2H), 7.55 (m, 2H); 7.25 (s, 1H), 6.95-7.15 (m, 4H), 5.20 (m, 1H), 4.10 (m, 1H), 3.30-3.50 (m, 2H), 2.85-3.0 (m, 2H), 2.70 (m, 1H). LC/MS: m/z=487 [M+H]⁺.

(S)-6-(2-carbamoylpyrrolidin-1-yl)-2-(4-(5-chloro-2-fluorophenoxy)phenyl)pyrimidine-4-carboxamide (Cpd No. 87)

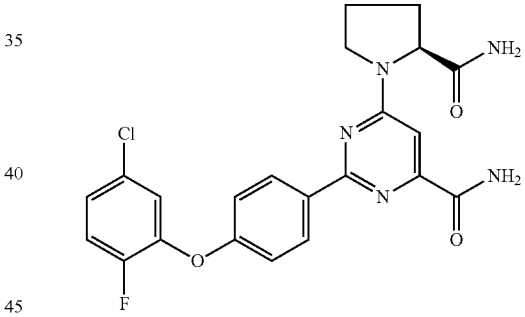

¹H NMR (CD₃OD): 8.40 (m, 2H), 6.75-7.20 (m, 6H), 4.55 (m, 1H), 3.30-3.70 (m, 2H), 1.95-2.35 (m, 4H). LC/MS: m/z=456 [M+H]

(S)-6-(2-carbamoylpyrrolidin-1-yl)-2-(4-((5-(trifluoromethyl)pyridin-2-yl)oxy)phenyl)pyrimidine-4-carboxamide (Cpd No. 88)

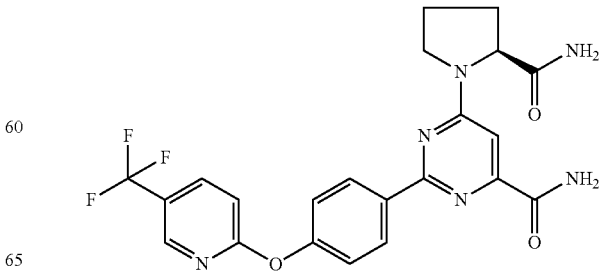

¹H NMR (CD₃OD): 8.49 (m, 2H), 8.30 (s, 1H), 8.15 (m, 1H), 6.95-7.20 (m, 3H), 4.55 (m, 1H), 3.40-3.60 (m, 2H), 1.90-2.40 (m, 4H). LC/MS: m/z=473 [M+H]⁺.

(S)-6-(2-carbamoylpyrrolidin-1-yl)-2-(4-(4-cyanophenoxy)phenyl)pyrimidine-4-carboxamide (Cpd No. 89)

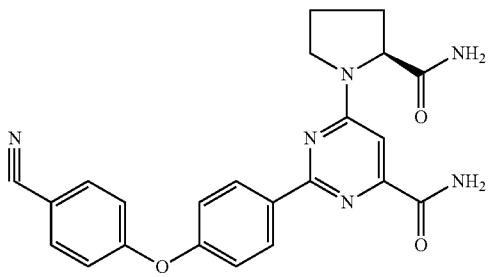 [SMILES: N#Cc1ccc(Oc2ccc(-c3nc(C(N)=O)cc(N4CCC[C@H]4C(N)=O)n3)cc2)cc1]

¹H NMR (CD₃OD): 8.49 (m, 2H), 7.65 (m, 2H), 7.05 (m, 5H), 4.55 (m, 1H), 3.30-3.70 (m, 2H), 1.90-2.40 (m, 4H). LC/MS: m/z=429 [M+H]⁺.

(S)-2-(4-(benzo[d][1,3]dioxol-5-yloxy)phenyl)-6-(2-carbamoylpyrrolidin-1-yl)pyrimidine-4-carboxamide (Cpd No. 90)

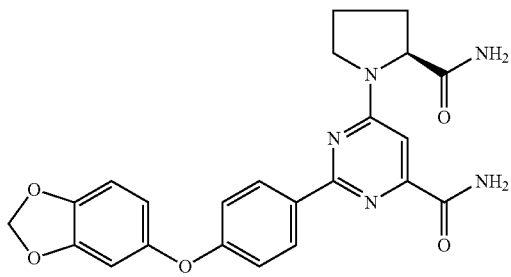 [SMILES: NC(=O)c1cc(N2CCC[C@H]2C(N)=O)nc(-c2ccc(Oc3ccc4c(c3)OCO4)cc2)n1]

¹H NMR (CD₃OD): 8.40 (m, 2H), 6.60-7.05 (m, 4H), 6.30-6.60 (m, 2H), 5.90 (s, 2H), 4.50 (m, 1H), 3.30-3.70 (m, 2H), 1.90-2.40 (m, 4H). LC/MS: m/z=448 [M+H]⁺.

(S)-6-(2-carbamoylpyrrolidin-1-yl)-2-(4-(4-(trifluoromethyl)phenoxy)phenyl)pyrimidine-4-carboxamide (Cpd No. 91)

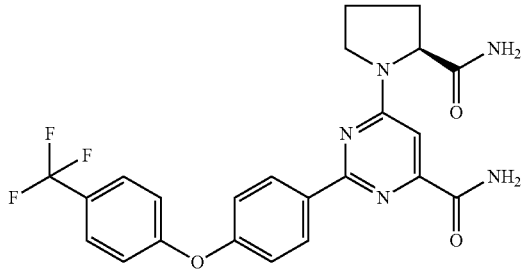

¹H NMR (CD₃OD): 8.45 (m, 2H), 7.50 (m, 2H), 6.90-7.05 (m, 4H), 4.60 (m, 1H), 3.40-3.70 (m, 2H), 1.90-2.40 (m, 4H). LC/MS: m/z=472[M+H]⁺.

(S)-6-((1-amino-1-oxopropan-2-yl)oxy)-2-(4-(4-chloro-2-fluorophenoxy)phenyl)pyrimidine-4-carboxamide (Cpd No. 92)

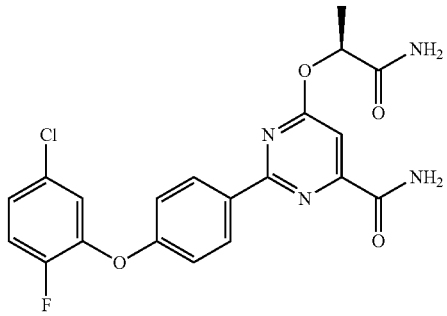 [SMILES: C[C@H](Oc1cc(C(N)=O)nc(-c2ccc(Oc3cc(Cl)ccc3F)cc2)n1)C(N)=O]

¹H NMR (CD₃OD): 8.45 (m, 2H), 7.25-7.35 (m, 2H), 7.05-7.15 (m, 2H), 6.85-6.95 (m, 2H), 5.40 (m, 1H), 1.50 (d, J=7.20 Hz, 3H). LC/MS: m/z=431 [M+H]⁺.

(S)-6-((1-amino-1-oxopropan-2-yl)oxy)-2-(4-(5-chloro-2-fluorophenoxy)phenyl)pyrimidine-4-carboxamide (Cpd No. 93)

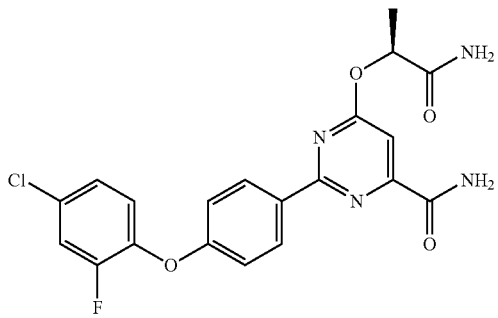 [SMILES: C[C@H](Oc1cc(C(N)=O)nc(-c2ccc(Oc3ccc(Cl)cc3F)cc2)n1)C(N)=O]

¹H NMR (CD₃OD): 8.45 (m, 2H), 7.30 (s, 1H), 7.05-7.20 (m, 3H), 6.85-6.95 (m 2H), 5.40 (m, 1H), 1.50 (d, J=7.20 Hz, 3H). LC/MS: m/z=431 [M+H]⁺.

(S)-2-(4-(4-fluorophenoxy)phenyl)-6-((1-morpholino-1-oxopropan-2-yl)amino)pyrimidine-4-carboxamide (Cpd No. 95)

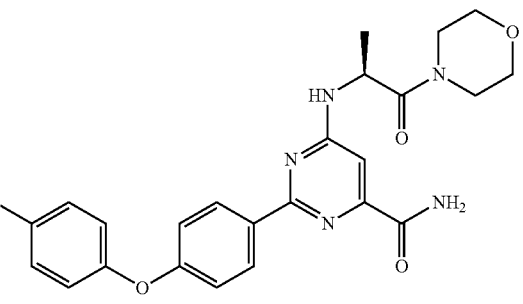

$^1$H NMR (CD$_3$OD): 8.40 (m, 2H), 6.95-7.20 (m, 7H), 5.15 (m, 1H), 3.45-3.85 (m, 8H), 1.50 (d, J=7.20 Hz, 3H). LC/MS: m/z=466 [M+H]$^+$.

(S)-6-((1-amino-1-oxopropan-2-yl)oxy)-2-(4-(4-(trifluoromethylmethyl)phenoxy)phenyl)pyrimidine-4-carboxamide (Cpd. No. 98)

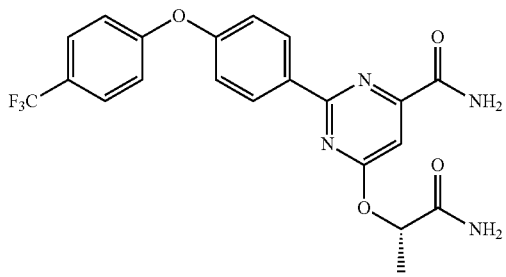

$^1$H NMR (400 MHz, DMSO-d$_6$): δ 8.66 (2H, d, J=9.2 Hz), 8.54 (1H, s), 7.98 (1H, s), 7.79 (2H, d, J=8.4 Hz), 7.71 (1H, s), 7.28 (1H, s), 7.27-7.20 (5H, m), 5.39 (1H, m), 1.54 (3H, d, J=6.8 Hz). LC/MS: m/z=447[M+H]$^+$.

(S)-6-((2-oxopyrrolidin-3-yl)amino)-2-(4-((5-(trifluoromethyl)pyridin-2-yl)oxy)phenyl)pyrimidine-4-carboxamide (Cpd. No. 99)

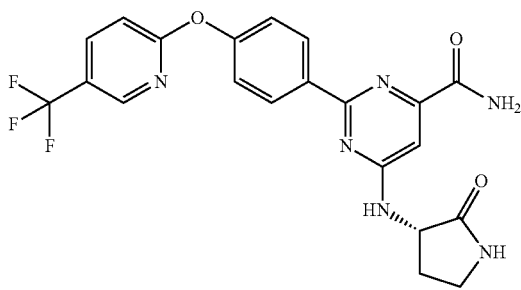 [SMILES: NC(=O)c1cc(N[C@H]2CCNC2=O)nc(-c2ccc(Oc3ccc(C(F)(F)F)cn3)cc2)n1]

$^1$H NMR (400 MHz, DMSO-d$_6$): δ 8.62-8.56 (3H, m), 8.33 (1H, s), 8.27 (1H, dd, J=8.8 Hz, 2.4 Hz), 8.12 (1H, d, J=6.8 Hz), 7.98 (1H, s), 7.76 (1H, s), 7.33-7.26 (3H, m), 7.09 (1H, s), 4.82-4.71 (1H, m), 3.35-3.25 (2H, m), 2.61-2.49 (1H, m, overlaps with DMSO peak), 2.07-1.94 (1H, m). LC/MS: m/z=459.1 [M+H]$^+$.

Example 35

Preparation of 6-(((S)-1-amino-1-oxopropan-2-yl)amino)-2-(4-(4-(trifluoromethyl)phenoxy)cyclohex-1-en-1-yl)pyrimidine-4-carboxamide (Cpd No. 103)

Scheme 77

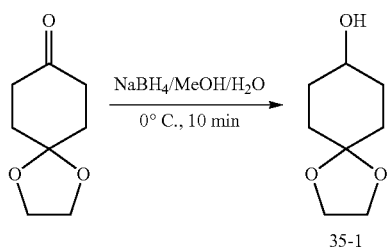

Synthesis of 1,4-dioxaspiro[4.5]decan-8-ol (compound 35-1)

NaBH$_4$ (370 mg, 10 mmol) in 5 mL H$_2$O was slowly added to 10 mL of MeOH solution of 1,4-dioxaspiro[4.5]decan-8-one (1.56 g, 10 mmol) at 0° C. After the addition, the methanol was removed and the residue was extracted with EtOAc (2×20 mL). The EtOAc layer was dried over MgSO4, filtered, and evaporated to give 1,4-dioxaspiro[4.5]decan-8-ol (compound 35-1), which was used in next step without further purification (1.56 g, yield 100%).

Scheme 78

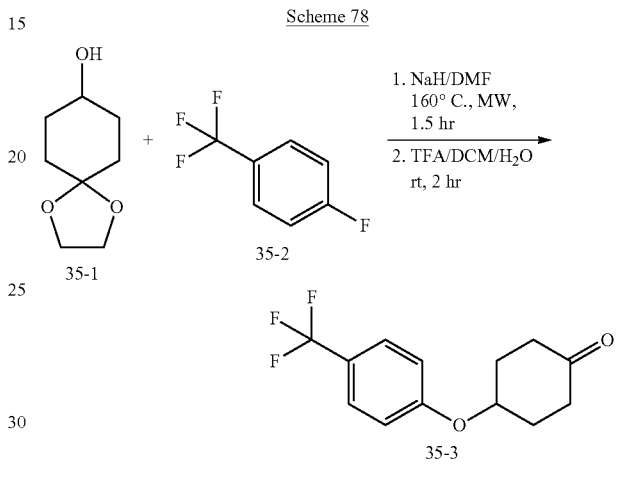

Synthesis of 4-(4-(trifluoromethyl)phenoxy)cyclohexanone (compound 35-3)

NaH (200 mg, 5 mmol) was added to a toluene solution of 1,4-dioxaspiro[4.5]decan-8-ol (compound 35-1) (730 mg, 5 mmol) at room temperature. The resulting mixture was stirred at 60° C. for 0.5 hr and then cooled to room temperature. A DMF solution of 1-fluoro-4-(trifluoromethyl)benzene (compound 35-2) (820 mg, 5 mmol) was added and the reaction mixture was heated at 160° C. for 1.5 hr in a microwave (Biotage initiator). The reaction mixture was then cooled to room temperature and extracted with EtOAc (2×20 mL). The crude product was treated with TFA/DCM/H$_2$O (2 mL/4 mL/0.6 mL) at room temperature for 2 hr and then extracted with EtOAc (2×20 mL). The EtOAc was removed and the residue was subjected to silica gel flash chromatography using EtOAc/hexanes as the eluent to give 4-(4-(trifluoromethyl)phenoxy)cyclohexanone (compound 35-3) as a colorless oil (0.52 g, yield 40%). LC/MS: m/z=259 [M+H]$^+$.

Scheme 79

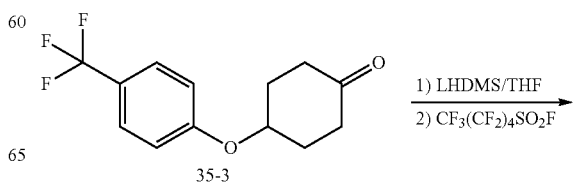

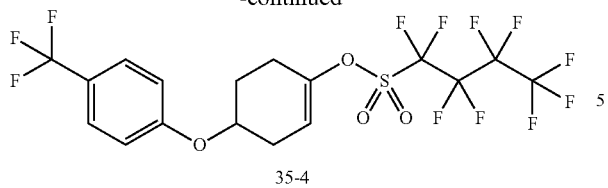

35-4

Synthesis of 4-(4-(trifluoromethyl)phenoxy)cyclohex-1-en-1-yl 1,1,2,2,3,3,4,4,4-nonafluorobutane-1-sulfonate (compound 35-4)

A LHDMS (1M in THF, 2.2 mmol, 2.2 mL) solution was added dropwise to a THF solution of 4-(4-(trifluoromethyl)phenoxy)cyclohexanone (compound 35-3) (0.52 g, 2 mmol) at −78° C. under argon, and the mixture was stirred for 1 hr after the addition was complete. $CF_3(CF_2)_3SO_2F$ (0.35 mL, 2 mmol) was added dropwise and the reaction mixture was allowed to warm up to room temperature over 2 hrs. The THF was removed and the residue was subjected to flash column using EtOAc/hexanes as the eluent to give 4-(4-(trifluoromethyl)phenoxy)cyclohex-1-en-1-yl 1,1,2,2,3,3,4,4,4-nonafluorobutane-1-sulfonate (compound 35-4) as a yellow oil (0.8 g, yield 74%).

Scheme 80

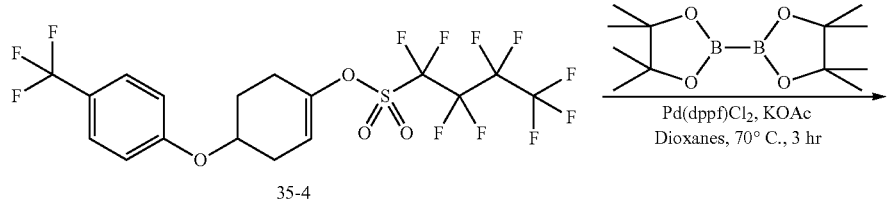

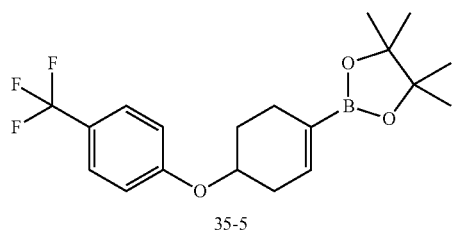

35-5

Synthesis of 4,4,5,5-tetramethyl-2-(4-(4-(trifluoromethyl)phenoxy)cyclohex-1-en-1-yl)-1,3,2-dioxaborolane (compound 35-5)

A mixture of 4-(4-(trifluoromethyl)phenoxy)cyclohex-1-en-1-yl 1,1,2,2,3,3,4,4,4-nonafluorobutane-1-sulfonate (compound 35-4) (0.8 g, 1.48 mmol), pinacol diborane (0.38 g, 1.48 mmol), KOAc (0.44 g, 4.5 mmol), and Pd(dppf)Cl₂ (60 mg, 0.07 mmol) was suspended in dioxanes (10 mL) and heated to 70° C. for 3 hrs. The reaction mixture was cooled to room temperature, extracted with EtOAc (2×20 mL), and dried over MgSO₄. Removal of EtOAc gave 4,4,5,5-tetramethyl-2-(4-(4-(trifluoromethyl)phenoxy)cyclohex-1-en-1-yl)-1,3,2-dioxaborolane (compound 35-5), which was used in the next step without further purification (0.5 g, crude yield 94%).

Scheme 81

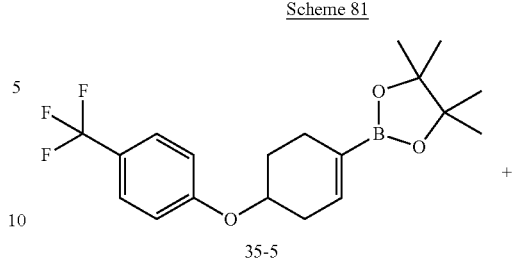

35-5 +

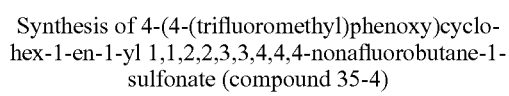

35-6

-continued

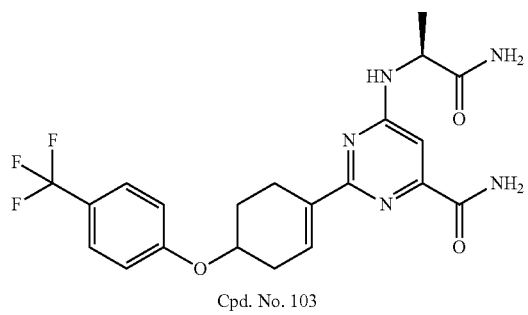

Cpd. No. 103

Synthesis of 6-(((S)-1-amino-1-oxopropan-2-yl)amino)-2-(4-(4-(trifluoromethyl)phenoxy)cyclohex-1-en-1-yl)pyrimidine-4-carboxamide (Cpd. No. 103)

A mixture of borate compound 35-5, (257 mg, 0.7 mmol), (S)-6-((1-amino-1-oxopropan-2-yl)amino)-2-chloropyrimidine-4-carboxamide (compound 35-6) (170 mg, 0.7 mmol), Pd(PPh₃)₂Cl2 (27 mg, 0.04 mmol), and Na₂CO₃ (2 M in H₂O, 0.7 mL) was suspended in DME/EtOH (2 mL/1 mL). The mixture was purged with N₂, heated at 100° C. for 14 hr, and then cooled to room temperature. The mixture was extracted with EtOAc (2×20 mL) and dried over MgSO₄. After the removal of ethyl acetate via rotary evaporator the residue was subjected to flash chromatography using DCM/MeOH as the eluent to give 6-(((S)-1-amino-1-oxopropan-2-yl)amino)-2-(4-(4-(trifluoromethyl)phenoxy)cyclohex-1-en-1-yl)pyrimidine-4-carboxamide (Cpd. No. 103) as a white solid (50 mg). ¹H NMR (CD₃OD) δ 7.50-7.60 (m, 2H), 7.20 (s, 1H), 6.95-7.15 (m, 3H), 4.80 (m, 1H), 4.40 (m, 1H), 2.60-2.90 (m, 3H), 2.40-2.50 (m, 1H), 1.95-2.15 (m, 2H), 1.50 (d, 3H). LC/MS: m/z=450[M+H]⁺.

Example 36

Preparation of 6-(((S)-2-oxopyrrolidin-3-yl)oxy)-2-(4-(4-(trifluoromethyl)phenoxy)cyclohex-1-en-1-yl)pyrimidine-4-carboxamide Scheme 82

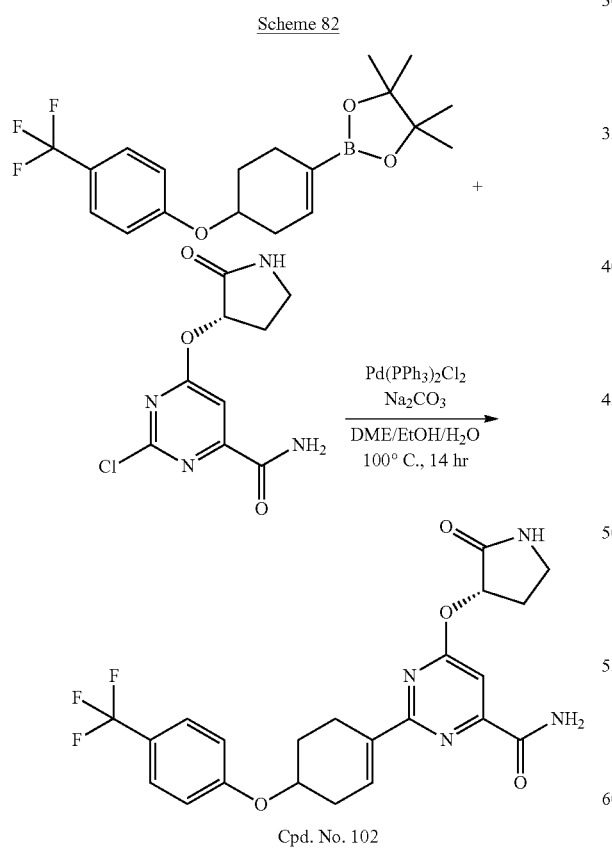

Cpd. No. 102

6-(((S)-2-oxopyrrolidin-3-yl)oxy)-2-(4-(4-(trifluoromethyl)phenoxy)cyclohex-1-en-1-yl)pyrimidine-4-carboxamide was prepared using the methodology described in EXAMPLE 35. ¹H NMR (CD₃OD) δ 7.35-7.45 (m, 2H), 7.22 (s, 1H), 7.15 (s, 1H), 6.95-7.10 (m, 2H), 5.65 (m, 1h), 4.70 (m, 1H), 3.20-3.35 (m, 2H), 2.60-2.80 (m, 4H), 2.35-2.40 (m, 1H), 1.85-2.15 (m, 3H). LC/MS: m/z=463 [M+H]⁺.

Example 37

Preparation of (S)-6-((1-amino-1-oxopropan-2-yl)amino)-2-(4-(4-cyanophenoxy)piperidin-1-yl)pyrimidine-4-carboxamide (Cpd. No. 100)

Scheme 83

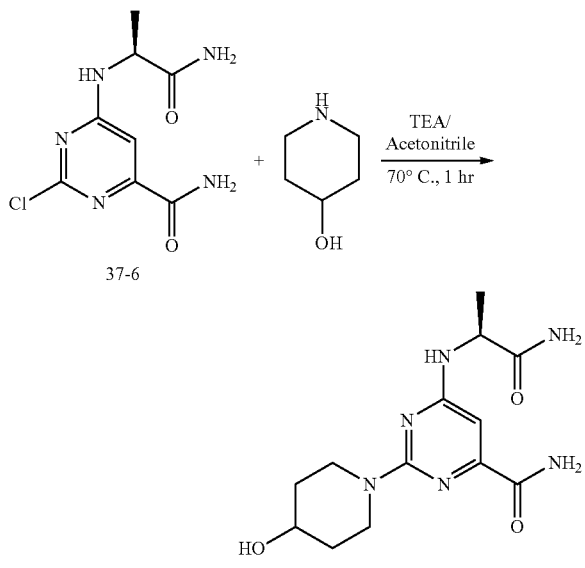

37-6

Synthesis of (S)-6-((1-amino-1-oxopropan-2-yl)amino)-2-(4-hydroxypiperidin-1-yl)pyrimidine-4-carboxamide (compound 37-7)

A mixture of (S)-6-((1-amino-1-oxopropan-2-yl)amino)-2-chloropyrimidine-4-carboxamide (compound 37-6) (243 mg, 1 mmol), 4-hydroxylpiperidine (101 mg, 1 mmol), and TEA (0.17 mL, 1.2 mmol) was dissolved in acetonitrile (5 mL) and stirred at 70° C. for 1 hr, extracted with EtOAc (2×20 ml), and dried over MgSO₄. The ethyl acetate was removed via rotary evaporator and the crude (S)-6-((1-amino-1-oxopropan-2-yl)amino)-2-(4-hydroxypiperidin-1-yl)pyrimidine-4-carboxamide (compound 37-7) was used in the next step without further purification.

Scheme 84

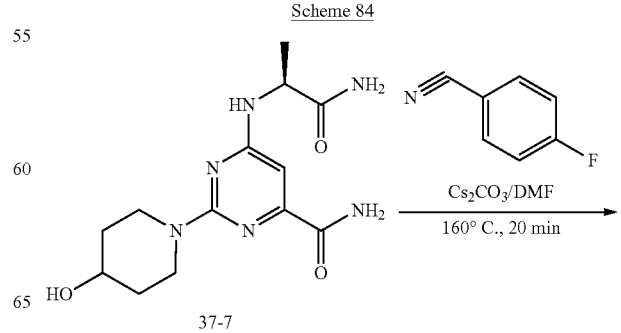

37-7

-continued

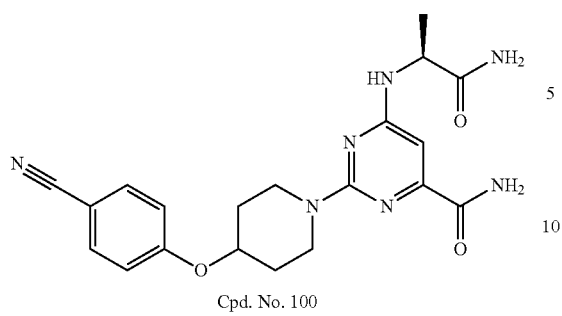

Cpd. No. 100

Synthesis of (S)-6-((1-amino-1-oxopropan-2-yl)amino)-2-(4-(4-cyanophenoxy)piperidin-1-yl)pyrimidine-4-carboxamide (Cpd. No. 100)

A mixture of 4-fluorobenzonitrile (121 mg, 1 mmol), compound 37-7 (308 mg, 1 mmol), and $Cs_2CO_3$ (326 mg, 1 mmol) in DMF (2 mL) was heated at 160° C. in a microwave (Biotage initiator) for 20 minutes. The mixture was extracted with EtOAc (2×20 mL) and dried over $MgSO_4$. After the removal of ethyl acetate via rotary evaporator the residue was subjected to flash chromatography using DCM/MeOH as the eluent to give S)-6-((1-amino-1-oxopropan-2-yl)amino)-2-(4-(4-cyanophenoxy)piperidin-1-yl)pyrimidine-4-carboxamide (Cpd. No. 100) as a white solid (150 mg). $^1$H NMR ($CD_3OD$) δ 7.55-7.65 (m, 2H), 7.12 (m, 2H), 6.40 (s, 1H), 4.80 (m, 1H), 4.30 (m, 1H), 3.95 (m, 2H), 3.68 (m, 2H), 1.98 (m, 2H), 1.75 (m, 2H), 1.40 (d, 3H). LC/MS: m/z=410 [M+H]$^+$.

Example 38

Preparation of (S)-6-((1-amino-1-oxopropan-2-yl)amino)-2-(3-(4-(trifluoromethoxy)phenyl)azetidin-1-yl)pyrimidine-4-carboxamide (Cpd. No. 101)

Scheme 85

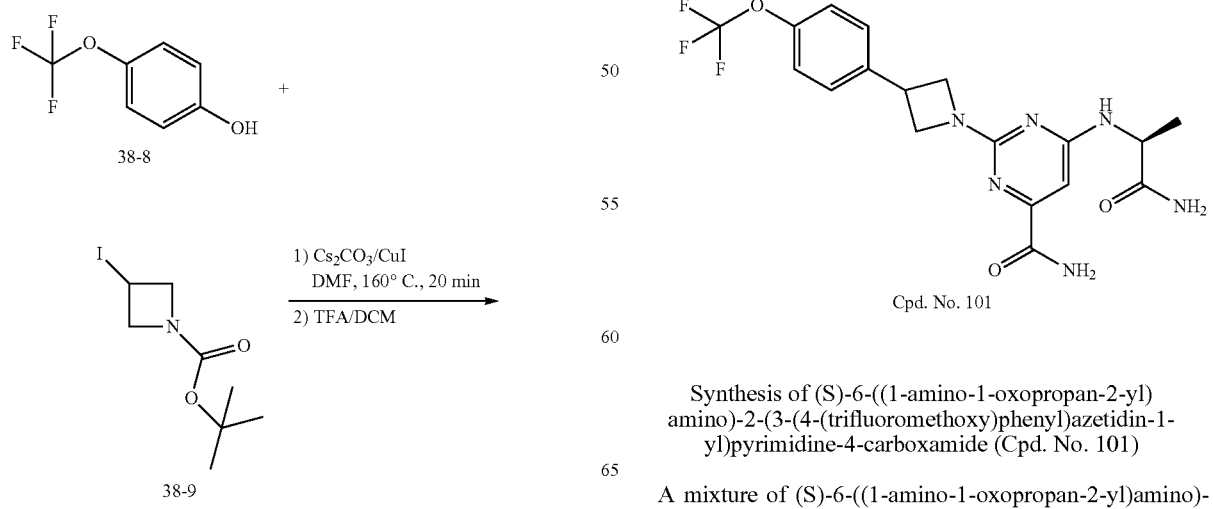

-continued

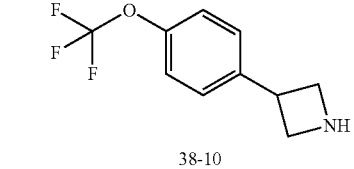

38-10

Synthesis of 3-(4-(trifluoromethoxy)phenyl)azetidine (compound 38-10)

A mixture of phenol compound 38-8 (356 mg, 2 mmol), iodide compound 389 (564 mg, 2 mmol), $Cs_2CO_3$ (652 mg, 2 mmol) and CuI (100 mg, 0.5 mmol) in DMF (3 mL) was capped in a microwavable vial and stirred at 160° C. in a microwave (Biotage initiator) for 20 minutes. After cooling to room temperature, the mixture was extracted with EtOAc (2×20 mL) and dried over $MgSO_4$. The EtOAc was removed under rotary evaporation and the residue was dissolved in TFA/DCM (5 mL/5 mL) and stirred at room temperature for 1 hr. The mixture was extracted with EtOAc (2×20 mL) and dried over $MgSO_4$. After the removal of ethyl acetate via rotary evaporation, the crude 3-(4-(trifluoromethoxy)phenyl) azetidine (compound 38-10) was used in the next step without further purification. LC/MS: m/z=218 [M+H]$^+$.

Scheme 86

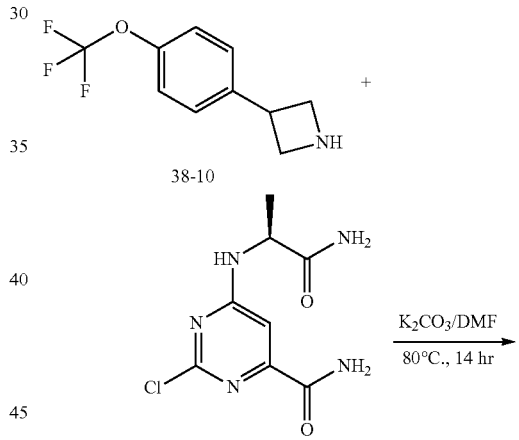

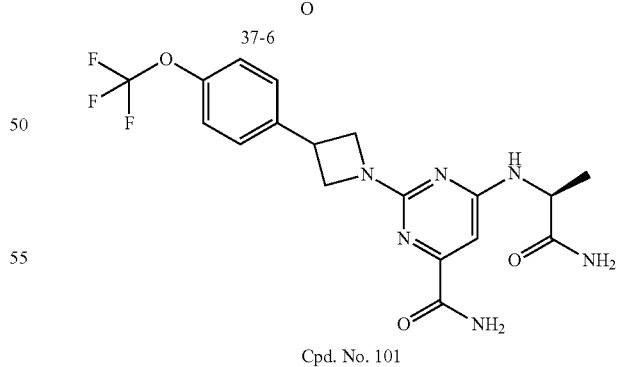

Cpd. No. 101

Synthesis of (S)-6-((1-amino-1-oxopropan-2-yl)amino)-2-(3-(4-(trifluoromethoxy)phenyl)azetidin-1-yl)pyrimidine-4-carboxamide (Cpd. No. 101)

A mixture of (S)-6-((1-amino-1-oxopropan-2-yl)amino)-2-chloropyrimidine-4-carboxamide (compound 37-6) (243 mg, 1 mmol), 3-(4-(trifluoromethoxy)phenyl)azetidine (1 mmol), and K$_2$CO$_3$ (138 mg, 1 mmol) was dissolved in DMF (3 mL), stirred at 80° C. for 14 hr, and then cooled to room temperature. The mixture was extracted with EtOAc (2×20 mL) and dried over MgSO$_4$. After the removal of ethyl acetate via rotary evaporation the residue was subjected to flash chromatography using DCM/MeOH as the eluent to give (S)-6-((1-amino-1-oxopropan-2-yl)amino)-2-(3-(4-(trifluoromethoxy)phenyl)azetidin-1-yl)pyrimidine-4-carboxamide (Cpd. No. 101) as a white solid (150 mg). $^1$H NMR (CD$_3$OD) δ 7.12 (m, 2H), 6.80 (m, 2H), 6.42 (s, 1H), 5.05 (m, 1H), 3.90-4.45 (m, 5H), 1.35 (d, 3H). LC/MS: m/z=425 [M+H]$^+$.

Example 39

Representative Compounds of the Invention have been tested in the FLIPR®, FLIPR$^{TETRA}$®, and/or electrophysiology (EP) assays for sodium channel blocking activity, which is described in detail above. Representative values are presented in TABLE 4.

TABLE 4

Evaluation of compounds as sodium channel (Na$_v$) blockers

| Compound Example No. | Na$_v$1.7 Activity (µM) | | |
|---|---|---|---|
| | FLIPR assay IC$_{50}$ | EP assay K$_i$ | EP assay K$_r$ |
| 1 | 0.42 | 0.057 | 4.22 |
| 2 | 0.4 | 0.59 | 10.12 |
| 3 | 0.39 | | |
| 4 | 1.4 | | |
| 5 | 0.26 | 0.078 | 7.95 |
| 6 | 0.13 | 0.25 | 4.78 |
| 7 | 0.17 | 0.053 | 1.89 |
| 8 | 0.42 | | |
| 9 | 0.35 | | |
| 10 | 0.18 | | |
| 11 | 0.72 | | |
| 12 | 0.4 | | |
| 13 | 0.99 | 0.42 | 168.67 |
| 14 | 0.17 | 0.024 | 0.84 |
| 15 | 0.86 | 0.35 | 10.42 |
| 16 | >20 | | |
| 17 | 0.10 | | |
| 18 | 0.20 | | |
| 19 | >20 | | |
| 20 | 0.22 | | |
| 21 | 0.60 | 0.23 | 7.25 |
| 22 | 0.55 | | |
| 23 | 0.3 | | |
| 24 | 10-20 | | |
| 25 | 0.36 | | |
| 26 | 0.26 | | |
| 27 | 0.26 | | |
| 28 | 10-20 | | |
| 29 | >20 | | |
| 30 | >20 | | |
| 31 | >20 | | |
| 32 | 2.00 | | |
| 33 | 0.97 | | |
| 34 | 1.15 | | |
| 35 | >20 | 20.50 | 102.0 |
| 36 | >20 | | |
| 37 | 10-20 | | |
| 38 | 0.11 | 0.067 | 1.55 |
| 39 | 0.95 | | |
| 40 | >20 | 41.05 | 109.5 |
| 41 | 0.037 | | |
| 42 | 0.069 | 0.024 | 2.04 |
| 43 | 0.15 | | |
| 44 | 0.11 | | |
| 45 | 0.22 | | |
| 46 | >20 | | |
| 47 | 0.46 | | |
| 48 | 0.17 | | |
| 49 | 0.17 | | |
| 50 | >20 | | |
| 51 | >20 | | |
| 52 | 0.088 | | |
| 53 | 0.14 | 0.27 | 4.08 |
| 54 | 1.75 | | |
| 55 | 2.09 | | |
| 56 | 0.22 | 0.053 | 5.04 |
| 57 | 3.25 | | |
| 58 | 1.27 | | |
| 59 | 2.04 | | |
| 60 | 1.66 | | |
| 61 | 6.46 | | |
| 62 | 2.98 | | |
| 63 | 0.79 | 0.60 | 27.96 |
| 64 | 0.18 | 0.016 | 0.73 |
| 65 | >20 | | |
| 66 | 0.41 | | |
| 67 | >20 | | |
| 68 | >20 | | |
| 69 | 6.10 | | |
| 70 | 3.76 | | |
| 71 | >20 | | |
| 72 | 1.42 | | |
| 73 | 1.80 | | |
| 74 | 0.25 | | |
| 75 | 0.12 | | |
| 76 | 0.16 | | |
| 77 | 0.29 | | |
| 78 | 0.12 | | |
| 79 | 0.41 | | |
| 80 | 0.38 | | |
| 81 | 0.49 | | |
| 82 | 0.34 | | |
| 83 | 0.31 | | |
| 84 | 0.18 | | |
| 85 | 0.21 | | |
| 86 | 0.36 | | |
| 87 | 0.14 | | |
| 88 | 1.18 | | |
| 89 | 0.41 | | |
| 90 | 0.54 | | |
| 91 | 0.20 | | |
| 92 | 0.27 | | |
| 93 | 0.083 | | |
| 94 | 1.59 | | |
| 95 | 0.43 | | |
| 96 | 0.53 | | |
| 97 | 5.72 | | |
| 98 | 0.17 | 0.054 | 1.16 |
| 99 | 0.57 | 0.083 | 4.65 |
| 100 | 4.57 | | |
| 101 | 0.87 | | |
| 102 | 0.22 | | |
| 103 | 1.08 | | |

Having now fully described this disclosure, it will be understood by those of ordinary skill in the art that the same can be performed within a wide and equivalent range of conditions, formulations and other parameters without affecting the scope of the disclosure or any embodiment thereof.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference in their entirety.

What is claimed is:

1. A compound having Formula I:

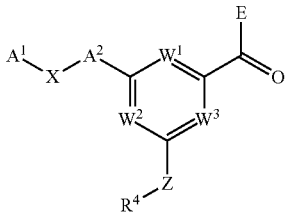

or a pharmaceutically acceptable salt, or solvate thereof, wherein:
$W^1$ and $W^2$ are N and $W^3$ is $CR^3$; or
$W^1$ and $W^3$ are N and $W^2$ is $CR^3$; or
$W^2$ and $W^3$ are N and $W^1$ is $CR^3$;
$A^1$ is selected from the group consisting of:
 a) optionally substituted aryl;
 b) optionally substituted heteroaryl;
 c) optionally substituted cycloalkyl;
 d) optionally substituted heterocyclo; and
 e) aralkyl;
X is
 —O—;
$A^2$ is selected from the group consisting of:
 a) optionally substituted aryl;
 b) optionally substituted heteroaryl;
 c) optionally substituted heterocyclo; and
 d) optionally substituted cycloalkyl; or
$A^2$ is absent;
E is selected from the group consisting of:
 a) hydroxy;
 b) alkoxy; and
 c) —NR$^1$R$^2$;
$R^1$ is selected from the group consisting of:
 a) hydrogen;
 b) alkyl;
 c) aralkyl;
 d) (heterocyclo)alkyl;
 e) (heteroaryl)alkyl;
 f) (amino)alkyl;
 g) (alkylamino)alkyl;
 h) (dialkylamino)alkyl;
 i) (carboxamido)alkyl;
 j) (cyano)alkyl;
 k) alkoxyalkyl;
 l) hydroxyalkyl; and
 m) heteroalkyl;
$R^2$ is selected from the group consisting of hydrogen and alkyl; or
 $R^1$ and $R^2$ taken together with the nitrogen atom to which they are attached form a 3- to 8-membered optionally substituted heterocyclo;
$R^3$ selected from the group consisting of:
 a) hydrogen;
 b) halo;
 c) nitro;
 d) cyano;
 e) hydroxy;
 f) amino;
 g) alkylamino;
 h) dialkylamino;
 i) haloalkyl;
 j) hydroxyalkyl;
 k) alkoxy;
 l) haloalkoxy; and
 m) alkoxyalkyl;
Z is selected from the group consisting of —NR$^5$— and —O—;
$R^4$ is selected from the group consisting of:
 a)

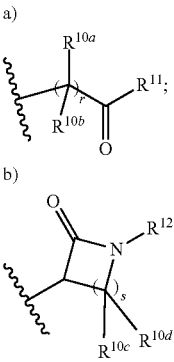

c) hydroxyalkyl;
 d) hydroxy(cycloalkyl)alkyl; and
 e) (heterocyclo)alkyl;
each $R^{10a}$, $R^{10b}$, $R^{10c}$, and $R_{10d}$ is independently selected from the group consisting of:
 a) hydrogen;
 b) hydroxy;
 c) optionally substituted alkyl;
 d) aralkyl;
 e) (heterocyclo)alkyl;
 f) (heteroaryl)alkyl;
 g) (amino)alkyl;
 h) (alkylamino)alkyl;
 i) (dialkylamino)alkyl;
 j) (carboxamido)alkyl;
 k) (cyano)alkyl;
 l) alkoxyalkyl;
 m) hydroxyalkyl;
 n) heteroalkyl;
 o) optionally substituted cycloalkyl;
 p) optionally substituted aryl;
 q) optionally substituted heterocyclo; and
 r) optionally substituted heteroaryl; or
 $R^{10a}$ and $R^{10b}$ taken together with the carbon atom to which they are attached form a 3- to 8-membered optionally substituted cycloalkyl or a 3- to 8-membered optionally substituted heterocyclo;
r is 1, 2, or 3;
s is 1, 2, or 3;
$R^{11}$ is selected from the group consisting of:
 a) hydroxy;
 b) alkoxy; and
 c) —NR$^{1a}$R$^{2a}$;
$R^{1a}$ is selected from the group consisting of:
 a) hydrogen;
 b) alkyl;
 c) aralkyl;
 d) (heterocyclo)alkyl;
 e) (heteroaryl)alkyl;
 f) (amino)alkyl;
 g) (alkylamino)alkyl;
 h) (dialkylamino)alkyl;
 i) (carboxamido)alkyl;

j) (cyano)alkyl;
k) alkoxyalkyl;
l) hydroxyalkyl; and
m) heteroalkyl;
$R^{2a}$ is selected from the group consisting of hydrogen and alkyl; or
$R^{1a}$ and $R^{2a}$ taken together with the nitrogen atom to which they are attached form a 3- to 8-membered optionally substituted heterocyclo;
$R^{12}$ is selected from the group consisting of:
a) hydrogen;
b) optionally substituted alkyl;
c) (amino)alkyl;
d) (alkylamino)alkyl;
e) (dialkylamino)alkyl;
f) (carboxamido)alkyl;
g) (cyano)alkyl;
h) alkoxyalkyl;
i) hydroxyalkyl; and
j) heteroalkyl;
$R^5$ is selected from the group consisting of:
a) hydrogen
b) alkyl;
c) hydroxyalkyl; and
d) alkylsulfonyl; or
$R^4$ and $R^5$ taken together with the nitrogen atom to which they are attached form a 3- to 8-membered optionally substituted heterocyclo;
with the proviso that when $R^4$ and $R^5$ taken together with the nitrogen atom to which they are attached form a 3- to 8-membered optionally substituted heterocyclo, then $R^1$ is selected from the group consisting of:
a) hydrogen;
b) (heterocyclo)alkyl;
c) (heteroaryl)alkyl;
d) (amino)alkyl;
e) (alkylamino)alkyl;
f) (dialkylamino)alkyl;
g) (carboxamido)alkyl;
h) (cyano)alkyl;
i) alkoxyalkyl;
j) hydroxyalkyl; and
k) heteroalkyl.

2. The compound of claim 1 having Formula II:

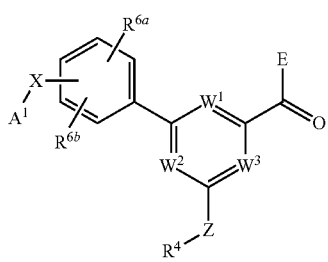

II or a pharmaceutically acceptable salt, or solvate thereof, wherein:
$R^{6a}$ and $R^{6b}$ are independently selected from the group consisting of:
a) hydrogen;
b) halo;
c) nitro;
d) cyano;
e) hydroxy;
f) amino;
g) alkylamino;
h) dialkylamino;
i) haloalkyl;
j) hydroxyalkyl;
k) alkoxy;
l) haloalkoxy;
m) carboxy; and
n) alkoxycarbonyl.

3. The compound of claim 1 having Formula IV:

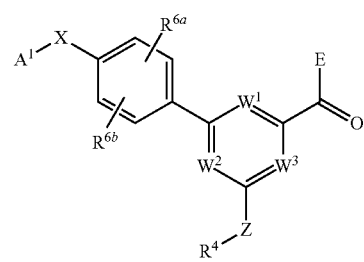

IV or a pharmaceutically acceptable salt, or solvate thereof.

4. The compound of claim 1 having Formula V:

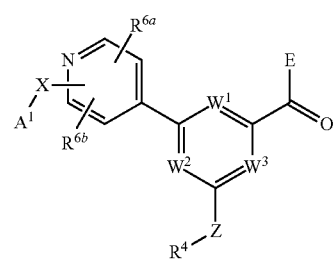

V or a pharmaceutically acceptable salt, or solvate thereof, wherein:
$R^{6a}$ and $R^{6b}$ are independently selected from the group consisting of:
a) hydrogen;
b) halo;
c) nitro;
d) cyano;
e) hydroxy;
f) amino;
g) alkylamino;
h) dialkylamino;
i) haloalkyl;
j) hydroxyalkyl;
k) alkoxy;
l) haloalkoxy;
m) carboxy; and
n) alkoxycarbonyl.

5. The compound of claim 1 having Formula VII:

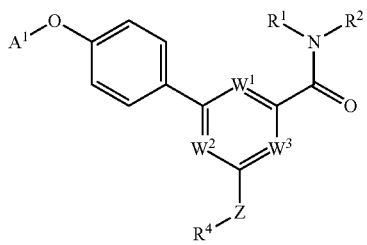

VII or a pharmaceutically acceptable salt, or solvate thereof.

6. The compound of claim 1, wherein:
$R^4$ is selected from the group consisting of:

a)

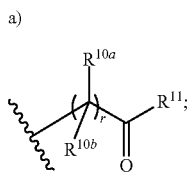

b) hydroxyalkyl; and
c) hydroxy(cycloalkyl)alkyl;
$R^{10a}$ is selected from the group consisting of:
  a) hydrogen;
  b) hydroxy;
  c) optionally substituted alkyl;
  d) aralkyl;
  e) (heteroaryl)alkyl;
  f) (amino)alkyl;
  g) (alkylamino)alkyl;
  h) (dialkylamino)alkyl;
  i) (carboxamido)alkyl;
  k) alkoxyalkyl; and
  l) hydroxyalkyl;
$R^{10b}$ is selected from the group consisting of hydrogen and alkyl; or
$R^{10a}$ and $R^{10b}$ taken together with the carbon atom to which they are attached form a 3- to 6-membered cycloalkyl;
r is 1 or 2;
or a pharmaceutically acceptable salt, or solvate thereof.

7. The compound of claim 1, wherein $R^4$ and $R^5$ taken together with the nitrogen to which they are attached form a 5- or 6-membered optionally substituted heterocyclo, and said optionally substituted 5- or 6-membered heterocyclo is selected from the group consisting of:

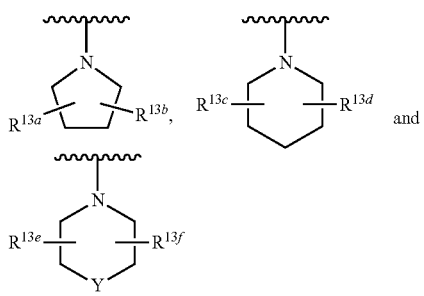

wherein:
$R^{13a}$, $R^{13b}$, $R^{13c}$, $R^{13d}$, $R^{13e}$, and $R^{13f}$ are independently selected from the group consisting of:
  a) hydrogen;
  b) hydroxy;
  c) hydroxyalkyl;
  d) carboxy;
  e) alkoxycarbonyl; and
  f) carboxamido;
Y is selected from the group consisting of O, S, and $NR^{14}$; and
$R^{14}$ is selected from the group consisting of hydrogen and alkyl,
or a pharmaceutically acceptable salt, or solvate thereof.

8. The compound of claim 1, wherein $R^4$ is:

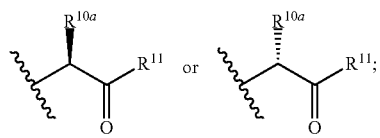

and
$R^{11}$ is $-NR^{1a}R^{2a}$,
or a pharmaceutically acceptable salt, or solvate thereof.

9. The compound of claim 1, wherein $R^4$ is:

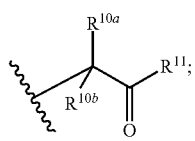

$R^{10a}$ and $R^{10b}$ taken together with the carbon atom to which they are attached form a 3- to 6-membered cycloalkyl; and
$R^{11}$ is $-NR^{1a}R^{2a}$,
or a pharmaceutically acceptable salt, or solvate thereof.

10. The compound of claim 1, wherein $R^4$ is selected from the group consisting of:

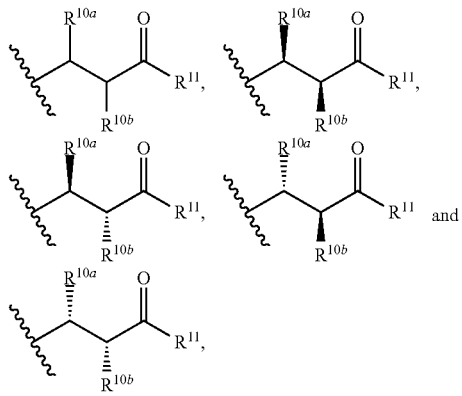

$R^{10}$ is selected from the group consisting of hydrogen and alkyl; and
$R^{10b}$ is selected from the group consisting of:
  a) hydrogen;
  b) hydroxy; and
  c) alkyl,
or a pharmaceutically acceptable salt, or solvate thereof.

11. The compound of claim 1, wherein R⁴ is hydroxyalkyl or hydroxy(cycloalkyl)alkyl, and said hydroxyalkyl or hydroxy(cycloalkyl)alkyl is selected from the group consisting of:

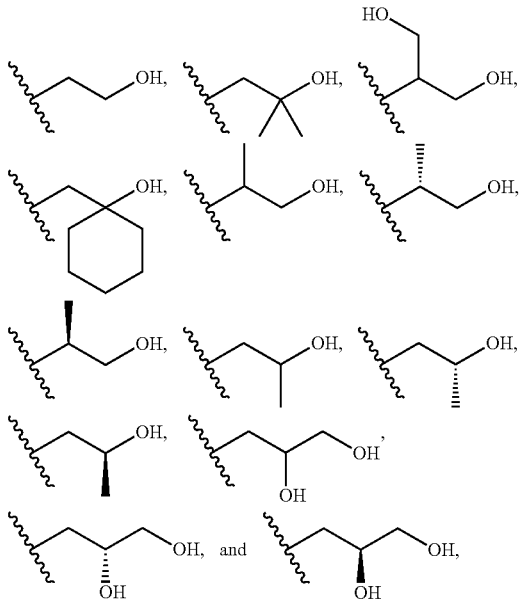

or a pharmaceutically acceptable salt, or solvate thereof.

12. The compound of claim 1, wherein A¹ is selected from the group consisting of substituted phenyl having one or two substituents and substituted pyridyl having one substituent, wherein each substituent is independently selected from the group consisting of halo, cyano, hydroxy, amino, haloalkyl, alkoxy, haloalkoxy, and alkyl, or a pharmaceutically acceptable salt, or solvate thereof.

13. The compound of claim 5 having Formula X:

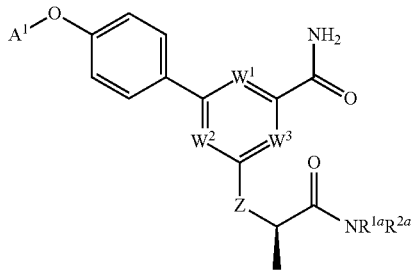

or a pharmaceutically acceptable salt, or solvate thereof.

14. The compound of claim 5 having Formula XI:

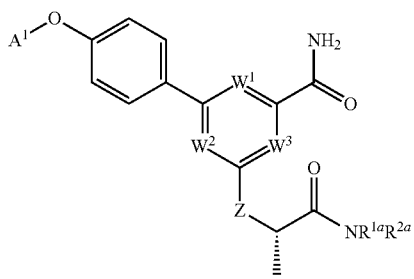

or a pharmaceutically acceptable salt, or solvate thereof.

15. The compound of claim 5 having Formula XIV:

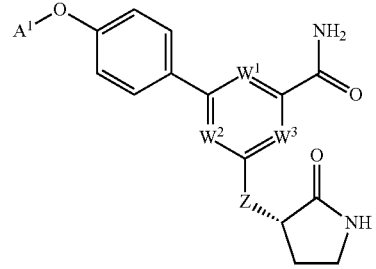

or a pharmaceutically acceptable salt, or solvate thereof.

16. The compound of claim 5 having Formula XV:

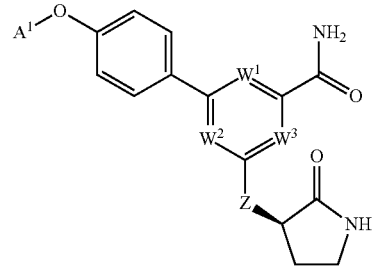

or a pharmaceutically acceptable salt, or solvate thereof.

17. The compound of claim 1 selected from the group consisting of:
- (S)-6-((1-amino-1-oxopropan-2-yl)amino)-2-(4-(4-fluorophenoxyl)phenyl)pyrimidine-4-carboxamide;
- 6-((2-amino-2-oxoethyl)amino)-2-(4-(4-fluorophenoxyl)phenyl)pyrimidine-4-carboxamide;
- (S)-6-((1-amino-4-methyl-1-oxopentan-2-yl)amino)-2-(4-(4-fluorophenoxyl)phenyl) pyrimidine-4-carboxamide;
- (S)-6-((1-amino-3-hydroxy-1-oxopropan-2-yl)amino)-2-(4-(4-fluorophenoxyl)phenyl) pyrimidine-4-carboxamide;
- (S)-6-(2-carbamoylpyrrolidin-1-yl)-2-(4-(4-fluorophenoxyl)phenyl)pyrimidine-4-carboxamide;
- (S)-6-((1-amino-3-(1-methyl-1H-imidazol-4-yl)-1-oxopropan-2-yl)amino)-2-(4-(4-fluorophenoxyl)phenyl) pyrimidine-4-carboxamide;
- (S)-2-(4-(4-fluorophenoxyl)phenyl)-6-((2-oxopyrrolidin-3-yl)amino)pyrimidine-4-carboxamide;
- 6-((1-carbamoylcyclopropyl)amino)-2-(4-(4-fluorophenoxyl)phenyl)pyrimidine-4-carboxamide;
- 6-((1-carbamoylcyclobutyl)amino)-2-(4-(4-fluorophenoxyl)phenyl)pyrimidine-4-carboxamide;
- 6-((1-amino-2-methyl-1-oxopropan-2-yl)amino)-2-(4-(4-fluorophenoxyl)phenyl) pyrimidine-4-carboxamide;
- (S)-6-((1-amino-1-oxopropan-2-yl)amino)-2-(4-(4-cyano-3-(trifluoromethyl)phenoxy)phenyl)pyrimidine-4-carboxamide;
- (S)-6-((1-amino-1-oxopropan-2-yl)amino)-2-(4-(3-cyano-4-(trifluoromethyl) phenoxy)phenyl)pyrimidine-4-carboxamide;
- (S)-6-((1-amino-1-oxopropan-2-yl)amino)-2-(4-((5-(trifluoromethyl)pyridin-2-yl)oxy)phenyl)pyrimidine-4-carboxamide;

(S)-6-((1-amino-1-oxopropan-2-yl)amino)-2-(4-(4-(trifluoromethyl)phenoxyl)phenyl) pyrimidine-4-carboxamide;
(S)-methyl 1-(6-carbamoyl-2-(4-(4-fluorophenoxyl)phenyl)pyrimidin-4-yl)pyrrolidine-2-carboxylate;
(S)-ethyl 1-(6-carbamoyl-2-(4-(4-fluorophenoxyl)phenyl)pyrimidin-4-yl)indoline-2-carboxylate;
ethyl 1-((6-carbamoyl-2-(4-(4-fluorophenoxyl)phenyl)pyrimidin-4-yl)amino)cyclopropanecarboxylate;
methyl 2-((6-carbamoyl-2-(4-(4-fluorophenoxyl)phenyl)pyrimidin-4-yl)amino)-2-methylpropanoate;
6-((3-amino-3-oxopropyl)amino)-2-(4-(4-fluorophenoxyl)phenyl)pyrimidine-4-carboxamide;
(S)-6-((1-amino-1-oxopropan-2-yl)(methyl)amino)-2-(4-(4-fluorophenoxyl)phenyl) pyrimidine-4-carboxamide;
(R)-6-((1-amino-1-oxopropan-2-yl)amino)-2-(4-(4-fluorophenoxyl)phenyl)pyrimidine-4-carboxamide;
6-((1-amino-1-oxopropan-2-yl)amino)-2-(4-(4-fluorophenoxyl)phenyl)pyrimidine-4-carboxamide;
6-((4-amino-4-oxobutan-2-yl)amino)-2-(4-(4-fluorophenoxyl)phenyl)pyrimidine-4-carboxamide;
6-(3-carbamoylpiperidin-1-yl)-2-(4-(4-fluorophenoxyl)phenyl)pyrimidine-4-carboxamide;
4-(6-carbamoyl-2-(4-(4-fluorophenoxyl)phenyl)pyrimidin-4-yl)morpholine-3-carboxamide;
4-(6-carbamoyl-2-(4-(4-fluorophenoxyl)phenyl)pyrimidin-4-yl)morpholine-2-carboxamide;
6-(2-carbamoylpiperazin-1-yl)-2-(4-(4-fluorophenoxyl)phenyl)pyrimidine-4-carboxamide;
(S)-2-((6-carbamoyl-2-(4-(4-fluorophenoxyl)phenyl)pyrimidin-4-yl)amino)propanoic acid;
(S)-6-(2-carboxypyrrolidin-1-yl)-2-(4-(4-fluorophenoxyl)phenyl)pyrimidine-4-carboxylic acid,
(S)-1-(6-carbamoyl-2-(4-(4-fluorophenoxyl)phenyl)pyrimidin-4-yl)pyrrolidine-2-carboxylic acid,
(S)-1-(6-carbamoyl-2-(4-(4-fluorophenoxyl)phenyl)pyrimidin-4-yl)indoline-2-carboxylic acid;
(S)-tert-butyl 2-(4-(4-fluorophenoxyl)phenyl)-6-((1-methoxy-1-oxopropan-2-yl)amino) pyrimidine-4-carboxylate;
(S)-2-(4-(4-fluorophenoxyl)phenyl)-6-((1-methoxy-1-oxopropan-2-yl)amino) pyrimidine-4-carboxylic acid;
(S)-tert-butyl 6-((1-amino-1-oxopropan-2-yl)amino)-2-(4-(4-fluorophenoxyl)phenyl) pyrimidine-4-carboxylate;
(S)-6-((1-amino-1-oxopropan-2-yl)amino)-2-(4-(4-fluorophenoxyl)phenyl)pyrimidine-4-carboxylic acid;
(S)-1-(6-carbamoyl-2-(4-(4-fluorophenoxyl)phenyl)pyrimidin-4-yl)indoline-2-carboxamide;
(S)-6-((1-amino-1-oxopropan-2-yl)amino)-2-(4-((5-cyanopyridin-2-yl)oxy)phenyl) pyrimidine-4-carboxamide;
S)-6-(((1-amino-1-oxopropan-2-yl)amino)-2-(4-(5-chloro-2-fluorophenoxyl)phenyl) pyrimidine-4-carboxamide;
(S)-methyl 2-(4-(4-fluorophenoxyl)phenyl)-6-((1-methoxy-1-oxopropan-2-yl)amino) pyrimidine-4-carboxylate;
(S)-6-((1-carboxyethyl)amino)-2-(4-(4-fluorophenoxyl)phenyl)pyrimidine-4-carboxylic acid,
2-(4-(4-fluorophenoxyl)phenyl)-6-(3-(hydroxymethyl)morpholino)pyrimidine-4-carboxamide;
(S)-2-(4-(4-fluorophenoxyl)phenyl)-6-((1-hydroxypropan-2-yl)amino)pyrimidine-4-carboxamide;
(S)-2-(4-(4-fluorophenoxyl)phenyl)-6-(2-(hydroxymethyl)pyrrolidin-1-yl)pyrimidine-4-carboxamide;
2-(4-(4-fluorophenoxyl)phenyl)-6-((2-hydroxy-2-methylpropyl)amino)pyrimidine-4-carboxamide;
2-(4-(4-fluorophenoxyl)phenyl)-6-(((1-hydroxycyclohexyl)methyl)amino)pyrimidine-4-carboxamide;
(S)-6-((2,3-dihydroxypropyl)amino)-2-(4-(4-fluorophenoxyl)phenyl)pyrimidine-4-carboxamide
6-((1,3-dihydroxypropan-2-yl)amino)-2-(4-(4-fluorophenoxyl)phenyl)pyrimidine-4-carboxamide;
2-(4-(4-fluorophenoxyl)phenyl)-6-(2-(hydroxymethyl)piperazin-1-yl)pyrimidine-4-carboxamide;
6-(3,4-dihydroxypyrrolidin-1-yl)-2-(4-(4-fluorophenoxyl)phenyl)pyrimidine-4-carboxamide;
(S)-6-((3-amino-2-hydroxy-3-oxopropyl)amino)-2-(4-(4-fluorophenoxyl)phenyl) pyrimidine-4-carboxamide;
(S)-3-((6-carbamoyl-2-(4-(4-fluorophenoxyl)phenyl)pyrimidin-4-yl)amino)-2-hydroxypropanoic acid;
6-(N-((2,2-dimethyl-1,3-dioxolan-4-yl)methyl)methylsulfonamido)-2-(4-(4-fluorophenoxyl)phenyl)pyrimidine-4-carboxamide;
6-(N-(2,3-dihydroxypropyl)methylsulfonamido)-2-(4-(4-fluorophenoxyl)phenyl) pyrimidine-4-carboxamide;
(S)-2-((1-amino-1-oxopropan-2-yl)amino)-6-(4-(4-fluorophenoxyl)phenyl)pyrimidine-4-carboxamide;
(S)-4-((1-amino-1-oxopropan-2-yl)amino)-6-(4-(4-fluorophenoxyl)phenyl)pyrimidine-2-carboxamide;
(S)-6-((1-amino-1-oxopropan-2-yl)oxy)-2-(4-(4-fluorophenoxyl)phenyl)pyrimidine-4-carboxamide;
(S)-6-((1-amino-1-oxopropan-2-yl)amino)-2-(4-((trifluoromethyl)pyridine-2-yl)oxy)phenyl)pyrimidine-4-carboxamide;
(S)-6-((1-amino-1-oxopropan-2-yl)amino)-2-(4-((3-trifluoromethyl)pyridine-2-yl)oxy)phenyl)pyrimidine-4-carboxamide;
(S)-6-((1-amino-1-oxopropan-2-yl)amino)-2-(4-((6-trifluoromethyl)pyridine-2-yl)oxy)phenyl)pyrimidine-4-carboxamide;
(S)-6-((1-amino-1-oxopropan-2-yl)amino)-2-(4-((6-trifluoromethyl)pyridine-3-yl)oxy)phenyl)pyrimidine-4-carboxamide;
(S)-6-((1-amino-1-oxopropan-2-yl)amino)-2-(4-((6-fluoropyridine-2-yl)oxy)phenyl) pyrimidine-4-carboxamide;
(S)-6-((1-amino-1-oxopropan-2-yl)amino)-2-(4-((5-fluoropyridine-2-yl)oxy)phenyl) pyrimidine-4-carboxamide;
(S)-6-((1-amino-1-oxopropan-2-yl)amino)-2-(4-((5-chloropyridine-2-yl)oxy)phenyl) pyrimidine-4-carboxamide;
(S)-6-((1-amino-1-oxopropan-2-yl)amino)-2-(4-(4-chloro-2-fluorophenoxy)phenyl) pyrimidine-4-carboxamide;
6-((S)-1-Carbamoyl-ethylamino)-2-[4-(4-cyano-phenoxy)-phenyl]-pyrimidine-4-carboxylic acid amide;
(S)-6-((1-amino-1-oxopropan-2-yl)amino)-2-(2-(2-aminopyridin-4-yl)-4-chlorophenoxy)pyrimidine-4-carboxamide;
(S)-6-((1-amino-1-oxopropan-2-yl)amino)-2-(2-(4-fluorophenoxyl)pyridin-4-yl)pyrimidine-4-carboxamide;
(S)-6-((1-amino-1-oxopropan-2-yl)amino)-2-(6-(4-fluorophenoxyl)pyridin-3-yl)pyrimidine-4-carboxamide;
(S)-6-((1-amino-1-oxopropan-2-yl)amino)-2-(2-(pyridazin-4-yl)-4-(trifluoromethyl) phenoxy)pyrimidine-4-carboxamide;
6-(3-carbamoylpiperazin-1-yl)-2-(4-(4-fluorophenoxyl)phenyl)pyrimidine-4-carboxamide;
(S)-2-(4-(4-chloro-2-fluorophenoxy)phenyl)-6-((2-oxopyrrolidin-3-yl)amino) pyrimidine-4-carboxamide;

(S)-6-((1-amino-1-oxopropan-2-yl)oxy)-2-(4-(4-(trifluoromethoxy)phenoxy)phenyl) pyrimidine-4-carboxamide;
(S)-6-((1-amino-1-oxopropan-2-yl)oxy)-2-(4-(4-cyanophenoxyl)phenyl)pyrimidine-4-carboxamide;
(S)-6-(2-carbamoylpyrrolidin-1-yl)-2-(4-(4-chloro-2-fluorophenoxy)phenyl) pyrimidine-4-carboxamide;
6-((3S,4S)-3,4-dihydroxypyrrolidin-1-yl)-2-(4-(4-fluorophenoxyl)phenyl)pyrimidine-4-carboxamide;
6-((3R,4R)-3,4-dihydroxypyrrolidin-1-yl)-2-(4-(4-fluorophenoxyl)phenyl)pyrimidine-4-carboxamide;
6-(2-carbamoyl-4-methylpiperazin-1-yl)-2-(4-(4-(trifluoromethyl)phenoxy)phenyl) pyrimidine-4-carboxamide;
6-(2-carbamoyl-4-methylpiperazin-1-yl)-2-(4-(4-fluorophenoxyl)phenyl)pyrimidine-4-carboxamide;
6-(2-carbamoyl-4-methylpiperazin-1-yl)-2-(4-(4-chloro-2-fluorophenoxy)phenyl) pyrimidine-4-carboxamide;
(S)-6-((1-amino-1-oxopropan-2-yl)amino)-2-(4-(4-(trifluoromethoxy)phenoxy)phenyl) pyrimidine-4-carboxamide;
(S)-6-((1-amino-1-oxopropan-2-yl)amino)-2-(4-(benzo[d][1,3]dioxol-5-yloxy)phenyl) pyrimidine-4-carboxamide;
6-(2-carbamoylpiperazin-1-yl)-2-(4-(4-(trifluoromethyl)phenoxy)phenyl)pyrimidine-4-carboxamide;
(S)-6-(2-carbamoylpyrrolidin-1-yl)-2-(4-(5-chloro-2-fluorophenoxy)phenyl) pyrimidine-4-carboxamide;
(S)-6-(2-carbamoylpyrrolidin-1-yl)-2-(4-((5-(trifluoromethyl)pyridin-2-yl)oxy)phenyl) pyrimidine-4-carboxamide;
(S)-6-(2-carbamoylpyrrolidin-1-yl)-2-(4-(4-cyanophenoxyl)phenyl)pyrimidine-4-carboxamide;
(S)-2-(4-(benzo[d][1,3]dioxol-5-yloxy)phenyl)-6-(2-carbamoylpyrrolidin-1-yl) pyrimidine-4-carboxamide;
(S)-6-(2-carbamoylpyrrolidin-1-yl)-2-(4-(4-(trifluoromethyl)phenoxy)phenyl)pyrimidine-4-carboxamide;
(S)-6-((1-amino-1-oxopropan-2-yl)oxy)-2-(4-(5-chloro-2-fluorophenoxy)phenyl) pyrimidine-4-carboxamide;
(S)-6-((1-amino-1-oxopropan-2-yl)oxy)-2-(4-(4-chloro-2-fluorophenoxy)phenyl) pyrimidine-4-carboxamide;
(S)-2-(4-(4-fluorophenoxyl)phenyl)-6-((1-((2-hydroxyethyl)amino)-1-oxopropan-2-yl)amino)pyrimidine-4-carboxamide;
(S)-2-(4-(4-fluorophenoxyl)phenyl)-6-((1-morpholino-1-oxopropan-2-yl)amino) pyrimidine-4-carboxamide;
(S)-methyl 5-(4-((1-amino-1-oxopropan-2-yl)amino)-6-carbamoylpyrimidin-2-yl)-2-(4-fluorophenoxyl)benzoate;
(S)-6-((1-amino-1-oxopropan-2-yl)amino)-2-(4-(4-fluorophenoxy)-3-(hydroxymethyl)phenyl)pyrimidine-4-carboxamide;
(S)-6-((1-amino-1-oxopropan-2-yl)oxy)-2-(4-(4-(trifluoromethyl)phenoxy)phenyl) pyrimidine-4-carboxamide;
(S)-6-((2-oxopyrrolidin-3-yl)amino)-2-(4-((5-(trifluoromethyl)pyridin-2-yl)oxy)phenyl)pyrimidine-4-carboxamide;
(S)-6-((1-amino-1-oxopropan-2-yl)amino)-2-(4-(4-cyanophenoxyl)piperidin-1-yl) pyrimidine-4-carboxamide;
(S)-6-((1-amino-1-oxopropan-2-yl)amino)-2-(3-(4-(trifluoromethoxy)phenoxy)azetidin-1-yl)pyrimidine-4-carboxamide;
6-(((S)-2-oxopyrrolidin-3-yl)oxy)-2-(4-(4-(trifluoromethyl)phenoxy)cyclohex-1-en-1-yl)pyrimidine-4-carboxamide; and
6-(((S)-1-amino-1-oxopropan-2-yl)amino)-2-(4-(4-(trifluoromethyl)phenoxy)cyclohex-1-en-1-yl)pyrimidine-4-carboxamide, or a pharmaceutically acceptable salt, or solvate thereof.

18. A pharmaceutical composition, comprising the compound of claim 1, or a pharmaceutically acceptable salt, or solvate thereof, and a pharmaceutically acceptable carrier.

19. A method for treating pain in a mammal, comprising administering an effective amount of a compound as claimed in claim 1, or a pharmaceutically acceptable salt or solvate thereof, to a mammal in need of such treatment.

20. The method of claim 19, wherein said pain is selected from the group consisting of chronic pain, inflammatory pain, neuropathic pain, acute pain, and surgical pain.

21. The compound of claim 1, wherein $R^4$ is selected from the group consisting of:

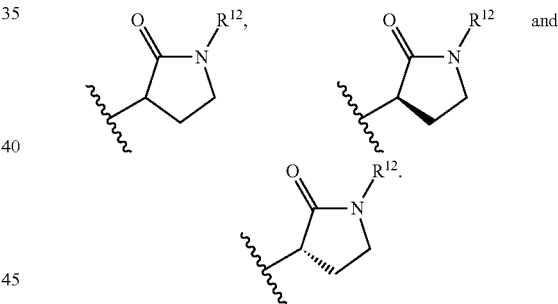

* * * * *